US008163746B2

(12) United States Patent
Sugasawa et al.

(10) Patent No.: US 8,163,746 B2
(45) Date of Patent: Apr. 24, 2012

(54) AZOLECARBOXAMIDE DERIVATIVE

(75) Inventors: Keizo Sugasawa, Tokyo (JP); Kenichi Kawaguchi, Tokyo (JP); Takaho Matsuzawa, Tokyo (JP); Ryushi Seo, Tokyo (JP); Hironori Harada, Tokyo (JP); Akira Suga, Tokyo (JP); Tomoaki Abe, Tokyo (JP); Hidenori Azami, Tokyo (JP); Shunichiro Matsumoto, Tokyo (JP); Takashi Shin, Tokyo (JP); Masayuki Tanahashi, Tokyo (JP); Toru Watanabe, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/297,275

(22) PCT Filed: Apr. 19, 2007

(86) PCT No.: PCT/JP2007/059009
§ 371 (c)(1),
(2), (4) Date: Oct. 15, 2008

(87) PCT Pub. No.: WO2007/123269
PCT Pub. Date: Nov. 1, 2007

(65) Prior Publication Data
US 2009/0286766 A1 Nov. 19, 2009

(30) Foreign Application Priority Data

Apr. 19, 2006 (JP) ................ 2006-115481

(51) Int. Cl.
*A61K 31/5355* (2006.01)
*A61K 31/496* (2006.01)
*A61K 31/451* (2006.01)
*A61K 31/4535* (2006.01)
*A61K 31/426* (2006.01)
*C07D 413/14* (2006.01)
*C07D 211/32* (2006.01)
*C07D 211/46* (2006.01)
*C07D 277/24* (2006.01)

(52) U.S. Cl. ............... 514/235.8; 514/236.8; 514/253.1; 514/254.02; 514/318; 514/326; 514/365; 544/130; 544/364; 544/369; 546/193; 546/208; 548/200

(58) Field of Classification Search .............. None
See application file for complete search history.

(56) References Cited

U.S. PATENT DOCUMENTS

| 2004/0157845 | A1  | 8/2004  | Doherty et al. |
| 2004/0220191 | A1  | 11/2004 | Schwink et al. |
| 2006/0084650 | A1  | 4/2006  | Dong et al. |
| 2006/0100201 | A1* | 5/2006  | Illig et al. ............. 514/227.5 |
| 2006/0247253 | A1  | 11/2006 | Leban et al. |
| 2007/0054939 | A1  | 3/2007  | Guedat et al. |
| 2007/0299077 | A1  | 12/2007 | Schwink et al. |
| 2009/0023758 | A1  | 1/2009  | Wahling et al. |
| 2010/0152219 | A1  | 6/2010  | Block et al. |

FOREIGN PATENT DOCUMENTS

| EP | 1 340 757 | | 9/2003 |
| EP | 1 881 001 | A1 | 1/2008 |
| EP | 1 942 105 | | 7/2008 |
| FR | 2 856 685 | | 12/2004 |
| JP | 2001 278872 | A | 10/2001 |
| JP | 2003-231687 | | 8/2003 |
| JP | 2007/091733 | A | 4/2007 |
| WO | 94/25456 | | 11/1994 |
| WO | WO 96/16954 | | 6/1996 |
| WO | 99/00121 | | 1/1999 |
| WO | 00/27823 | | 5/2000 |
| WO | 00/62778 | | 10/2000 |
| WO | 01/14380 | | 3/2001 |
| WO | 01/32653 | | 5/2001 |
| WO | 01/78698 | | 10/2001 |
| WO | 02/20479 | | 3/2002 |
| WO | 02/20513 | | 3/2002 |
| WO | 02/064558 | | 8/2002 |
| WO | 03/013484 | | 2/2003 |
| WO | 03/027111 | | 4/2003 |
| WO | 2004/002948 | | 1/2004 |
| WO | WO 2004/018428 | A1 | 3/2004 |
| WO | WO 2004/072025 | A2 | 8/2004 |
| WO | 2004/096795 | | 11/2004 |
| WO | WO 2005/003128 | * | 1/2005 |

(Continued)

OTHER PUBLICATIONS

"Pain," Merck Manuals Online Medical Library: Home Edition. Accessed Mar. 24, 2009. <http://www.merck.com/mmhe/sec06/ch078/ch078a.html>.*
Stillman, Mark. "Clinical approach to patients with neuropathic pain." Cleveland Clinic Journal of Medicine, 73 (8), pp. 726-730, 733-739.*
Joanne C. Conover, et al., "Neurotrophin Regulation of the Developing Nervous System: Analyses of Knockout Mice", *Reviews in the Neurosciences*, 8, 13-27 (1997).
E.M. Lowe, et al., "Increased nerve growth factor levels in the urinary bladder of women with idiopathic sensory urgency and interstitial cystitis", *British Journal of Urology* (1997), 79, 572-577.

(Continued)

*Primary Examiner* — Rebecca Anderson
*Assistant Examiner* — Alicia L Otton
(74) *Attorney, Agent, or Firm* — Oblon, Spivak, McClelland, Maier & Neustadt, L.L.P.

(57) ABSTRACT

Provided is an agent for treating or preventing urinary frequency, urinary urgency and urinary, incontinence which are associated with overactive bladder, a lower urinary tract disease such as interstitial cystitis and chronic prostatitis accompanied by lower urinary tract pain, and various diseases accompanied by pain. A novel azolecarboxamide derivative in which an azole ring such as thioazole or oxazole is bonded to a benzene ring, pyridine ring or pyrimidine ring through carboxamide was confirmed to have a potent trkA receptor-inhibitory activity and found to be an agent for treating or preventing lower urinary tract disease and various diseases accompanied by pain, which is excellent in efficacy and safety, and thus the present invention was accomplished.

16 Claims, No Drawings

FOREIGN PATENT DOCUMENTS

| | | |
|---|---|---|
| WO | 2005/030704 | 4/2005 |
| WO | 2005/030705 | 4/2005 |
| WO | 2005/042488 | 5/2005 |
| WO | 2005/049033 | 6/2005 |
| WO | WO 2005/049018 A1 | 6/2005 |
| WO | 2005/076695 | 8/2005 |
| WO | 2005/103010 | 11/2005 |
| WO | 2006/018280 | 2/2006 |
| WO | 2006/020767 | 2/2006 |
| WO | 2006/047479 | 5/2006 |
| WO | 2006/047503 | 5/2006 |
| WO | 2006/047504 | 5/2006 |
| WO | 2006/116355 | 11/2006 |
| WO | 2006/122011 | 11/2006 |
| WO | 2007/000582 | 1/2007 |
| WO | 2007/017144 | 2/2007 |
| WO | WO 2007/014926 A1 | 2/2007 |
| WO | 2007/026959 | 3/2007 |
| WO | 2007/031440 | 3/2007 |
| WO | WO 2007/035478 A2 | 3/2007 |
| WO | 2007/049532 | 5/2007 |
| WO | 2007/060140 | 5/2007 |
| WO | WO 2007/060140 | * 5/2007 |
| WO | 2007/103550 | 9/2007 |
| WO | 2008/054701 | 5/2008 |
| WO | 2008/054702 | 5/2008 |
| WO | 2008/054749 | 5/2008 |
| WO | WO 2008/054702 | * 5/2008 |
| WO | WO 2008/054749 | * 5/2008 |

OTHER PUBLICATIONS

N. Dmitrieva, et al., "The Role of Nerve Growth Factor in a Model of Visceral Inflammation", *Neuroscience* vol. 78, No. 2, pp. 449-459, 1997.

Jordan D. Dimitrakov, et al. "Efficacy and Safety of Recombinant Human Anti-NGF Antibody in the Treatment of IC", General outline preliminarily described for the 99*th* American Urology Association, (San Francisco), 2004, #363.

Vivian Y. Hu, et al., "Decrease in Bladder Overactivity with REN1820 in Rats with Cyclophosphamide Induced Cystitis", *The Journal of Urology*, vol. 173, 1016-1021, Mar. 2005.

M. Theodosiou, et al., "Hyperalgesia due to nerve damage: role of nerve growth factor", *Pain* 81 (1999), 245-255.

David L. Shelton, et al., "Nerve growth factor mediates hyperalgesia and cachexia in auto-immune arthritis", *Pain* 116 (2005), 8-16.

Daniel J. George, et al. "Sustained in Vivo Regression of Dunning H Rat Prostate Cancers Treated with Combinations of Androgen Ablation and Trk Tyrosine Kinase Inhibitors, CEP-751 (KT-6587) or CEP-701 (KT-5555)", *Cancer Research*, 59, 2395-2401, (1999).

Jagabandhu Das et al., "2-Aminothiazole as a Novel Kinase Inhibitor Template. Structure—Activity Relationship Studies toward the Discovery of N-(2-Chloro-6-methylphenyl)-2-[[6-[4-(2-hydroxyethyl)-1-piperanzinyl)]-2-methyl-4-pyrimidinyl]amino)]-1,3-thiazole-5-carboxamide (Dasatinib, BMS-354825) as a Potent *pan*-Src Kinase Inhibitor", *Journal of Medicinal Chemistry*, 2006, 49, 6819-6832.

U.S. Appl. No. 12/739,433, filed Apr. 23, 2010, Sugasawa, et al.

Extended European Search Report issued Jul. 18, 2011, in Patent Application No. 08842145.8.

Rogelio P. Frutos, et al., "Practical Synthesis of 2-(2-Isopropylaminothiazol-4-yl)-7-methoxy-1*H*-quinolin-4-one: Key Intermediate for the Synthesis of Potent HCV NS3 Protease Inhibitor BILN 2061", Synthesis, No. 15, XP 2507667, Aug. 1, 2006, pp. 2563-2567.

Tao Wang, et al., "Trk kinase inhibitors as new treatments for cancer and pain", Expert Opinion on Therapeutic Patents, Informa Healthcare, vol. 19, No. 3, XP 2557234, Mar. 1, 2009, pp. 305-319.

Jianke Li, et al., "Preparation of novel antibacterial agents. Replacement of the central aromatic ring with heterocycles", Bioorganic & Medicinal Chemistry Letters, vol. 17, No. 8, XP 22009263, 2007, pp. 2347-2350.

Office Action issued Apr. 29, 2011 in European Patent Application No. 07 742 444.8-1211.

Chinese Office Action for Patent Application No. 200780014053.7 filed Apr. 19, 2006 (w/English Translation).

Chinese Office Action issued on Apr. 25, 2011 in corresponding Chinese Application No. 200780014053.7 filed on Apr. 19, 2007 (with an English Translation).

* cited by examiner

AZOLECARBOXAMIDE DERIVATIVE

TECHNICAL FIELD

The present invention relates to an azolecarboxamide derivative which is useful as a medicine, particularly as an agent for treating urinary frequency, urinary urgency, urinary incontinence, lower urinary tract pain, which are associated with various lower urinary tract diseases including overactive bladder, and various diseases accompanied by pain.

BACKGROUND ART

Overactive bladder refers to a clinical condition complaining urinary urgency regardless of incontinence, which is usually accompanied by urinary frequency and nocturia (Non-Patent Document 1). Currently, an anticholinergic agent is mainly used for the treatment thereof, and certain therapeutic outcome has been shown. However, it is known to cause side-effects such as dry mouth, constipation and blurred vision and it has been reported that the anticholinergic agent is difficult to be used for patients with prostatic hypertrophy or elderly patients because of a risk of urinary retention. In addition, there are patients showing no improvement with the anticholinergic agent. From the above facts, there is a great expectation for a drug with new mechanism of action against overactive bladder.

Nerve Growth Factor (NGF) is one of humoral factors named generically as a neurotrophic factor, which plays an important role in the development, differentiation and function maintenance of neurons in an organism. As the receptor of NGF, the high-affinity trkA receptor (receptor tyrosine kinase) and the low-affinity p75 receptor have been known. It has been reported that p75 binds to all of nerve growth factors, and is involved in apoptosis in the process of neuron development, but its role has not yet been fully elucidated. It has been known that NGF and trkA receptor-knockout mice show the same phenotype (Non-Patent Document 1), and it is believed that a physiological action of NGF is exhibited mainly through the trkA receptor.

It has been known that the NGF level in bladder is high in a patient with overactive bladder or interstitial cystitis (Non-Patent Document 2), and it has been reported that an intravesical instillation of NGF reduces a bladder capacity of rat and that an inhibition of NGF improves urinary functions in the urinary frequency model rat (Non-Patent Document 3). In addition, there have been reported that the inhibition of NGF improved urinary frequency or incontinence in patients with interstitial cystitis (Non-Patent Document 4), and thus it is believed that a trkA receptor inhibitor is useful as an agent for treating urinary frequency/urinary urgency, and urinary incontinence which are associated with overactive bladder, and lower urinary tract diseases such as interstitial cystitis and prostatitis.

Moreover, a trkA receptor inhibitor has a different mechanism of action, and thus side effects which are characteristic to the anticholinergic agent are expected to be avoided and also an effect on patients who showed no improvement with the anticholinergic agent is expected. In addition, this agent is expected to show more potent effects on subjective symptoms by acting on sensory nerves. Furthermore, this agent has been reported to exhibit an effect of improving morbid conditions without lowering the urinary pressure in the urinary frequency model rat (Non-Patent Document 5), and thus it is expected that this agent can be administered safely to a patient with prostatic hypertrophy or an elderly patient.

It has been also known that administration of NGF to human or rat induces pain, and that algesthesia in the trkA knockout mice is lost. Consequently, NGF is believed to be strongly related in expression of pain. An NGF inhibition shows efficacy to the model animals with neuropathic pain or inflammatory pain, such as a model with pain induced by injury to sciatic nerve (Non-Patent Document 6) and a model with pain induced by damage to knee joint (Non-Patent Document 7), and the trkA receptor inhibitor is believed to be useful as an agent for treating a lower urinary tract disease accompanied by lower urinary tract pain and various kinds of pains such as an osteoarthritis.

As the compound mentioned above, there have been known an indolocarbazole derivative (Non-Patent Document 8), a pyrrolocarbazole derivative (Patent Document 1), a pyrazolone derivative (Patent Document 2), an oxyindole derivative (Patent Document 3 and 4), an azaoxyindole derivative (Patent Document 5), a pyrazolyl condensed ring compound (Patent Document 6), a pyrazole derivative (Patent Document 7 and 8), a tricyclic derivative (Patent Document 9) and ALE-0540 (Patent Document 10).

In addition to the above Non-Patent Document 8 and Patent Documents 1 to 10, as the compound having relatively similar structure, a compound represented by the following general formula (XV) is disclosed as a c-fms kinase inhibitor in Patent Document 11. However, a trkA receptor-inhibitory activity in the present invention is not mentioned at all. Furthermore, in this publication, there is no specific disclosure in Examples and so forth as for the compound having thiazole or oxazole skeleton wherein 2-position is substituted.

[Chem. 12]

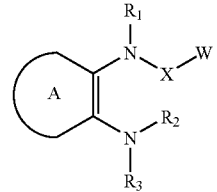

(XV)

(In the formula, A is phenyl, naphthyl, or biphenyl which may respectively be substituted; or a 5 to 7-membered aromatic monoheterocyclic group or a 8 to 10-membered aromatic biheterocyclic group which may respectively be substituted and have 1 to 4 N, O, or S; $R_1$ is —H, aryl, or the like; X is —CO—, —C(=NH)—, —CS—, or the like; $R_2$ and $R_3$ are each independently —H, $C_{1-6}$ alkyl, aryl, cycloalkyl, or the like, while $R_2$ and $R_3$ may, together with the nitrogen to which $R_2$ and $R_3$ are bonded, form a 5 to 7-membered heterocyclic group or aromatic heterocyclic group, and the heterocyclic group may be substituted and contain 1 to 3 N, O or S; W is phenyl, naphthyl or biphenyl which may respectively be substituted, or a 5 or 6-membered monocyclic or 8 to 10-membered bicyclic heterocyclic group or aromatic heterocyclic ring, which may respectively be substituted and contain 1 to 4 N, O or S. For details, refer to the publication).

Non-Patent Document 1: 'Reviews in the Neurosciences', (England), 1997, vol 8, p. 13 to 27
Non-Patent Document 2: 'British Journal of Urology', (England), 1997, vol 79, p. 572 to 7
Non-Patent Document 3: 'Neuroscience', (U.S.A.), 1997, vol. 78, No. 2, p. 449 to 59

Non-Patent Document 4: 'General Outline preliminarily described for the 99th American Urology Association', (San Francisco), 2004, #363

Non-Patent Document 5: 'The Journal of Urology', (U.S.A.), 2005, vol 173, p. 1016 to 21

Non-Patent Document 6: 'Pain', (U.S.A.), 1999, vol 81, p. 245 to 55

Non-Patent Document 7: 'Pain', (U.S.A.), 2005, vol 116, p. 8 to 16

Non-Patent Document 8: 'Cancer Research', 1999, vol 59, p. 2395 to 2401

Patent Document 1: International Publication pamphlet WO01/14380

Patent Document 2: International Publication pamphlet WO01/32653

Patent Document 3: International Publication pamphlet WO02/20479

Patent Document 4: International Publication pamphlet WO02/20513

Patent Document 5: International Publication pamphlet WO03/027111

Patent Document 6: Japan Patent Application Publication 2003-231687

Patent Document 7: International Publication pamphlet WO2005/049033

Patent Document 8: International Publication pamphlet WO2005/103010

Patent Document 9: International Publication pamphlet WO2005/076695

Patent Document 10: International Publication pamphlet WO01/78698

Patent Document 11: International Publication pamphlet WO2004/096795

DISCLOSURE OF THE INVENTION

Problems to be Solved by the Invention

As described above, existing agents for treating urinary frequency, urinary urgency, urinary incontinence which are associated with overactive bladder, and various lower urinary tract diseases accompanied by pain in the lower urinary tract such as interstitial cystitis and chronic prostatitis, are not satisfactory in the points of efficacy, safety, etc. Thus, an agent for treating lower urinary tract disease which is excellent in efficacy and safety has been demanded.

Means for Solving the Problems

As described above, a trkA receptor inhibitor is expected to be a highly safe therapeutic agent with few side effects such as dry mouth and urinary retention, for a lower urinary tract disease. The inventors of the present invention made extensive studies on a compound having a trkA receptor-inhibitory activity in order to provide a novel compound useful for treating a lower urinary tract disease and so forth. As a result, they found that an azolecarboxamide derivative represented by the following general formula (I) exhibits potent trkA receptor-inhibitory activity, thus they completed the invention.

That is, the present invention relates to a novel azolecarboxamide derivative or a salt thereof, the derivative represented by the following general formula (I):

[Chem. 13]

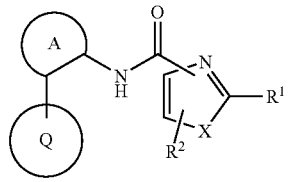

(I)

(In the formula, symbols have the following meanings;

X: S or O,

A: phenylene which may be substituted, pyridinediyl which may be substituted, pyrimidinediyl which may be substituted, thiophenediyl which may be substituted, pyrazolediyl which may be substituted, or pyridonediyl which may be substituted, Q: a monocyclic or bicyclic alicyclic nitrogen-containing heterocyclic group which may be substituted, $R^1$: halogen, lower alkylcarbonyl, $C_1$-$C_7$ alkyl which may be substituted, lower cycloalkyl which may be substituted, lower alkoxy which may be substituted, aryl which may be substituted, heteroaryl which may be substituted, a group represented by the general formula (II), the general formula (III), or the general formula (IV):

[Chem. 14]

(II)

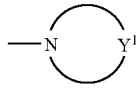

(III)

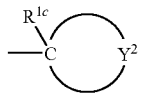

(IV)

$R^{1a}$ and $R^{1b}$: each independently —H, lower alkyl which may be substituted, lower cycloalkyl, a saturated heterocyclic group which may be substituted, lower alkylcarbonyl, lower alkoxycarbonyl, aryl, or heteroaryl, $R^{1c}$: —H or lower alkyl, $Y^1$: lower alkylene which may be substituted in which —O—, —S—, —SO—, —SO$_2$—, or —N(—$R^{1d}$)— may be contained between carbons thereof, $R^{1d}$: —H, lower alkyl, lower alkylcarbonyl, lower alkoxycarbonyl, or aryl-lower alkyl, $Y^2$: lower alkylene in which —O—, —S—, —SO$_2$—, —N(—$R^{1e}$)—, —N(—CO—$R^{1f}$)—, —N(—CO—NH—$R^{1g}$)—, —N(—CS—NH—$R^{1g}$)—, or —N(—SO$_2$—$R^{1h}$)— may be contained between carbons thereof, $R^{1e}$: —H or lower alkyl which may be substituted, $R^{1f}$: lower alkyl which may be substituted, lower cycloalkyl, lower alkoxy, aryl which may be substituted, heteroaryl which may be substituted, or aryl-lower alkenyl, $R^{1g}$: —H, lower alkyl, aryl, or aryl-lower alkyl, $R^{1h}$: lower alkyl, lower cycloalkyl, lower cycloalkyl-lower alkyl, aryl which may be substituted, heteroaryl, or aryl-lower alkyl, $R^2$ is —H, halogen, or a nitrogen-containing saturated heterocyclic group. The same shall be applied hereinafter).

Effects of the Invention

The compound of the present invention has a potent trkA receptor-inhibitory activity, urinary symptom-improving action, and analgesic action, and thus is useful as an agent for treating or preventing, for example, urinary frequency, urinary urgency, urinary incontinence which are associated with various lower urinary tract diseases including overactive bladder, and various lower urinary tract diseases accompanied by pain in the lower urinary tract such as interstitial cystitis and chronic prostatitis, as well as various diseases accompanied by pain.

Since the compound of the present invention has different mechanism of action from the anticholinergic agent, an effect on patients who showed no improvement with the anticholinergic agent can be expected, and it is expected to be served as a very safe agent for treating a lower urinary tract disease by avoiding side effects which are characteristic to the anticholinergic agent.

BEST MODE FOR CARRYING OUT THE INVENTION

Hereinafter, the present invention will be described in more detail.

As used in the definition of the general formulae in the present specification, the term "lower" means a linear or branched carbon chain having 1 to 6 carbon atoms (hereinafter simply referred to as $C_{1-6}$), unless otherwise specifically mentioned. Accordingly, the "lower alkyl" is $C_{1-6}$ alkyl, preferably linear alkyl such as methyl, ethyl, n-propyl, and n-butyl groups, and a branched alkyl such as isopropyl, isobutyl, tert-butyl, and neopentyl groups. More preferred is $C_{1-4}$ alkyl, and particularly preferred are methyl, ethyl, n-propyl, isopropyl, and tert-butyl groups. The "lower alkylene" is a divalent group of $C_{1-6}$ alkyl, preferably $C_{1-3}$ alkylene, such as methylene, ethylene, methyl methylene, ethyl methylene, and trimethylene.

The "lower alkenyl" means $C_{2-6}$ alkenyl, preferred are vinyl and allyl, and particularly preferred is allyl.

The "lower alkoxy" means —O-lower alkyl, preferred is $C_{1-4}$ alkoxy, and particularly preferred are methoxy, ethoxy, and tert-butoxy.

The "halogen" means F, Cl, Br, and I. The "halogeno-lower alkyl" means $C_{1-6}$ alkyl substituted with one or more halogen, preferred is $C_{1-6}$ alkyl substituted with one or more F or Cl, and more preferred are chloropropyl, fluoroethyl, trifluoromethyl, trifluoroethyl, and trifluoropropyl groups.

The "cycloalkyl" is a $C_{3-10}$ saturated hydrocarbon ring group, which may have bridge(s). Preferred is $C_{3-8}$ cycloalkyl, and particularly preferred are cyclopropyl, cyclobutyl, cyclopentyl, and cyclohexyl groups.

The "aryl" is a $C_{6-14}$ mono- to tricyclic aromatic hydrocarbon ring group, preferred are phenyl and naphthyl groups. More preferred is phenyl. The aryl may be condensed with monocyclic, oxygen-containing, saturated heterocyclic or monocyclic cycloalkyl. The "aryl-lower alkyl", the "aryl-lower alkenyl", the "aryloxy", the "arylamino", and the "arylcarbonyl" represent "lower alkyl substituted with aryl", "lower alkenyl substituted with aryl", "oxy substituted with aryl", "amino substituted with aryl", and "carbonyl substituted with aryl", respectively.

The "heteroaryl" collectively means a 5 to 8-membered, preferably 5- to 6-membered monocyclic aromatic ring group (monocyclic heteroaryl) each of which has 1 to 3 heteroatom(s) selected from O, S, and N, or a bicyclic or tricyclic heteroaryl having the monocyclic heteroaryl groups condensed with each other, having a benzene ring condensed with the monocyclic heteroaryl group, or having a benzene ring condensed with the heterocyclic group. Preferable examples of the monocyclic heteroaryl include pyridyl, pyridazinyl, pyrimidinyl, pyrazinyl, pyrrolyl, imidazolyl, triazolyl, thienyl, furyl, thiazolyl, pyrazolyl, isothiazolyl, oxazolyl, isooxazolyl, and oxadiazolyl groups, and more preferably pyridyl, pyridazinyl, pyrimidinyl, pyrazinyl, pyrrolyl, thienyl, and furyl groups. Preferable examples of the bicyclic heteroaryl include dihydrobenzofuranyl.

In the "heteroaryl", the ring atom S may be oxidized to form an oxide or dioxide, and N may be oxidized to form an oxide. The "heteroaryl-lower alkyl" means "lower alkyl substituted with heteroaryl".

The "saturated heterocyclic group" means a 4- to 8-membered, preferably 5- to 6-membered saturated heterocyclic group containing one heteroatom of N or O, and a 5- to 8-membered saturated heterocyclic group containing one N atom, and one heteroatom selected from N, O, and S. Preferred are azetidinyl, pyrrolidinyl, piperidinyl, azepanyl, piperazinyl, diazepanyl, tetrahydrofuryl, tetrahydropyranyl, morpholinyl, oxazepanyl, and thiomorpholinyl groups.

In the "saturated heterocycle", the ring atom S may be oxidized to form an oxide or dioxide, and N may be oxidized to form an oxide.

The "alicyclic heterocyclic group" means a corresponding heterocyclic group having double bonds in the above-mentioned saturated heterocyclic group or its structure. Preferred are azetidinyl, pyrrolidinyl, piperidinyl, azepanyl, piperazinyl, diazepanyl, tetrahydrofuryl, tetrahydropyranyl, morpholinyl, oxazepanyl, thiomorpholinyl, pyrrolinyl, and tetrahydropyridyl groups.

The "monocyclic or bicyclic, alicyclic nitrogen-containing heterocyclic group" means a saturated or partially unsaturated 4- to 8-membered, preferably 5- to 6-membered monocyclic nitrogen-containing heterocyclic group, or a 4- to 8-membered, preferably 5- to 6-membered nitrogen-containing heterocyclic group having one bridge. More preferred are azetidinyl, pyrrolidinyl, piperidinyl, azepanyl, piperazinyl, diazepanyl, morpholinyl, thiomorpholinyl, 2,5-diazabicycloheptyl, and tetrahydropyridyl groups.

Preferred embodiments in the compound of the present invention represented by the general formula (I) are described in the following.

1) The compound, wherein X is S or O, and the general formula (I) is represented by the following formula:

[Chem. 15]

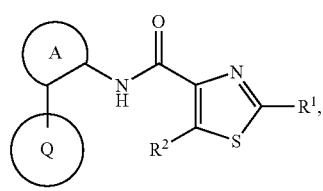

(Ia)

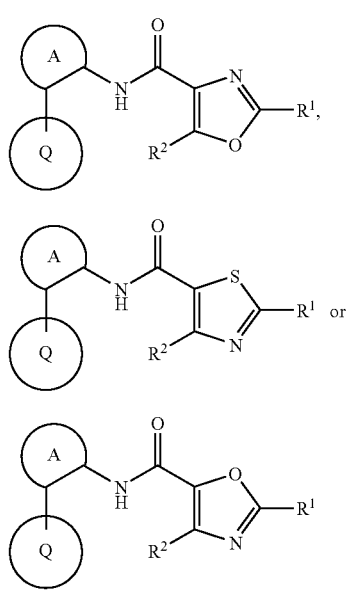

2) The compound as described in 1), wherein A is a divalent group represented by the following formula:
A:

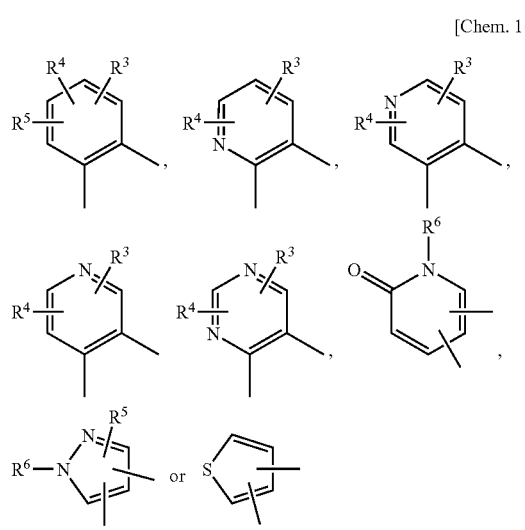

(The symbols in the formula have the following meanings:
R³: —H, halogen, lower alkyl, cyano, cyano lower alkyl, hydroxy-lower alkyl, lower alkoxy, halogeno-lower alkoxy, lower alkoxy-lower alkyl, lower alkenyl, cyano lower alkenyl, carboxy, carbamoyl, lower alkoxy-carbonyl, carboxy-lower alkyl, lower alkoxy-carbonyl-lower alkyl, carbamoyl-lower alkyl, lower alkyl-aminocarbonyl-lower alkyl, lower alkyl-sulfonyl, aminosulfonyl, or lower alkylsulfinyl, R⁴: —H, halogen, or lower alkoxy, R³ and R⁴ in combination may be bridged as —O-lower alkylene, R⁵: —H or halogen, R⁶: —H or lower alkyl. The same shall be applied hereinafter.)

3) More preferably, the compound as described in 2), wherein A is a divalent group represented by the following formula:

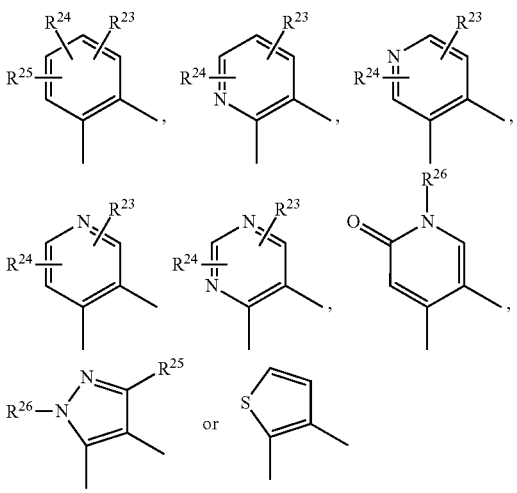

4) Even more preferably, the compound as described in 3), wherein A is as described in 3) and the symbols in the formula have the following meanings:

R²³: —H, fluoro, chloro, bromo, methyl, ethyl, vinyl, cyano, cyanomethyl, cyanoethyl, cyanovinyl, hydroxymethyl, methoxy, difluoromethoxy, trifluoromethoxy, methoxymethyl, methoxycarbonyl, carboxy, carbamoyl, mesyl, aminosulfonyl, methylsulfinyl, or -Alk-CO—R²³ᵃ, -Alk-: methylene or ethylene, R²³ᵃ: hydroxy, amino, tert-butylamino, methoxy, or ethoxy, R²⁴: —H, fluoro, chloro, bromo, or methoxy, R²³ and R²⁴ in combination may be bridged as a —O-ethylene, R²⁵: —H or bromo, R²⁶: —H or methyl).

5) The compound as described in 2), wherein Q is a cyclic group selected from the groups represented by the general formulae (V), (VI), (VII), (VIII), and (IX):

-continued (VIII)

(IX)

(The symbols in the formula have the following meanings:
$V^1$, $V^2$: each independently $C_{1-3}$ alkylene,
$V^3$: methylene or ethylene,
W: —CH(—$R^9$)—, —N(—$R^9$)—, —O—, —S—, —SO—, or —SO$_2$—,
$R^7$ and $R^8$: each independently —H, halogen, hydroxy, lower alkyl, hydroxy-lower alkyl, carboxy, lower alkoxycarbonyl, lower alkylcarbonyloxy, carbamoyl, aryl, aryl-lower alkyl, a saturated heterocyclic group which may be substituted with lower alkyl, or an -Alk-saturated heterocyclic group,
-Alk-: lower alkylene, and
two of $R^7$, $R^8$, and $R^9$ in combination may be bridged as a lower alkylene,
$R^7$ and $R^8$ may be substituted with the same carbon atoms, or in combination may form an oxo group, or a nitrogen-containing saturated heterocyclic group having spiro bonds, wherein the nitrogen-containing saturated heterocyclic group may be substituted with a lower alkyl or oxo group,
$R^9$: —H, lower alkyl, cyano, hydroxy, lower alkoxy, lower alkenyl, lower alkoxycarbonyl-lower alkenyl, lower alkylsulfonyl, -Alk-$R^{9a}$, —CO—$R^{9b}$, Alk-CO—$R^{9b}$, —CO-Alk-$R^{9c}$, —NR$^{9d}$R$^{9e}$, aryl, aryloxy, or a saturated heterocyclic group, wherein the saturated heterocyclic group may be substituted with a lower alkyl, hydroxy, or oxo group,
-Alk-: lower alkylene,
$R^{9a}$: cyano, hydroxy, lower alkoxy, mono- or dihydroxy lower alkyl, aryl, aryloxy, arylcarbonyloxy, amino which may be substituted with lower alkyl, lower alkoxy-carbonylamino, heteroaryl, or saturated heterocyclic group, wherein the heteroaryl may be substituted with a lower alkyl or oxo group, and the saturated heterocyclic group may be substituted with a lower alkyl group,
$R^{9b}$: lower alkyl, hydroxy, lower alkoxy, —NR$^{9f}$R$^{9g}$ or alicyclic heterocyclic group, wherein the alicyclic heterocyclic group may be substituted with lower alkyl, hydroxy, carboxy, lower alkoxycarbonyl, mono- or di-lower alkylamino, a saturated heterocyclic group, or an -Alk-saturated heterocyclic group,
-Alk-: lower alkylene,
$R^{9f}$ and $R^{9g}$: each independently —H, lower alkyl, hydroxy-lower alkyl, lower cycloalkyl which may be substituted with amino, lower alkoxy-lower alkyl, mono- or di-lower alkyl-amino-lower alkyl, lower alkylsulfonyl, heteroaryl, a saturated heterocyclic group,
wherein the saturated heterocyclic group may be substituted with lower alkyl or aryl-lower alkyl, or
an -Alk-saturated heterocyclic group,
-Alk-: lower alkylene,
$R^{9c}$: lower alkoxy, lower alkylcarbonyloxy or saturated heterocyclic group, wherein the saturated heterocyclic group may be substituted with a lower alkyl or oxo group, and $R^{9d}$ and $R^{9e}$: each independently —H, lower alkyl, lower alkylcarbonyl, or carbamoyl-lower alkyl).

6) More preferably, the compound as described in 5), wherein Q is a cyclic group represented by the following formula:

[Chem. 19]

(The symbols in the formula have the following meanings:
$R^{27}$ and $R^{28}$: each independently —H, fluoro, hydroxy, oxo, methyl, hydroxymethyl, carboxy, carbamoyl, acetoxy, methoxycarbonyl, phenyl, benzyl, pyrrolidinylmethyl, or piperidinyl which may be substituted with methyl, $R^{27}$ and $R^{28}$ in combination may be bonded with the same Q ring-constituting carbon atom to form a pyrrolidine ring which may be substituted with methyl and oxo, and thus may have a spiro bond.

$R^{29}$: —H, hydroxy, cyano, methyl, ethyl, isopropyl, isopentyl, allyl, methoxy, methoxycarbonylallyl, ethoxycarbonylallyl, phenyl, phenoxy, piperidinyl which may be substituted with a methyl group, piperazinyl which may be substituted with a methyl group or an oxo group, morpholinyl, methylsulfonyl, tetrahydrofuryl which may be substituted with hydroxy, -Alk-$R^{29a}$, —CO—$R^{29a}$, -Alk-CO—$R^{29b}$, CO-Alk-$R^{29c}$, or —$NR^{29d}R^{29e}$, -Alk-: methylene, ethylene, methylmethylene, trimethylene, tetramethylene, or pentamethylene, $R^{29a}$: methoxy, cyano, hydroxy, phenyl, phenoxy, benzoyloxy, pyridyl, thiazolyl, oxazolyl, oxadiazolyl, triazolyl which may be substituted with oxo, imidazolyl which may be substituted with methyl, pyrrolidinyl which may be substituted with methyl, piperidinyl which may be substituted with methyl, morpholinyl, oxazepanyl, 1,2-dihydroxyethyl, 1-hydroxypropyl, amino, dimethylamino, diethylamino, or tert-butoxycarbonylamino, $R^{29b}$: methyl, hydroxy, methoxy, ethoxy, butoxy, pyrrolidinyl which may have a substituent selected from the following Group $G_{5-1}$, pyrrolinyl, piperidinyl which may have a substituent selected from the following Group $G_{5-2}$, piperazinyl which may have a substituent selected from the following Group $G_{5-3}$, diazepanyl which may be substituted with methyl, morpholinyl, tetrahydropyranyl, or —$NR^{29f}R^{29g}$, $R^{29f}$: —H, methyl, ethyl, hydroxyethyl, methoxyethyl, tetrahydropyranyl, morpholinylethyl, dimethylaminoethyl, mesyl, pyridyl, cyclohexyl which may be substituted with amino, piperidinyl which may be substituted with methyl, or pyrrolidinyl which may have a substituent selected from the following Group $G_{5-4}$, $R^{29g}$: —H, methyl, or ethyl, Group $G_{5-1}$: hydroxy, methyl, dimethylamino, and pyrrolidinylmethyl, Group $G_{5-2}$: methyl, carboxy, ethoxycarbonyl, and pyrrolidinyl, Group $G_{5-3}$: methyl and propyl, Group $G_{5-4}$: methyl and benzyl, $R^{29c}$: methoxy, acetoxy, pyrrolidinyl, piperazinyl which may be substituted with methyl, morpholinyl, or thiomorpholinyl which may be substituted with oxo, $R^{29d}$ and $R^{29e}$: each independently —H, methyl, ethyl, acetyl, or carbamoylmethyl).

7) The compound as described in 5), wherein $R^1$ is represented by the following formula:

$R^1$: halogen, lower alkylcarbonyl, lower cycloalkyl which may be substituted with hydroxy, or lower alkoxy which may be substituted with lower alkoxy, $C_1$-$C_7$ alkyl which may have a substituent selected from the following Group $G_{6-1}$, aryl, heteroaryl, a group represented by the general formula (X), (XI), (XII), (XIII), or (XIV), wherein the aryl and the heteroaryl may have one or two substituents selected from the following Group $G_{6-2}$, and the two substituents in combination may form a cyclic structure, Group $G_{6-1}$: hydroxy, lower alkoxy, N-lower alkyl-N-lower alkoxy-lower alkyl-amino, mono- or di-lower alkyl amino, a saturated heterocyclic group, aryl, and aryloxy, wherein the aryl or the aryloxy may be substituted with halogen or halogeno-lower alkyl, Group $G_{6-2}$: halogen, hydroxy, oxo, lower alkyl, halogeno-lower alkyl, lower alkoxy, cyano, carboxy, carbamoyl, and —$NR^{1i}R^{1j}$, $R^{1i}$ and $R^{1j}$: each independently —H, lower alkyl, lower alkoxy-lower alkyl, or lower alkoxycarbonyl,

[Chem. 20]

(X)

(XI)

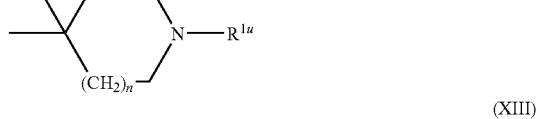

(XII)

(XIII)

(XIV)

$R^{1p}$, $R^{1q}$: each independently —H, lower cycloalkyl, lower alkylcarbonyl, lower alkoxycarbonyl, aryl, heteroaryl, a saturated heterocyclic group, or lower alkyl which may have a substituent selected from the following Group $G_{6-3}$, wherein the saturated heterocyclic group may have a substituent selected from the group consisting of lower alkyl which may be substituted with one or two aryl, and aryl-lower alkoxycarbonyl, Group $G_{6-3}$: halogen, hydroxy, cyano, lower alkoxy, lower alkoxy-lower alkoxy, aryl, heteroaryl, a saturated heterocyclic group, carboxy, lower alkoxycarbonyl, lower alkylsulfanyl, lower alkylsulfinyl, lower alkylsulfonyl, carbamoyl which may be substituted with lower alkyl, and —$NR^{1k}R^{1l}$, $R^{1k}$ and $R^{1l}$: each independently —H, lower alkyl, lower alkylcarbonyl, lower alkoxycarbonyl, or lower alkylsulfonyl, k: 0, 1, or 2, $Y^3$: single bond, —$CH_2$—, —O—, —N(—$R^{1m}$), —S—, —SO—, or —$SO_2$—

$R^{1m}$: —H, lower alkyl, lower alkylcarbonyl, lower alkoxycarbonyl, or aryl-lower alkyl, $R^{1r}$, $R^{1s}$: each independently —H, halogen, hydroxy, lower alkyl, lower alkoxy, hydroxy-lower alkyl, lower alkoxy-lower alkyl, lower alkylcarbonyloxy, carboxy, lower alkoxycarbonyl, carbamoyl, mono- or di-lower alkyl-amino-lower alkyl, aryl, or —CO—NH-Alk-$R^{1n}$, -Alk-: lower alkylene, $R^{1n}$: hydroxy or a saturated heterocyclic group, wherein $R^{1r}$ and $R^{1s}$ in combination may be bridged as a lower alkylene, and $R^{1r}$ and $R^{1s}$ may be substituted with the same carbon atom, and may form an oxo group, m=0, 1, or 2, and n=1, 2, 3, or 4, preferably, m=0, 1, or 2, and n=2 or 3, more preferably, in a case of m=0, n=3, in a case of m=1, n=3, and in a case of m=2, n=2, $R^{1t}$: —H or lower alkyl, $R^{1u}$: —H, lower alkyl, -Alk-$R^{1w}$, —CO—$R^{1x}$, —SO$_2$—$R^{1y}$, or —CS—NH—$R^{1z}$, -Alk-: lower alkylene, $R^{1w}$: lower cycloalkyl, lower alkoxy, carboxy, carbamoyl, a saturated heterocyclic group, aryl, or heteroaryl, wherein the aryl may have a substituent selected from the group consisting of lower alkyl, lower alkoxy, and carboxy groups, $R^{1x}$: lower alkyl, lower cycloalkyl, hydroxy-lower alkyl, lower alkoxy, lower alkoxy-lower alkyl, amino, lower alkylamino, arylamino, aryl-lower alkyl amino, mono- or di-lower alkyl-amino-lower alkyl, aryl, aryl-lower alkyl which may be substituted with halogen, aryl-lower alkenyl, heteroaryl, heteroaryl-lower alkyl, wherein the aryl or the heteroaryl may have a substituent selected from the group consisting of halogen, lower alkyl, lower alkoxy, and aryl, $R^{1y}$: lower alkyl, lower cycloalkyl, lower cycloalkyl-lower alkyl, aryl, aryl-lower alkyl, heteroaryl, wherein the aryl may have a substituent selected from the group consisting of halogen and aryl, $R^{1z}$: lower alkyl, aryl, aryl-lower alkyl, $R^{1v}$: —H or lower alkoxycarbonyl, $Y^4$: —O—, —S— or —SO$_2$—, h: 0 or 1).

8) More preferably, the compound as described in 7), wherein $R^1$ is a group represented by the following (a) to (l):

(a) bromo, methyl, ethyl, propyl, butyl, pentyl, hexyl, heptyl, cyclopentyl, cyclohexyl which may be substituted with hydroxy, acetyl, or methoxyethoxy, (b) lower alkyl having a substituent selected from the following Group $G_{7-1}$, Group $G_{7-1}$: hydroxy, methoxy, propoxy, phenoxy which may be substituted with butyl, phenyl which may be substituted with chloro or trifluoro methyl, morpholinyl, dimethylamino, and methoxyethyl(methyl)amino, (c) phenyl, pyridyl, or pyrazolyl, wherein these groups may be substituted with one or two groups selected from the following Group $G_{7-2}$, Group $G_{7-2}$: fluoro, chloro, bromo, hydroxy, oxo, methyl, trifluoromethyl, methoxy, cyano, carboxy, carbamoyl, amino, methylamino, dimethylamino, methoxyethyl(methyl)amino, and tert-butoxycarbonylamino, (d) pyrimidinyl, pyrazinyl, pyridazinyl which may be substituted with methoxy, oxodihydropyridyl, pyrrolyl, furyl, thienyl, or dihydrobenzofuranyl, (e) —N$R^{11p}R^{11q}$ $R^{11p}$: —H, methyl, ethyl, propyl, isopropyl, cyclobutyl, trifluoromethyl, or methoxyethyl, $R^{11q}$: —H, cyclopropyl, cyclobutyl, acetyl, tert-butoxycarbonyl, phenyl, pyridyl, tetrahydropyranyl, tetrahydrofuryl, oxetanyl, pyrrolidinyl, methylpyrrolidinyl, benzyloxycarbonylpyrrolidinyl, diphenylmethylazetidinyl, or $C_1$-$C_4$ alkyl which may have a substituent selected from the following Group $G_{7-3}$, Group $G_{7-3}$: fluoro, chloro, hydroxy, cyano, methoxy, ethoxy, methoxyethoxy, amino, methylamino, dimethylamino, acetylamino, mesylamino, tert-butoxycarbonylamino, carboxy, carbamoyl, dimethylaminocarbonyl, methoxycarbonyl, phenyl, pyridyl, furyl, tetrahydrofuryl, methylthio, methylsulfinyl, and mesyl, (f) 4-morpholinyl, wherein the morpholinyl may have a substituent selected from the following Group $G_{7-4}$, Group $G_{7-4}$: methyl, hydroxymethyl, methoxymethyl, and dimethylaminomethyl, (g) 1-piperazinyl or 1-diazepanyl, wherein these groups may be substituted with a group selected from the following Group $G_{7-5}$ for a nitrogen atom, and may have a group selected from the following Group $G_{7-6}$, Group $G_{7-5}$: methyl, propyl, acetyl, benzyl, or tert-butoxycarbonyl, Group $G_{7-6}$: fluoro, hydroxy, hydroxymethyl, methoxy, methoxymethyl, oxo, methylamino, or phenyl, (h) 1-piperidinyl, wherein the piperidinyl may be substituted with one or two group selected from the following $G_{7-7}$, Group $G_{7-7}$: fluoro, hydroxy, hydroxymethyl, methoxy, ethoxy, acetyloxy, oxo, carboxy, carbamoyl, ethoxycarbonyl, hydroxypropylcarbamoyl, or tetrahydrofurylmethylcarbamoyl, (i) 1-pyrrolidinyl or 1-azetidinyl wherein these groups may be substituted with one or two groups selected from the following Group $G_{7-8}$, Group $G_{7-8}$: fluoro, hydroxy, hydroxymethyl, methoxy, methoxymethyl, oxo, methylamino, or phenyl, (j) 3-morpholinyl, 3-piperidinyl, 2-pyrrolidinyl, or 3-pyrrolidinyl, wherein these groups may be substituted with a group selected the following $G_{7-9}$ for a nitrogen atom, Group $G_{7-9}$: acetyl, tert-butoxycarbonyl, or benzyl, (k) 4-oxazepanyl, 4-thiomorpholinyl, 1-oxothiomorpholin-4-yl, 1,1-dioxothiomorpholin-4-yl, 2,5-diazabicycloheptan-1-yl, 2-oxa-5-azabicyclo[2.2.1]heptan-5-yl, tetrahydrofuryl, tetrahydropyranyl, thiacyclohexyl, or 1,1-dioxothiacyclohexyl, (l) a group represented by the following formula:

[Chem. 21]

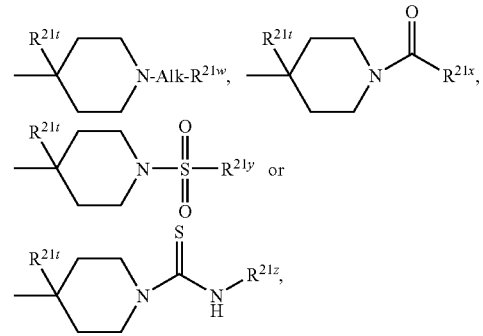

(The symbols in the formula have the following meanings:

$R^{21t}$: —H or methyl,

-Alk-: methylene, ethylene, trimethylene, tetramethylene, pentamethylene, methyltrimethylene, $R^{21w}$: —H, cyclopropyl, methoxy, carboxy, carbamoyl, tetrahydrofuryl, pyridyl, or phenyl, wherein the phenyl may have a substituent selected from the group consisting of methyl, methoxy, and carboxy, $R^{21x}$: methyl, ethyl, propyl, butyl, pentyl, isopropyl, ethylpropyl, cyclobutyl, cyclopentyl, cyclohexyl, pyrrolyl which may be substituted with methyl, pyridyl, pyridazinyl, pyrimidinyl, thienyl, phenyl, tert-butoxy, amino, isopropylamino, phenylamino or benzylamino, phenylvinyl, phenylpropenyl, or -Alk$^{31x}$-$R^{31x}$, wherein the phenyl may have a substituent selected from the group consisting of fluoro, methyl, methoxy, and phenyl, -Alk$^{31x}$-: methylene, ethylene, trimethylene, or tetramethylene, R$^{31x}$: phenyl or pyridyl, each of which may be substituted with hydroxy, methoxy, dimethylamino, or fluoro, R$^{21y}$: methyl, ethyl, propyl, butyl, isopropyl, cyclopropyl, cyclohexyl, cyclohexylmethyl, phenyl, benzyl, phenylethyl, or thienyl, wherein the phenyl may have a substituent selected from the group consisting of fluoro and phenyl, R$^{21z}$: methyl, isopropyl, phenyl, or benzyl).

9) The compound as described in 7), wherein R$^2$ is a group represented by the following:

R$^2$: —H, halogen, or a nitrogen-containing saturated heterocyclic group.

10) More preferably, the compound as described in 9), wherein R$^2$ is as follows:

R$^2$: —H, bromo, or a pyrrolidinyl group.

In the specification, the substituent acceptable by the term "may be substituted" may be any of the groups that are usually used in the technical field as a substituent of a respective group, and each of the groups may have at least one substituent.

In A of the general formula (I), examples of the substituent of the "phenylene which may be substituted, pyridinediyl which may be substituted, or pyrimidinediyl which may be substituted" include halogen, lower alkyl, cyano, cyano-lower alkyl, hydroxy-lower alkyl, lower alkoxy, halogeno-lower alkyl, lower alkoxy-lower alkyl, lower alkenyl, cyano-lower alkenyl, carboxy, carbamoyl, lower alkoxycarbonyl, carboxy-lower alkyl, lower alkoxycarbonyl-lower alkyl, carbamoyl-lower alkyl, lower alkylaminocarbonyl-lower alkyl, lower alkylsulfonyl, aminosulfonyl, or lower alkylsulfinyl.

Examples of the substituent of the "thiophenediyl which may be substituted, pyrazoldiyl which may be substituted, or pyridonediyl which may be substituted" in A of the general formula (I), in which two substituents in combination may be bridged as —O-lower alkylene, include halogen and lower alkyl.

Examples of the substituent of the "monocyclic or bicyclic, alicyclic nitrogen-containing heterocyclic group which may be substituted" in Q of the general formula (I) include halogen, hydroxy, oxo, cyano, lower alkyl, lower alkenyl, lower alkoxycarbonyl-lower alkenyl, lower alkylcarbonyloxy, lower alkylsulfonyl, aryl, aryloxy, a saturated heterocyclic group, and groups represented by -Alk-R$^{9a}$, —CO—R$^{9b}$, -Alk-CO—R$^{9b}$, —CO-Alk-R$^{9c}$, and —NR$^{9d}$R$^{9e}$. Here, the saturated heterocyclic group may be substituted with a lower alkyl, hydroxy, or oxo group, or may have a spiro bond.

The symbols in the formula have the following meanings:
-Alk-: lower alkylene,

R$^{9a}$: cyano, hydroxy, lower alkoxy, mono- or dihydroxy-lower alkyl, aryl, aryloxy, arylcarbonyloxy, amino which may be substituted with lower alkyl, heteroaryl, or a saturated heterocyclic group, wherein the heteroaryl may be substituted with a lower alkyl or oxo group, and the saturated heterocyclic group may be substituted with lower alkyl, R$^{9b}$: lower alkyl, hydroxy, lower alkoxy, an alicyclic heterocyclic group, or —NR$^{9f}$R$^{9g}$, wherein the alicyclic heterocyclic group may be substituted with lower alkyl, hydroxy, carboxy, lower alkoxycarbonyl, mono- or di-lower alkylamino, a saturated heterocyclic group, or an -Alk-saturated heterocyclic group, -Alk-: lower alkylene, R$^{9f}$ and R$^{9g}$: each independently —H, lower alkyl, hydroxy-lower alkyl, lower cycloalkyl which may be substituted with amino, lower alkoxy-lower alkyl, mono- or di-lower alkyl-amino-lower alkyl, lower alkylsulfonyl, heteroaryl, a saturated heterocyclic group, wherein the saturated heterocyclic group may be substituted with lower alkyl or aryl-lower alkyl, or an -Alk-saturated heterocyclic group,
-Alk-: lower alkylene, R$^{9c}$: lower alkoxy, lower alkylcarbonyloxy, or a saturated heterocyclic group, wherein the saturated heterocyclic group may be substituted with lower alkyl or oxo, R$^{9d}$ and R$^{9e}$: each independently —H, lower alkyl, lower alkylcarbonyl, or carbamoyl-lower alkyl).

Examples of the substituent of the "C$_1$-C$_7$ alkyl which may be substituted" in R$^1$ of the general formula (I) include hydroxy, lower alkoxy, N-lower alkyl-N-lower alkoxy lower alkyl-amino, mono- or di-lower alkylamino, a saturated heterocyclic group, aryl, and aryloxy.

Here, the aryl or aryloxy may be substituted with halogen or halogeno-lower alkyl.

Examples of the substituent of the "lower cycloalkyl which may be substituted" in R$^1$ of the general formula (I) include hydroxy.

Examples of the substituent of the "lower alkoxy which may be substituted" in R$^1$ of the general formula (I) include lower alkoxy.

Examples of the substituent of the "aryl which may be substituted" and the "heteroaryl which may be substituted" in R$^1$ of the general formula (I) include halogen, hydroxy, oxo, lower alkyl, halogeno-lower alkyl, lower alkoxy, cyano, carboxy, carbamoyl, and —NR$^{1i}$R$^{1j}$.

The symbols in the formula have the following meanings:
R$^{1i}$ and R$^{1j}$: each independently —H, lower alkyl, lower alkoxy-lower alkyl, or lower alkoxycarbonyl).

Examples of the substituent of the "lower alkyl which may be substituted" in R$^{1a}$ and R$^{1b}$ in the general formula (II) include halogen, hydroxy, cyano, lower alkoxy, lower alkoxy-lower alkoxy, aryl, heteroaryl, a saturated heterocyclic group, carboxy, lower alkoxycarbonyl, lower alkylsulfanyl, lower alkylsulfinyl, lower alkylsulfonyl, carbamoyl which may be substituted with lower alkyl, and —NR$^{1k}$R$^{1l}$.

The symbols in the formula have the following meanings:
R$^{1k}$ and R$^{1l}$: each independently —H, lower alkyl, lower alkylcarbonyl, lower alkoxycarbonyl or lower alkylsulfonyl).

Examples of the substituent of the "saturated heterocyclic group which may be substituted" in R$^{1a}$ and R$^{1b}$ in the general formula (II) include lower alkyl which may be substituted with aryl, and aryl-lower alkoxycarbonyl.

Examples of the substituent of the "lower alkylene which may be substituted" in Y in the general formula (III) include halogen, hydroxy, oxo, lower alkyl, lower alkoxy, hydroxy-lower alkyl, lower alkoxy-lower alkyl, aryl, aryl-lower alkyl, carboxy, lower alkylcarbonyl, lower alkoxycarbonyloxy, lower alkoxycarbonyl, carbamoyl, mono- or di-lower alkyl-amino-lower alkyl, and —CO—NH-Alk-R$^{1n}$. Here, two substituents in combination may be bridged as lower alkylene, and two substituents may be substituted on the same carbon atom.

The symbols in the formula have the following meanings:
-Alk-: lower alkylene,

R$^{1n}$: hydroxy or a saturated heterocyclic group).

Examples of the substituent of the "lower alkyl which may be substituted" of R$^{1e}$ in Z of the general formula (IV) include lower cycloalkyl, lower alkoxy, carboxy, carbamoyl, a saturated heterocyclic group, aryl, and heteroaryl, wherein the aryl may have a substituent selected from the group consisting of lower alkyl, lower alkoxy, and carboxy groups, Examples of the substituent of the "lower alkyl which may be substituted" of $R^{1f}$ in Z of the general formula (IV) include hydroxy, lower alkoxy, mono- or di-lower alkyl amino, aryl which may be substituted with halogen, and heteroaryl.

Examples of the substituent of the "aryl which may be substituted" and the "heteroaryl which may be substituted" of $R^{1f}$ in Z of the general formula (IV) include halogen, lower alkyl, lower alkoxy, and aryl.

Examples of the substituent of the "aryl which may be substituted" of $R^{1h}$ in Z of the general formula (IV) include halogen and aryl.

The compound of the present invention represented by the general formula (I) may have asymmetric carbons depending on the kind of the substituents, and thus optical isomers may be present. The present invention includes the isolated counterparts of either of a mixture of these optical isomers, and an isolated form thereof. The compound of the present invention may have tautomers, and the present invention also encompasses isolated isomers or a mixture thereof. Examples of these tautomers include a tautomer of 2-hydroxypyridine and 2-pyridone. Also, the labeled compounds, that is, the compounds having at least one element in the compounds of the present invention substituted with radioactive isotopes or non-radioactive isotopes are also included in the present invention.

Furthermore, the "pharmaceutically acceptable prodrugs" of the compounds represented by the general formula (I) are also included in the present invention. The "pharmaceutically acceptable prodrug" is a compound having a group which is converted into a group such as $CO_2H$, $NH_2$, and OH by solvolysis or under a physiological condition to produce the compound (I) of the present invention. Examples of the group capable of forming a prodrug include those as described in "Prog. Med., 5, 2157-2161 (1985), and "Iyakuhin no Kaihatsu (Development of Drugs) (Hirokawa Shoten, 1990), vol. 7, Bunshi Sekkei (Molecular Design)", 163-198.

The salt of compounds (I) of the present invention are the pharmaceutically acceptable salts, and specific examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid. Depending on the kind of substituents, the compounds may form a salt with a base, and examples thereof include salts with inorganic bases such as sodium, potassium, magnesium, calcium, aluminum, and lithium, and with organic bases such as methylamine, ethylamine, ethanolamine, lysine, and ornithine, and ammonium salts.

In addition, the compound (I) of the present invention and a salt thereof also include various hydrates and solvates, and polymorphic substances thereof.

(Preparation Methods)

The compound according to the present invention and a pharmaceutically acceptable salt thereof can be prepared by applying various known synthetic methods, utilizing characteristics based on their basic skeletons or the type of the substituents. Representative preparation methods are exemplified hereinafter. Further, depending on the type of the functional groups, it is in some cases effective from the viewpoint of the preparation techniques to protect the functional group with an appropriate protecting group, or to replace it by a group which may be easily converted into the functional group, during the steps of from starting materials to intermediates. Thereafter, if desired, the protecting group may be removed to obtain a desired compound. Examples of such a functional group include a hydroxyl group, a carboxyl group, and an amino group, and examples of a protecting group thereof include those as described in "Protective Groups in Organic Synthesis", edited by T. W. Greene and P. G. M. Wuts, (USA), $3^{rd}$ edition, 1999, which may be optionally selected and used in response to the reaction conditions. In such a method, the desired compound can be obtained by introducing the protecting group to carry out the reaction, and then, if desired, removing the protecting group or converting it into a desired group.

In addition, a prodrug of the compound (I) or a salt thereof can be prepared by introducing a specific group during the stage of from starting materials to intermediates, similar to the aforementioned protecting groups, or by carrying out the reaction using the obtained compound (I). The reaction can be carried out by employing a method conventionally known to a person skilled in the art, such as common esterification, amidation, and acylation.

(First Preparation Method)

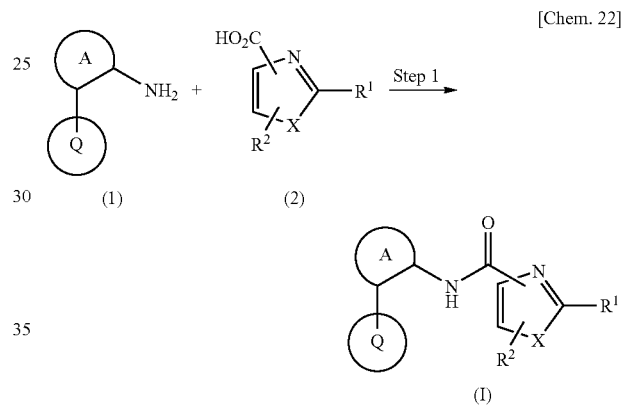

[Chem. 22]

(wherein X, A, Q, $R^1$, and $R^2$ have the same meanings as defined above, respectively. The same shall be applied hereinafter.)

(Step 1)

This step is a process for preparing a compound (I) by subjecting a compound (2) or a reactive derivative thereof, and a compound (1) or a salt thereof to amidation by a conventional method, and then if desired, removing the protecting group.

Examples of the reactive derivative of the compound (2) include a common ester such as methyl ester, ethyl ester, and tert-butyl ester; an acid halide such as acid chloride and acid bromide; an acid azide; an active ester with 1-hydroxybenzotriazole, p-nitrophenol, N-hydroxysuccinimide, or the like; a symmetric acid anhydride; a mixed acid anhydride of a halocarboxylic acid alky ester such as an alkyl halocarbonate, a pivaloyl halide, a p-toluenesulfonyl chloride, and the like; and a mixed acid anhydride such as a phosphoric mixed acid anhydride obtained by the reaction of diphenylphosphoryl chloride with N-methylmorpholine.

If the compound (2) is reacted as a free acid, or is reacted without isolation of an active ester, or the like, amidation that can be usually used by a person skilled in the art can be used, but a method in which a condensing agent such as 1-ethyl-3-(3-dimethylaminopropyl)carbodiimide hydrochloride (WSC-HCl), or dicyclohexylcarbodiimide (DCC), carbonyldiimidazole (CDI), diphenylphosphoryl azide (DPPA), diethylphosphorylcyanide (DEPC), O-(7-azabenzotriazol-1-yl)-

N,N,N',N'-tetramethyluronium hexafluorophosphate (HATU) are allowed to undergo the reaction in the presence of 1-hydroxybenzotriazole (HOBt), a method in which phosphorus oxychloride is allowed to undergo the reaction in a pyridine solvent, or a condensing agent-carrying polystyrene resin such as a PS-carbodiimide (Argonaut Technologies, Inc., USA) or a PL-DCC resin (Polymer Laboratories, UK) are appropriately used.

Also, in some cases, it is preferable to use an isocyanate-carrying polystyrene resin, such as PS-Isocyanate (Argonaut Technologies, Inc., USA), in order to remove an excessive amount of amine after completion of the reaction. In addition, it is preferable in some cases to use a quaternary ammonium salt-carrying polystyrene resin, such as MP-Carbonate (Argonaut Technologies, Inc., USA), in order to remove an excessive amount of carboxylic acid, and the aforementioned additive such as HOBt after completion of the reaction.

Particularly, in the present invention, an acid chloride method, and a method for performing a reaction in the coexistence of an active esterifying agent and a condensing agent are convenient.

The reaction varies depending on the reactive derivatives, condensing agents, or the like to be used, but usually, this is carried out under cooling, from under cooling to at room temperature, or from at room temperature to under heating, in a solvent inert to the reaction, such as halogenated hydrocarbons such as dichloromethane, dichloroethane and chloroform; aromatic hydrocarbons such as benzene, toluene, and xylene; ethers such as ether and tetrahydrofuran (THF); esters such as ethyl acetate (EtOAc); acetonitrile, N,N-dimethylformamide (DMF), N,N-dimethylacetamide (DMA), and dimethyl sulfoxide (DMSO).

Furthermore, in the reaction, it is in some cases advantageous in advancing the reaction smoothly to carry out the reaction with an excess amount of the compound (1) or in the presence of a base such as N-methylmorpholine, trimethylamine, triethylamine, diisopropylethylamine, N,N-dimethylaniline, pyridine, 4-(N,N-dimethylamino)pyridine, picoline, and lutidine. Also, a salt formed from a weak base and a strong acid, such as pyridine hydrochloride, pyridine p-toluenesulfonate, and N,N-dimethylaniline hydrochloride, may be used. Pyridine may be used as a solvent.

Particularly, it is preferable to carry out the reaction in the presence of a base such as triethylamine in a solvent such as THF and DMF.

(Second Preparation Method)

[Chem. 23]

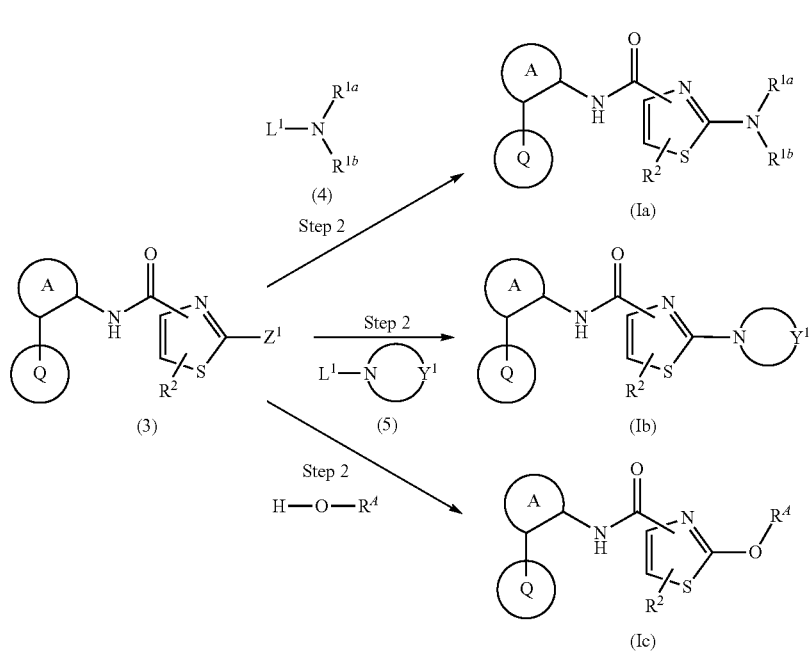

(wherein $Z^1$ represents halogen, SMe, SOMe, $SO_2Me$, $SO_3H$, or OTf. $L^1$ represents hydrogen or methyl. $R^4$ can be any one of the substituents that are usually used, preferably lower alkyl, and more preferably lower alkoxy-lower alkyl. $Y^1$, $R^{1a}$, and $R^{1b}$ have the same meanings as defined above, respectively. The same shall be applied hereinafter)

The nucleophilic substitution reaction of this step can be carried out in a solvent inert to the reaction, such as halogenated hydrocarbons, aromatic hydrocarbons, ethers, esters, alcohols such as methanol, ethanol, and isopropanol, acetonitrile, DMF, DMA, and DMSO, in the presence of an organic base such as triethylamine and diisopropylethylamine, and/or an inorganic base such as potassium carbonate, sodium carbonate, cesium carbonate, sodium hydrogen carbonate, and sodium hydride, by allowing the compound (4), (5), or HO—$R^{1A}$ to undergo the reaction with the compound (3). Further, in order to accelerate the reaction, a catalyst such as dimethylaminopyridine may be added. Also, instead of the organic base and/or the inorganic base, the compound (4) or (5) may be used in an excessive amount. The reaction varies depending on the base to be used, but it can be carried out from under cooling to at room temperature, from at room temperature to under heating, or from at room temperature to under reflux.

Also, in some cases, it is preferable to use an isocyanate-carrying polystyrene resin, such as PS-Isocyanate (Argonaut Technologies, Inc., USA), in order to remove an excessive amount of amine after completion of the reaction.

(Third Preparation Method)

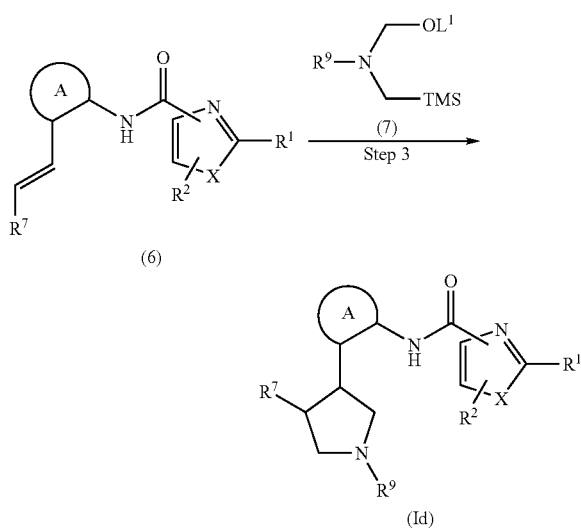

(wherein $L^1$ represents lower alkyl. $R^7$ and $R^9$ have the same meanings as defined above, respectively. The same shall be applied hereinafter.)

The 1,3-dipolar cycloaddition reaction of this step is a step for carrying out cycloaddition by azomethine ylide generated in the reaction system for the compound (6). For various alkoxymethylsilyl methylamine, the reaction can be carried out by allowing the compound (6) to undergo the reaction in the presence of an organic acid such as trifluoroacetic acid, or a Lewis acid such as trimethylsilyl trifluoromethane sulfonate, cesium fluoride, lithium fluoride, tetrabutylammonium fluoride, and zinc chloride, in an organic solvent inert to the reaction, such as halogenated hydrocarbons, aromatic hydrocarbons, ethers, esters, acetonitrile, DMF, DMA, and DMSO. The reaction varies depending on the acid or the solvent to be used, but it can be carried out from under cooling to at room temperature, from at room temperature to under heating, or from at room temperature to under reflux.

(Fourth Preparation Method)

Furthermore, the compound of the present invention having various functional groups represented in the formula (I) can be prepared from the compound of the present invention obtained by First Preparation Method, Second Preparation Method, or Third Preparation Method, by any combination of well-known processes that can be usually employed by a person skilled in the art, such as alkylation, acylation, substitution reaction, oxidation, reduction, and hydrolysis. This step is not limited to a one-step reaction, but it may be consisted of a multi-step reaction. Further, the processes that can be usually employed by a person skilled in the art are not limited to the application for the compound of the present invention, but they may be used in the application for the preparation intermediates.

Representative reactions are exemplified hereinafter.

(1) Amidation

A compound having an amide group among the compounds (I) of the present invention can be prepared by reacting a compound having an amino group as a starting material with a carboxylic acid and a reactive derivative thereof, or by reacting a compound having carboxylic acid as a starting material with an amine. The reaction can be carried out in accordance with Step A of First Preparation Method, for example, with reference to a method as described in "Jikken Kagaku Koza (Courses in Experimental Chemistry) (4$^{th}$ edition)", vol. 22 (1992) (Maruzen), or "Compendium of Organic Synthetic Methods", vols. 1 to 3, or the like.

(2) Sulfonylation

A compound having a sulfonamide group among the compounds (I) of the present invention can be prepared by reacting a compound having an amino group as a starting material with a reactive derivative of sulfonic acid. The reaction can be carried out, for example, with reference to a method as described in "Jikken Kagaku Koza (Courses in Experimental Chemistry) (4$^{th}$ edition)", edited by The Chemical Society of Japan, vol. 24 (1992) (Maruzen).

(3) Synthesis of Carbamate

A compound having a carbamate group among the compounds (I) of the present invention can be prepared by reacting a compound having an amino group as a starting material with a carbonate derivative. The reaction can be carried out, for example, with reference to a method as described in "Jikken Kagaku Koza (Courses in Experimental Chemistry) (4$^{th}$ edition)", edited by The Chemical Society of Japan, vol. 20 (1992) (Maruzen).

(4) Synthesis of Urea and Thiourea

A compound having an urea group among the compounds (I) of the present invention can be prepared by reacting a compound having an amino group as a starting material with an isocyanate compound, an aminocarbonyl halide, or the like.

A compound having a thiourea group among the compounds (I) of the present invention can be prepared by reacting a compound having an amino group as a starting material with a thioisocyanate compound, etc.

The reaction can be carried out, for example, with reference to a method as described in "Jikken Kagaku Koza (Courses in Experimental Chemistry) (4$^{th}$ edition)", edited by The Chemical Society of Japan, vol. 20 (1992) (Maruzen).

(5) O-Acylation

A compound having an ester group among the compounds (I) of the present invention can be prepared by reacting a compound having an alcohol group as a starting material with a carboxylic acid derivative. The reaction can be carried out, for example, with reference to a method as described in "Jikken Kagaku Koza (Courses in Experimental Chemistry) (4$^{th}$ edition)", edited by The Chemical Society of Japan, vol. 22 (1992) (Maruzen).

(6) N-Alkylation

A compound having a secondary amine or a tertiary amine among the compounds (I) of the present invention can have an alkyl group introduced thereinto by reacting a compound having a primary amino group or a secondary amino group as a starting material with another alkylating agent or an epoxy derivative. As the alkylating agent, alkyl halide, an organic sulfonic ester of alcohol, and the like are preferred.

The reaction is carried out by mixing the materials from under cooling to under heating in a solvent inert to the reaction, such as aromatic hydrocarbons, halogenated hydrocarbons, ethers, ketones such as acetone and 2-butanone, acetonitrile, ethyl acetate, DMF, DMA, and NMP. It is sometimes advantageous in smoothly advancing the reaction to carry out the reaction in the presence of an organic base or an inorganic base.

(7) Reductive Alkylation

A compound having a secondary amine or a tertiary amine among the compounds (I) of the present invention can have an alkyl group introduced thereinto by reacting a compound having a primary amino group or a secondary amino group as a starting material with an aldehyde and a ketone for performing reductive alkylation, in the presence of an reducing agent such as sodium borohydride and sodium triacetoxy borohydride, or under a catalytic reduction condition by palladium-carbon under a hydrogen atmosphere. This can exemplified by a method as described in "Jikken Kagaku Koza (Courses in Experimental Chemistry) ($4^{th}$ edition)", edited by The Chemical Society of Japan, vol. 20 (1992) (Maruzen), or the like. It is sometimes preferable to use a reducing agent-carrying polystyrene resin, such as MP-Triacetoxyborohydride (Argonaut Technologies, Inc., USA) as a reducing agent.

(8) Oxidation

A compound having a sulfonyl group or a sulfenyl group among the compounds (I) of the present invention can be prepared by subjecting a compound having a sulfide group to an oxidation reaction. The compound having an adjacent diol can be prepared by subjecting a corresponding olefin product to an Os oxidation, etc. The reaction can be carried out, for example, with reference to a method as described in "Jikken Kagaku Koza (Courses in Experimental Chemistry) ($4^{th}$ edition)", edited by The Chemical Society of Japan, vol. 23 (1992) (Maruzen).

(9) Reduction Reaction

A compound having a primary alcohol group among the compounds (I) of the present invention can be prepared by subjecting a corresponding compound having a carboxyl group to a reduction reaction. The reaction can be carried out, for example, with reference to a method as described in "Jikken Kagaku Koza (Courses in Experimental Chemistry) ($4^{th}$ edition)", edited by The Chemical Society of Japan, vol. 26 (1992) (Maruzen).

(10) Catalytic Reduction Reaction

In the synthesis of the compound of the present invention, a corresponding reduced product can be prepared by subjecting a compound having double bonds, and a compound having a halogen group as starting materials to catalytic reduction reaction. The reaction can be carried out, for example, with reference to a method as described in "Jikken Kagaku Koza (Courses in Experimental Chemistry) ($4^{th}$ edition)", edited by The Chemical Society of Japan, vol. 26 (1992) (Maruzen).

(11) ipso Substitution Reaction

A compound having an alkoxypyridine or aminopyridine skelton among the compounds (I) of the present invention can be prepared by reacting a corresponding compound having a chloropyridyl group as a starting material with an alkoxides, an amine, or the like. The reaction can be carried out, for example, with reference to Step A of Second Preparation Method. Further, under the same condition, an azide group can be once introduced by sodium azide, and then a catalytic reduction, or the like can be carried out to convert the group to a primary amino group.

(12) Palladium Coupling Reaction

A compound having a cyanoaryl group among the compounds (I) of the present invention can be prepared by cross-coupling a corresponding compound having a halogenated aryl group as a starting material with zinc cyanide, or the like in the presence of a palladium catalyst. Further, a compound having an alkenylaryl group or an alkylaryl group can be prepared by cross-coupling a corresponding compound having a halogenated aryl group as a starting material with an organic tin reagent, boric acid, or the like in the presence of a palladium catalyst. The reaction can be carried out, for example, with reference to a method as described in "Jikken Kagaku Koza (Courses in Experimental Chemistry) ($4^{th}$ edition)", edited by The Chemical Society of Japan, vol. 25 (1992) (Maruzen).

(13) Addition Reaction Via Lithiation

A compound having a carboxylphenyl group among the compounds (I) of the present invention can be prepared by subjecting a compound having a bromophenyl group as a starting material to a lithium-halogen exchange reaction by allowing alkyl lithium to undergo the reaction, and then reacting the resultant with carbon dioxide. The reaction can be carried out, for example, with reference to a method as described in "Jikken Kagaku Koza (Courses in Experimental Chemistry) ($4^{th}$ edition)", edited by The Chemical Society of Japan, vol. 20 (1992) (Maruzen).

(14) Hydrolysis Reaction

A compound having a carboxyl group or an amide group among the compounds (I) of the present invention can be prepared by subjecting a corresponding compound having an ester group, an amide group, or a cyano group to hydrolysis. The reaction can be carried out, for example, with reference to a method as described in "Protective Groups in Organic Synthesis ($3^{rd}$ edition)" as described above, or "Jikken Kagaku Koza (Courses in Experimental Chemistry) ($4^{th}$ edition)", edited by The Chemical Society of Japan, vol. 22 (1992) (Maruzen).

(15) Dehydration Reaction

A compound having a cyano group among the compounds (I) of the present invention can be prepared by subjecting a compound having a carboxamide group to a dehydration reaction. The reaction can be carried out, for example, with reference to a method as described in "Jikken Kagaku Koza (Courses in Experimental Chemistry) ($4^{th}$ edition)", edited by The Chemical Society of Japan, vol. 20 (1992) (Maruzen).

In various reactions as described above, it is in some cases preferable to use a primary amine-carrying polystyrene resin, such as PS-Trisamine (Argonaut Technologies, Inc., USA), or the like, in order to remove an electrophilic reagent (acid chloride, sulfonyl chloride, isocyanate, or the like), or to use a strong cationic exchanger, such as BondElut® SCX (Varian Ltd., USA) to purify basic substances, or the like.

The starting materials used in the preparation of the compounds of the present invention can be prepared, for example, by using the methods described in Reference Examples as described below, well-known methods, or methods apparent to a person skilled in the art, or variations thereof.

(Starting Material Synthesis 1)

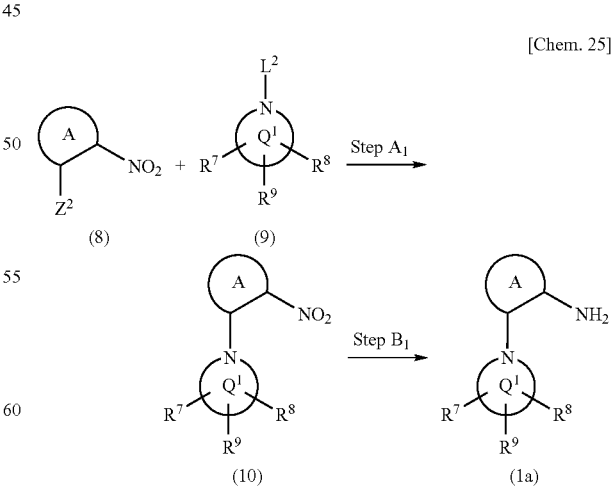

[Chem. 25]

(wherein $Z^2$ represents halogen or —O—$SO_2CF_3$. $L^2$ represents hydrogen or methyl. The ring of $Q^1$ has a nitrogen atom as a ring-forming atom, and represents an alicyclic heterocycle that bonds with the ring of A at the nitrogen atom. $R^7$, $R^8$, and $R^9$ have the same meanings as defined above, respectively. The same shall be applied hereinafter.)

<Step $A_1$>

This step is a process for preparing a compound (10) by carrying out a substitution reaction at an ortho position of the nitro group of the compound (8). The substitution reaction of this step can be carried out in the same manner as in Step 2 of Second Preparation Method.

<Step $B_1$>

This step is a process for preparing a compound (1a) by subjecting the nitro compound (10) to reduction. The reduction reaction of this step can be carried out by using a reduction reaction for a nitro group, which can be usually employed by a person skilled in the art. For example, it can be exemplified by a reduction reaction using an reducing agent such as reduced iron and tin chloride, and a hydrogenation reaction using palladium-carbon, rhodium-carbon, or the like as a catalyst. The reaction can be carried out, for example, with reference to a method as described in "Jikken Kagaku Koza (Courses in Experimental Chemistry) ($4^{th}$ edition)", edited by The Chemical Society of Japan, vol. 26 (1992) (Maruzen).

(Starting Material Synthesis 2)

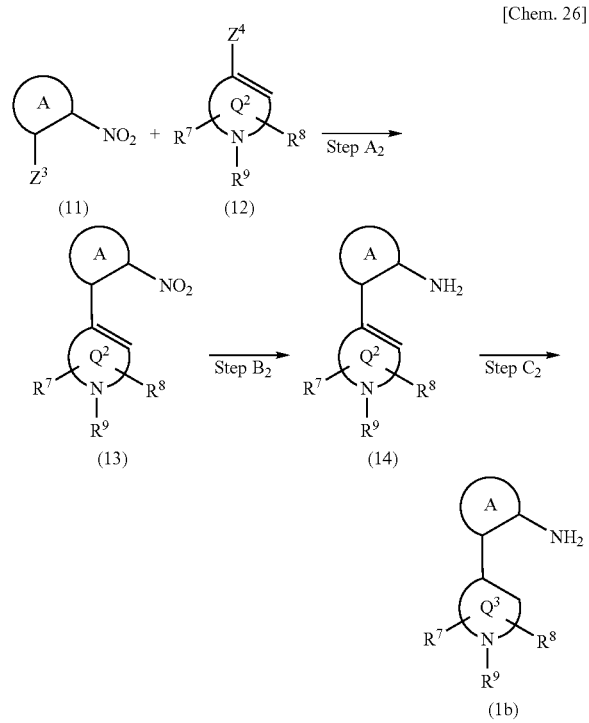

[Chem. 26]

(wherein $Z^3$ represents halogen or —O—$SO_2CF_3$, and $Z^4$ represents —$B(OH)_2$, dialkylboron, dialkoxyboron, or trialkyltin. Alternatively, $Z^3$ may represent —$B(OH)_2$, dialkyl boron, dialkoxyboron, or trialkyltin, and $Z^4$ may represent halogen or —O—$SO_2CF_3$. The rings of $Q^2$ and $Q^3$ represent aliphatic nitrogen-containing heterocycles that bond with the ring of A at the carbon atom, respectively. The same shall be applied hereinafter.)

<Step $A_2$>

This step is a reaction of two cyclic skeltons comprising a combination of the compound (11) and the compound (12), preferably in the presence of a transition metal catalyst and a suitable additive to form a carbon-carbon bond. Representative methods thereof include a method as described in "Jikken Kagaku Koza (Courses in Experimental Chemistry) ($4^{th}$ edition)", edited by The Chemical Society of Japan, vol. 25 (1992) (Maruzen). As the transition metal catalyst, various palladium complexes such as tetrakis(triphenylphosphine) palladium, and various nickel complexes such as dibromobis (triphenylphosphine)nickel can be preferably used. As the additive, various ligands such as triphenylphosphine, sodium carbonate, and zinc can be preferably used, but it is preferable to suitably select an additive depending on the employed methods. Usually, this reaction is carried out in a solvent from at room temperature to under heating.

<Step $B_2$>

This step is a process for preparing a compound (14) by subjecting the nitro compound (13) to reduction. The reduction of the nitro group in this step can be carried out in the same manner as in Step $B_1$, of Starting Material Synthesis 1, but particularly preferred is a reduction reaction using a reducing agent such as reduced iron and tin chloride.

<Step $C_2$>

This step is a process for preparing a compound (1b) by subjecting the double bonds of the compound (14) to reduction. For the reduction reaction of this step, a reduction reaction that can be usually employed by a person skilled in the art can be used. For example, the reaction can be exemplified by a catalytic reduction reaction using palladium-carbon, or the like as a catalyst under a hydrogen atmosphere.

(Starting Material Synthesis 3)

[Chem. 27]

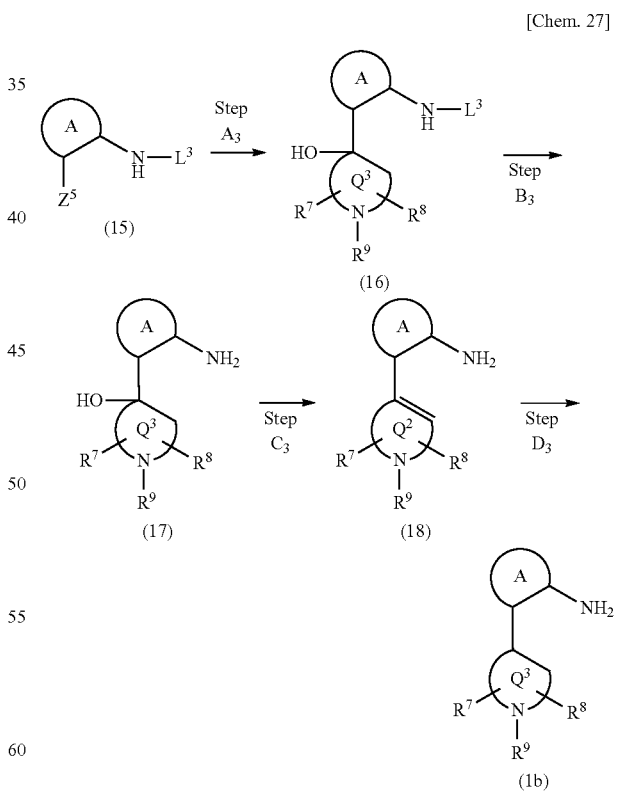

(wherein $Z^5$ represents halogen or hydrogen, and $L^3$ represents a protecting group for amine. $Q^2$ and $Q^3$ have the same meanings as defined above, respectively. The same shall be applied hereinafter.)

<Step A₃>

This step is a process for preparing a compound (16) by allowing alkyl lithium to undergo the reaction with the compound (15) for a lithium-halogen exchange or deprotonation reaction to produce aryl lithium, and then subjecting the ketone to an addition reaction. A method as described in "Jikken Kagaku Koza (Courses in Experimental Chemistry) (4$^{th}$ edition)", edited by The Chemical Society of Japan, vol. 25 (1992) (Maruzen), and an equivalent method.

<Step B₃>

This step is a process for preparing a compound (17) by subjecting a substituent L³ on nitrogen of the compound (16) to deprotection. For the reaction, a deprotection condition by a conventional method corresponding to the substituent L³ can be used, and for example, a method as described in the deprotection reaction of an amino group in "Protective Groups in Organic Synthesis (3rd edition)", or the like can be applied.

<Step C₃>

This step is a method for preparing an olefinic product by subjecting a hydroxy group of the compound (17) to a hydroxy group-elimination reaction. The reaction can be carried out under a basic condition via halogenation and sulfonation in addition to an acid catalyst dehydration reaction. A method as described in "Jikken Kagaku Koza (Courses in Experimental Chemistry) (4$^{th}$ edition)", edited by The Chemical Society of Japan, vol. 19 (1992) (Maruzen) or an equivalent method can be employed.

<Step D₃>

This step is a process for preparing a compound (1b) by subjecting the double bonds of the compound (18) to reduction. The reduction reaction of this step can be carried out in the same manner as in Step C₂ of Starting Material Synthesis 2.

Furthermore, these Steps B₃ to D₃ can be carried out in varying order depending on the need. For example, a method in which from the compound (16), a dehydration reaction is carried out in Step C₃, deprotection of the substituent L³ on nitrogen is carried out in Step B₃, and then reduction of the double bonds carried out in Step D₃, or other methods can be exemplified.

(Starting Material Synthesis 4)

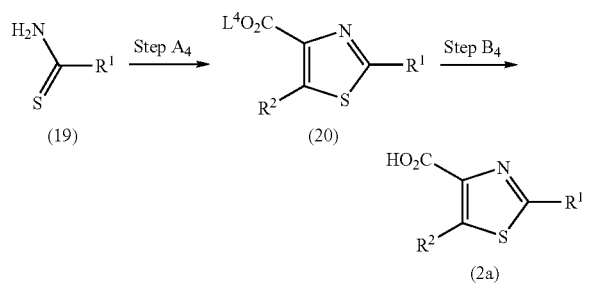

[Chem. 28]

(wherein L⁴ represents a protecting group for carboxylic acid. The same shall be applied hereinafter.)

<Step A₄>

This step is a method for constructing a thiazole ring by allowing an α-haloketone, representatively such as bromopyruvic ester, to undergo the reaction with a thioamide or thiourea. Those methods as described "Comprehensive Organic Chemistry", vol. 4, or an equivalent method can be employed.

In addition, it is in some cases preferable to add trifluoroacetic anhydride in order to promote a cyclization reaction.

<Step B₄>

This step is a process for preparing a carboxylic acid derivative (2a) by subjecting a carboxylic acid ester derivative (20) to hydrolysis. For this reaction, a hydrolysis condition by a conventional method can be used, and for example, a method as described in the deprotection reaction of a carboxyl group in "Protective Groups in Organic Synthesis (3rd edition)" as described above, or the like can be applied.

(Starting Material Synthesis 5)

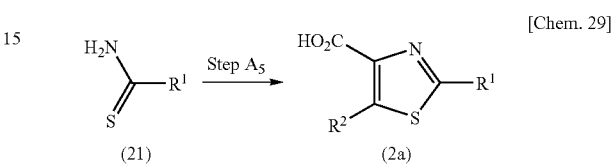

[Chem. 29]

<Step A₅>

This step is a method for constructing a thiazole ring by allowing an α-haloketone, representatively such as bromopyruvic acid, to undergo the reaction with a thioamide or thiourea. The reaction can be carried out in the same manner as in Step A₄ of Starting Material Synthesis 4.

(Starting Material Synthesis 6)

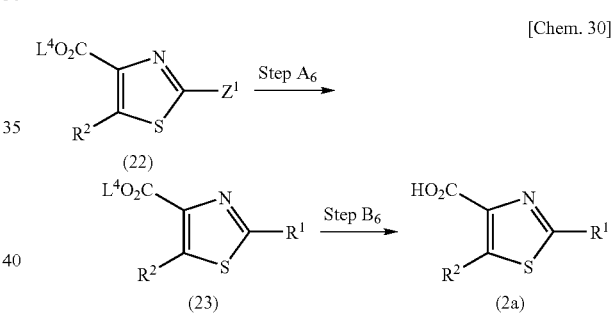

[Chem. 30]

<Step A₆>

This step is a process for preparing a compound (23) by carrying out a substitution reaction of the compound (22) at a 2 position of the thiazole. The substitution reaction of this step can be carried out in the same manner as in Step 2 of Second Preparation Method.

<Step B₆>

This step is a process for preparing a compound (2a) by subjecting the carboxylic acid ester derivative (23) to hydrolysis. The hydrolysis reaction of this step can be carried out in the same manner as in Step B₄ of Starting Material Synthesis 4.

(Starting Material Synthesis 7)

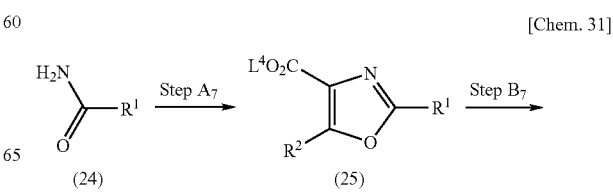

[Chem. 31]

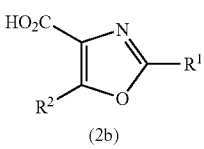

<Step A₇>

This step is a method for constructing an oxazole ring by allowing an α-haloketone, representatively such as bromopyruvic acid ester, to undergo the reaction with an amide or urea. A method as described in "Heterocyclic Compounds" edited by Turchi, vol. 45, or "Heterocyclic Compounds" edited by Palmer, vol. 60, Part A, or an equivalent method can be employed.

<Step B₇>

This step is a process for preparing a compound (2b) by subjecting the carboxylic acid ester derivative (25) to hydrolysis. The hydrolysis reaction of this step can be carried out in the same manner as in Step B₄ of Starting Material Synthesis 4.

(Starting Material Synthesis 8)

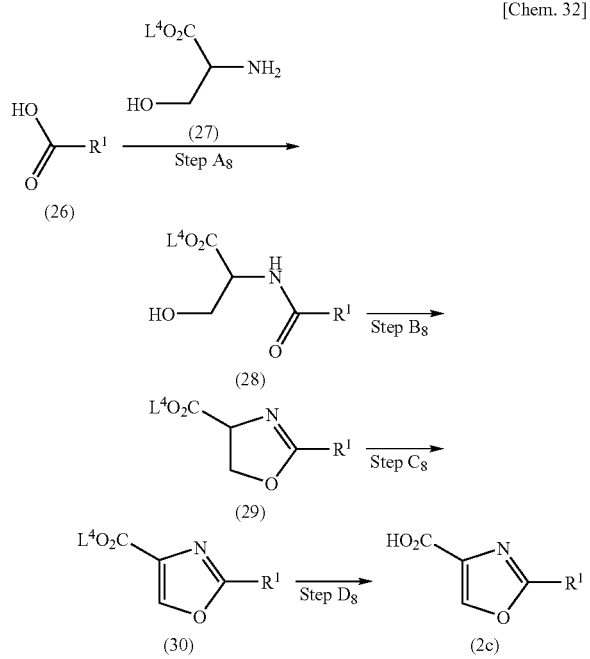

<Step A₈>

This step is a process for carrying out an amidation reaction from the compound (26) and the compound (27). The reaction can be carried out in accordance with Step 1 in First Preparation Method, for example, with reference to a method as described in "Jikken Kagaku Koza (Courses in Experimental Chemistry) (4th edition)", edited by The Chemical Society of Japan, vol. 22 (1992) (Maruzen), or "Compendium of Organic Synthetic Methods" as described above, vols. 1 to 3, or the like.

<Step B₈>

This step is a method for constructing an oxazoline ring by carrying out a dehydration-cyclization reaction from the compound (28). The cyclization of this step can be carried out, for example, with reference to a method as described in Phillips, A. J.; Wipf, P.; Williams, D. R.; et al., Org Lett, 2000, 2(8), 1165-1168, "Heterocyclic Compounds" as described above, vol. 60, Part A, Part B, etc.

<Step C₈>

This step is a method for constructing an oxazole ring by carrying out an oxidation reaction from the compound (29). The cyclization of this step can be carried out, for example, with reference to a method as described in Phillips, A. J.; Wipf, P.; Williams, D. R.; et al., Org Lett, 2000, 2(8), 1165-1168, or "Heterocyclic Compounds" as described above, vol. 60, Part A, or the like.

<Step D₈>

This step is a process for preparing a compound (2c) by subjecting the carboxylic acid ester derivative (30) to hydrolysis. The hydrolysis reaction of this step can be carried out in the same manner as in Step B₄ of Starting Material Synthesis 4.

(Starting Material Synthesis 9)

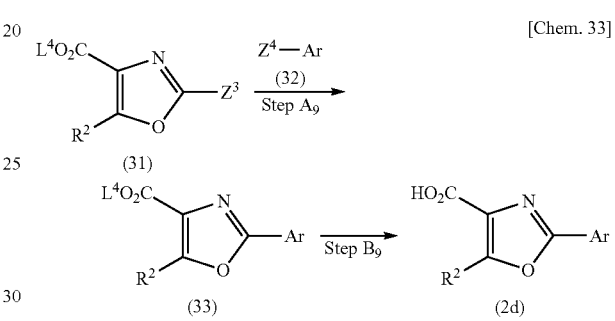

(wherein Ar represents aryl which may be substituted, or heteroaryl which may be substituted, and bonds with an oxazole ring at the carbon atoms on the ring. $Z^3$ and $Z^4$ have the same meanings as defined above, respectively. The same shall be applied hereinafter.)

<Step A₉>

This step is a method for synthesizing a biaryl compound from the compound (31) and the compound (32). The reaction of this step can be carried out, for example, in accordance with HODGETTS, K. J.; KERSHAW, M. T.; Org Lett, 2002, 4(17), 2905-2907.

<Step B₉>

This step is a process for preparing a compound (2d) by subjecting the carboxylic acid ester derivative (33) to hydrolysis. The hydrolysis reaction of this step can be carried out in the same manner as in Step B₄ of Starting Material Synthesis 4.

Furthermore, in Starting Material Syntheses 1 to 9, the substituents to bond with the compound (I) of the present invention can be converted in a suitable period of time in the above-described step for proceeding in the next step. Examples of the method for the aforesaid conversion include a method in which of Starting Material Synthesis 3, a Boc group is introduced to the position of $R^9$, and an alkylation reaction is carried out at a suitable periods of time, before Step B₃, before Step C₃, or before Step D₃, and after deprotection of the Boc group, to conversion into a partial structure $R^9$ of the compound according to the present invention.

The reaction products obtained by each of Preparation Methods can be isolated and purified as their free compounds, and salts or various solvates thereof, such as hydrates. The salts can be prepared after carrying out a conventional salt formation treatment.

The isolation and purification can be carried out by employing common chemical operations such as extraction, concentration, removal by distillation, crystallization, filtration, recrystallization, and various chromatography.

Various isomers can be isolated in the standard method making use of the differences in physicochemical properties among isomers. For example, optical isomers can be separated by general optical resolution, for example, by fractional crystallization, chromatography, or the like. In addition, the optical isomers can also be prepared from appropriate optically active starting material compounds.

The effects of the compounds of the present invention were confirmed by the following pharmacological tests.

1. Experiment to Measure a Receptor Inhibitory Activity Using Cells Expressing a Nerve Growth Factor Receptor The nerve growth factor receptor inhibitory activity was measured by using the increase in a ligand-dependent calcium concentration in cells as an index. HEK293 cells (American Type Culture Collection) that stably expressed Human nerve growth factor receptor were dispensed onto a 96-well poly-D-lysine-coated plate (Product Name: Biocoat, PDL96W black/clear, by Nippon Becton Dickinson) to a $2 \times 10^4$ cells/well at the day before the experiment, and incubated overnight at 37° C. under 5% carbon dioxide ($CO_2$) in a culture medium containing 10% fetal bovine serum (FBS) (Product Name: DMEM, Invitrogen Corporation). The culture medium was replaced by a washing solution: a Hank's balanced salt solution)(HBSS), containing a 1.5 μM loading buffer (fluorescent indicator (Product Name: Fluo-4-AM, Tong Ren Tang Technologies Co. Ltd.)), 20 mM 2-[4-(2-hydroxyethyl)-1-piperazinyl]ethanesulfonic acid (HEPES)-sodium hydroxide (NaOH), 2.5 mM Probenecid, 0.1% bovine serum albumin (BSA), and left to stand at room temperature for 3 hours, and the cells were washed using a plate washer (Product Name: ELx405, BIO-TEK instrument Corporation) in which a washing solution had been set up. The compound that had been preliminarily dissolved and diluted in a washing solution was added thereto, and set up in a system for measuring a calcium (Ca) concentration in a cell (Product Name: FLIPR, Molecular Devices Corporation). After 5 minutes, a nerve growth factor (NGF, mouse derived 2.5S, Alomone) corresponding on 80% stimulation of a maximum response was added (to a final concentration of about 100 to 150 ng/ml) to measure the change in Ca concentrations in cells. A difference between a maximum value and a minimum value in Ca concentrations in cells was determined, and kept as measurement data. With a response upon addition of NGF being set at 0%, and a response upon addition of a buffer being set at 100%, the concentration causing 50% inhibition was determined as an $IC_{50}$ value. The results are shown in the following Table 1. In the table, Ex represents Compound No. of Examples as described later. From the results of this test, it was confirmed that the compound of the present invention has a nerve growth factor receptor inhibitory activity.

TABLE 1

| Ex | $IC_{50}$ (nM) |
|---|---|
| 11 | 4.3 |
| 69 | 4.7 |
| 151 | 11 |
| 311 | 2.6 |
| 356 | 8.8 |
| 380 | 9.5 |
| 382 | 11 |
| 449 | 2.4 |
| 492 | 2.3 |
| 501 | 12 |
| 662 | 2.4 |
| 942 | 4.6 |

2. Evaluation of the Inhibitory Activity of the Compound on Enhanced Vascular Permeability Caused by NGF in Rat The in vivo trkA receptor inhibitory activity of the compound was examined. A Wistar female rat (SLC) were forced to be orally administered with the compound (0.5% methylcellulose solution) 10 mg/3 ml/kg or a vehicle (0.5% methylcellulose solution) 3 ml/kg. Under ether anesthesia performed at 60 min after administration, physiological saline or 1 ug/ml NGF (NGF, mouse derived 2.5S, Alomone) was intracutaneously administered to the back at 50 ul/site, and then immediately a 1% Evans blue solution (dissolved in physiological saline) was administered through caudal vein at 3 ml/kg. At a time point of 10 min after the administration, the skin on the back was taken, and shaken in formamide for 16 hours. After shaking, an absorption of Evans blue extracted with formamide was measured by an absorption meter (wavelength: 620 nm), and the concentration was determined by a calibration curve method. A value obtained by subtracting the concentration of Evans blue at a site administered with physiological saline from the concentration of Evans blue at a site administered with NGF has a function dependent on NGF, and an inhibitory rate of the compound group was determined with a group administered with vehicle being set at 100%. The results are shown in the following Table 2. In this test, it was confirmed that the compound of the present invention has an excellent inhibitory activity on enhanced vascular permeability caused by NGF in rat.

TABLE 2

| Ex | Inhibition rate (%) |
|---|---|
| 151 | 93 |
| 311 | 90 |
| 356 | 97 |
| 380 | 88 |
| 382 | 92 |
| 492 | 91 |
| 501 | 85 |
| 862 | 91 |
| 942 | 95 |

3. Effects of the Compound on the Cyclophosphamide (CPA)-Induced Urinary Frequency in Rat CPA (150 mg/5 ml/kg) was intraperitoneally administered to a Wistar female rat (Charles river laboratories), and after two days, the experiment was carried out. It was forced to be orally administered with distilled water (30 ml/kg), and then placed in a metabolic cage, and the voided urine weight and the urination frequency were continuously measured for 1 hour. The compound (0.5% methylcellulose solution) 3 or 10 mg/5 ml/kg, or a vehicle (0.5% methylcellulose solution) 5 ml/kg was orally administered, and after 5 to 30 min, the urinary functions were measured after loading water in the same manner as described above. A total voided urine weight was divided by the total urination frequency to determine an effective bladder capacity. With the value before administration of the compound being set at 100%, a rate of change in the effective bladder capacity caused by administration of the compound was determined. The results are shown in the following Table 3.

In this test, at 2 days after CPA treatment, the effective bladder capacity was decreased (about 0.5 ml), indicating urinary frequency condition. On the other hand, the compound of the present invention improved the urinary frequency condition. For example, Example 492 increased the effective bladder capacity up to 177%.

TABLE 3

| Ex | Dose (mg/kg) | Duration of evaluation after administration (min.) | Change rate of effective bladder capacity (%) |
|---|---|---|---|
| 151 | 10 | 30-90 | 147 |
| 356 | 10 | 30-90 | 180 |
| 380 | 10 | 30-90 | 152 |
| 382 | 3 | 5-65 | 134 |
| 477 | 3 | 5-65 | 161 |
| 492 | 10 | 30-90 | 177 |
| 501 | 10 | 30-90 | 157 |
| 599 | 3 | 5-65 | 147 |
| 942 | 3 | 5-65 | 153 |

4. Effects of the Compound on Acetic Acid-Induced Painful Behaviors in Rat

1% Acetic acid (99% distilled water) was intraperitoneally administered to a Wistar male rat (Charles river laboratories), and the frequency of pain behavior (writhing) between 10 min and 20 min after administration was measured. The compound (10 mg/5 ml/kg) or a vehicle (0.5% methylcellulose solution) was orally administered 5 mins before the administration of 1% acetic acid. With the frequency of the group administered with the vehicle being set at 100%, the inhibition rate of the writhing behavior frequency by the compound administration was determined. The results are shown in the following Table 4. In this test, the compound of the present invention exhibited an excellent analgesic action.

TABLE 4

| Ex | Inhibition rate (%) |
|---|---|
| 151 | 53 |
| 380 | 44 |
| 382 | 38 |
| 501 | 55 |

From the results as described above, it was demonstrated that the compound of the present invention has a potent in vitro and in vivo trkA receptor inhibitory activity, and has a urinary symptom-improving action and an analgesic action. Accordingly, it can be expected that the compound of the present invention is useful as a therapeutic or prophylactic drug for various lower urinary tract diseases accompanied by urinary symptoms, and various pain diseases.

A pharmaceutical composition containing the compound (I) of the present invention or a salt thereof is prepared by using a carrier, an excipient or other additives that are usually used in the preparation of drugs.

Administration may be made in any one form for either oral administration by tablets, pills, capsules, granules, powders, and liquids, or for parenteral administration by injections for intravenous injection, and intramuscular injection, suppositories, percutaneous preparations, transnasal preparations, inhalations or the like. The dose is appropriately decided in response to an individual case by taking the symptoms, age and sex of the subject and the like into consideration, but is usually from about 0.001 mg/kg to about 100 mg/kg per day per adult in the case of oral administration, and this is administered in one portion or dividing it into 2 to 4 portions. Also, in the case of intravenous administration according to the symptoms, this is administered usually within the range of from 0.0001 mg/kg to 10 mg/kg per day per adult, once a day or two or more times a day. In addition, in the case of inhalation, this is administered generally within the range of from 0.0001 mg/kg to 1 mg/kg per adult, once a day or two or more times a day.

Regarding the solid composition of the present invention for oral administration, tablets, powders, granules, or the like are used. In such a solid composition, one or more active substances are mixed with at least one inactive excipient(s) such as lactose, mannitol, glucose, hydroxypropylcellulose, microcrystalline cellulose, starch, polyvinyl pyrrolidone, and magnesium aluminometasilicate. In a conventional method, the composition may contain inactive additives such as lubricants such as magnesium stearate, disintegrators such as carboxymethylstarch sodium, and solubilization assisting agents. As occasion demands, tablets or pills may be coated with a sugar coating, or a gastric or enteric coating agent.

The liquid composition for oral administration includes pharmaceutically acceptable emulsions, solutions, suspensions, syrups, elixirs, and the like, and contains a generally used inert solvent such as purified water or ethanol. In addition to the inert solvent, this composition may contain auxiliary agents such as solubilization assisting agents, moistening agents, and suspending agents, sweeteners, correctives, aromatics and antiseptics.

Injections for parenteral administration include aseptic aqueous or non-aqueous solutions, suspensions and emulsions. As the aqueous solvent, for example, distilled water for injection and physiological saline are included. Examples of the non-aqueous solvent include propylene glycol, polyethylene glycol, plant oils such as olive oil, alcohols such as ethanol, and Polysorbate 80 (Pharmacopeia). Such a composition may further contain tonicity agents, antiseptics, moistening agents, emulsifying agents, dispersing agents, stabilizing agents, and solubilization assisting agent. These are sterilized, for example, by filtration through bacteria retaining filter, blending of germicides or irradiation. In addition, these can also be used by producing sterile solid compositions, and dissolving or suspending it in sterile water or a sterile solvent for injection prior to their use.

Regarding transmucosal agents such as inhalers and transnasal agents, those in a solid, liquid or semi-solid state are used, and may be produced in accordance with conventionally known methods. For example, excipients such as lactose and starch, and also pH adjusting agents, antiseptics, surfactants, lubricants, stabilizers, thickeners, and the like may be optionally added thereto. For their administration, an appropriate device for inhalation or insufflation can be used. For example, a compound may be administered alone or as a powder of prescribed mixture, or as a solution or suspension by combining it with a pharmaceutically acceptable carrier, using conventionally known devices or sprayer, such as metered-dose inhalers. The dry powder inhaler or the like may be for single or multiple administration use, and a dry powder or a powder-containing capsule can be used. Alternatively, this may be in a form such as a high pressure aerosol spray which uses an appropriate propellant, for example, a suitable gas such as chlorofluoroalkane, hydrofluoroalkane, and carbon dioxide.

In the preparation of the suppositories, a low melting point wax such as a mixture of fatty acid glycerides, or cocoa butter is dissolved, and an active ingredient is added thereto, followed by uniformly dispersing under stirring. Thereafter, it was poured into an appropriate mold and cooled for solidification. The liquid preparation includes solutions, suspensions, oil retention enemas, and emulsions, such as a solution in water or propyleneglycol.

EXAMPLES

Hereinafter, the compounds of the present invention will be described in more detail with reference to Examples. Also, the preparation methods of the starting material compounds are shown in Reference Examples. Further, the preparation methods of the compounds of the present invention are not limited to the preparation methods of the specific Examples as below, and any combination of the preparation methods or well-known preparation methods can be used for preparation.

The following abbreviations are used in Reference Examples and Examples.

Me: methyl, Et: ethyl, Ac: acetyl, Ms: mesyl, Ph: phenyl, Boc: tert-butoxycarbonyl, TBS: tert-butyldimethylsilyl, Tf: trifluoromethanesulfonyl, HOBt: 1-hydroxybenzotriazole, WSC-HCl: 1-ethyl-3-(3-dimethylaminopropyl)carbodiimide hydrochloride, DCC: dicyclohexylcarbodiimide, CDI: carbonyldiimidazole, DPPA: diphenylphosphorylazide, DEPC: diethylphosphorylcyanide, THF: tetrahydrofuran, EtOAc: ethyl acetate, DMF: N,N-dimethylformamide, DMA: N,N-dimethylacetamide, DMSO: dimethylsulfoxide.

Reference Example 1

2,4-Difluoro-6-nitrophenol was allowed to undergo the reaction with trifluoromethanesulfonic anhydride in pyridine to prepare 2,4-difluoro-6-nitrophenyl trifluoromethane sulfonic acid ester.

Reference Example 8

4-Chloro-3-nitrophenyl methylsulfide was allowed to undergo the reaction with m-chloroperbenzoic acid in chloroform for performing oxidation of sulfide to prepare 4-chloro-3-nitrophenyl methylsulfoxide.

Reference Example 9

1,2,3-Trifluoro-4-nitrobenzene was allowed to undergo the reaction with potassium hydroxide and ethyl cyanoacetate in DMSO, and then with acetic acid and hydrochloric acid to prepare (2,3-difluoro-4-nitrophenyl)acetonitrile.

Reference Example 10

3-Chloro-2,6-difluorophenylacetonitrile was allowed to undergo the reaction with tetramethylammonium nitrate and trifluoromethanesulfonic anhydride in methylene chloride to prepare (3-chloro-2,6-difluoro-5-nitrophenyl)acetonitrile.

Reference Example 11

4-Chloro-3-nitrophenol was allowed to undergo the reaction with sodium chlorodifluoroacetate and cesium carbonate in DMF-water to prepare 1-chloro-4-(difluoromethoxy)-2-nitrobenzene.

Reference Examples 12 and 13

4-Chloro-5-nitropyridin-2(1H)-one was allowed to undergo the reaction with silver carbonate and methyl iodide in methylene chloride to prepare 4-chloro-2-methoxy-5-nitropyridine and 4-chloro-1-methyl-5-nitropyridin-2(1H)-one.

Reference Example 14

(2R,5S)-2,5-Dimethylpiperazine-1-carboxylic acid tert-butyl ester was allowed to undergo the reaction with potassium carbonate and bromoacetamide in DMF to prepare (2R, 5S)-4-(2-amino-2-oxoethyl)-2,5-dimethylpiperazine-1-carboxylic acid tert-butyl ester.

Reference Example 15

4-Oxopiperidine-1-carboxylic acid tert-butyl ester was allowed to undergo the reaction with N-methylglycinamide and sodium triacetoxyborohydride in dichloroethane to prepare 4-[(2-amino-2-oxoethyl)(methyl)amino]piperidine-1-carboxylic acid tert-butyl ester.

Reference Example 19

4-Oxoazepane-1-carboxylic acid tert-butyl ester was allowed to undergo the reaction with sodium cyanide in an aqueous sodium hydrogen sulfite solution to prepare 4-cyano-4-hydroxyazepane-1-carboxylic acid tert-butyl ester.

Reference Example 20

4-Cyano-4-hydroxyazepane-1-carboxylic acid tert-butyl ester was allowed to undergo the reaction with 10% hydrogen chloride/methanol to prepare 4-hydroxyazepane-4-carboxylic acid methyl ester hydrochloride.

Reference Example 21

4-(2-Amino-2-oxoethyl)piperazine-1-carboxylic acid tert-butyl ester was allowed to undergo the reaction with 4 M hydrogen chloride/dioxane to prepare 2-piperazin-1-ylacetamide dihydrochloride.

Reference Example 27

2,4-Difluoronitrobenzene was allowed to undergo the reaction with 2-piperazin-1-ylacetamide and triethylamine in acetonitrile to prepare 2-[4-(5-fluoro-2-nitrophenyl)piperazin-1-yl]acetamide.

Reference Example 130

4-Oxoazepane-1-carboxylic acid tert-butyl ester was allowed to undergo the reaction with lithium diisopropylamide and 1,1,1-trifluoro-N-phenyl-N-[(trifluoromethyl)sulfonyl]methanesulfonamide in THF to prepare 4-{[(trifluoromethyl)sulfonyl]oxo}-2,3,6,7-tetrahydro-1H-azepine-1-carboxylic acid tert-butyl ester.

Reference Example 132

(4-Aminophenyl)acetonitrile was allowed to undergo the reaction with bis(pyridine)iodonium tetrafluoroborate in methylene chloride to prepare (4-amino-3-iodophenyl)acetonitrile.

Reference Example 135

2-Fluoro-6-nitrophenyl-trifluoromethane sulfonic acid ester was allowed to undergo the reaction with [1,1'-bis(diphenylphosphino)ferrocene]-dichloropalladium (II), potassium phosphate, and 4-(4,4,5,5-tetramethyl-1,3,2-dioxaboroloran-2-yl)-3,6-dihydropyridine-1(2H)-carboxylic acid tert-butyl ester in DMF to prepare 4-(2-fluoro-6-nitrophenyl)-3,6-dihydropyridine-1(2H)-carboxylic acid tert-butyl ester.

Reference Example 140

4-Amino-3-bromobenzonitrile was allowed to undergo the reaction with triethylamine, palladium acetate, 2-(dicyclohexylphosphino)biphenyl, and bis(pinacolato)diboron in dioxane, and then with 4-{[(trifluoromethyl)sulfonyl]oxo}-3,6-dihydropyridine-1(2H)-carboxylic acid tert-butyl ester, barium hydroxide and water to prepare 4-(2-amino-5-cyanophenyl)-3,6-dihydropyridine-1(2H)-carboxylic acid tert-butyl ester.

Reference Example 171

1-(2-Nitrophenyl)-2,5-dihydro-1H-pyrrole was allowed to undergo the reaction with N-methylmorpholine-N-oxide, and a catalytic amount of osmium tetroxide in THF-water to prepare cis-1-(2-nitrophenyl)pyrrolidine-3,4-diol.

Reference Example 173

2-[4-(2-Bromo-4-fluoro-6-nitrophenyl)piperazin-1-yl]acetamide was allowed to undergo the reaction with zinc cyanide and tetrakistriphenylphosphinepalladium in DMF to prepare 2-[4-(2-cyano-4-fluoro-6-nitrophenyl)piperazin-1-yl]acetamide.

Reference Example 174

1-(5-Bromo-2-nitrophenyl)-4-hydroxypiperidine-4-carboxylic acid methyl ester was allowed to undergo the reaction with phosphorus oxychloride in pyridine to prepare 1-(5-bromo-2-nitrophenyl)-1,2,3,6-tetrahydropyridine-4-carboxylic acid methyl ester.

Reference Example 175

2-[4-(4-Formyl-2-nitrophenyl)piperazin-1-yl]acetamide was allowed to undergo the reaction with ethyl diethylphosphonoacetate and potassium carbonate in DMF to prepare ethyl (2E)-3-{4-[4-(2-amino-2-oxoethyl)piperazin-1-yl]-3-nitrophenyl}acrylate.

Reference Example 176

1-(3-Nitropyridine-2-yl)piperidine-4-carboxamide was allowed to undergo the reaction with palladium-carbon in a methanol-THF mixed solution, under a hydrogen atmosphere for performing reduction of a nitro group to prepare 1-(3-aminopyridine-2-yl)piperidine-4-carboxamide.

Reference Examples 276 and 277

2-[4-(6-Chloro-3-nitropyridine-2-yl)piperazin-1-yl]acetamide was allowed to undergo the reaction with potassium carbonate and ethyl cyanoacetate in DMF, and then with trifluoroacetic acid. This was allowed to undergo the reaction with 10% palladium-carbon and hydrogen in methanol to prepare 2-{4-[3-amino-6-(cyanomethyl)pyridin-2-yl]piperazin-1-yl}acetamide and 2-{5-amino-6-[4-(2-amino-2-oxoethyl)piperazin-1-yl]pyridin-2-yl}-N-tert-butylacetamide.

Reference Example 278

2-[4-(4-Bromo-2-nitrophenyl)piperazin-1-yl]acetamide was allowed to undergo the reaction with rhodium-carbon in a methanol-THF mixed solution under a hydrogen atmosphere for performing reduction of a nitro group to prepare 2-[4-(2-amino-4-bromophenyl)piperazin-1-yl]acetamide.

Reference Example 284

2-[4-(6-Amino-3-chloro-2-cyanophenyl)piperazin-1-yl]acetamide was allowed to undergo the reaction with palladium-carbon in methanol under a hydrogen atmosphere for performing dechlorination to prepare 2-[4-(2-amino-6-cyanophenyl)piperazin-1-yl]acetamide hydrochloride.

Reference Example 286

2-[4-(4-Chloro-2-nitrophenyl)piperazin-1-yl]acetamide was allowed to undergo the reaction with reduced iron in acetic acid for performing reduction of a nitro group to prepare 2-[4-(4-chloro-2-aminophenyl)piperazin-1-yl]acetamide.

Reference Example 303

1-(4-Nitro-1-oxidepyridin-3-yl)piperidine-4-carboxamide was allowed to undergo the reaction with reduced iron in acetic acid to prepare 1-(4-aminopyridin-3-yl)piperidine-4-carboxamide.

Reference Example 304

1-Benzyl-3-(2-nitrophenyl)pyrrolidine was allowed to undergo the reaction with palladium-carbon in methanol under a hydrogen atmosphere for performing reduction of a nitro group, and then ammonium formate was added thereto for performing debenzylation. This was allowed to undergo the reaction with di-tert-butyl dicarbonate to prepare 3-(2-aminophenyl)pyrrolidine-1-carboxylic acid tert-butyl ester.

Reference Example 305

1-(2-Aminophenyl)-3-pyrrolidinecarboxylic acid methyl ester was allowed to undergo the reaction with formamide and sodium methoxide in DMF under an argon atmosphere to prepare 1-(2-aminophenyl)-3-pyrrolidine carboxamide.

Reference Example 308

2-Bromopyridine-3-amine was allowed to undergo the reaction with trifluoroacetic anhydride in THF to prepare N-(2-bromopyridin-3-yl)-2,2,2-trifluoroacetamide.

Reference Example 309

Methyllithium and butyllithium were added to a solution of N-(2-Bromophenyl)-2,2,2-trifluoroacetamide in THF, followed by allowing to undergo the reaction with 4-oxo-1-piperidinecarboxylic acid tert-butyl ester to prepare 4-hydroxy-4-[2-[(trifluoroacetyl)amino]phenyl]-1-piperidinecarboxylic acid tert-butyl ester.

Reference Example 312

A THF-methanol solution of 4-hydroxy-4-{2-[(trifluoroacetyl)amino]phenyl}-1-piperidinecarboxylic acid tert-butyl ester was allowed to undergo the reaction with a 15% aqueous sodium hydroxide solution to prepare 4-(2-aminophenyl)-4-hydroxy-1-piperidinecarboxylic acid tert-butyl ester.

Reference Example 316

A solution of 4-(2-Aminophenyl)-4-hydroxy-1-piperidinecarboxylic acid tert-butyl ester in ethanol was allowed to undergo the reaction with a 4 M hydrogen chloride/dioxane solution to prepare 2-(1,2,3,6-tetrahydro-4-pyridinyl)aniline dihydrochloride.

Reference Example 318

A solution of N-(3-methoxyphenyl)-2,2-dimethylpropanamide in tetrahydrofuran was allowed to undergo the reaction with butyllithium, and then 4-oxo-1-piperidinecarboxylic acid tert-butyl ester was added thereto. The reaction solution was concentrated, and the residue was allowed to undergo the reaction with sulfuric acid to prepare 3-methoxy-2-(1,2,3,6-tetrahydropyridin-4-yl)aniline.

Reference Examples 322 and 323

4-(3-Aminopyridine-2-yl)piperidin-4-ol hydrochloride was allowed to undergo the reaction with 20% sulfuric acid. This was allowed to undergo the reaction with potassium carbonate and 2-bromoacetamide in acetonitrile to obtain 2-(3-amino-3',6'-dihydro-2,4'-bipyridine-1'(2'H)-yl)acetamide and 2-[4-(3-aminopyridine-2-yl)-4-hydroxypiperidin-1-yl]acetamide.

Reference Example 324

A solution of 5-fluoro-2-(1,2,3,6-tetrahydro-4-pyridinyl) aniline dihydrochloride in pyridine was allowed to undergo the reaction with 4-morpholinecarbonylchloride to prepare 5-fluoro-2-[1-(4-morpholinylcarbonyl)-1,2,3,6-tetrahydro-4-pyridinyl]aniline.

Reference Example 325

A 4 M hydrogen chloride/EtOAc solution was added to a solution of 2-[4-(2-aminophenyl)-3,6-dihydro-1(2H)-pyridinyl]acetamide in ethanol, and followed by reacting with palladium-carbon under a hydrogen atmosphere for performing reduction of double bonds to prepare 2-[4-(2-aminophenyl)-1-piperidinyl]acetamide dihydrochloride.

Reference Example 333

3-Methyldihydrofuran-2(3H)-one was allowed to undergo the reaction with aqueous ammonia to prepare 4-hydroxy-2-methylbutanamide.

Reference Example 334

Triethylamine and 4-dimethylaminopyridine were added to a solution of 2-methylbutanamide in dichloromethane, and followed by reacting with benzoyl chloride to prepare 4-amino-3-methyl-4-oxobutylbenzoate.

Reference Example 335

A solution of [(1R)-2-hydroxy-1-methylethyl]carbamic acid tert-butyl ester in acetonitrile was allowed to undergo the reaction with methyl iodide in the presence of silver oxide (I) for alkylation to prepare [(1R)-2-methoxy-1-methylethyl] carbamic acid tert-butyl ester.

Reference Example 336

A solution of (S)-1-methoxy-2-propylamine in tetrahydrofuran was allowed to undergo the reaction with ethyl chloroformate in the presence of triethylamine to obtain [(1S)-2-methoxy-1-methylethyl]carbamic acid ethyl ester.

Reference Example 337

[(1R)-2-methoxy-1-methylethyl]carbamic acid tert-butyl ester was allowed to undergo the reaction with lithium aluminum hydride in tetrahydrofuran to obtain (2R)-1-methoxy-N-methylpropane-2-amine hydrochloride.

Reference Example 339

A 4 M hydrogen chloride/EtOAc solution was added to 2-methoxynicotinonitrile, and followed by reacting with dithiophosphoric acid O,O-diethyl ester to prepare 2-hydroxythionicotinamide.

Reference Example 340

4-(Benzyloxy)butanamide was allowed to undergo the reaction with 2,4-bis(4-methoxyphenyl)-1,3,2,4-dithiadiphosphetane-2,4-disulfide in THF to prepare 4-(benzyloxy) butanethioamide.

Reference Example 347

A 4 M hydrogen chloride/EtOAc solution was added to 6-methoxypyridazine-3-carbonitrile, and followed by reacting with dithiophosphoric acid O,O-diethyl ester to prepare 6-methoxypyridazine-3-carbothioamide.

Reference Example 349

(S)-3-Hydroxypiperidine hydrochloride was subject to thioamidation using benzoylthioisocyanate in toluene to prepare N-{[(3S)-3-hydroxypiperidin-1-yl] carbonothioyl}benzamide.

Reference Example 364

N-{[(3S)-3-hydroxypiperidin-1-yl] carbonothioyl}benzamide was reacted with a methylamine-methanol solution in methanol to prepare (3S)-3-hydroxypiperidine-1-carbothioamide.

Reference Example 381

Furan-3-carbothioamide was allowed to undergo the reaction with 3-bromo-2-oxopropanoic acid ethyl ester in ethanol to prepare 2-(3-furyl)-1,3-thiazole-4-carboxylic acid ethyl ester.

Reference Example 425

Tetrahydro-2H-pyrane-4-carbothioamide was allowed to undergo the reaction with 3-bromo-2-oxopropanoic acid ethyl ester in ethanol. The reaction liquid was concentrated and the residue was allowed to undergo the reaction with pyridine and trifluoroacetic anhydride in 1,2-dimethoxyethane, to prepare 2-(tetrahydro-2H-pyran-4-yl)-1,3-thiazolecarboxylic acid ethyl ester.

Reference Example 427

2-(2-Hydroxy-3-pyridinyl)-1,3-thiazole-4-carboxylic acid ethyl ester was allowed to undergo the reaction with phosphorus oxychloride to prepare 2-(2-chloro-3-pyridinyl)-1,3-thiazole-4-carboxylic acid ethyl ester.

Reference Example 428

1-[4-(Ethoxycarbonyl)-1,3-thiazol-2-yl]piperidine-4-carboxylic acid was allowed to undergo the reaction with CDI in THF, and then 28% aqueous ammonia was added thereto to prepare 2-[4-(aminocarbonyl)piperidin-1-yl]-1,3-thiazole-4-carboxylic acid ethyl ester.

Reference Example 431

6-Methoxypyridine-3-carbothioamide hydrochloride was allowed to undergo the reaction with 3-bromo-2-oxopropanoic acid ethyl ester in ethanol to prepare 2-(6-hydroxy-3-pyridinyl)-1,3-thiazole-4-carboxylic acid ethyl ester.

Reference Example 437

{[(2R)-2-Amino-3-hydroxypropanoyl]amino}acetic acid methyl ester was allowed to undergo the reaction with acetic acid, benzaldehyde, and sodium triacetoxyborohydride in a mixed solvent of methylene chloride and DMF to prepare (6R)-1-benzyl-6-(hydroxymethyl)piperazine-2,5-dione.

Reference Example 439

[(2S)-1-Benzylpiperazin-2-yl]methanol was allowed to undergo the reaction with di-tert-butyl dicarbonate in a THF solution to prepare (3S)-4-benzyl-3-(hydroxymethyl)piperazine-1-carboxylic acid tert-butyl ester.

Reference Example 440

(3S)-4-Benzyl-3-(hydroxymethyl)piperazine-1-carboxylic acid tert-butyl ester was allowed to undergo the reaction with sodium hydride and methyl iodide to prepare (3S)-4-benzyl-3-(methoxymethyl)piperazine-1-carboxylic acid-tert-butyl ester.

Reference Example 442

(3S)-4-Benzyl-3-(methoxymethyl)piperazine-1-carboxylic acid tert-butyl ester was allowed to undergo the reaction with 10% palladium-carbon and formic acid in methanol to prepare (3S)-3-(methoxymethyl)piperazine-1-carboxylic acid tert-butyl ester.

Reference Example 448

Benzyl methyl(oxetan-3-yl)carbamate was allowed to undergo the reaction with palladium-carbon and a hydrogen gas in methanol, and then with a 0.4 M hydrogen chloride/EtOAc solution to prepare N-methyloxetan-3-aminehydrochloride.

Reference Example 449

2-Bromo-1,3-thiazole-4-carboxylic acid ethyl ester was allowed to undergo the reaction with 4-(hydroxymethyl)-4-piperidinol trifluoroacetate and potassium carbonate in DMF to prepare 2-[4-hydroxy-4-(hydroxymethyl)piperidin-1-yl]-1,3-thiazole-4-carboxylic acid ethyl ester.

Reference Example 456

Under an argon atmosphere, 2-bromo-1,3-thiazole-4-carboxylic acid ethyl ester was allowed to undergo the reaction with copper iodide (I), N,N-dimethylethane-1,2-diamine, potassium carbonate, and pyrrolidin-2-one in dioxane to prepare 2-(2-oxopyrrolidin-1-yl)-1,3-thiazole-4-carboxylic acid ethyl ester.

Reference Example 470

2-[3-(Benzoyloxy)-1,1-dimethylpropyl]-1,3-thiazole-4-carboxylic acid ethyl ester was allowed to undergo the reaction with sodium ethoxide in ethanol to prepare 2-(3-hydroxy-1,1-dimethylpropyl)-1,3-thiazole-4-carboxylic acid ethyl ester.

Reference Example 474

2-(Chloromethyl)-1,3-thiazole-4-carboxylic acid ethyl ester was allowed to undergo the reaction with 2-methoxy-N-methylethaneamine in DMF to prepare 2-{[(methoxyethyl)(methyl)amino]methyl}-1,3-thiazole-4-carboxylic acid ethyl ester.

Reference Example 475

2-(chloromethyl)-1,3-thiazole-4-carboxylic acid ethyl ester was allowed to undergo the reaction with 2-bromophenol and potassium carbonate in DMF to prepare 2-[(2-bromophenoxy)methyl]-1,3-thiazole-4-carboxylic acid ethyl ester.

Reference Example 476

A solution of 2-phenyl-1,3-thiazole-4-carboxylic acid ethyl ester in chloroform was allowed to undergo the reaction with N-bromosuccinimide to prepare 5-bromo-2-phenyl-1,3-thiazole-4-carboxylic acid ethyl ester.

Reference Example 477

5-Bromo-2-phenyl-1,3-thiazole-4-carboxylic acid ethyl ester was allowed to undergo the reaction with pyrrolidine to prepare 2-phenyl-5-(1-pyrrolidinyl)-1,3-thiazole-4-carboxylic acid ethyl ester.

Reference Example 554

A solution of 2-(4-hydroxy-1-piperidinyl)-1,3-thiazole-4-carboxylic acid in pyridine was allowed to undergo the reaction with acetic anhydride to prepare 2-[4-(acetyloxy)-1-piperidinyl]-1,3-thiazole-4-carboxylic acid.

Reference Example 555

1-(Aminocarbonothioyl)piperidine-4-carboxylic acid ethyl ester was allowed to undergo the reaction with sodium hydrogen carbonate and 3-bromo-2-oxopropanoic acid in dimethoxyethane to prepare 2-[4-(ethoxycarbonyl)piperidin-1-yl]-1,3-thiazole-4-carboxylic acid.

Reference Example 556

(2-Methoxyethyl)methylamine was reacted with potassium cyanate in a 6 M aqueous hydrochloric acid solution to prepare N-(2-methoxyethyl)-N-methylurea.

Reference Example 558

N-(2-Methoxyethyl)-N-methylurea was reacted with 3-bromo-2-oxopropanoic acid ethyl ester in ethanol to prepare 2-[(2-methoxyethyl)(methyl)amino]-1,3-oxazole-4-carboxylic acid ethyl ester.

Reference Example 564

2-[(tert-Butoxycarbonyl)amino]isonicotinic acid was allowed to undergo the reaction with L-serine methyl hydrochloride, WSC-HCl, HOBt, and triethylamine in DMF to prepare (2S)-2-({2-[(tert-butoxycarbonyl)amino]isonicotinoyl}amino)-3-hydroxypropionic acid methyl ester.

Reference Example 566

4-Pyridazinecarbonyl chloride was allowed to undergo the reaction with L-serine methyl hydrochloride and triethylamine in acetonitrile to prepare (2S)-3-hydroxy-2-[(pyridazin-4-ylcarbonyl)amino]propionic acid methyl ester.

Reference Example 577

(2S)-2-({2-[(tert-Butoxycarbonyl)amino]isonicotinoyl}amino)-3-hydroxypropionic acid methyl ester was allowed to undergo the reaction with 2-methoxy-N-(2-methoxyethyl)-N-(trifluorosulfanyl)ethaneamine, and then with bromotrichloromethane and 1,8-diazabicyclo[5.4.0]-7-undecene in methylene chloride to prepare 2-{2-[(tert-butoxycarbonyl)amino]pyridin-4-yl}-1,3-oxazole-4-carboxylic acid methyl ester.

Reference Example 592

2-[(2R)-Pyrrolidin-2-yl]-1,3-oxazole-4-carboxylic acid methyl ester was allowed to undergo the reaction with acetic anhydride and pyridine in dichloromethane to prepare 2-[(2R)-1-acetylpyrrolidin-2-yl]-1,3-oxazole-4-carboxylic acid methyl ester.

Reference Example 593

2-(4-{[tert-Butyl(dimethyl)silyl]oxy}cyclohexyl)-1,3-oxazole-4-carboxylic acid methyl ester was allowed to undergo the reaction with tetra n-butylammonium fluoride in THF to prepare 2-(4-hydroxycyclohexyl)-1,3-oxazole-4-carboxylic acid methyl ester.

Reference Example 596

2-Chloro-1,3-oxazole-4-carboxylic acid ethyl ester was allowed to undergo the reaction with 3-furylboronic acid, tetrakistriphenylphosphine palladium (O), and an aqueous potassium carbonate solution in toluene to prepare 2-(3-furyl)-1,3-oxazole-4-carboxylic acid ethyl ester.

Reference Example 600

2-Vinyl-1,3-oxazole-4-carboxylic acid ethyl ester was allowed to undergo the reaction with N-benzyl-1-methoxy-N-[(trimethylsilyl)methyl]methaneamine and trifluoroacetic acid in toluene to prepare 2-(1-benzylpyrrolidin-3-yl)-1,3-oxazole-4-carboxylic acid ethyl ester.

Reference Example 601

1,3-Oxazole-4-carbonyl chloride was allowed to undergo the reaction with 2-amino-2-methyl-1-propanol and triethylamine in methylene chloride to prepare N-(2-hydroxy-1,1,-dimethylethyl)-1,3-oxazole-4-carboxamide.

Reference Example 602

N-(2-Hydroxy-1,1-dimethylethyl)-1,3-oxazole-4-carboxamide was allowed to undergo the reaction with thionyl chloride in methylene chloride to prepare 4,4-dimethyl-4,5-dihydro-2,4'-bi-1,3-oxazole.

Reference Example 603

4,4-Dimethyl-4,5-dihydro-2,4'-bi-1,3-oxazole was allowed to undergo the reaction with n-butyllithium, benzaldehyde in THF to prepare (4,4-dimethyl-4,5-dihydro-2,4'-bi-1,3-oxazole-2'-yl)(phenyl)methanol.

Reference Example 604

(4,4-Dimethyl-4,5-dihydro-2,4'-bi-1,3-oxazole-2'-yl)(phenyl)methanol was allowed to undergo the reaction with methyl iodide, and then with a 2 M aqueous sodium hydroxide solution to prepare 2-[hydroxy(phenyl)methyl]-1,3-oxazole-4-carboxylic acid.

Reference Example 605

2-Morpholin-4-yl-1,3-oxazole-4-carboxylic acid ethyl ester was allowed to undergo the reaction with 1.7 ml of a 1 M aqueous sodium hydroxide solution in ethanol for performing hydrolysis to prepare 2-morpholin-4-yl-1,3-oxazole-4-carboxylic acid.

Reference Example 629

2-(6-Methoxypyridin-3-yl)-1,3-oxazole-4-carboxylic acid methyl ester was allowed to undergo the reaction with 48% hydrobromic acid in ethanol, and then with a 4 M aqueous sodium hydroxide solution in methanol to prepare 2-(6-oxo-1,6-dihydropyridin-3-yl)-1,3-oxazole-4-carboxylic acid.

The structures and the physiochemical data of the compounds of Reference Examples 1 to 629 are shown in Table 5. In addition to the description on the preparation methods in Reference Examples as above, the compounds of the Reference Example Nos. were prepared in the same manner as the methods of Reference Examples of the numbers shown in Syn of Tables, using each corresponding starting materials.

In the tables of Reference Examples as described later, the following abbreviations are used.

Rex in the left-hand columns in the Tables represents Reference Example No., and the Str cells in the middle columns show the structural formulae of Reference Example compounds. The structural formulae marked with * in the cells of the tables indicate that the compounds are optically active.

The tops in each cell of in the right columns show the Reference Example Nos. with reference to the preparation methods as Syn. For example, "27→14" as described in the preparation methods means that the same preparation method as in the preparation method of Reference Example 27 is performed, and then the same preparation method as in the preparation method of Reference Example 14 is performed. The materials horizontally described in the right hand of Syn, that is, (Sal) represents salts, and the materials without such a description represents free compounds. (HCl) represents hydrochloride, (Na) represents a sodium salt, (HBr) represents a hydrobromide, and ($CF_3CO_2H$) represents a trifluoroacetate. At the bottoms in the right columns show values by mass analysis as Dat (physiochemical data). However, in Reference Example 424 and Reference Example 553, NMR data are shown.

TABLE 5

| REx | Str | Syn (Sal) Dat |
|---|---|---|
| 1 | (2,4-difluoro-6-nitrophenyl trifluoromethanesulfonate) | 1 MS(FAB) m/z: 308 ([M + H]+) |
| 2 | (4-methoxy-2-nitrophenyl trifluoromethanesulfonate) | 1 MS(FAB) m/z: 302 ([M + H]+) |
| 3 | (2-bromo-4-fluoro-6-nitrophenyl trifluoromethanesulfonate) | 1 MS(ESI) m/z: 367 ([M + H]+) |
| 4 | (2-nitro-1,4-phenylene bis(trifluoromethanesulfonate)) | 1 MS(ESI) m/z: 355 ([M + H]+) |
| 5 | (2-bromo-4-methoxy-6-nitrophenyl trifluoromethanesulfonate) | 1 MS(FAB) m/z: 381 ([M + H]+) |
| 6 | (6-nitro-2,3-dihydrobenzofuran-5-ol) | 10 → 442 MS(EI) m/z: 181 ([M]+) |
| 7 | (6-nitro-2,3-dihydrobenzofuran-5-yl trifluoromethanesulfonate) | 1 MS(FAB) m/z: 313 ([M + H]+) |

TABLE 5-continued

| REx | Str | Syn (Sal) Dat |
|---|---|---|
| 8 | (1-chloro-4-(methylsulfinyl)-2-nitrobenzene) | 8 MS(FAB) m/z: 220 ([M + H]+) |
| 9 | (2-(2,3-difluoro-4-nitrophenyl)acetonitrile) | 9 MS(ESI) m/z: 199 ([M + H]+) |
| 10 | (2-(3-chloro-2,6-difluoro-5-nitrophenyl)acetonitrile) | 10 MS(ESI) m/z: 231 ([M − H]−) |
| 11 | (1-chloro-4-(difluoromethoxy)-2-nitrobenzene) | 11 MS(ESI) m/z: 223 ([M + H]+) |
| 12 | (4-chloro-2-methoxy-5-nitropyridine) | 12 MS(EI) m/z: 188 ([M]+) |
| 13 | (4-chloro-1-methyl-5-nitropyridin-2(1H)-one) | 13 MS(EI) m/z: 188 ([M]+) |
| 14 | (tert-butyl (2S,5R)-4-(2-amino-2-oxoethyl)-2,5-dimethylpiperazine-1-carboxylate) | 14 MS(FAB) m/z: 272 ([M + H]+) |
| 15 | (tert-butyl 4-((2-amino-2-oxoethyl)(methyl)amino)piperidine-1-carboxylate) | 15 MS(FAB) m/z: 272 ([M + H]+) |
| 16 | (tert-butyl 3-((2-amino-2-oxoethyl)(methyl)amino)piperidine-1-carboxylate) | 15 MS(FAB) m/z: 272 ([M + H]+) |
| 17 | (tert-butyl 3-((2-amino-2-oxoethyl)(methyl)amino)pyrrolidine-1-carboxylate) | 15 MS(FAB) m/z: 258 ([M + H]+) |

TABLE 5-continued

| REx | Str | Syn (Sal) Dat |
|---|---|---|
| 18 | Boc-azepane-N(Me)CH₂CONH₂ | 15<br>MS(FAB) m/z:<br>286 ([M + H]⁺) |
| 19 | Boc-azepane-4-OH, 4-CN | 19<br>MS(FAB) m/z:<br>241 ([M + H]⁺) |
| 20 | azepane-4-CO₂Me, 4-OH | 20 (HCl)<br>MS(FAB) m/z:<br>174 ([M + H]⁺) |
| 21 | piperazine-CH₂CONH₂ | 21 (2HCl)<br>MS(ESI) m/z:<br>144 ([M + H]⁺) |
| 22 | (2R,5S)-dimethylpiperazine-CH₂CONH₂ | 21 (2HCl)<br>MS(FAB) m/z:<br>172 ([M + H]⁺) |
| 23 | piperidine-3-N(Me)CH₂CONH₂ | 21 (2HCl)<br>MS(FAB) m/z:<br>172 ([M + H]⁺) |
| 24 | pyrrolidine-3-N(Me)CH₂CONH₂ | 21 (2HCl)<br>MS(ESI) m/z:<br>158 ([M + H]⁺) |
| 25 | piperidine-4-N(Me)CH₂CONH₂ | 21 (2HCl)<br>MS(FAB) m/z:<br>172 ([M + H]⁺) |
| 26 | azepane-4-N(Me)CH₂CONH₂ | 21 (2HCl)<br>MS(ESI) m/z:<br>186 ([M + H]⁺) |
| 27 | 2-nitro-5-fluoro-pyridin-3-yl piperazine-CH₂CONH₂ | 27<br>MS(FAB) m/z:<br>283 ([M + H]⁺) |
| 28 | 2-nitrophenyl-piperazin-3-one | 27<br>MS(ESI) m/z:<br>222 ([M + H]⁺) |
| 29 | 4-CO₂Me-2-NO₂-phenyl piperidine-4-CONH₂ | 27<br>MS(FAB) m/z:<br>308 ([M + H]⁺) |
| 30 | 3-nitropyridin-4-yl piperidine-4-CONH₂ | 27<br>MS(FAB) m/z:<br>251 ([M + H]⁺) |
| 31 | 4-F-2-NO₂-phenyl piperazine-CH₂CONH₂ | 27<br>MS(FAB) m/z:<br>283 ([M + H]⁺) |
| 32 | 4-Me-2-NO₂-phenyl piperazine-CH₂CONH₂ | 27<br>MS(FAB) m/z:<br>279 ([M + H]⁺) |
| 33 | 5-Me-2-NO₂-phenyl piperazine-CH₂CONH₂ | 27<br>MS(FAB) m/z:<br>279 ([M + H]⁺) |
| 34 | 3-F-2-NO₂-phenyl piperazine-CH₂CONH₂ | 27<br>MS(FAB) m/z:<br>283 ([M + H]⁺) |
| 35 | 3-CONH₂-2-NO₂-phenyl 4-Me-piperazine | 27<br>MS(ESI) m/z:<br>265 ([M + H]⁺) |

TABLE 5-continued

| REx | Str | Syn (Sal) Dat |
|---|---|---|
| 36 | (structure) | 27 MS(ESI) m/z: 337 ([M + H]⁺) |
| 37 | (structure) * | 27 MS(FAB) m/z: 293 ([M + H]⁺) |
| 38 | (structure) | 27 MS(API) m/z: 277 ([M + H]⁺) |
| 39 | (structure) | 27 MS(ESI) m/z: 253 ([M + H]⁺) |
| 40 | (structure) | 27 MS(ESI) m/z: 343 ([M + H]⁺) |
| 41 | (structure) | 27 MS(FAB) m/z: 292 ([M + H]⁺) |
| 42 | (structure) | 27 MS(ESI) m/z: 327 ([M + H]⁺) |
| 43 | (structure) | 27 MS(ESI) m/z: 301 ([M + H]⁺) |
| 44 | (structure) | 27 MS(ESI) m/z: 344 ([M + H]⁺) |
| 45 | (structure) | 27 MS(ESI) m/z: 301 ([M + H]⁺) |
| 46 | (structure) | 27 MS(FAB) m/z: 305 ([M + H]⁺) |
| 47 | (structure) * | 27 MS(ESI) m/z: 225 ([M + H]⁺) |
| 48 | (structure) | 27 MS(FAB) m/z: 266 ([M + H]⁺) |
| 49 | (structure) | 27 MS(FAB) m/z: 269 ([M + H]⁺) |

TABLE 5-continued

| REx | Str | Syn (Sal) Dat |
|---|---|---|
| 50 | 3-fluoro-6-nitro-2-(4-(carbamoylmethyl)piperazin-1-yl)benzonitrile | 27 MS(FAB) m/z: 308 ([M + H]+) |
| 51 | 4-(4-(carbamoylmethyl)piperazin-1-yl)-3-nitrobenzonitrile | 27 MS(ESI) m/z: 290 ([M + H]+) |
| 52 | methyl 2-(4-(carbamoylmethyl)piperazin-1-yl)-3-nitrobenzoate | 27 MS(FAB) m/z: 323 ([M + H]+) |
| 53 | (1-(3-nitropyridin-2-yl)-4-hydroxypiperidin-4-yl)methanol | 27 MS(ESI) m/z: 254 ([M + H]+) |
| 54 | 1-(6-chloro-5-nitropyrimidin-4-yl)piperidine-4-carboxamide | 27 MS(FAB) m/z: 286 ([M + H]+) |
| 55 | 3-chloro-6-nitro-2-(4-(carbamoylmethyl)piperazin-1-yl)benzonitrile | 27 MS(FAB) m/z: 324 ([M + H]+) |
| 56 | 4-chloro-2-nitro-1-(4-(carbamoylmethyl)piperazin-1-yl)benzene | 27 MS(FAB) m/z: 299 ([M + H]+) |
| 57 | 5-chloro-2-nitro-1-(4-(carbamoylmethyl)piperazin-1-yl)benzene | 27 MS(FAB) m/z: 299 ([M + H]+) |
| 58 | 5-bromo-2-nitro-1-(4-(carbamoylmethyl)piperazin-1-yl)benzene | 27 MS(ESI) m/z: 343 ([M + H]+) |
| 59 | 1-(4-nitropyridin-3-yl)piperidine-4-carboxamide N-oxide | 27 MS(FAB) m/z: 267 ([M + H]+) |
| 60 | (S)-1-Boc-4-(2-nitrophenyl)piperazine-2-carboxylic acid methyl ester * | 27 MS(FAB) m/z: 366 ([M + H]+) |
| 61 | (R)-1-Boc-4-(2-nitrophenyl)piperazine-2-carboxylic acid methyl ester * | 27 MS(FAB) m/z: 366 ([M + H]+) |
| 62 | methyl 2-(4-(4-carbamoylpiperidin-1-yl)-3-nitrophenyl)acetate | 27 MS(ESI) m/z: 322 ([M + H]+) |
| 63 | 5-methoxy-2-nitro-1-(4-(carbamoylmethyl)piperazin-1-yl)benzene | 27 MS(ESI) m/z: 295 ([M + H]+) |

TABLE 5-continued

| REx | Str | Syn (Sal) Dat |
|---|---|---|
| 64 | 2-NO₂, 6-F-C₆H₃-N(piperazine)-CH₂-CONH₂ | 27 MS(FAB) m/z: 283 ([M + H]⁺) |
| 65 | 2-NO₂-C₆H₄-N(bicyclic diazabicyclo)-NH | 27 MS(EI) m/z: 219 ([M]⁺) |
| 66 | 2-NO₂-C₆H₄-N(trans-2,5-dimethylpiperazine)-NH | 27 MS(ESI) m/z: 236 ([M + H]⁺) |
| 67 | 2-NO₂-C₆H₄-N(2,5-dimethyl-4-Boc-piperazine) | 27 MS(FAB) m/z: 336 ([M + H]⁺) |
| 68 | 4-OHC-2-NO₂-C₆H₃-N(piperazine)-CH₂-CONH₂ | 27 MS(ESI) m/z: 293 ([M + H]⁺) |
| 69 | 2-NO₂-C₆H₄-N(1,2,3,6-tetrahydropyridine) | 27 MS(ESI) m/z: 205 ([M + H]⁺) |
| 70 | 2-NO₂-C₆H₄-N(2,5-dihydropyrrole) | 27 MS(API) m/z: 191 ([M + H]⁺) |
| 71 | 2-NO₂-C₆H₄-N(piperidine)-4-CO₂Et | 27 MS(FAB) m/z: 279 ([M + H]⁺) |
| 72 | 2-NO₂-C₆H₄-N(piperidine)-4-CONH₂ | 27 MS(ESI) m/z: 250 ([M + H]⁺) |
| 73 | 2-NO₂-C₆H₄-N(3-hydroxymethyl-4-methylpiperazine) | 27 MS(ESI) m/z: 252 ([M + H]⁺) |
| 74 | 2-NO₂-C₆H₄-N(piperidine)-3-CO₂Et | 27 MS(ESI) m/z: 279 ([M + H]⁺) |
| 75 | 2-NO₂-C₆H₄-N(piperidine)-4-CH₂-CO₂Et | 27 MS(ESI) m/z: 293 ([M + H]⁺) |
| 76 | 2-NO₂-C₆H₄-N(piperidine)-3-OH | 27 MS(ESI) m/z: 223 ([M + H]⁺) |
| 77 | 2-NO₂-C₆H₄-N(azetidine)-3-CO₂Me | 27 MS(API) m/z: 237 ([M + H]⁺) |
| 78 | 2-NO₂-C₆H₄-N(4-methyl-2-oxopiperazine) | 27 MS(ESI) m/z: 236 ([M + H]⁺) |
| 79 | 2-NO₂-C₆H₄-N(pyrrolidine)-3-CO₂Me | 27 MS(API) m/z: 251 ([M + H]⁺) |
| 80 | 2-NO₂-C₆H₄-N(pyrrolidine)-3-N(Me)-CH₂-CONH₂ | 27 MS(FAB) m/z: 279 ([M + H]⁺) |

TABLE 5-continued

| REx | Str | Syn (Sal) Dat |
|---|---|---|
| 81 | (1-(2-nitrophenyl)-1,4-diazepan-5-one) | 27 MS(EI) m/z: 235 ([M]+) |
| 82 | 2-(4-(5-fluoro-3-nitropyridin-2-yl)piperazin-1-yl)acetamide | 27 MS(EI) m/z: 283 ([M]+) |
| 83 | 2-(4-(6-fluoro-3-nitropyridin-2-yl)piperazin-1-yl)acetamide | 27 MS(EI) m/z: 283 ([M]+) |
| 84 | 1-(6-fluoro-3-nitropyridin-2-yl)piperidine-4-carboxamide | 27 MS(EI) m/z: 268 ([M]+) |
| 85 | 2-(4-(2-bromo-4-fluoro-6-nitrophenyl)piperazin-1-yl)acetamide | 27 MS(ESI) m/z: 361 ([M + H]+) |
| 86 | methyl 4-hydroxy-1-(2-nitrophenyl)piperidine-4-carboxylate | 27 MS(API) m/z: 281 ([M + H]+) |
| 87 | 2-(4-(4-bromo-5-fluoro-2-nitrophenyl)piperazin-1-yl)acetamide | 27 MS(ESI) m/z: 361 ([M + H]+) |
| 88 | * (2-nitrophenyl)pyrrolidin-2-yl methanol | 27 MS(FAB) m/z: 223 ([M + H]+) |
| 89 | methyl 4-hydroxy-1-(3-nitropyridin-2-yl)piperidine-4-carboxylate | 27 MS(ESI) m/z: 282 ([M + H]+) |
| 90 | 2-(4-(3-nitrothiophen-2-yl)piperazin-1-yl)acetamide | 27 MS(FAB) m/z: 271 ([M + H]+) |
| 91 | 2-(4-(3-bromo-1-methyl-4-nitro-1H-pyrazol-5-yl)piperazin-1-yl)acetamide | 27 MS(ESI) m/z: 347 ([M + H]+) |
| 92 | methyl 1-(4-bromo-2-nitrophenyl)-4-hydroxypiperidine-4-carboxylate | 27 MS(FAB) m/z: 359 ([M + H]+) |
| 93 | 2-(4-(6-chloro-3-nitropyridin-2-yl)piperazin-1-yl)acetamide | 27 MS(ESI) m/z: 300 ([M + H]+) |
| 94 | 4-(2-nitrophenyl)-1,4-oxazepane | 27 MS(FAB) m/z: 223 ([M + H]+) |

TABLE 5-continued

| REx | Str | Syn (Sal) Dat |
|---|---|---|
| 95 | (pyridine-N, 3-NO2)-azepane-4,5-diol | 171 → 448 → 27 MS(FAB) m/z: 254 ([M + H]+) |
| 96 | (2-nitrophenyl)-azepane-4,5-diol | 171 → 448 → 27 MS(EI) m/z: 252 ([M]+) |
| 97 | (3-nitropyridin-2-yl)-[1,4]diazepan-5-one | 27 MS(FAB) m/z: 237 ([M + H]+) |
| 98 | 4-hydroxy-1-(3-nitro-6-fluoropyridin-2-yl)piperidine-4-carboxylic acid methyl ester | 27 MS(ESI) m/z: 300 ([M + H]+) |
| 99 | 4-hydroxy-1-(3-nitro-5-fluoropyridin-2-yl)piperidine-4-carboxylic acid methyl ester | 27 MS(ESI) m/z: 300 ([M + H]+) |
| 100 | 2-{methyl-[1-(2-nitrophenyl)piperidin-3-yl]amino}acetamide | 27 MS(FAB) m/z: 293 ([M + H]+) |
| 101 | 2-{methyl-[1-(2-nitrophenyl)azepan-4-yl]amino}acetamide | 27 MS(FAB) m/z: 307 ([M + H]+) |
| 102 | 2-{methyl-[1-(2-nitrophenyl)piperidin-4-yl]amino}acetamide | 27 MS(ESI) m/z: 293 ([M + H]+) |
| 103 | * (3R)-1-(2-nitrophenyl)pyrrolidin-3-ol | 27 MS(FAB) m/z: 209 ([M + H]+) |
| 104 | 2-[4-(4-bromo-2-nitrophenyl)piperazin-1-yl]acetamide | 27 MS(ESI) m/z: 343 ([M + H]+) |
| 105 | 1-(3-nitropyridin-2-yl)piperidine-4-carboxylic acid ethyl ester | 27 MS(FAB) m/z: 280 ([M + H]+) |
| 106 | 1-(4-fluoro-2-nitrophenyl)piperidine-4-carboxylic acid ethyl ester | 27 MS(FAB) m/z: 297 ([M + H]+) |
| 107 | 2-[4-(4-cyanomethyl-2-nitrophenyl)piperazin-1-yl]acetamide | 27 MS(ESI) m/z: 304 ([M + H]+) |
| 108 | 2-[4-(4-cyanomethyl-3-fluoro-2-nitrophenyl)piperazin-1-yl]acetamide | 27 MS(FAB) m/z: 322 ([M + H]+) |
| 109 | 1-(5-chloro-3-nitropyridin-2-yl)piperidine-4-carboxamide | 27 MS(FAB) m/z: 285 ([M + H]+) |

TABLE 5-continued

| REx | Str | Syn (Sal) Dat |
|---|---|---|
| 110 | CONH₂-CH₂-piperazine-N-(5-bromo-3-nitropyridin-2-yl) | 27 MS(ESI) m/z: 344 ([M + H]⁺) |
| 111 | CONH₂-CH₂-piperazine-N-(5-chloro-3-nitropyridin-2-yl) | 27 MS(ESI) m/z: 300 ([M + H]⁺) |
| 112 | CONH₂-CH₂-piperazine-N-(5-methyl-3-nitropyridin-2-yl) | 27 MS(ESI) m/z: 280 ([M + H]⁺) |
| 113 | CONH₂-piperidine-N-(5-bromo-3-nitropyridin-2-yl) | 27 MS(FAB) m/z: 329 ([M + H]⁺) |
| 114 | CONH₂-piperidine-N-(5-methyl-3-nitropyridin-2-yl) | 27 MS(ESI) m/z: 265 ([M + H]⁺) |
| 115 | CONH₂-piperidine-N-(5-cyano-3-nitropyridin-2-yl) | 27 MS(ESI) m/z: 276 ([M + H]⁺) |
| 116 | CONH₂-piperidine-N-(5-methoxycarbonyl-3-nitropyridin-2-yl) | 27 MS(FAB) m/z: 309 ([M + H]⁺) |
| 117 | CONH₂-piperidine-N-(6-chloro-3-nitropyridin-4-yl) | 27 MS(FAB) m/z: 285 ([M + H]⁺) |
| 118 | 4-hydroxy-4-methoxycarbonyl-azepan-1-yl-(3-nitropyridin-2-yl) | 27 MS(ESI) m/z: 296 ([M + H]⁺) |
| 119 | CO₂Et-piperidine-N-(4-chloro-2-nitrophenyl) | 27 MS(ESI) m/z: 313 ([M + H]+) |
| 120 | (2S,4R)-4-hydroxy-2-hydroxymethyl-pyrrolidine-N-(3-nitropyridin-2-yl) * | 27 MS(ESI) m/z: 240 ([M + H]⁺) |
| 121 | CO₂Et-piperidine-N-(4-methoxy-2-nitrophenyl) | 27 MS(ESI) m/z: 309 ([M + H]⁺) |

TABLE 5-continued

| REx | Str | Syn (Sal) Dat |
|---|---|---|
| 122 | (piperazine with CH2CONH2, linked to phenyl bearing NO2 and OCF3) | 27 MS(ESI) m/z: 349 ([M + H]+) |
| 123 | (piperidine-4-CONH2 attached to 3-nitro-6-methoxypyridine) | 27 MS(FAB) m/z: 281 ([M + H]+) |
| 124 | (piperidine-4-CONH2 attached to 5-nitro-1-methyl-2-pyridone) | 27 MS(FAB) m/z: 281 ([M + H]+) |
| 125 | (BocNH-CH2-piperidine N-linked to 2-nitrophenyl) | 27 MS(FAB) m/z: 336 ([M + H]+) |
| 126 | (piperazine-CH2CONH2 attached to phenyl with NO2, Cl, F, CH2CN) | 27 MS(ESI) m/z: 356 ([M + H]+) |
| 127 | (2,3-dihydrobenzofuran with piperazine and NO2) | 27 MS(ESI) m/z: 250 ([M + H]+) |
| 128 | (piperazine attached to phenyl with NO2, OMe, Br) | 128 MS(ESI) m/z: 318 ([M + H]+) |
| 129 | (ethyl piperidine-4-carboxylate N-linked to 3-nitro-5-fluoropyridine) | 27 MS(ESI) m/z: 298 ([M + H]+) |
| 130 | (N-Boc azepane with triflate ester) | 130 MS(ESI) m/z: 368 ([M + Na]+) |
| 131 | (N-Boc tetrahydroazepine with triflate) | 130 MS(ESI) m/z: 368 ([M + Na]+) |
| 132 | (2-iodo-4-cyanomethyl aniline) | 132 MS(EI) m/z: 258 [M]+ |
| 133 | (ethyl piperidine-4-carboxylate N-linked to 3-nitro-5-methylpyridine) | 27 MS(ESI) m/z: 294 ([M + H]+) |
| 134 | (piperazine-CH2CONH2 attached to phenyl with NO2 and OCHF2) | 27 MS(ESI) m/z: 331 ([M + H]+) |
| 135 | (N-Boc tetrahydropyridine attached to 2-nitro-6-fluorophenyl) | 135 MS(FAB) m/z: 323 ([M + H]+) |
| 136 | (N-Boc azepine attached to 2-nitrophenyl) | 135 MS(FAB) m/z: 319 ([M + H]+) |
| 137 | (N-Boc azepine attached to 2-nitrophenyl, isomer) | 135 MS(FAB) m/z: 319 ([M + H]+) |

TABLE 5-continued

| REx | Str | Syn (Sal) Dat |
|---|---|---|
| 138 | [structure: Boc-tetrahydropyridine attached to 2-NO2-4,6-difluorophenyl] | 135 MS(ESI) m/z: 341 ([M + H]+) |
| 139 | [structure: Boc-tetrahydropyridine attached to 2-NO2-5,6-difluorophenyl] | 135 MS(ESI) m/z: 341 ([M + H]+) |
| 140 | [structure: Boc-tetrahydropyridine attached to 2-NH2-5-CN-phenyl] | 140 MS(FAB) m/z: 300 ([M + H]+) |
| 141 | [structure: Boc-tetrahydropyridine attached to 2-NH2-5-CH2CN-phenyl] | 140 MS(FAB) m/z: 312 ([M − H]−) |
| 142 | [structure: trans-2,5-dimethylpiperazine with 2-nitrophenyl] | 21 MS(FAB) m/z: 236 ([M + H]+) |
| 143 | [structure: tetrahydropyridine with 2-NO2-6-F-phenyl] | 21 (CF3CO2H) MS(ESI) m/z: 223 ([M + H]+) |
| 144 | [structure: hexahydroazepine with 2-nitrophenyl] | 21 (HCl) MS(ESI) m/z: 219 ([M + H]+) |
| 145 | [structure: tetrahydropyridine with 2-NH2-5-F-phenyl] | 21 MS(EI) m/z: 192 ([M]+) |
| 146 | [structure: tetrahydropyridine with 4-CN-2-NH2-phenyl] | 21 MS(EI) m/z: 199 ([M]+) |
| 147 | [structure: tetrahydropyridine with 4-CH2CN-2-NH2-phenyl] | 21 MS(EI) m/z: 213 ([M]+) |
| 148 | [structure: tetrahydropyridine with 2,3-difluoro-6-nitrophenyl] | 21 (HCl) MS(ESI) m/z: 241 ([M + H]+) |
| 149 | [structure: hexahydroazepine with 2-nitrophenyl] | 21 (HCl) MS(ESI) m/z: 219 ([M + H]+) |
| 150 | [structure: tetrahydropyridine with 2,6-difluoro-3-nitrophenyl] | 21 (HCl) MS(ESI) m/z: 241 ([M + H]+) |
| 151 | [structure: piperazine with 2-nitrophenyl and CH2CONH2] | 14 MS(ESI) m/z: 265 ([M + H]+) |
| 152 | [structure: diazabicyclic with 2-nitrophenyl and CH2CONH2] | 14 MS(FAB) m/z: 277 ([M + H]+) |
| 153 | [structure: trans-2,5-dimethylpiperazine with 2-nitrophenyl and CH2CONH2] | 14 MS(FAB) m/z: 293 ([M + H]+) |

| REx | Str | Syn (Sal) Dat |
|---|---|---|
| 154 |  | 14 MS(FAB) m/z: 293 ([M + H]+) |
| 155 | 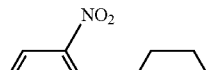 | 14 MS(FAB) m/z: 280 ([M + H]+) |
| 156 | 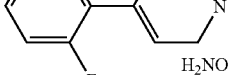 | 14 MS(ESI) m/z: 375 ([M + 2H]+) |
| 157 |  | 14 MS(ESI) m/z: 307 ([M + H]+) |
| 158 | 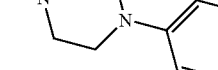 | 14 MS(ESI) m/z: 298 ([M + H]+) |
| 159 | 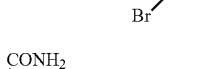 | 14 MS(FAB) m/z: 276 ([M + H]+) |
| 160 | 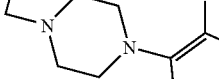 | 14 MS(FAB) m/z: 276 ([M + H]+) |
| 161 |  | 14 MS(EI) m/z: 249 ([M]+) |
| 162 | | 14 MS(ESI) m/z: 257 ([M + H]+) |
| 163 | | 14 MS(ESI) m/z: 271 ([M + H]+) |
| 164 | | 14 MS(EI) m/z: 233 ([M]+) |
| 165 | | 14 MS(EI) m/z: 297 ([M]+) |
| 166 | | 27 → 14 MS(ESI) m/z: 297 ([M + H]+) |
| 167 | | 27 → 14 MS(ESI) m/z: 279 ([M + H]+) |
| 168 | | 27 → 14 MS(FAB) m/z: 296 ([M + H]+) |
| 169 | | 27 → 14 MS(ESI) m/z: 280 ([M + H]+) |

TABLE 5-continued

| REx | Str | Syn (Sal) Dat |
|---|---|---|
| 170 | (structure) | 27 → 14 MS(ESI) m/z: 295 ([M + H]⁺) |
| 171 | (structure) | 171 MS(API) m/z: 225 ([M + H]⁺) |
| 172 | (structure) | 171 MS(ESI) m/z: 239 ([M + H]⁺) |
| 173 | (structure) | 173 MS(ESI) m/z: 308 ([M + H]⁺) |
| 174 | (structure) | 174 MS(ESI) m/z: 343 ([M + H]⁺) |
| 175 | (structure) | 175 MS(FAB) m/z: 363 ([M + H]⁺) |
| 176 | (structure) | 176 MS(FAB) m/z: 221 ([M + H]⁺) |
| 177 | (structure) | 176 MS(ESI) m/z: 192 ([M + H]⁺) |
| 178 | (structure) | 176 MS(ESI) m/z: 235 ([M + H]⁺) |
| 179 | (structure) | 176 MS(FAB) m/z: 278 ([M + H]⁺) |
| 180 | (structure) | 176 MS(FAB) m/z: 292 ([M + H]⁺) |
| 181 | (structure) | 176 MS(FAB) m/z: 275 ([M + H]⁺) |
| 182 | (structure) | 176 MS(FAB) m/z: 221 ([M + H]⁺) |
| 183 | (structure) | 176 MS(ESI) m/z: 253 ([M + H]⁺) |
| 184 | (structure) | 176 MS(FAB) m/z: 249 ([M + H]⁺) |
| 185 | (structure) | 176 MS(FAB) m/z: 249 ([M + H]⁺) |

TABLE 5-continued

| REx | Str | Syn (Sal) Dat |
|---|---|---|
| 186 | 2-amino-4-fluorophenyl piperazinyl-CH2-CONH2 | 176 MS(ESI) m/z: 253 ([M + H]$^+$) |
| 187 | 2-amino-4-methoxyphenyl piperazinyl-CH2-CONH2 | 176 MS(FAB) m/z: 265 ([M + H]$^+$) |
| 188 | 2-amino-3-fluorophenyl piperazinyl-CH2-CONH2 | 176 MS(FAB) m/z: 253 ([M + H]$^+$) |
| 189 | 3-(H2NOC)-2-amino-phenyl-(4-methylpiperazinyl) | 176 MS(FAB) m/z: 235 ([M + H]$^+$) |
| 190 | 2-amino-6-fluorophenyl piperazinyl-CH2-CONH2 | 176 MS(FAB) m/z: 253 ([M + H]$^+$) |
| 191 | 3-amino-4-piperazinylphenyl-CH2CH2-CO2Et, piperazinyl-CH2-CONH2 | 176 MS(ESI) m/z: 335 ([M + H]$^+$) |
| 192 | 2-amino-5-(CH2CO2Me)phenyl piperazinyl-CH2-CONH2 | 176 MS(ESI) m/z: 307 ([M + H]$^+$) |
| 193 | 2-aminophenyl-(diazabicyclo)-CH2-CONH2 | 176 MS(FAB) m/z: 247 ([M + H]$^+$) |
| 194 | 2-aminophenyl-(2,5-dimethylpiperazinyl)-CH2-CONH2 | 176 MS(FAB) m/z: 263 ([M + H]$^+$) |
| 195 | 2-aminophenyl-(2,5-dimethylpiperazinyl, stereo*)-CH2-CONH2 | 176 MS(FAB) m/z: 263 ([M + H]$^+$) |
| 196 | 2-aminophenyl-(2,5-dimethylpiperazinyl, stereo*)-CH2-CONH2 | 176 MS(FAB) m/z: 263 ([M + H]$^+$) |
| 197 | 2-aminophenyl-(homopiperazinyl)-CH2-CONH2 | 176 MS(FAB) m/z: 249 ([M + H]$^+$) |
| 198 | 2-aminophenyl-piperazinyl(N-Boc)(CO2Me)* | 176 MS(FAB) m/z: 336 ([M + H]$^+$) |
| 199 | 2-aminophenyl-piperazinyl(N-Boc)(CO2Me)* | 176 MS(FAB) m/z: 336 ([M + H]$^+$) |
| 200 | 2-aminophenyl-(3,4-dihydroxypiperidinyl) | 176 MS(ESI) m/z: 209 ([M + H]$^+$) |
| 201 | 2-aminophenyl-piperazinone-CH2-CONH2 | 176 MS(API) m/z: 247 ([M − H]$^−$) |

TABLE 5-continued

| REx | Str | Syn (Sal) Dat |
|---|---|---|
| 202 | 2-aminophenyl-piperidine with 4,4-(OH)(CH2OH) | 176 MS(ESI) m/z: 223 ([M + H]+) |
| 203 | 2-amino-4-(methylsulfonyl)phenyl-piperazine-CH2CONH2 | 176 MS(ESI) m/z: 313 ([M + H]+) |
| 204 | 2-aminophenyl-piperidine-4-morpholine | 176 MS(FAB) m/z: 262 ([M + H]+) |
| 205 | 2-amino-4-(methylsulfinyl)phenyl-piperazine-CH2CONH2 | 176 MS(ESI) m/z: 297 ([M + H]+) |
| 206 | 2-amino-4,6-difluorophenyl-piperazine-CH2CONH2 | 176 MS(ESI) m/z: 271 ([M + H]+) |
| 207 | 3-amino-4-(piperazinyl)benzenesulfonamide-CH2CONH2 | 176 MS(FAB) m/z: 314 ([M + H]+) |
| 208 | 2-amino-5,6-difluorophenyl-piperazine-CH2CONH2 | 176 MS(FAB) m/z: 271 ([M + H]+) |
| 209 | 2-aminophenyl-piperidine-4-(3-oxopiperazine) | 176 MS(FAB) m/z: 275 ([M + H]+) |
| 210 | 2-amino-6-fluorophenyl-homopiperazine-CH2CONH2 | 176 MS(ESI) m/z: 267 ([M + H]+) |
| 211 | 2-aminophenyl-pyrrolidine-3,4-diol * | 176 MS(ESI) m/z: 195 ([M + H]+) |
| 212 | 3-amino-2-pyridyl-piperazine-CH2CONH2 | 176 MS(FAB) m/z: 236 ([M + H]+) |
| 213 | 3-amino-5-fluoro-2-pyridyl-piperidine-4-CONH2 | 176 MS(EI) m/z: 238 ([M]+) |
| 214 | 2-amino-6-fluoro-3-cyanophenyl-piperazine-CH2CONH2 | 176 MS(FAB) m/z: 276 ([M − H]−) |
| 215 | 3-amino-6-methoxy-2-pyridyl-piperazine-CH2CONH2 | 176 MS(ESI) m/z: 266 ([M + H]+) |
| 216 | 3-amino-4-(piperazinyl)benzonitrile-CH2CONH2 | 176 MS(ESI) m/z: 260 ([M + H]+) |
| 217 | 2-amino-6-(methoxycarbonyl)phenyl-piperazine-CH2CONH2 | 176 MS(FAB) m/z: 293 ([M + H]+) |
| 218 | 3-amino-2-pyridyl-piperidine-4,4-(OH)(CH2OH) | 176 MS(ESI) m/z: 224 ([M + H]+) |

TABLE 5-continued

| REx | Str | Syn (Sal) Dat |
|---|---|---|
| 219 | 4-amino-pyrimidine-piperidine-4-carboxamide | 176 MS(FAB) m/z: 222 ([M + H]+) |
| 220 | 2-amino-6-chloro-3-cyanophenyl-piperazine-N-acetamide | 176 MS(FAB) m/z: 294 ([M + H]+) |
| 221 | 2-aminophenyl-pyrrolidine-3-carboxylic acid methyl ester | 176 MS(ESI) m/z: 221 ([M + H]+) |
| 222 | 2-aminophenyl-piperidine-4-carboxylic acid ethyl ester | 176 MS(FAB) m/z: 249 ([M + H]+) |
| 223 | 2-aminophenyl-piperidine-4-carboxamide | 176 MS(ESI) m/z: 220 ([M + H]+) |
| 224 | 2-aminophenyl-3,4-dihydroxypyrrolidine | 176 MS(ESI) m/z: 195 ([M + H]+) |
| 225 | 2-aminophenyl-4-methyl-2-hydroxymethylpiperazine | 176 MS(FAB) m/z: 222 ([M + H]+) |
| 226 | 2-aminophenyl-piperidine-3-carboxylic acid ethyl ester | 176 MS(ESI) m/z: 249 ([M + H]+) |
| 227 | 2-aminophenyl-piperidine-4-acetic acid ethyl ester | 176 MS(ESI) m/z: 263 ([M + H]+) |
| 228 | 2-aminophenyl-3-hydroxypiperidine | 176 MS(API) m/z: 193 ([M + H]+) |
| 229 | 2-aminophenyl-azetidine-3-carboxylic acid methyl ester | 176 MS(ESI) m/z: 207 ([M + H]+) |
| 230 | 2-aminophenyl-4-methyl-3-oxopiperazine | 176 MS(ESI) m/z: 206 ([M + H]+) |
| 231 | 6-fluoro-3-amino-2-pyridyl-piperidine-4-carboxamide | 176 MS(FAB) m/z: 239 ([M + H]+) |
| 232 | 3-amino-5-fluoro-2-pyridyl-piperazine-N-acetamide | 176 MS(FAB) m/z: 254 ([M + H]+) |
| 233 | 2-cyano-4-fluoro-6-pyridylpiperazine-N-acetamide | 176 MS(ESI) m/z: 278 ([M + H]+) |
| 234 | 2-aminophenyl-4-hydroxy-piperidine-4-carboxylic acid methyl ester | 176 MS(API) m/z: 251 ([M + H]+) |
| 235 | 2-aminophenyl-(S)-2-hydroxymethylpyrrolidine * | 176 MS(EI) m/z: 192 ([M]+) |

TABLE 5-continued

| REx | Str | Syn (Sal) Dat |
|---|---|---|
| 236 | (structure) | 176 MS(ESI) m/z: 252 ([M + H]+) |
| 237 | (structure) | 176 (2HBr) MS(ESI) m/z: 317 ([M + H]+) |
| 238 | (structure) | 176 (HCl) MS(ESI) m/z: 193 ([M + H]+) |
| 239 | (structure) | 176 MS(ESI) m/z: 250 ([M + H]+) |
| 240 | (structure) | 176 MS(EI) m/z: 205 ([M]+) |
| 241 | (structure) | 176 MS(EI) m/z: 206 ([M]+) |
| 242 | (structure) | 176 MS(EI) m/z: 222 ([M]+) |
| 243 | (structure) | 176 MS(ESI) m/z: 270 ([M + H]+) |
| 244 | (structure) | 176 MS(EI) m/z: 262 ([M]+) |
| 245 | (structure) | 176 MS(EI) m/z: 248 ([M]+) |
| 246 | (structure) | 176 MS(FAB) m/z: 265 ([M + H]+) |
| 247 | (structure) | 176 MS(ESI) m/z: 263 ([M + H]+) |
| 248 | (structure) | 176 MS(EI) m/z: 276 ([M]+) |
| 249 | (structure) | 176 MS(FAB) m/z: 250 ([M + H]+) |
| 250 | (structure) | 176 MS(FAB) m/z: 267 ([M + H]+) |
| 251 | (structure) | 176 MS(ESI) m/z: 274 ([M + H]+) |

TABLE 5-continued

| REx | Str | Syn (Sal) Dat |
|---|---|---|
| 252 | [structure: piperazine with CH2CONH2, linked to 2-amino-5-methylpyridine] | 176 MS(ESI) m/z: 249 ([M + H]+) |
| 253 | [structure: 4-carbamoylpiperidine linked to 3-amino-5-methylpyridin-2-yl] | 176 MS(ESI) m/z: 235 ([M + H]+) |
| 254 | [structure: 4-carbamoylpiperidine linked to 3-amino-5-cyanopyridin-2-yl] | 176 MS(ESI) m/z: 245 ([M + H]+) |
| 255 | * [structure: 2-aminophenyl-(3-hydroxypyrrolidin-1-yl)] | 176 MS(FAB) m/z: 179 ([M + H]+) |
| 256 | [structure: piperidine-4-carboxamide linked to 3-amino-5-(methoxycarbonyl)pyridin-2-yl] | 176 MS(ESI) m/z: 279 ([M + H]+) |
| 257 | [structure: piperazinyl-CH2CONH2 on amino-fluoro-cyanomethyl benzene] | 176 MS(ESI) m/z: 292 ([M + H]+) |
| 258 | [structure: 3-aminopyridin-2-yl linked to 4-hydroxy-4-(methoxycarbonyl)azepane] | 176 MS(ESI) m/z: 266 ([M + H]+) |
| 259 | [structure: 3-amino-6-methoxypyridin-4-yl linked to 4-carbamoylpiperidine] | 176 MS(EI) m/z: 250 ([M]+) |
| 260 | [structure: piperazine CH2CONH2 linked to 2-amino-4-(trifluoromethoxy)phenyl] | 176 MS(ESI) m/z: 319 ([M + H]+) |
| 261 | [structure: 4-(ethoxycarbonyl)piperidine linked to 2-amino-4-methoxyphenyl] | 176 MS(ESI) m/z: 279 ([M + H]+) |
| 262 | * [structure: (3-hydroxy-5-hydroxymethyl)pyrrolidinyl linked to 3-aminopyridin-2-yl] | 176 MS(ESI) m/z: 210 ([M + H]+) |
| 263 | [structure: 4-(Boc-aminomethyl)piperidine linked to 2-aminophenyl] | 176 MS(FAB) m/z: 306 ([M + H]+) |
| 264 | [structure: piperazine CH2CONH2 linked to amino-dihydrobenzofuran] | 176 MS(EI) m/z: 276 ([M]+) |
| 265 | [structure: 4-(ethoxycarbonyl)piperidine linked to 3-amino-5-methylpyridin-2-yl] | 176 MS(EI) m/z: 263 ([M]+) |
| 266 | [structure: 4-(ethoxycarbonyl)piperidine linked to 3-amino-5-fluoropyridin-2-yl] | 176 MS(EI) m/z: 267 ([M]+) |

TABLE 5-continued

| REx | Str | Syn (Sal) Dat |
|---|---|---|
| 267 | (4-(difluoromethoxy)-2-aminophenyl)piperazine with N-CH2CONH2 | 176 MS(ESI) m/z: 301 ([M + H]+) |
| 268 | 3-amino-6-fluoropyridin-2-yl attached to 4-hydroxy-4-(CO2Me)piperidine | 176 MS(FAB) m/z: 270 ([M + H]+) |
| 269 | 3-amino-6-fluoropyridin-2-yl piperazine with CH2CONH2 | 176 MS(FAB) m/z: 254 ([M + H]+) |
| 270 | 3-aminopyridin-2-yl azepane with trans-4,5-diOH | 176 MS(EI) m/z: 223 ([M]+) |
| 271 | 2-aminophenyl pyrrolidine with trans-3,4-diOH * | 27 → 176 MS(ESI) m/z: 195 ([M + H]+) |
| 272 | 2-aminophenyl 3-hydroxypyrrolidine | 27 → 176 MS(ESI) m/z: 179 ([M + H]+) |
| 273 | 2-aminophenyl 4-hydroxyazepane | 27 → 176 MS(API) m/z: 207 ([M + H]+) |
| 274 | 3-aminopyridin-2-yl 4-hydroxypiperidine | 176 MS(API) m/z: 194 ([M + H]+) |
| 275 | 3-amino-pyridin-2-yl 4-fluoro-4-CO2Et-piperidine | 27 → 176 MS(ESI) m/z: 268 ([M + H]+) |
| 276 | 3-amino-6-(CH2CN)pyridin-2-yl piperazine with CH2CONH2 | 276 MS(ESI) m/z: 275 ([M + H]+) |
| 277 | 3-amino-6-(CH2C(O)NH-tBu)pyridin-2-yl piperazine with CH2CONH2 | 277 MS(ESI) m/z: 349 ([M + H]+) |
| 278 | 4-bromo-2-aminophenyl piperazine with CH2CONH2 | 278 MS(API) m/z: 313 ([M + H]+) |
| 279 | 5-amino-2-chloropyridin-4-yl 4-CONH2-piperidine | 278 MS(ESI) m/z: 255 ([M + H]+) |
| 280 | 2-amino-4-chlorophenyl 4-CO2Et-piperidine | 278 MS(ESI) m/z: 282 ([M + H]+) |
| 281 | 5-amino-1-methyl-2-oxo-1,2-dihydropyridin-4-yl 4-CONH2-piperidine | 278 MS(ESI) m/z: 251 ([M + H]+) |

TABLE 5-continued

| REx | Str | Syn (Sal) Dat |
|---|---|---|
| 282 | (structure) | 278 MS(ESI) m/z: 326 ([M + H]$^+$) |
| 283 | (structure) | 278 MS(ESI) m/z: 343 ([M + H]$^+$) |
| 284 | (structure) | 284 (HCl) MS(FAB) m/z: 260 ([M + H]$^+$) |
| 285 | (structure) | 27 → 176 → 284 MS(FAB) m/z: 278 ([M + H]$^+$) |
| 286 | (structure) | 286 MS(ESI) m/z: 269 ([M + H]$^+$) |
| 287 | (structure) | 286 MS(FAB) m/z: 269 ([M + H]$^+$) |
| 288 | (structure) | 286 MS(ESI) m/z: 313 ([M + H]$^+$) |
| 289 | (structure) | 286 MS(EI) m/z: 261 ([M]$^+$) |
| 290 | (structure) | 286 MS(EI) m/z: 249 ([M]$^+$) |
| 291 | (structure) | 286 MS(ESI) m/z: 241 ([M + H]$^+$) |
| 292 | (structure) | 286 MS(ESI) m/z: 331 ([M + H]$^+$) |
| 293 | (structure) | 286 MS(ESI) m/z: 329 ([M + H]$^+$) |
| 294 | (structure) | 286 MS(ESI) m/z: 313 ([M + H]$^+$) |
| 295 | (structure) | 286 MS(ESI) m/z: 268 ([M + H]$^+$) |
| 296 | (structure) | 286 MS(EI) m/z: 269 ([M]$^+$) |

TABLE 5-continued

| REx | Str | Syn (Sal) Dat |
|---|---|---|
| 297 | | 286 MS(EI) m/z: 254 ([M]⁺) |
| 298 | | 286 MS(ESI) m/z: 314 [M + H]⁺ |
| 299 | | 286 MS(ESI) m/z: 299 ([M + H]⁺) |
| 300 | | 286 MS(FAB) m/z: 246 ([M + H]⁺) |
| 301 | | 286 MS(FAB) m/z: 246 ([M + H]+) |
| 302 | | 286 MS(ESI) m/z: 268 (]M + H]⁺) |
| 303 | | 303 MS(FAB) m/z: 221 ([M + H]⁺) |
| 304 | | 304 MS(FAB) m/z: 262 ([M]⁺) |
| 305 | | 305 MS(ESI) m/z: 206 ([M + H]⁺) |
| 306 | | 14 MS(FAB) m/z: 260 ([M + H]⁺) |
| 307 | | 14 MS(FAB) m/z: 261 ([M + H]⁺) |
| 308 | | 308 MS(FAB) m/z: 269 ([M + H]⁺) |
| 309 | | 309 MS(FAB) m/z: 389 ([M + H]⁺) |
| 310 | | 309 MS(ESI) m/z: 390 ([M + H]⁺) |
| 311 | | 309 MS(FAB) m/z: 407 ([M + H]⁺) |
| 312 | | 312 MS(FAB) m/z: 293 ([M + H]⁺) |

TABLE 5-continued

| REx | Str | Syn (Sal) Dat |
|---|---|---|
| 313 | (structure) | 312 MS(FAB) m/z: 310 ([M]+) |
| 314 | (structure) | 312 MS(ESI) m/z: 294 ([M + H]+) |
| 315 | (structure) | 21 (HCl) MS(ESI) m/z: 194 ([M + H]+) |
| 316 | (structure) | 316 (2HCl) MS(FAB) m/z: 175 ([M + H]+) |
| 317 | (structure) | 316 (2HCl) MS(FAB) m/z: 193 ([M + H]+) |
| 318 | (structure) | 318 MS(ESI) m/z: 205 ([M + H]+) |
| 319 | (structure) | 14 MS(FAB) m/z: 232 ([M + H]+) |
| 320 | (structure) | 14 MS(FAB) m/z: 250 ([M + H]+) |
| 321 | (structure) | 14 MS(FAB) m/z: 262 ([M + H]+) |
| 322 | (structure) | 322 MS(ESI) m/z: 233 ([M + H]+) |
| 323 | (structure) | 323 MS(ESI) m/z: 251 ([M + H]+) |
| 324 | (structure) | 324 MS(FAB) m/z: 306 ([M + H]+) |
| 325 | (structure) | 325 (2HCl) MS(FAB) m/z: 234 ([M + H]+) |
| 326 | (structure) | 325 MS(EI) m/z: 251 ([M]+) |
| 327 | (structure) | 325 MS(ESI) m/z: 252 ([M + H]+) |
| 328 | (structure) | 325 MS(ESI) m/z: 252 ([M + H]+) |
| 329 | (structure) | 325 MS(FAB) m/z: 248 ([M + H]+) |

TABLE 5-continued

| REx | Str | Syn (Sal) Dat |
|---|---|---|
| 330 | CONH2, 3,5-dichlorophenyl | 566 MS(EI) m/z: 203 ([M]+) |
| 331 | Ph-CH2-O-(CH2)3-C(=O)NH2 | 564 MS(ESI) m/z: 194 ([M + H]+) |
| 332 | PhC(=O)O-CH2-C(Me)(Me)-C(=O)NH2 | 564 MS(ESI) m/z: 222 ([M + H]+) |
| 333 | H2N-C(=O)-CH(Me)-CH2-CH2-OH | 333 MS(API) m/z: 118 ([M + H]+) |
| 334 | H2N-C(=O)-CH(Me)-CH2-CH2-O-C(=O)Ph | 334 MS(ESI) m/z: 222 ([M + H]+) |
| 335 | Boc-NH-CH(Me)-CH2-OMe * | 335 MS(CI) m/z: 190 ([M + H]+) |
| 336 | EtO-C(=O)-NH-CH(Me)-CH2-OMe * | 336 MS(CI) m/z: 162 ([M + H]+) |
| 337 | MeNH-CH(Me)-CH2-OMe * | 337 (HCl) MS(FAB) m/z: 104 ([M + H]+) |
| 338 | MeNH-CH(Me)-CH2-OMe * | 337 (HCl) MS(FAB) m/z: 104 ([M + H]+) |
| 339 | 2-hydroxy-pyridine-3-thiocarboxamide | 339 MS(FAB) m/z: 155 ([M + H]+) |
| 340 | Ph-CH2-O-(CH2)3-C(=S)NH2 | 340 MS(ESI) m/z: 208 ([M − H]−) |
| 341 | MeO-(CH2)3-C(=S)NH2 | 340 MS(API) m/z: 132 ([M − H]−) |
| 342 | PhC(=O)O-CH2-C(Me)(Me)-C(=S)NH2 | 340 MS(ESI) m/z: 238 ([M + H]+) |
| 343 | H2N-C(=S)-CH(Me)-CH2-CH2-O-C(=O)Ph | 340 MS(API) m/z: 238 ([M + H]+) |
| 344 | 1-Boc-4-Me-piperidine-4-thiocarboxamide | 340 MS(FAB) m/z: 259 ([M + H]+) |
| 345 | 3,5-dichlorophenyl-CH2-C(=S)NH2 | 340 MS(FAB) m/z: 220 ([M + H]+) |
| 346 | H2N-C(=S)-C(Me)(Me)-CH2-CH2-O-C(=O)Ph | 333 → 334 → 340 MS(ESI) m/z: 274 ([M + Na]+) |
| 347 | 6-methoxy-pyridazine-3-thiocarboxamide | 347 MS(EI) m/z: 169 ([M]+) |

TABLE 5-continued
| REx | Str | Syn (Sal) Dat |
|---|---|---|
| 348 | 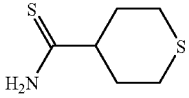 | 347 MS(ESI) m/z: 160 ([M − H]−) |
| 349 | 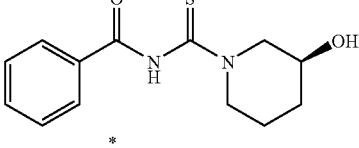 * | 349 MS(ESI) m/z: 263 ([M − H]−) |
| 350 | 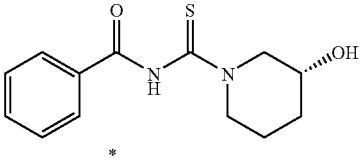 * | 349 MS(ESI) m/z: 265 ([M + H]+) |
| 351 | 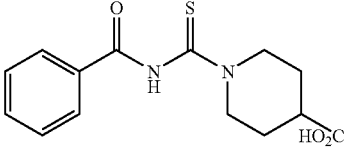 | 349 MS(ESI) m/z: 293 ([M + H]+) |
| 352 | 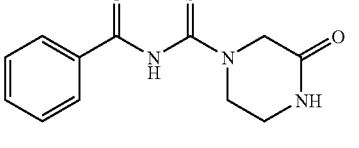 | 349 MS(FAB) m/z: 264 ([M + H]+) |
| 353 | 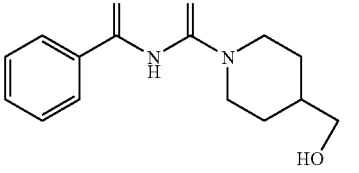 | 349 MS(FAB) m/z: 279 ([M + H]+) |
| 354 | 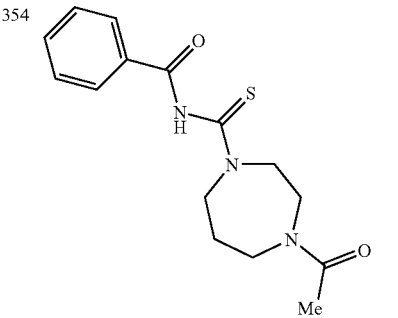 | 349 MS(FAB) m/z: 306 ([M + H]+) |
| 355 | 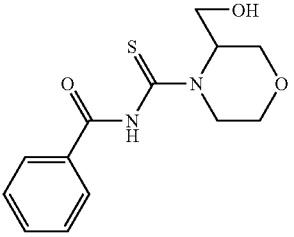 | 349 MS(ESI) m/z: 279 ([M − H]−) |
| 356 | 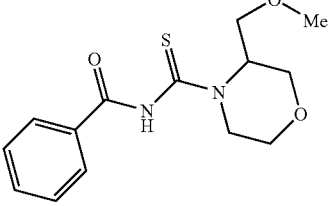 | 349 MS(ESI) m/z: 293 ([M − H]−) |
| 357 | 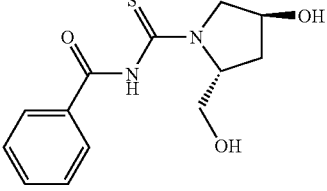 | 349 MS(ESI) m/z: 279 ([M − H]−) |
| 358 | 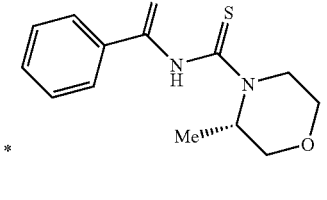 * | 349 MS(FAB) m/z: 265 ([M + H]+) |
| 359 | * 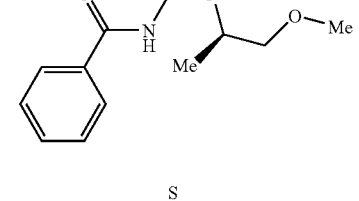 | 349 MS(FAB) m/z: 267 ([M + H]+) |
| 360 | * 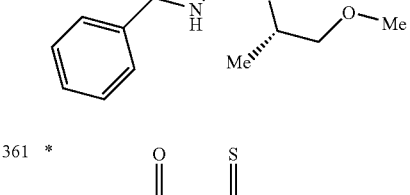 | 349 MS(FAB) m/z: 267 ([M + H]+) |
| 361 | *  | 349 MS(FAB) m/z: 263 ([M + H]+) |

TABLE 5-continued

| REx | Str | Syn (Sal) Dat |
|---|---|---|
| 362 | (structure) | 349 MS(ESI) m/z: 265 ([M + H]$^+$) |
| 363 | (structure) | 349 MS(FAB) m/z: 295 ([M + H]$^+$) |
| 364 | (structure) | 364 MS(ESI) m/z: 161 ([M + H]$^+$) |
| 365 | (structure) | 364 MS(ESI) m/z: 161 ([M + H]$^+$) |
| 366 | (structure) | 364 MS(ESI) m/z: 187 ([M − H]$^-$) |
| 367 | (structure) | 364 MS(ESI) m/z: 158 ([M − H]$^-$) |
| 368 | (structure) | 364 MS(FAB) m/z: 175 ([M + H]$^+$) |
| 369 | (structure) | 364 MS(FAB) m/z: 202 ([M + H]$^+$) |
| 370 | (structure) | 349 → 364 MS(ESI) m/z: 147 ([M − H]$^-$) |
| 371 | (structure) | 364 MS(API) m/z: 191 ([M + H]$^+$) |
| 372 | (structure) | 364 MS(ESI) m/z: 175 ([M − H]$^-$) |
| 373 | (structure) | 364 MS(ESI) m/z: 175 ([M − H]$^-$) |
| 374 | (structure) | 364 MS(API) m/z: 161 ([M + H]$^+$) |
| 375 | (structure) | 364 MS(FAB) m/z: 161 ([M + H]$^+$) |
| 376 | (structure) | 364 MS(FAB) m/z: 163 ([M + H]$^+$) |
| 377 | (structure) | 364 MS(FAB) m/z: 163 ([M + H]+) |
| 378 | (structure) | 364 MS(CI) m/z: 159 ([M + H]$^+$) |
| 379 | (structure) | 364 MS(EI) m/z: 190 ([M]$^+$) |

TABLE 5-continued

| REx | Str | Syn (Sal) Dat |
|---|---|---|
| 380 | (thiourea with N-Me, N-CH2CH2OMe) | 349 → 364 MS(ESI) m/z: 149 ([M + H]+) |
| 381 | EtO2C-thiazole-2-(furan-3-yl) | 381 MS(FAB) m/z: 224 ([M + H]+) |
| 382 | EtO2C-thiazole-2-(2-bromophenyl) | 381 MS(FAB) m/z: 314 ([M + H]+) |
| 383 | EtO2C-thiazole-2-(3-dimethylaminophenyl) | 381 MS(FAB) m/z: 277 ([M + H]+) |
| 384 | CO2Et-thiazole-2-(4-dimethylaminophenyl) | 381 MS(FAB) m/z: 276 ([M]+) |
| 385 | EtO2C-thiazole-2-(pyrimidin-4-yl) | 381 MS(ESI) m/z: 236 ([M + H]+) |
| 386 | EtO2C-thiazole-2-(pyrimidin-5-yl) | 381 MS(FAB) m/z: 236 ([M + H]+) |
| 387 | EtO2C-thiazole-2-(pyridazin-4-yl) | 381 MS(ESI) m/z: 236 ([M + H]+) |
| 388 | EtO2C-thiazole-2-(2-oxo-1,2-dihydropyridin-3-yl) | 431 MS(FAB) m/z: 251 ([M + H]+) |
| 389 | EtO2C-thiazole-2-((3S)-3-hydroxypiperidin-1-yl) | 381 MS(ESI) m/z: 257 ([M + H]+) |
| 390 | EtO2C-thiazole-2-((3R)-3-hydroxypiperidin-1-yl) | 381 MS(ESI) m/z: 257 ([M + H]+) |
| 391 | EtO2C-thiazole-2-(4-hydroxymethylpiperidin-1-yl) | 381 MS(FAB) m/z: 271 ([M + H]+) |
| 392 | EtO2C-thiazole-2-(3-carboxypiperidin-1-yl) | 381 MS(ESI) m/z: 285 ([M + H]+) |
| 393 | EtO2C-thiazole-2-(3-oxopiperazin-1-yl) | 381 MS(ESI) m/z: 256 ([M + H]+) |
| 394 | CO2Et-thiazole-2-(4-methyl-1,4-diazepan-1-yl) | 381 MS(FAB) m/z: 270 ([M + H]+) |
| 395 | CO2Et-thiazole-2-(4-acetyl-1,4-diazepan-1-yl) | 381 MS(FAB) m/z: 298 ([M + H]+) |
| 396 | CO2Et-thiazole-2-(1-ethylpropyl... 2,4-dimethylpentan-3-yl) | 381 MS(ESI) m/z: 228 ([M + H]+) |
| 397 | CO2Et-thiazole-2-heptyl | 381 MS(ESI) m/z: 256 ([M + H]+) |
| 398 | CO2Et-thiazole-2-(tetrahydrofuran-3-yl) | 381 MS(ESI) m/z: 228 ([M + H]+) |
| 399 | CO2Et-thiazole-2-cyclopentyl | 381 MS(ESI) m/z: 226 ([M + H]+) |

| REx | Str | Syn (Sal) Dat |
|---|---|---|
| 400 | (thiazole-4-CO₂Et, 2-(tetrahydrothiopyran-4-yl)) | 381 MS(ESI) m/z: 258 ([M + H]⁺) |
| 401 | (thiazole-4-CO₂Et, 2-(3-benzyloxypropyl)) | 381 MS(ESI) m/z: 306 ([M + H]⁺) |
| 402 | (thiazole-4-CO₂Et, 2-(3-methoxypropyl)) | 381 MS(ESI) m/z: 230 ([M + H]⁺) |
| 403 | (thiazole-4-CO₂Et, 2-(2-methyl-2-(benzoyloxymethyl)propyl)) | 381 MS(API) m/z: 334 ([M + H]⁺) |
| 404 | (thiazole-4-CO₂Et, 2-(6-methoxypyridazin-3-yl)) | 381 MS(ESI) m/z: 266 ([M + H]⁺) |
| 405 | (thiazole-4-CO₂Et, 2-(3-benzoyloxy-1-methylpropyl)) | 381 MS(ESI) m/z: 334 ([M + H]⁺) |
| 406 | (thiazole-4-CO₂Et, 2-(N-methyl-N-(2-hydroxypropyl)amino)) | 381 MS(API) m/z: 245 ([M + H]⁺) |
| 407 | (thiazole-4-CO₂Et, 2-(2-methyl-4-benzoyloxy-2-butyl)) | 381 MS(ESI) m/z: 348 ([M + H]⁺) |
| 408 | (thiazole-4-CO₂Et, 2-(3-methoxymethylmorpholin-4-yl)) | 381 MS(ESI) m/z: 287 ([M + H]⁺) |
| 409 | (thiazole-4-CO₂Et, 2-(3-hydroxymethylmorpholin-4-yl)) | 381 MS(ESI) m/z: 273 ([M + H]⁺) |
| 410 | (thiazole-4-CO₂Et, 2-((2S,4R)-4-hydroxy-2-hydroxymethylpyrrolidin-1-yl)) | 381 MS(ESI) m/z: 273 ([M + H]⁺) |
| 411 | (thiazole-4-CO₂Et, 2-(4-Boc-2-methoxymethylpiperazin-1-yl)) | 381 MS(FAB) m/z: 386 ([M + H]⁺) |
| 412 | (thiazole-4-CO₂Et, 2-(3-methoxypyrrolidin-1-yl)) | 381 MS(ESI) m/z: 257 ([M + H]⁺) |
| 413 | (thiazole-4-CO₂Et, 2-(1-Boc-4-methylpiperidin-4-yl)) | 381 MS(FAB) m/z: 355 ([M + H]⁺) |
| 414 | (thiazole-4-CO₂Et, 2-(3,5-dichlorobenzyl)) | 381 MS(FAB) m/z: 316 ([M + H]⁺) |
| 415 | (thiazole-4-CO₂Et, 2-(3-methylmorpholin-4-yl)) | 381 MS(FAB) m/z: 257 ([M + H]⁺) |
| 416 | (thiazole-4-CO₂Et, 2-(N-methyl-N-((1S)-1-methyl-2-methoxyethyl)amino)) | 381 MS(FAB) m/z: 259 ([M + H]⁺) |
| 417 | (thiazole-4-CO₂Et, 2-(N-methyl-N-((1R)-1-methyl-2-methoxyethyl)amino)) | 381 MS(EI) m/z: 258 ([M]⁺) |

TABLE 5-continued

| REx | Str | Syn (Sal) Dat |
|---|---|---|
| 418 | [structure] | 381 MS(FAB) m/z: 255 ([M + H]+) |
| 419 | [structure] | 381 MS(FAB) m/z: 287 ([M + H]+) |
| 420 | [structure] | 349 → 364 → 381 MS(API) m/z: 273 ([M + H]+) |
| 421 | [structure] | 349 → 364 → 381 MS(ESI) m/z: 313 ([M + H]+) |
| 422 | [structure] | 349 → 364 → 381 MS(FAB) m/z: 285 ([M + H]+) |
| 423 | [structure] | 349 → 364 → 381 MS(API) m/z: 261 ([M + H]+) |
| 424 | [structure] | 349 → 364 → 381 NMR: (CDCl3) 0.79-0.92 (4H, m), 1.36 (3H, t, J = 7.1 Hz), 2.69-2.76 (1H, m), 3.33 (3H, s), 3.67 (2H, t, J = 5.3 Hz), 3.83 (2H, t, J = 5.3 Hz), 4.34 (2H, q, J = 7.1 Hz), 7.44 (1H, s) |
| 425 | [structure] | 425 MS(ESI) m/z: 242 ([M + H]+) |
| 426 | [structure] | 308 → 337 → 349 → 364 → 381 MS(ESI) m/z: 325 ([M + H]+) |
| 427 | [structure] | 427 MS(FAB) m/z: 269 ([M + H]+) |
| 428 | [structure] | 428 MS(ESI) m/z: 284 ([M + H]+) |
| 429 | [structure] | 564 MS(ESI) m/z: 342 ([M + H]+) |
| 430 | [structure] | 564 MS(ESI) m/z: 368 ([M + H]+) |
| 431 | [structure] | 431 MS(EI) m/z: 250 ([M]+) |
| 432 | [structure] | 335 MS(ESI) m/z: 231 ([M + H]+) |
| 433 | [structure] | 21 (HCl) MS(ESI) m/z: 132 ([M + H]+) |

TABLE 5-continued

| REx | Str | Syn (Sal) Dat |
|---|---|---|
| 434 | | 21 (HCl) MS(ESI) m/z: 118 ([M + H]+) |
| 435 | | 564 MS(FAB) m/z: 277 ([M + H]+) |
| 436 | | 21 (HCl) MS(FAB) m/z: 177 ([M + H]+) |
| 437 | | 437 MS(FAB) m/z: 235 ([M + H]+) |
| 438 | | 337 MS(FAB) m/z: 207 ([M + H]+) |
| 439 | | 439 MS(FAB) m/z: 307 ([M + H]+) |
| 440 | | 440 MS(FAB) m/z: 321 ([M + H]+) |
| 441 | | 21 (2HCl) MS(FAB) m/z: 221 ([M + H]+) |
| 442 | | 442 MS(FAB) m/z: 231 ([M + H]+) |
| 443 | | 440 MS(ESI) m/z: 216 ([M + H]+) |
| 444 | | 21 (HCl) MS(ESI) m/z: 116 ([M + H]+) |
| 445 | | 335 MS(ESI) m/z: 268 ([M + H]+) |
| 446 | | 442 MS(ESI) m/z: 102 ([M + H]+) |
| 447 | | 336 → 440 MS(ESI) m/z: 244 ([M + Na]+) |
| 448 | | 448 MS(FAB) m/z: 88 ([M + H]+) |
| 449 | | 449 MS(ESI) m/z: 287 ([M + H]+) |
| 450 | | 449 MS(API) m/z: 245 ([M + H]+) |
| 451 | | 449 MS(ESI) m/z: 243 ([M + H]+) |
| 452 | | 449 MS(ESI) m/z: 241 ([M + H]+) |
| 453 | | 449 MS(API) m/z: 271 ([M + H]+) |

TABLE 5-continued

| REx | Str | Syn (Sal) Dat |
|---|---|---|
| 454 | (structure) | 449 MS(EI) m/z: 270 ([M]+) |
| 455 | (structure) | 449 MS(ESI) m/z: 257 ([M + H]+) |
| 456 | (structure) | 456 MS(ESI) m/z: 241 ([M + H]+) |
| 457 | (structure) | 449 MS(ESI) m/z: 225 ([M + H]+) |
| 458 | (structure) | 171 MS(ESI) m/z: 259 ([M + H]+) |
| 459 | (structure) | 8 MS(ESI) m/z: 251 ([M + H]+) |
| 460 | (structure) | 8 MS(ESI) m/z: 275 ([M + H]+) |
| 461 | (structure) | 8 MS(ESI) m/z: 291 ([M + H]+) |
| 462 | (structure) | 8 MS(API) m/z: 277 ([M + H]+) |
| 463 | (structure) | 8 MS(API) m/z: 293 ([M + H]+) |
| 464 | (structure) | 8 MS(FAB) m/z: 290 ([M + H]+) |
| 465 | (structure) | 440 MS(API) m/z: 244 ([M + H]+) |
| 466 | (structure) | 440 MS(ESI) m/z: 244 ([M + H]+) |
| 467 | (structure) | 440 MS(ESI) m/z: 216 ([M + H]+) |
| 468 | (structure) | 440 → 605 MS(API) m/z: 216 ([M + H]+) |
| 469 | (structure) | 440 MS(API) m/z: 258 ([M + H]+) |
| 470 | (structure) | 470 MS(ESI) m/z: 244 ([M + H]+) |
| 471 | (structure) | 442 MS(API) m/z: 216 ([M + H]+) |
| 472 | (structure) | 470 MS(ESI) m/z: 230 ([M + H]+) |
| 473 | (structure) | 470 MS(ESI) m/z: 230 ([M + H]+) |
| 474 | (structure) | 474 MS(FAB) m/z: 259 ([M + H]+) |
| 475 | (structure) | 475 MS(FAB) m/z: 342 ([M + H]+) |

TABLE 5-continued

| REx | Str | Syn (Sal) Dat |
|---|---|---|
| 476 | 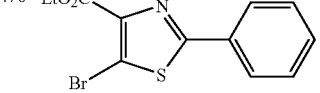 | 476 MS(FAB) m/z: 314 ([M + H]$^+$) |
| 477 | 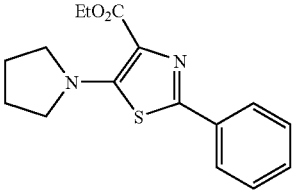 | 477 MS(FAB) m/z: 303 ([M + H]$^+$) |
| 478 | 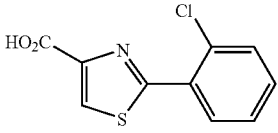 | 605 MS(FAB) m/z: 240 ([M + H]$^+$) |
| 479 | 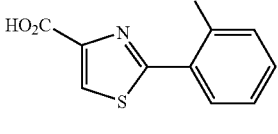 | 605 MS(ESI) m/z: 286 ([M + H]$^+$) |
| 480 | 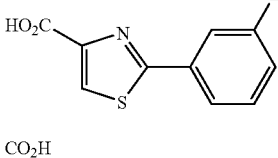 | 605 MS(FAB) m/z: 286 ([M + H]$^+$) |
| 481 | 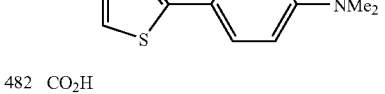 | 605 MS(FAB) m/z: 248 ([M]$^+$) |
| 482 | 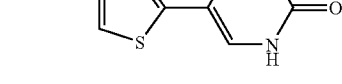 | 605 MS(FAB) m/z: 223 ([M + H]$^+$) |
| 483 | 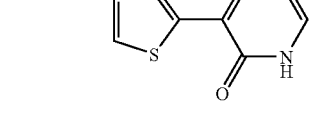 | 605 MS(ESI) m/z: 223 ([M + H]$^+$) |
| 484 | 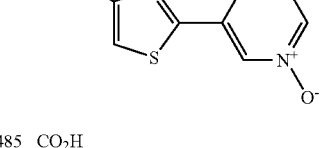 | 605 MS(FAB) m/z: 223 ([M + H]$^+$) |
| 485 | 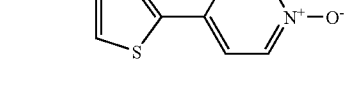 | 605 MS(ESI) m/z: 223 ([M + H]$^+$) |
| 486 | 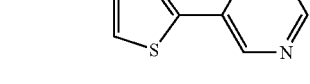 | 605 MS(FAB) m/z: 208 ([M + H]$^+$) |
| 487 | 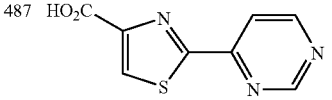 | 605 MS(EI) m/z: 207 ([M]$^+$) |
| 488 | 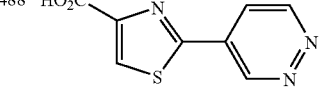 | 605 MS(ESI) m/z: 208 ([M + H]$^+$) |
| 489 | 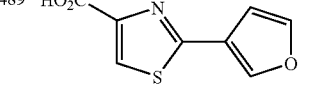 | 605 MS(ESI) m/z: 196 ([M + H]$^+$) |
| 490 | 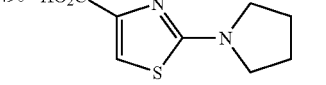 | 605 MS(ESI) m/z: 199 ([M + H]$^+$) |
| 491 | 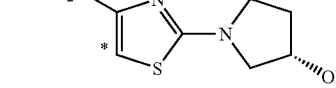 | 605 MS(ESI) m/z: 215 ([M + H]$^+$) |
| 492 | 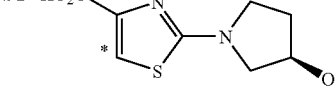 | 605 MS(ESI) m/z: 215 ([M + H]$^+$) |
| 493 | 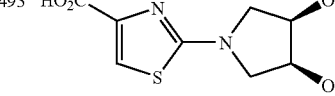 | 605 MS(ESI) m/z: 231 ([M + H]$^+$) |
| 494 | 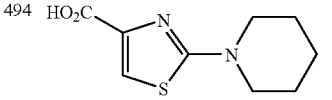 | 605 MS(FAB) m/z: 213 ([M + H]$^+$) |
| 495 | 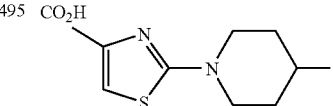 | 605 MS(ESI) m/z: 229 ([M + H]$^+$) |
| 496 | 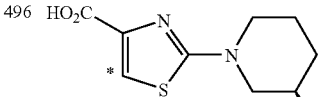 | 605 MS(ESI) m/z: 229 ([M + H]$^+$) |
| 497 | 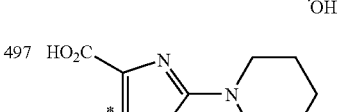 | 605 MS(ESI) m/z: 229 ([M + H]$^+$) |
| 498 |  | 605 MS(ESI) m/z: 259 ([M + H]$^+$) |

TABLE 5-continued

| REx | Str | Syn (Sal) Dat |
|---|---|---|
| 499 | thiazole-4-carboxylic acid, 2-morpholino | 605 MS(ESI) m/z: 215 ([M + H]$^+$) |
| 500 | thiazole-4-carboxylic acid, 2-thiomorpholino | 605 MS(API) m/z: 229 ([M − H]$^-$) |
| 501 | thiazole-4-carboxylic acid, 2-(1-oxidothiomorpholino) | 605 MS(API) m/z: 247 ([M + H]$^+$) |
| 502 | thiazole-4-carboxylic acid, 2-(1,1-dioxidothiomorpholino) | 605 MS(API) m/z: 263 ([M + H]$^+$) |
| 503 | thiazole-4-carboxylic acid, 2-(4-carbamoylpiperidin-1-yl) | 605 MS(ESI) m/z: 256 ([M + H]$^+$) |
| 504 | thiazole-4-carboxylic acid, 2-[4-(3-hydroxypropylcarbamoyl)piperidin-1-yl] | 605 MS(ESI) m/z: 314 ([M + H]$^+$) |
| 505 | thiazole-4-carboxylic acid, 2-[4-((tetrahydrofuran-2-yl)methylcarbamoyl)piperidin-1-yl] | 605 MS(ESI) m/z: 340 ([M + H]$^+$) |
| 506 | thiazole-4-carboxylic acid, 2-(3-oxopiperazin-1-yl) | 605 MS(ESI) m/z: 228 ([M + H]$^+$) |
| 507 | thiazole-4-carboxylic acid, 2-[N-isopropyl-N-(2-methoxyethyl)amino] | 605 MS(API) m/z: 245 ([M + H]$^+$) |
| 508 | thiazole-4-carboxylic acid, 2-[N-cyclobutyl-N-(2-methoxyethyl)amino] | 605 MS(API) m/z: 257 ([M + H]$^+$) |
| 509 | thiazole-4-carboxylic acid, 2-[N-(2,2,2-trifluoroethyl)-N-(2-methoxyethyl)amino] | 605 MS(ESI) m/z: 285 ([M + H]$^+$) |
| 510 | 2-phenyl-5-(pyrrolidin-1-yl)thiazole-4-carboxylic acid | 605 MS(FAB) m/z: 273 ([M − H]$^-$) |
| 511 | 2-(pentan-3-yl)thiazole-4-carboxylic acid | 605 MS(ESI) m/z: 200 ([M + H]$^+$) |
| 512 | 2-heptylthiazole-4-carboxylic acid | 605 MS(API) m/z: 228 ([M + H]$^+$) |
| 513 | 2-(tetrahydro-2H-pyran-4-yl)thiazole-4-carboxylic acid | 605 MS(ESI) m/z: 214 ([M + H]$^+$) |
| 514 | 2-(tetrahydrofuran-3-yl)thiazole-4-carboxylic acid | 605 MS(ESI) m/z: 200 ([M + H]$^+$) |
| 515 | 2-cyclopentylthiazole-4-carboxylic acid | 605 MS(ESI) m/z: 198 ([M + H]$^+$) |
| 516 | 2-(tetrahydro-2H-thiopyran-4-yl)thiazole-4-carboxylic acid | 605 MS(ESI) m/z: 230 ([M + H]$^+$) |
| 517 | 2-(1,1-dioxidotetrahydro-2H-thiopyran-4-yl)thiazole-4-carboxylic acid | 605 MS(FAB) m/z: 262 ([M + H]$^+$) |

TABLE 5-continued

| REx | Str | Syn (Sal) Dat |
|---|---|---|
| 518 | thiazole-CO2H with -(CH2)3OH | 605 MS(API) m/z: 188 ([M + H]+) |
| 519 | thiazole-CO2H with -(CH2)3OMe | 605 MS(ESI) m/z: 202 ([M + H]+) |
| 520 | thiazole-CO2H with -CH(Me)OMe | 605 MS(API) m/z: 188 ([M + H]+) |
| 521 | thiazole-CO2H with -C(Me)2CH2OMe | 605 MS(API) m/z: 216 ([M + H]+) |
| 522 | thiazole-CO2H with -C(Me)2CH2OH | 605 MS(ESI) m/z: 202 ([M + H]+) |
| 523 | thiazole-CO2H with pyridazine-OMe | 605 MS(ESI) m/z: 238 ([M + H]+) |
| 524 | thiazole-CO2H with -CH(Me)CH2CH2OH | 605 MS(ESI) m/z: 200 ([M − H]−) |
| 525 | thiazole-CO2H with -CH2-morpholine | 605 MS(FAB) m/z: 229 ([M + H]+) |
| 526 | thiazole-CO2H with -CH2N(Me)CH2CH2OMe | 605 MS(FAB) m/z: 231 ([M + H]+) |
| 527 | thiazole-CO2H with -C(Me)2CH2CH2OH | 605 MS(ESI) m/z: 214 ([M − H]−) |
| 528 | thiazole-CO2H with morpholine-CH2OMe | 605 MS(ESI) m/z: 259 ([M + H]+) |
| 529 | thiazole-CO2H with morpholine-CH2OH | 605 MS(ESI) m/z: 245 ([M + H]+) |
| 530 | thiazole-CO2H with pyrrolidine (OH, CH2OH) * | 605 MS(ESI) m/z: 245 ([M + H]+) |
| 531 | Boc-piperazine-thiazole-CO2H with CH2OMe * | 605 MS(FAB) m/z: 358 ([M + H]+) |
| 532 | thiazole-CO2H with pyrrolidine-OMe * | 605 MS(ESI) m/z: 229 ([M + H]+) |
| 533 | thiazole-CO2H with piperidine(Me)-N-Boc | 605 MS(ESI) m/z: 325 ([M − H]−) |
| 534 | thiazole-CO2H with -CH2O-C6H4-Br | 605 MS(FAB) m/z: 314 ([M + H]+) |
| 535 | thiazole-CO2H with -CH2-C6H3(Cl)2 | 605 MS(FAB) m/z: 288 ([M + H]+) |

TABLE 5-continued

| REx | Str | Syn (Sal) Dat |
|---|---|---|
| 536 | (thiazole-CO2H)-N-azetidine-OMe | 605 MS(ESI) m/z: 215 ([M + H]+) |
| 537 | (thiazole-CO2H)-N-pyrrolidinone | 605 MS(ESI) m/z: 213 ([M + H]+) |
| 538 | (thiazole-CO2H)-N-pyrrolidine-Me* | 605 MS(ESI) m/z: 213 ([M + H]+) |
| 539 | (thiazole-CO2H)-N-pyrrolidine-F* | 605 MS(ESI) m/z: 217 ([M + H]+) |
| 540 | (thiazole-CO2H)-N-piperidine-OMe | 605 MS(ESI) m/z: 243 ([M + H]+) |
| 541 | (thiazole-CO2H)-N(Me)-tetrahydrofuran | 605 MS(EI) m/z: 228 ([M]+) |
| 542 | (thiazole-CO2H)-N-morpholine-Me* | 605 MS(ESI) m/z: 229 ([M + H]+) |
| 543 | (thiazole-CO2H)-N(Me)-CH(Me)-CH2-OMe* | 605 MS(FAB) m/z: 231 ([M + H]+) |
| 544 | (thiazole-CO2H)-N(Me)-CH(Me)-CH2-OMe* | 605 MS(EI) m/z: 230 ([M]+) |
| 545 | (thiazole-CO2H)-N-piperidine-OMe* | 605 MS(FAB) m/z: 243 ([M + H]+) |
| 546 | (thiazole-CO2H)-N-bicyclic-O* | 605 MS(FAB) m/z: 227 ([M + H]+) |
| 547 | (thiazole-CO2H)-N-morpholine-CH2OMe* | 605 MS(FAB) m/z: 259 ([M + H]+) |
| 548 | (thiazole-CO2H)-N(Me)-CH2CH2-OMe | 381 → 605 (HCl) MS(ESI) m/z: 217 ([M + H]+) |
| 549 | (thiazole-CO2H)-NH-CH2CH2-OMe | 381 → 605 (HBr) MS(ESI) m/z: 203 ([M + H]+) |
| 550 | (thiazole-CO2H)-piperidine-NBoc | 381 → 605 MS(ESI) m/z: 311 ([M − H]−) |
| 551 | (thiazole-CO2H)-C(Me)2-CH2CH2-OMe | 440 → 605 MS(ESI) m/z: 230 ([M + H]+) |
| 552 | (thiazole-CO2H)-N(cyclopropyl)-CH2CH2-OMe | 605 MS(ESI) m/z: 243 ([M + H]+) |
| 553 | (thiazole-CO2H)-N(Me)-CH2-CH(Me)-OMe | 349 → 364 → 381 → 605 (HCl) NMR: (DMSO-d6) 1.08 (3H, d, J = 5.9 Hz), 3.07 (3H, s), 3.24 (3H, s), 3.45 (2H, d, J = 6.0 Hz), 3.64 (1H, dd, J = 5.9, 6.0 Hz), 7.53 (1H, s), 11.77 (1H, brs) |

TABLE 5-continued

| REx | Str | Syn (Sal) Dat |
|---|---|---|
| 554 | [thiazole-CO2H with N-piperidine-OAc] | 554 MS(FAB) m/z: 271 ([M + H]+) |
| 555 | [thiazole-CO2H with N-piperidine-CO2Et] | 555 MS(FAB) m/z: 285 ([M + H]+) |
| 556 | H2N-C(O)-N(Me)-CH2CH2-OMe | 556 MS(ESI) m/z: 133 ([M + H]+) |
| 557 | H2N-C(O)-N-piperidine-OEt | 556 MS(ESI) m/z: 173 ([M + H]+) |
| 558 | [oxazole-CO2Et with N(Me)CH2CH2OMe] | 558 MS(ESI) m/z: 229 ([M + H]+) |
| 559 | [oxazole-CO2Et with N-piperidine-OH] | 558 MS(ESI) m/z: 241 ([M + H]+) |
| 560 | [oxazole-EtO2C with N-piperidine] | 558 MS(ESI) m/z: 225 ([M + H]+) |
| 561 | [oxazole-CO2Et with N-piperidine-OEt] | 558 MS(ESI) m/z: 270 ([M + H]+) |
| 562 | [oxazole-CO2Et with tetrahydropyran] | 558 MS(ESI) m/z: 226 ([M + H]+) |
| 563 | TBSO-cyclohexane-CO2H | 605 MS(ESI) m/z: 257 ([M − H]−) |
| 564 | BocHN-pyridine-C(O)NH-CH(CH2OH)-CO2Me | 564 MS(FAB) m/z: 340 ([M + H]+) |
| 565 | MeO-pyridine-C(O)NH-CH(CH2OH)-CO2Me | 564 MS(ESI) m/z: 255 ([M + H]+) |
| 566 | HO-CH2-CH(CO2Me)-NH-C(O)-pyridazine | 566 MS(ESI) m/z: 226 ([M + H]+) |
| 567 | HO-CH2-CH(CO2Me)-NH-C(O)-pyrimidine | 566 MS(ESI) m/z: 226 ([M + H]+) |
| 568 | HO-CH2-CH(CO2Me)-NH-C(O)-(2-Cl-pyridine) | 566 MS(FAB) m/z: 259 ([M + H]+) |
| 569 | TBSO-cyclohexane-C(O)NH-CH(CH2OH)-CO2Me | 564 MS(ESI) m/z: 360 ([M + H]+) |
| 570 | TBSO-cyclohexane-C(O)NH-CH(CH2OH)-CO2Me | 564 MS(ESI) m/z: 360 ([M + H]+) |
| 571 | N-Boc-pyrrolidine-C(O)NH-CH(CH2OH)-CO2Me | 564 MS(FAB) m/z: 317 ([M + H]+) |
| 572 | N-Boc-morpholine-C(O)NH-CH(CH2OH)-CO2Me | 564 MS(ESI) m/z: 333 ([M + H]+) |

TABLE 5-continued

| REx | Str | Syn (Sal) Dat |
|---|---|---|
| 573 | [structure: TBS-O-cyclohexyl-C(O)-NH-CH(CO2Me)-CH2OH] | 564 MS(ESI) m/z: 360 ([M + H]+) |
| 574 | [structure: *-C(O)-CH2-O-(2-Br-phenyl), amide with serine methyl ester] | 564 MS(FAB) m/z: 332 ([M + H]+) |
| 575 | [structure: MeO-CH2-C(O)-NH-CH(CO2Me)-CH2OH] | 564 MS(FAB) m/z: 192 ([M + H]+) |
| 576 | [structure: Me2CH-O-CH2-C(O)-NH-CH(CO2Me)-CH2OH, with *] | 564 MS(FAB) m/z: 220 ([M + H]+) |
| 577 | [structure: 4-CO2Me-oxazole-2-yl-pyridine-NHBoc] | 577 MS(FAB) m/z: 320 ([M + H]+) |
| 578 | [structure: MeO2C-oxazole-pyridine-Cl] | 577 MS(EI) m/z: 238 ([M]+) |
| 579 | [structure: MeO2C-oxazole-4-pyridyl] | 577 MS(FAB) m/z: 205 ([M + H]+) |
| 580 | [structure: MeO2C-oxazole-pyridazinyl] | 577 MS(FAB) m/z: 206 ([M + H]+) |
| 581 | [structure: MeO2C-oxazole-pyrimidinyl] | 577 MS(ESI) m/z: 206 ([M + H]+) |
| 582 | [structure: CO2Me-oxazole-pyridine-OMe] | 577 MS(FAB) m/z: 235 ([M + H]+) |
| 583 | [structure: CO2Me-oxazole-morpholine-Boc] | 577 MS(FAB) m/z: 313 ([M + H]+) |
| 584 | [structure: TBS-O-cyclohexyl-oxazole-CO2Me] | 577 MS(ESI) m/z: 340 ([M + H]+) |
| 585 | [structure: TBS-O-cyclohexyl-oxazole-CO2Me] | 577 MS(ESI) m/z: 340 ([M + H]+) |
| 586 | [structure: TBS-O-cyclohexyl-oxazole-CO2Me] | 577 MS(ESI) m/z: 340 ([M + H]+) |
| 587 | [structure: N-Boc-pyrrolidinyl-oxazole-CO2Me, with *] | 577 MS(ESI) m/z: 297 ([M + H]+) |
| 588 | [structure: 2-Br-phenyl-O-CH2-oxazole-CO2Me] | 577 MS(FAB) m/z: 311 ([M + H]+) |
| 589 | [structure: Me2CH-O-CH2-oxazole-CO2Me] | 577 MS(CI) m/z: 200 ([M + H]+) |
| 590 | [structure: MeO-CH2-oxazole-CO2Me] | 577 MS(FAB) m/z: 172 ([M + H]+) |
| 591 | [structure: *-CO2Me-oxazole-pyrrolidinyl] | 21 MS(ESI) m/z: 197 ([M + H]+) |

TABLE 5-continued

| REx | Str | Syn (Sal) Dat |
|---|---|---|
| 592 | (structure) | 592 MS(ESI) m/z: 239 ([M + H]$^+$) |
| 593 | (structure) | 593 MS(ESI) m/z: 226 ([M + H]$^+$) |
| 594 | (structure) | 593 MS(ESI) m/z: 226 ([M + H]$^+$) |
| 595 | (structure) | 593 MS(ESI) m/z: 226 ([M + H]$^+$) |
| 596 | (structure) | 596 MS(ESI) m/z: 208 ([M + H]$^+$) |
| 597 | (structure) | 596 MS(ESI) m/z: 224 ([M + H]$^+$) |
| 598 | (structure) | 596 MS(ESI) m/z: 208 ([M + H]$^+$) |
| 599 | (structure) | 596 MS(ESI) m/z: 307 ([M + H]$^+$) |
| 600 | (structure) | 600 MS(API) m/z: 301 ([M + H]$^+$) |
| 601 | (structure) | 601 MS(FAB) m/z: 185 ([M + H]$^+$) |
| 602 | (structure) | 602 MS(EI) m/z: 166 ([M]$^+$) |
| 603 | (structure) | 603 MS(FAB) m/z: 273 ([M + H]$^+$) |
| 604 | (structure) | 604 MS(FAB) m/z: 220 ([M + H]$^+$) |
| 605 | (structure) | 605 MS(ESI) m/z: 197 ([M − H]$^-$) |
| 606 | (structure) | 605 MS(ESI) m/z: 213 ([M + H]$^+$) |
| 607 | (structure) | 605 MS(ESI) m/z: 197 ([M + H]$^+$) |
| 608 | (structure) | 605 MS(ESI) m/z: 201 ([M + H]$^+$) |
| 609 | (structure) | 605 MS(ESI) m/z: 191 ([M + H]$^+$) |
| 610 | (structure) | 605 MS(ESI) m/z: 192 ([M + H]$^+$) |
| 611 | (structure) | 605 MS(ESI) m/z: 192 ([M + H]$^+$) |
| 612 | (structure) | 605 MS(FAB) m/z: 223 ([M − H]$^-$) |
| 613 | (structure) | 605 MS(FAB) m/z: 304 ([M − H]$^-$) |

TABLE 5-continued

| REx | Str | Syn (Sal) Dat |
|---|---|---|
| 614 | HO₂C-oxazole-furan | 605 MS(ESI) m/z: 180 ([M + H]⁺) |
| 615 | HO₂C-oxazole-thiophene | 605 MS(ESI) m/z: 196 ([M + H]⁺) |
| 616 | HO₂C-oxazole-furan | 605 MS(FAB) m/z: 180 ([M + H]⁺) |
| 617 | CO₂H-oxazole-cyclohexyl-OH | 605 MS(ESI) m/z: 212 ([M + H]⁺) |
| 618 | CO₂H-oxazole-tetrahydropyran | 605 MS(ESI) m/z: 198 ([M + H]⁺) |
| 619 | CO₂H-oxazole-cyclohexyl-OH | 605 MS(ESI) m/z: 210 ([M − H]⁻) |
| 620 | CO₂H-oxazole-thiophene | 605 MS(FAB) m/z: 196 ([M + H]⁺) |
| 621 | CO₂H-oxazole-morpholine-Boc | 605 MS(ESI) m/z: 297 ([M − H]⁻) |
| 622 | CO₂H-oxazole-pyrrolidine-benzyl | 605 MS(ESI) m/z: 273 ([M + H]⁺) |
| 623 | CO₂H-oxazole-cyclohexyl-OH | 605 MS(ESI) m/z: 210 ([M − H]⁻) |
| 624 | CO₂H-oxazole-CH₂-O-phenyl-Br | 605 MS(FAB) m/z: 298 ([M + H]⁺) |
| 625 | CO₂H-oxazole-CH₂-O-CH(Me)₂ | 605 MS(FAB) m/z: 186 ([M + H]⁺) |
| 626 | CO₂H-oxazole-CH₂-O-Me | 605 MS(FAB) m/z: 158 ([M + H]⁺) |
| 627 | Na⁺ salt, oxazole-piperidine-O-Et | 605 (Na) MS(ESI) m/z: 241 ([M + H]⁺) |
| 628 | CO₂H-oxazole-pyrrolidine-C(O)Me | 605 MS(ESI) m/z: 223 ([M − H]⁻) |
| 629 | HO₂C-oxazole-pyridinone | 629 MS(ESI) m/z: 207 ([M + H]⁺) |

Hereinafter, the representative preparation methods are described with reference to Examples. Example 1 to Example 1202 as described in Tables 6 to 68 can be prepared in the same manner as any one of the following representative preparation methods of Examples, and Example No. corresponding to each is shown as Syn of Tables.

Example 17

To a solution of 950 mg of N-[2-(aminocarbonyl)-6-(4-methylpiperazin-1-yl)phenyl]-2-phenyl-1,3-thiazole-4-carboxamide in 10.0 ml of acetic acid was added 10.0 ml of concentrated sulfuric acid. A solution of 310 mg sodium nitrite in 3.00 ml of water was added thereto under ice-cooling, followed by stirring at room temperature for 5 hours. To the reaction liquid was added water, followed by extraction with chloroform. The organic layer was dried over magnesium sulfate, a solvent was evaporated under reduced pressure, and the residue was purified by silica gel column chromatography (chloroform:methanol=95:5) to prepare 123 mg of 3-(4-methylpiperazin-1-yl)-2-{[(2-phenyl-1,3-thiazol-4-yl)carbonyl]amino}benzoic acid.

Example 28

300 mg of 2-phenyl-N-(2-piperazin-1-ylphenyl)-1,3-thiazole-4-carboxamide and 200 μl of pyridine were dissolved in 10 ml of dichloroethane, and 180 μl of acetylchloride was added dropwise thereto at room temperature, followed by stirring for one day. To the reaction liquid was added an aqueous sodium hydrogen carbonate solution, followed by extraction with chloroform, and drying over magnesium sulfate. A solvent was evaporated under reduced pressure, and the residue was purified by silica gel column chromatography (chloroform:methanol=100:1) to prepare 230 mg of N-[2-(4-acetylpiperazin-1-yl)phenyl]-2-phenyl-1,3-thiazole-4-carboxamide.

Example 29

300 mg of 2-phenyl-N-(2-piperazin-1-ylphenyl)-1,3-thiazole-4-carboxamide and 600 µl of pyridine were dissolved in 10 ml of dichloroethane, and 708 µl of ethyl chloroformate was added dropwise thereto at room temperature, followed by stirring at room temperature for one day. To the reaction liquid was added an aqueous sodium hydrogen carbonate solution, followed by extraction with chloroform, and drying over magnesium sulfate. A solvent was evaporated under reduced pressure, and the residue was purified by silica gel column chromatography (chloroform:methanol=100:1) to prepare 213 mg of 4-(2-{[(2-phenyl-1,3-thiazol-4-yl) carbonyl]amino}phenyl)-1-piperazinecarboxylic acid ethyl ester.

Example 31

300 mg of 2-phenyl-N-(2-piperazin-1-ylphenyl)-1,3-thiazole-4-carboxamide, and 600 µl of pyridine were dissolved in 10 ml of dichloroethane, and 570 µl of methanesulfonyl chloride was added dropwise thereto at room temperature, followed by stirring at room temperature for one day. To the reaction liquid was added an aqueous sodium hydrogen carbonate solution, followed by extraction with chloroform and drying over magnesium sulfate. A solvent was evaporated under reduced pressure, and the residue was purified by silica gel column chromatography (chloroform:methanol=100:1) to prepare 315 mg of N-{2-[4-(methanesulfonyl)piperazin-1-yl]phenyl}-2-phenyl-1,3-thiazole-4-carboxamide.

Example 36

2.18 g of 1-(2-{[(2-phenyl-1,3-thiazol-4-yl)carbonyl]amino}phenyl)piperidine-4-carboxylic acid ethyl ester was dissolved in 100 ml of methanol, 20 ml of a 1M aqueous sodium hydroxide solution was added dropwise thereto at room temperature, followed by stirring at 50° C. for 3 hours. To the reaction liquid was added dropwise 20 ml of a 1M aqueous hydrochloric acid solution, followed by extraction with chloroform and drying over magnesium sulfate. A solvent was evaporated under reduced pressure to prepare 1.82 g of 1-(2-{[(2-phenyl-1,3-thiazol-4-yl)carbonyl]amino}phenyl)piperidine-4-carboxylic acid.

Example 63

To a suspension of 300 mg of 1-(4-(2-amino-2-oxoethyl)-2-{(2-phenyl-1,3-thiazol-4-yl)carbonyl]amino}phenyl)piperidine-4-carboxamide in 6.00 ml of THF was added 200 mg of triethylamine, and 500 µl of trifluoroacetic anhydride was added thereto at 0° C., followed by stirring at room temperature for 3 days. The reaction liquid was adsorbed on silica gel, followed by purification using column chromatography (chloroform:methanol=95:5) to prepare 239 mg of N-[5-(cyanomethyl)-2-(4-cyanopiperidin-1-yl)phenyl]-2-phenyl-1,3-thiazole-4-carboxamide.

Example 68

To a solution of 500 mg of 1-(2-aminophenyl)pyrrolidine-3-carboxylic acid methyl ester in 20 ml of DMF were added 562 mg of 2-phenyl-1,3-thiazole-4-carboxylic acid, 653 mg of WSC-HCl, and 460 mg of HOBt at room temperature, followed by stirring for 8 hours. To the reaction liquid was added a saturated aqueous sodium hydrogen carbonate solution, followed by extraction with chloroform, drying over sodium sulfate, and filtration. A solvent was evaporated under reduced pressure, and the residue was purified by silica gel column chromatography (hexane:EtOAc=4:1) to prepare 1.169 g of 1-(2-{[(2-phenyl-1,3-thiazol-4-yl) carbonyl]amino}phenyl)pyrrolidine-3-carboxylic acid methyl ester.

Subsequently, 969 mg of this product was dissolved in 30 ml of methanol and 10 ml of THF, and 4.76 ml of a 1 M aqueous sodium hydroxide solution was added dropwise thereto at room temperature, followed by stirring at 50° C. for one day. To the reaction liquid was added dropwise 4.76 ml of a 1 M aqueous hydrochloric acid solution, followed by extraction with chloroform and drying over magnesium sulfate. A solvent was evaporated under reduced pressure to prepare 708 mg of 1-(2-{[(2-phenyl-1,3-thiazol-4-yl)carbonyl]amino}phenyl)-3-pyrrolidinecarboxylic acid.

Example 76

To a solution of 700 mg of 2-phenyl-N-[2-(4-thiomorpholinyl)phenyl]-1,3-thiazole-4-carboxamide in 40 ml of chloroform was added 301 mg of m-chloroperbenzoic acid, followed by stirring at room temperature for 4 hours. To the reaction liquid was added a saturated aqueous sodium hydrogen carbonate solution, followed by extraction with chloroform, and the organic layer was washed with saturated brine, dried over sodium sulfate, and then filtered. A solvent was evaporated under reduced pressure, and the residue was purified by silica gel column chromatography (chloroform), and crystallized from 9 ml of ethanol to prepare 457 mg of N-[2-(1-oxide-4-thiomorpholinyl)phenyl]-2-phenyl-1,3-thiazole-4-carboxamide.

Examples 77 and 78

To a solution of 300 mg of N-[2-(1-oxide-4-thiomorpholinyl)phenyl]-2-phenyl-1,3-thiazole-4-carboxamide in 20 ml of chloroform was added 124 mg of m-chloroperbenzoic acid, followed by stirring at room temperature for 29 hours. To the reaction liquid was added a saturated aqueous sodium hydrogen carbonate solution, followed by extraction with chloroform, and the organic layer was washed with saturated brine, dried over sodium sulfate, and then filtered. A solvent was evaporated under reduced pressure, and the residue was purified by silica gel column chromatography (chloroform: methanol=10:1) to prepare 104 mg of N-[2-(1,1-dioxide-4-thiomorpholinyl)phenyl]-2-phenyl-1,3-thiazole-4-carboxamide (Example 77) and 56 mg of N-[2-(1,4-dioxide-4-thiomorpholinyl)phenyl]-2-phenyl-1,3-thiazole-4-carboxamide (Example 78).

Example 85

To a suspension of 200 mg of 2-phenyl-N-[2-(4-piperidinyl)phenyl]-1,3-thiazole-4-carboxamide hydrochloride in 9 ml of DMF-3 ml of ethanol were added 280 mg of potassium carbonate and 108 µl of (2-bromoethoxy)-tert-butyldimethylsilane, followed by stirring at room temperature for 24 hours. To the reaction liquid was added 100 ml of water, followed by extraction with chloroform, and the organic layer was washed with saturated brine, dried over sodium sulfate, and then filtered. A solvent was evaporated under reduced pressure, and the residue was purified by silica gel column chromatography (chloroform:methanol=40:1) to prepare 118 mg of N-{2-[1-(2-{[tert-butyl(dimethyl)silyl]oxy}ethyl)-4-piperidinyl]phenyl}-2-phenyl-1,3-thiazole-4-carboxamide.

This was suspended in 2 ml of ethanol, and 0.2 ml of a 37% aqueous hydrochloric acid solution was added thereto, followed by stirring at room temperature for 35 min. A solvent was evaporated under reduced pressure, followed by washing with diethyl ether to prepare 49 mg of N-{2-[1-(2-hydroxyethyl)-4-piperidinyl]phenyl}-2-phenyl-1,3-thiazole-4-carboxamide hydrochloride.

Example 94

A solution of 2.19 g of (2E)-3-(2-{[(2-phenyl-1,3-thiazol-4-yl) carbonyl]amino}phenyl)acrylic acid methyl ester and 1.57 g of N-benzyl-1-methoxy-N-[(trimethylsilyl)methyl] methaneamine in 40.0 ml of toluene was warmed to 50° C. To this was added portionwise and dropwise a solution of 46.3 µl of trifluoroacetic acid in 10.0 ml of toluene, followed by stirring at the same temperature for 18 hours. The reaction liquid was concentrated, and the residue was purified by silica gel column chromatography (chloroform:methanol=97:3). This was dissolved in ethanol, a 4 M hydrogen chloride/ethyl acetate solution was added thereto, and a solvent was evaporated under reduced pressure to prepare 2.35 g of trans-1-benzyl-4-(2-{[(2-phenyl-1,3-thiazol-4-yl)carbonyl]amino}phenyl)pyrrolidine-3-carboxylic acid methyl ester hydrochloride.

Example 95

To 2.35 g of trans-1-benzyl-4-(2-{[(2-phenyl-1,3-thiazol-4-yl)carbonyl]amino}phenyl)pyrrolidine-3-carboxylic acid methyl ester hydrochloride was added a saturated aqueous sodium hydrogen carbonate solution, followed by extraction with chloroform. The organic layer was dried over magnesium sulfate, and a solvent was evaporated under reduced pressure. The residue was dissolved in dichloroethane, 542 mg of 1-chloroethylchlorocarbonate was added thereto, followed by heating under reflux for 1 hour, and then the reaction liquid was evaporated under reduced pressure. Thereafter, to the residue was added methanol, followed by heating under reflux for 3 hours. The reaction liquid was concentrated, and the residue was purified by silica gel column chromatography (chloroform:methanol=92:8) to prepare 123 mg of trans-4-(2-{[(2-phenyl-1,3-thiazol-4-yl)carbonyl]amino}phenyl)pyrrolidine-3-carboxylic acid methyl ester.

Example 99

To a suspension of 170 mg of 2-phenyl-N-[2-(1,2,3,6-tetrahydro-4-pyridinyl)phenyl]-1,3-thiazole-4-carboxamide hydrochloride in 7 ml of THF was added 0.30 ml of Et3N, and then 170 µl of trimethylsilylisocyanate was added thereto under ice-cooling, followed by stirring at room temperature for 8 days. To the reaction liquid was added 100 ml of water, followed by extraction with EtOAc, and the organic layer was washed with saturated brine, dried over sodium sulfate, and then filtered. A solvent was evaporated under reduced pressure, and the residue was washed with 10 ml of chloroform to prepare 172 mg of 4-(2-{[(2-phenyl-1,3-thiazol-4-yl)carbonyl]amino}phenyl)-3,6-dihydro-1(2H)-pyridinecarboxamide.

Example 100

To a suspension of 170 mg of 2-phenyl-N-[2-(1,2,3,6-tetrahydro-4-pyridinyl)phenyl]-1,3-thiazole-4-carboxamide hydrochloride in 7 ml of THF was added 0.30 ml of triethylamine, and 60 µl of 4-morpholinecarbonylchloride was added thereto under ice-cooling, followed by stirring at room temperature for 2 hours. To the reaction liquid was added 100 ml of water, followed by extraction with EtOAc, and the organic layer was washed with saturated brine, dried over sodium sulfate, and then filtered. A solvent was evaporated under reduced pressure, and the residue was recrystallized from 5 ml of ethanol to obtain 165 mg of N-{2-[1-(4-morpholinylcarbonyl)-1,2,3,6-tetrahydro-4-pyridinyl]phenyl}-2-phenyl-1,3-thiazole-4-carboxamide.

Example 119

To a solution of 414 mg of 2-(4-pyridinyl)-1,3-thiazole-4-carboxylic acid ethyl ester in 10 ml of methanol was added 2 ml of a 4 M aqueous lithium hydroxide solution, followed by stirring at room temperature for 2 hours, and then to the reaction liquid was added a 1 M aqueous hydrochloric acid solution, followed by acidification of the system. A solvent was evaporated under reduced pressure, to the residue was added 20 ml of thionyl chloride, followed by stirring overnight at 80° C., the reaction liquid was evaporated under reduced pressure, the residue was suspended in 10 ml of dichloromethane, and 329 mg of 1-(2-aminophenyl)-4-piperidinecarboxamide and 1.25 ml of triethylamine were added thereto, followed by stirring overnight at room temperature. To the reaction liquid were added a saturated aqueous sodium hydrogen carbonate solution and chloroform, the insolubles was collected by filtration, and suspended in chloroform-methanol, and then the insolubles were removed by filtration. To the obtained solution was added a 4 M hydrogen chloride/EtOAc solution, followed by evaporation under reduced pressure, and then the residue was crystallized from diethyl ether to obtain 320 mg of 1-[2-({[2-(4-pyridinyl)-1,3-thiazol-4-yl]carbonyl}amino)phenyl]-4-piperidinecarboxamide hydrochloride.

Example 130

To 125 mg of N-{2-[4-(2-amino-2-oxoethyl)piperazin-1-yl]phenyl}-2-(6-methoxypyridin-3-yl)-1,3-thiazole-4-carboxamide was added dropwise 3.00 ml of a 48% hydrogen bromide solution, followed by stirring at room temperature for 25 min. The reaction liquid was concentrated under reduced pressure, and the obtained residue was washed with ethanol to prepare 123 mg of N-{2-[4-(2-amino-2-oxoethyl) piperazin-1-yl]phenyl}-2-(6-oxo-1,6-dihydropyridin-3-yl)-1,3-thiazole-4-carboxamide hydrobromide.

Example 142

To 360 mg of 2-(6-hydroxy-3-pyridinyl)-1,3-thiazole-4-carboxylic acid was added 8.0 ml of phosphorus oxychloride, followed by stirring at 90° C. for 8 hours. A solvent was evaporated under reduced pressure, then the residue was suspended in 5 ml of pyridine, and 355 mg of 1-(2-aminophenyl)-4-piperidinecarboxamide was added thereto, followed by stirring overnight at room temperature. To the reaction liquid was added a saturated aqueous sodium hydrogen carbonate solution, followed by extraction with EtOAc, and then the organic layer was washed a 1 M aqueous hydrochloric acid solution. A solvent was evaporated under reduced pressure, and the residue was purified by silica gel column chromatography (hexane:EtOAc=1:0 to 1:1) to prepare 79 mg of 2-(6-chloro-3-pyridinyl)-N-[2-(4-cyano-1-piperidinyl)phenyl]-1,3-thiazole-4-carboxamide.

Example 146

To 17.1 g of 4-(2-{[(2-morpholin-4-yl-1,3-thiazol-4-yl)carbonyl]amino}phenyl)piperazine-1-carboxylic acid tert-butyl ester was added 100 ml of a 4 M hydrogen chloride/dioxane, followed by stirring at room temperature for 4 hours. The reaction liquid was concentrated, and recrystallized from methanol to prepare 8.33 g of 2-morpholin-4-yl-N-(2-piperazin-1-ylphenyl)-1,3-thiazole-4-carboxamide hydrochloride.

Example 167

To a solution of 105 mg of morpholine in 4.00 ml of DMF were added 500 mg of sodium [4-(2-{[(2-morpholin-4-yl-1,3-thiazol-4-yl)carbonyl]amino}phenyl)piperazin-1-yl]acetate, 275 mg of WSC-HCl, 194 mg of HOBt at room temperature, followed by stirring for 6 hours. To the reaction liquid was added water, the insolubles were collected by filtration, and dissolved in ethanol, a 4 M hydrogen chloride/EtOAc solution was added thereto, and a solvent was evaporated under reduced pressure to prepare 564 mg of 2-morpholin-4-yl-N-[2-{4-(2-morpholin-4-yl-2-oxoethyl)piperazin-1-yl]phenyl}-1,3-thiazole-4-carboxamide hydrochloride.

Example 169

To a mixed solution of 400 mg of N-(2-{4-[2-(2,5-dihydro-1H-pyrrol-1-yl)-2-oxoethyl]piperazin-1-yl}phenyl)-2-morpholin-4-yl-1,3-thiazole-4-carboxamide in 4.00 ml of THF and 1.00 ml of water was added 120 mg of 4-methylmorpholine-4-oxide and 1.00 ml of a 0.08 M solution of osmium tetroxide in tert-butanol, followed by stirring at room temperature for 24 hours. A saturated aqueous sodium thiosulfate solution was added thereto, followed by extraction with EtOAc, and the organic layer was washed with saturated brine, and then dried over magnesium sulfate. A solvent was evaporated under reduced pressure, and the residue was purified by silica gel column chromatography (chloroform:methanol=95:5). This was dissolved in ethanol, a 4 M hydrogen chloride/EtOAc solution was added thereto, and then a solvent was evaporated under reduced pressure to prepare 51.0 mg of N-(2-{4-[2-(cis-3,4-dihydroxypyrrolidin-1-yl)-2-oxoethyl]piperazin-1-yl}phenyl)-2-morpholin-4-yl-1,3-thiazole-4-carboxamide hydrochloride.

Example 185

To a solution of 300 mg of 2-morpholin-4-yl-N-(2-piperazin-1-ylphenyl)-1,3-thiazole-4-carboxamide hydrochloride in 15.0 ml of DMF were added 350 mg of potassium carbonate and 95.0 mg of 3-(chloromethyl)-1,2,4-oxadiazole, followed by stirring at room temperature for 18 hours. The reaction liquid was concentrated, and a saturated aqueous sodium hydrogen carbonate solution was added thereto, followed by extraction with chloroform. The organic layer was dried over magnesium sulfate, a solvent was evaporated under reduced pressure, and the residue was purified by silica gel column chromatography (chloroform:methanol=96:4). This was dissolved in ethanol, a 4 M hydrogen chloride/EtOAc solution was added thereto, and a solvent was evaporated under reduced pressure to prepare 62.0 mg of 2-morpholin-4-yl-N-[2-{4-(1,2,4-oxadiazol-3-ylmethyl)-2-piperazin-1-yl]phenyl}-1,3-thiazole-4-carboxamide hydrochloride.

Example 191

To a suspension of 600 mg of 2-morpholin-4-yl-N-(2-piperazin-1-ylphenyl)-1,3-thiazole-4-carboxamide hydrochloride in 10.0 ml of acetonitrile were added 25.0 µl of acetic acid, 293 mg of tetrahydro-4H-pyran-4-one, and 1.55 g of sodium triacetoxyborohydride, followed by stirring at room temperature for 7 days. To the reaction liquid was added a saturated aqueous sodium hydrogen carbonate solution, and the resulting insolubles were collected by filtration, and washed with acetonitrile. This was dissolved in ethanol, a 4 M hydrogen chloride/EtOAc solution was added thereto, and then a solvent was evaporated under reduced pressure to prepare 224 mg of 2-morpholin-4-yl-N-{2-[4-(tetrahydro-2H-pyran-4-yl)piperazin-1-yl]phenyl}-1,3-thiazole-4-carboxamide hydrochloride.

Example 192

To a solution of 300 mg of 2-morpholin-4-yl-N-(2-piperazin-1-ylphenyl)-1,3-thiazole-4-carboxamide hydrochloride in 10.0 ml of dioxane were added 300 µl of triethylamine and 315 mg of 3,6-dioxabicyclo[3.1.0]hexane, followed by heating under reflux for 3 days. The reaction liquid was concentrated, and the residue was purified by silica gel column chromatography (chloroform:methanol=96:4). This was dissolved in ethanol, a 4 M hydrogen chloride/EtOAc solution was added thereto, and then a solvent was evaporated under reduced pressure to prepare 38.0 mg of N-{2-[4-(trans-4-hydroxytetrahydrofuran-3-yl)piperazin-1-yl]phenyl}-2-morpholin-4-yl-1,3-thiazole-4-carboxamide hydrochloride.

Example 206

To a suspension of 204 mg of N-{2-[4-(2-amino-2-oxoethyl)piperazin-1-yl]-4-bromophenyl}-2-morpholin-4-yl-1,3-thiazole-4-carboxamide and 47.0 mg of zinc cyanide in 2.00 ml of DMF was added 13.8 mg of tetrakistriphenylphosphine palladium, followed by radiation with microwave and stirring at 190° C. for 30 min, and then at 200° C. for 90 min. After cooling to room temperature, EtOAc and a 28% aqueous ammonia solution were added thereto, and the insolubles was filtered through celite. The organic layer was separated and dried over magnesium sulfate, a solvent was evaporated under reduced pressure, and the residue was purified by silica gel column chromatography (chloroform:methanol=96:4). This was dissolved in ethanol, a 4 M hydrogen chloride/EtOAc solution was added thereto, and then a solvent was evaporated under reduced pressure to prepare 108 mg of N-{2-[4-(2-amino-2-oxoethyl)piperazin-1-yl]-4-cyanophenyl}-2-morpholin-4-yl-1,3-thiazole-4-carboxamide hydrochloride.

Example 234

455 mg of 2-(morpholin-4-yl)-1,3-thiazole-4-carboxylic acid and a catalytic amount of 16 µl of DMF were dissolved in 20 ml of dichloroethane, and 740 µl of oxalylchloride was added dropwise thereto, followed by stirring at room temperature for 30 min. A solvent was evaporated under reduced pressure, and the residue was added dropwise to a solution of 316 mg of 1-(3-aminopyridin-2-yl)-4-(hydroxymethyl)-4-piperidinol and 789 µl of triethylamine in 20 ml of tetrahydrofuran, followed by stirring at room temperature for 15 min. To the reaction liquid was added an aqueous sodium hydrogen carbonate solution, followed by extraction with chloroform and drying over magnesium sulfate. A solvent was evaporated under reduced pressure, and the residue was purified by silica gel column chromatography (chloroform:methanol=50:1 to 10:1). This was suspended in EtOAc, a 4 M hydrogen chloride/EtOAc solution was added thereto, and then a solvent was evaporated under reduced pressure to prepare 555 mg of N-{2-[4-hydroxy-4-(hydroxymethyl)piperidin-1-yl]pyridin-3-yl}-2-(morpholin-4-yl)-1,3-thiazole-4-carboxamide hydrochloride.

Example 266

To a solution of 220 mg of 1-(4-fluoro-2-{[(2-morpholin-4-yl-1,3-thiazol-4-yl)carbonyl]amino}phenyl)piperidine-4-carboxylic acid and 59 mg of methanesulfonamide in 8 ml of DMF were added 120 mg of WSC-HCl and 13 mg of 4-dimethylaminopyridine, followed by stirring at room temperature for 17 hours.
To the reaction liquid was added water, followed by extraction with EtOAc, and the organic layer was washed with a 10% citric acid solution and then with saturated brine, and dried over sodium sulfate. A solvent was evaporated under reduced pressure, and the residue was purified by silica gel column chromatography (chloroform:methanol=100:1). This was recrystallized from 15 ml of methanol to obtain 68 mg of 1-(4-fluoro-2-{[(2-morpholin-4-yl-1,3-thiazol-4-yl)carbonyl]amino}phenyl)-N-(methylsulfonyl)piperidine-4-carboxamide.

Example 267

To a solution of 247 mg of 1-(6-fluoro-3-{[(2-morpholin-4-yl-1,3-thiazol-4-yl)carbonyl]amino}pyridin-2-yl)-4-hydroxypiperidine-4-carboxylic acid in 8.50 ml of THF was added 500 mg of CDI, followed by stirring at room temperature for 12 hours, and then at 60° C. for 3 hours. Thereafter, a solution of 165 mg of sodium borohydride in 3.40 ml of water was added dropwise thereto under ice-cooling, followed by stirring at room temperature for 4 hours. The reaction liquid was concentrated, and to the residue was added water, followed by extraction with EtOAc. The organic layer was dried over magnesium sulfate, a solvent was evaporated under reduced pressure, and the residue was recrystallized from ethanol to prepare 132 mg of N-{6-fluoro-2-[4-hydroxy-4-(hydroxymethyl)piperidin-1-yl]pyridin-3-yl}-2-morpholin-4-yl-1,3-thiazole-4-carboxamide.

Example 281

To a solution of 195 mg of 1-(5-bromo-3-{[(2-morpholin-4-yl-1,3-thiazol-4-yl)carbonyl]amino}pyridin-2-yl)piperidine-4-carboxamide in 1.95 ml of DMF were added 33.0 mg of sodium acetate, 50 µl of acrylonitrile, 9.0 mg of tri-o-tolylphosphine, and 9.0 mg of palladium acetate, followed by radiation with microwave and stirring at 200° C. for 10 min. To the reaction liquid was added water, followed by extraction with EtOAc, and the organic layer was washed with saturated brine. The organic layer was dried over magnesium sulfate, a solvent was evaporated under reduced pressure, and the residue was purified by silica gel column chromatography (chloroform:methanol=96:4) to prepare 85.2 mg of 1-(5-[(E)-2-cyanovinyl]-3-{[(2-morpholin-4-yl-1,3-thiazol-4-yl)carbonyl]amino}pyridin-2-yl)piperidine-4-carboxamide.

Example 287

To a mixed solution of 71.0 mg of 1-(5-[(E)-2-cyanovinyl]-3-{[(2-morpholin-4-yl-1,3-thiazol-4-yl)carbonyl]amino}pyridin-2-yl)piperidine-4-carboxamide in 2.0 ml of methanol and 2.0 ml of THF was added 10.0 mg of 10% palladium/carbon, followed by stirring under a hydrogen atmosphere for 15 hours. The reaction liquid was filtered through celite, the mother liquor was concentrated, and the residue was recrystallized from ethanol to prepare 51.3 mg of 1-(5-[-2-cyanoethyl]-3-{[(2-morpholin-4-yl-1,3-thiazol-4-yl)carbonyl]amino}pyridin-2-yl)piperidine-4-carboxamide.

Example 288

To a suspension of 500 mg of N-{2-[4-(2-amino-2-oxoethyl)piperazin-1-yl]-5-bromophenyl}-2-morpholin-4-yl-1,3-thiazole-4-carboxamide in 3.00 ml of propanol were added 40.0 mg of [1,1'-bis(diphenylphosphino)ferrocene]-dichloropalladium (II), 400 mg of potassium vinyltrifluoroborate and 0.15 ml of triethylamine, followed by radiation with microwave and stirring at 120° C. for 15 min. The precipitate was separated by filtration, and washed with ethanol, and the mother liquor was concentrated under reduced pressure. The obtained residue was diluted in 30 ml of saturated brine, and extracted with chloroform. The organic layer was dried over sodium sulfate, and then concentrated under reduced pressure, and the residue was purified by silica gel column chromatography (chloroform:methanol=96:4) to prepare 360 mg of N-{2-[4-(2-amino-2-oxoethyl)piperazin-1-yl]-5-vinylphenyl}-2-morpholin-4-yl-1,3-thiazole-4-carboxamide.

Example 293

To a solution of 200 mg of N-{2-[4-(2-amino-2-oxoethyl)piperazin-1-yl]-5-bromophenyl}-2-morpholin-4-yl-1,3-thiazole-4-carboxamide in 1.00 ml of DMF were added 14.0 mg of dichlorobis(triphenylphosphine)palladium (II) and 200 mg of tributyl(methoxymethyl)tin, followed by radiation with microwave and heating at 200° C. for 15 min. To the reaction liquid were added EtOAc and a saturated aqueous potassium fluoride solution, followed by stirring for a while. The organic layer was separated, dried over sodium sulfate, and then concentrated under reduced pressure, and the residue was purified by silica gel column chromatography (chloroform:methanol=95:5) to prepare 16.2 mg of N-{2-[4-(2-amino-2-oxoethyl)piperazin-1-yl]-5-(methoxymethyl)phenyl}-2-morpholin-4-yl-1,3-thiazole-4-carboxamide.

Example 356

300 mg of N-{2-[4-(2-amino-2-oxoethyl)piperazin-1-yl]phenyl}-2-bromo-1,3-thiazole-4-carboxamide was dissolved in 20 ml of dioxane, and 380 µl of (2-methoxyethyl)methylamine was added dropwise thereto at room temperature, followed by stirring at 100° C. for 3 days. To the reaction liquid was added an aqueous sodium hydrogen carbonate solution, followed by extraction with chloroform and drying over magnesium sulfate. A solvent was evaporated under reduced pressure, and the residue was purified by silica gel column chromatography (chloroform:methanol=50:1). After this was suspended in EtOAc, a 4 M hydrogen chloride/EtOAc solution was added thereto, and then a solvent was evaporated under reduced pressure to prepare 206 mg of N-{2-[4-(2-amino-2-oxoethyl)-piperazin-1-yl]phenyl}-2-[(2-methoxyethyl)(methyl)amino]-1,3-thiazole-4-carboxamide hydrochloride.

Example 394

To a solution of 200 mg of 1-(3-aminopyridin-2-yl)-4-(hydroxymethyl)piperidin-4-ol in 10 ml of DMF were added 453 mg of 2-[(2-methoxyethyl)(methyl)amino]-1,3-thiazole-4-carboxylic acid hydrochloride, 515 mg of WSC-HCl, 363 mg of HOBt, and 0.50 ml of triethylamine, followed by stirring at room temperature for one day. Thereafter, 4.00 ml of methanol and 4.00 ml of a 4 M aqueous sodium hydroxide solution were added thereto, followed by stirring at room temperature for 1 hour. To the reaction liquid was added water, followed by extraction with chloroform, drying over magnesium sulfate, and filtration. A solvent was evaporated under reduced pressure, and the residue was purified by silica gel column chromatography (chloroform:methanol=50:1) to prepare 210 mg of N-{2-[4-hydroxy-4-(hydroxymethyl)piperidin-1-yl]pyridin-3-yl}-2-[(2-methoxyethyl)(methyl)amino]-1,3-thiazole-4-carboxamide hydrochloride.

Example 501

To a solution of 119 mg of 2-morpholin-4-yl-1,3-oxazole-4-carboxylic acid in 6.00 ml of DMF were added 132 mg of 1-(3-aminopyridin-2-yl)piperidine-4-carboxamide, 150 mg of WSC-HCl, and 105 mg of HOBt, followed by stirring at room temperature for 3 days. The reaction liquid was concentrated under reduced pressure, and an aqueous sodium hydrogen carbonate solution was added thereto, followed by extraction with chloroform. The organic layer was washed with saturated brine, and then dried over magnesium sulfate. A solvent was evaporated under reduced pressure, and the residue was purified by silica gel column chromatography (chloroform:methanol=50:1), and further recrystallized from acetonitrile. This was suspended in EtOAc, a 4 M hydrogen chloride/EtOAc solution was added thereto, and then a solid was collected by filtration to prepare 95 mg of 1-(3-{[(2-morpholin-4-yl-1,3-oxazol-4-yl)carbonyl]amino}pyridin-2-yl)piperidine-4-carboxamide hydrochloride.

Example 529

To a solution of 230 mg of 2-morpholin-4-yl-1,3-oxazole-4-carboxylic acid and 200 mg of 2-[4-(2-amino-5-bromo-4-fluorophenyl)piperazin-1-yl]acetoamide in 1.00 ml of pyridine was added 0.61 ml of phosphorus oxychloride at −20° C., followed by stirring at room temperature for 15 hours. To the reaction liquid was added water, followed by extraction with EtOAc, drying over sodium sulfate, and concentration under reduced pressure, and the residue was purified by silica gel column chromatography (chloroform:methanol=95:5) to prepare 180 mg of N-{2-[4-(2-amino-2-oxoethyl)piperazin-1-yl]-4-bromo-5-fluorophenyl}-2-morpholin-4-yl-1,3-oxazole-4-carboxamide.

Example 537

To a solution of 150 mg of N-{5-[4-(2-amino-2-oxoethyl)piperazin-1-yl]-3-bromo-1-methyl-1H-pyrazol-4-yl}-2-morpholin-4-yl-1,3-oxazole-4-carboxamide in 8.00 ml methanol was added 20.0 mg of 10% palladium-carbon, followed by stirring for 15 hours under a hydrogen atmosphere. The reaction liquid was filtered through celite, the mother liquor was concentrated, and the residue was recrystallized from ethanol to prepare 85.0 mg of N-{5-[4-(2-amino-2-oxoethyl)piperazin-1-yl]-1-methyl-1H-pyrazol-4-yl}-2-morpholin-4-yl-1,3-oxazole-4-carboxamide.

Example 635

Under an argon atmosphere, a solution of 820 mg of 2-(3-bromophenyl)-N-[2-(4-methyl-1-piperazinyl)phenyl]-1,3-thiazole-4-carboxamide in 10 ml of THF was cooled to −78° C., and 2.6 ml of a 1.5 M n-butyllithium-hexane solution was added thereto, followed by stirring for 30 min. Subsequently, to the reaction liquid was added dry ice, followed by elevating the temperature to room temperature and stirring for 3 hours, and then water, a 1 M aqueous hydrochloric acid solution, and water were added thereto in this order to obtain a precipitate, which was collected by filtration. This was purified by silica gel column chromatography (chloroform:methanol=:100:0 to 90:10), and then dissolved in chloroform, and a 4 M hydrogen chloride/EtOAc solution was added thereto. A solvent was evaporated under reduced pressure, and then washed with diethyl ether to prepare 170 mg of 2-[4-({[2-(4-methyl-1-piperazinyl)phenyl]amino}carbonyl)-1,3-thiazol-2-yl]benzoic acid hydrochloride.

Example 662

To a solution of 480 mg of 2-(3-furyl)-1,3-thiazole-4-carboxylic acid ethyl ester in 10 ml of methanol was added 1.61 ml of a 4 M aqueous lithium hydroxide solution, followed by stirring at room temperature for 3 hours, and then to the reaction liquid was added a 1 M aqueous hydrochloric acid solution for acidification of the system. A solvent was evaporated under reduced pressure, the residue was suspended in 10 ml of DMF, and 471 mg of 1-(2-aminophenyl)-4-piperidinecarboxamide, 348 mg of HOBt, 493 mg of WSC.HCl, and 0.90 ml of triethylamine were added thereto, followed by stirring overnight at room temperature. To the reaction liquid was added a saturated aqueous sodium hydrogen carbonate solution, followed by extraction with EtOAc, and then the organic layer was washed with a 1 M aqueous hydrochloric acid solution, and saturated brine in this order. A solvent was evaporated under reduced pressure, and the residue was purified by silica gel column chromatography (chloroform:methanol=100:0 to 93:7) to prepare 315 mg of 1-[2-({[2-(3-furyl)-1,3-thiazol-4-yl]carbonyl}amino)phenyl]-4-piperidine carboxamide.

Example 664

To a solution of 290 mg of 1-(2-{[(2-pyrrolidin-1-yl-1,3-thiazol-4-yl)carbonyl]amino}phenyl)piperidine-4-carboxylic acid in 9.00 ml of THF was added 350 mg of CDI, followed by stirring at 50° C. for 30 min. The reaction liquid was returned to room temperature, and 500 μl of 28% aqueous ammonia was added thereto, followed by continuously stirring at the same temperature for 1.5 hours. The reaction liquid was concentrated under reduced pressure, water was added thereto, and then the precipitated white solid was collected by filtration to prepare 264 mg of 1-(2-{[(2-pyrrolidin-1-yl-1,3-thiazol-4-yl)carbonyl]amino}phenyl)piperidine-4-carboxamide.

Example 691

To a solution of 90.4 mg of N-{2-[4-(2-amino-2-oxoethyl)-1-piperazinyl]phenyl}-2-(2-methoxy-4-pyridinyl)-1,3-thiazole-4-carboxamide in 2.5 ml of chloroform was added a 4 M hydrogen chloride/EtOAc solution. The precipitate was collected by filtration, and dried under reduced pressure to prepare 66.9 mg of N-{2-[4-(2-amino-2-oxoethyl)-1-piperazinyl]phenyl}-2-(2-methoxy-4-pyridinyl)-1,3-thiazole-4-carboxamide hydrochloride.

To a solution of 74.8 mg of N-{2-[4-(2-amino-2-oxoethyl)-1-piperazinyl]phenyl}-2-(2-methoxy-4-pyridinyl)-1,3-thiazole-4-carboxamide hydrochloride in 2 ml of dichloromethane was added 0.57 ml of a 1 M tribromoborane dichloromethane solution, followed by stirring overnight at room temperature. To the obtained mixture were further added 2 ml of dichloromethane and a 0.57 ml of 1 M tribromoborane dichloromethane solution, followed by stirring overnight at room temperature. To the mixture was added a saturated aqueous sodium hydrogen carbonate solution, followed by extraction with chloroform. The organic layer was dried over magnesium sulfate, and then concentrated under reduced pressure. The residue was purified by preparative TLC, and then a 4 M hydrogen chloride/EtOAc solution in EtOAc was added thereto. The solution was concentrated and dried to prepare 25.3 mg of N-{2-[4-(2-amino-2-oxoethyl)-1-piperazinyl]phenyl}-2-(2-hydroxy-4-pyridinyl)-1,3-thiazole-4-carboxamide hydrochloride.

Example 692

To a solution of 317 mg of N-{2-[4-(2-amino-2-oxoethyl)-1-piperazinyl]phenyl}-2-(2-chloro-4-pyridinyl)-1,3-thiazole-4-carboxamide in 2.0 ml of DMSO was added 375 mg of sodium methoxide, followed by stirring at 140° C. for 14 hours. The mixture was concentrated under reduced pressure, and dried, and to the mixture were added chloroform and water, followed by stirring and separation. The aqueous layer was extracted with chloroform, and the combined organic layer was dried over magnesium sulfate, and then concentrated under reduced pressure. The residue was purified by HPLC, and then 5.5 ml of EtOAc and 7.5 ml of hexane were added thereto. The mixture was heated to 60° C., filtered at room temperature, and dried under reduced pressure to prepare 143.6 mg of N-{2-[4-(2-amino-2-oxoethyl)-1-piperazinyl]phenyl}-2-(2-methoxy-4-pyridinyl)-1,3-thiazole-4-carboxamide.

Example 693

To a solution of 151 mg of N-{2-[4-(2-amino-2-oxoethyl)-1-piperazinyl]phenyl}-2-(2-chloro-4-pyridinyl)-1,3-thiazole-4-carboxamide in 1.5 ml of DMSO was added 86 mg of sodium azide, and the mixture was stirred at 90° C. for 2 hours, and then at 120° C. for 24 hours. To the obtained mixture was added water, followed by stirring for a while, and then the precipitate was filtered and dried. To the obtained powder was added methanol, followed by stirring at 80° C. for 1 hour, filtration, and drying at room temperature to prepare 44 mg of N-{2-[4-(2-amino-2-oxoethyl)-1-piperazinyl]phenyl}-2-(2-azide-4-pyridinyl)-1,3-thiazole-4-carboxamide.
To a solution of 53 mg of N-{2-[4-(2-amino-2-oxoethyl)-1-piperazinyl]phenyl}-2-(2-azide-4-pyridinyl)-1,3-thiazole-4-carboxamide in 15.9 ml of methanol and 5.3 ml of THF was added 78 mg of 10% palladium-carbon, and a 4 M hydrogen chloride/EtOAc solution was added thereto, followed by stirring overnight at room temperature under a hydrogen atmosphere. The mixture was filtered, and the filtrate was concentrated under reduced pressure. To a solution of the residue in chloroform and methanol was added a saturated aqueous sodium hydrogen carbonate solution, concentrated under reduced pressure, and dried. The residue was thoroughly washed with a mixed solvent of methanol and chloroform (10:90), and the washing liquid was concentrated under reduced pressure. The residue was purified by preparative TLC, and a 4 M hydrogen chloride/EtOAc solution in a mixed solution of methanol and chloroform was added thereto, followed by concentration under reduced pressure. The residue was washed with a mixed solvent of methanol and isopropyl ether to prepare 24 mg of N-{2-[4-(2-amino-2-oxoethyl)-1-piperazinyl]phenyl}-2-(2-amino-4-pyridinyl)-1,3-thiazole-4-carboxamide dihydrochloride.

Example 695

A solution of 100 mg of N-{2-[4-(2-amino-2-oxoethyl)-1-piperazinyl]phenyl}-2-(2-chloro-4-pyridinyl)-1,3-thiazole-4-carboxamide, 350 mg of dimethylamine hydrochloride, and 0.61 ml of triethylamine in 1.2 ml of DMSO was stirred overnight at 140° C. To the mixture was added water, followed by extraction with chloroform. The extract solution was washed with saturated brine, dried over magnesium sulfate, and then concentrated under reduced pressure. The residue was purified using preparative TLC, a 4 M hydrogen chloride/EtOAc solution in a mixed solution of methanol and chloroform was added thereto, and then the solution was concentrated. The residue was washed with a mixed solvent of methanol and isopropyl ether, and dried under reduced pressure to prepare 47.7 mg of N-{2-[4-(2-amino-2-oxoethyl)-1-piperazinyl]phenyl}-2-(2-(dimethylamino)-4-pyridinyl)-1,3-thiazole-4-carboxamide dihydrochloride.

Example 698

To a solution of 46 mg of N-{2-[4-(2-amino-2-oxoethyl)-1-piperazinyl]phenyl}-2-(2-cyano-4-pyridinyl)-1,3-thiazole-4-carboxamide in 1 ml of DMSO were added 71 mg of powdered potassium carbonate and 0.015 ml of 30% aqueous hydrogen peroxide at 0° C. The mixture was stirred at room temperature for 1.5 hours, and then at 120° C. for 24 hours, to the mixture was added water, and then the precipitate was collected, filtered, and then dried. To the residue was added a 4 M hydrogen chloride/EtOAc solution in a mixed solution of methanol and chloroform, and the solution was concentrated. The residue was washed with a mixed solvent of methanol and isopropyl ether to prepare 44 mg of 4-{4-[({2-([4-(2-amino-2-oxoethyl)-1-piperazinyl]phenyl}amino)carbonyl]-1,3-thiazol-2-yl}-2-pyridinecarboxamide hydrochloride.

Example 703

A solution of 203.6 mg of N-{2-[4-(2-amino-2-oxoethyl)-1-piperazinyl]phenyl}-2-bromo-1,3-thiazole-4-carboxamide and 687.1 mg of 1,4-dioxa-8-azaspiro[4.5]decane in 1.02 ml of DMA was stirred overnight at 100° C., and then the mixture was concentrated and dried under reduced pressure. To the residue was added 30 ml of water, and stirred at room temperature for 2 hours. The precipitate was collected by filtration, dried under reduced pressure at 50° C., and purified by preparative TLC to obtain 200 mg of a solid. To a solution of the resulting product in 30 ml of acetone was added 228 mg of p-toluenesulfonic acid hydrate. The mixture was stirred at room temperature for 4 hours, and then at 40° C. for 3 days, and then to the mixture was added a saturated aqueous sodium hydrogen carbonate solution, followed by extraction with chloroform. The organic layer was washed with saturated brine, dried over magnesium sulfate, and then concentrated under reduced pressure. The residue was purified by preparative TLC, and dissolved in a mixed solution of methanol and chloroform, and a 4 M hydrogen chloride/EtOAc solution was added thereto. The solution was concentrated, and the residue was washed with a mixed solvent of ethanol and isopropyl ether, and dried under reduced pressure to prepare 170.6 mg of N-{2-[4-(2-amino-2-oxomethyl)-1-piperazinyl]phenyl}-2-(4-oxo-1-piperidinyl)-1,3-thiazole-4-carboxamide hydrochloride.

Examples 718 and 734

A solution of 151 mg of N-{2-[4-(2-amino-2-oxoethyl)-1-piperazinyl]phenyl}-2-bromo-1,3-thiazole-4-carboxamide, 333 mg of azetidine hydrochloride, and 0.5 ml of triethylamine in 1.02 ml of DMA was stirred overnight at 100° C., and then the mixture was concentrated and dried under reduced pressure. To the residue was added 30 ml of water, and then the aqueous layer was extracted with chloroform. The organic layer was dried over magnesium sulfate, and concentrated. The residue was purified using preparative TLC, and then a 4 M hydrogen chloride/EtOAc solution in a mixed solution of methanol and chloroform was added thereto. The solution was concentrated, and the obtained residue was washed with mixed solvent of ethanol and isopropyl ether, and dried under reduced pressure to obtain a mixture of two kinds of compounds. To this was added a saturated aqueous sodium hydrogen carbonate solution for neutralization, and then extracted with chloroform. The organic layer was washed with saturated brine, dried over magnesium sulfate, concentrated, and isolated using preparative TLC.

The upper fraction was washed with a mixed solvent of ethanol and isopropyl ether to prepare 17.2 mg of N-{2-[4-(2-amino-2-oxoethyl)-1-piperazinyl]phenyl}-2-(1-azetidinyl)-1,3-thiazole-4-carboxamide.

The lower fraction was dissolved in ethyl acetate, and a 4 M hydrogen chloride/EtOAc solution was allowed to act thereon, followed by washing with a mixed solvent of ethanol and isopropyl ether to prepare 82.3 mg of N-{2-[4-(2-amino-2-oxoethyl)-1-piperazinyl]phenyl}-2-[(3-chloropropyl)amino]-1,3-thiazole-4-carboxamide hydrochloride.

Example 723

To a solution of 296 mg of 2-(1-oxidethiomorpholin-4-yl)-1,3-thiazole-4-carboxylic acid in 10.0 ml of THF was added 260 μl of 4-methylmorpholine and 170 μl of isobutylchloridecarbonate under ice-cooling at 0° C. for 5 min, followed by warming to room temperature, and stirring for 15 min. The reaction liquid was ice cooled again, and a solution of 281 mg of 2-[4-(2-aminophenyl)piperazin-1-yl]acetoamide in 8.00 ml of THF was added dropwise thereto, followed by stirring at 0° C. for 1 hour, and then warmed at room temperature, followed by stirring for 8 hours. To the reaction liquid was added an aqueous sodium hydrogen carbonate solution, followed by extraction with chloroform. At this time, the insolubles partitioned between the aqueous layer and the organic layer were separated by filtration. The organic layer was washed with saturated brine, and then dried over magnesium sulfate. A solvent was evaporated under reduced pressure, the residue was mixed with the above-described insolubles, and this was subject to a recrystallization operation using ethanol to precipitate a solid, which was collected by filtration. This was suspended in ethanol, a 4 M hydrogen chloride/EtOAc solution was added thereto, and the solid was collected by filtration to prepare 281 mg of N-{2-[4-(2-amino-2-oxoethyl)piperazin-1-yl]phenyl}-2-(1-oxidothiomorpholin-4-yl)-1,3-thiazole-4-carboxamide hydrochloride.

Example 792

269 mg of 2-methoxyethanol was dissolved in 6 ml of DMF, and 141 mg of 60% sodium hydride was added thereto under ice-cooling, followed by stirring for 30 min. A solution of 300 mg of N-{2-[4-(2-amino-2-oxoethyl)piperazin-1-yl]phenyl}-2-bromo-1,3-thiazole-4-carboxamide in DMF was added thereto, followed by stirring at 60° C. for 30 min. To the reaction liquid was added an aqueous sodium hydrogen carbonate solution, followed by extraction with chloroform, and the solvent was evaporated under reduced pressure. The residue was purified by silica gel column chromatography (chloroform:methanol=50:1). This was dissolved in ethanol, a 4 M hydrogen chloride/EtOAc solution was added thereto, and then the precipitated solid was collected by filtration to prepare 137 mg of N-{2-[4-(2-amino-2-oxoethyl)piperazin-1-yl]phenyl}-2-(2-methoxyethoxy)-1,3-thiazole-4-carboxamide hydrochloride.

Example 793

155 mg of N-{2-[4-(2-amino-2-oxoethyl)piperazin-1-yl]phenyl}-2-piperazin-1-yl-1,3-thiazole-4-carboxamide and 26 μl of propionaldehyde were suspended in 2 ml of methylene chloride, and 62 μl of acetic acid was added thereto, followed by stirring at room temperature for 1 hour. 76 mg of sodium triacetoxyborohydride was added thereto, followed by further stirring for 15 min. To the reaction liquid was added an aqueous sodium hydrogen carbonate solution, followed by extraction with chloroform, and the solvent was evaporated under reduced pressure. The residue was purified by silica gel column chromatography (chloroform:methanol=20:1). This was dissolved in ethanol, a 4 M hydrogen chloride/EtOAc solution was added thereto, and then the precipitated solid was collected by filtration to prepare 96 mg of N-{2-[4-(2-amino-2-oxoethyl)piperazin-1-yl]phenyl}-2-(4-propylpiperazin-1-yl)-1,3-thiazole-4-carboxamide hydrochloride.

Example 815

28 mg of N-{2-[4-(2-amino-2-oxoethyl)piperazin-1-yl]phenyl}-2-[(3S)-4-benzyl-3-(methoxymethyl)piperazin-1-yl]-1,3-thiazole-4-carboxamide was dissolved in 1 ml of methanol, and 28 mg of 10% palladium-carbon and 57 μl of formic acid were added thereto, followed by stirring at room temperature for 7 hours. The reaction liquid was filtered through celite, and the mother liquor was evaporated under reduced pressure. To the residue was added an aqueous sodium hydrogen carbonate solution, followed by extraction with chloroform:2-propanol=3:1, and the solvent was evaporated under reduced pressure. The residue was purified by basic silica gel column chromatography (chloroform:methanol=300:1). This was dissolved in ethanol, a 4 M hydrogen chloride/EtOAc solution was added thereto, and then the precipitated solid was collected by filtration to prepare 7 mg of N-{2-[4-(2-amino-2-oxoethyl)piperazin-1-yl]phenyl}-2-[(3S)-3-(methoxymethyl)piperazin-1-yl]-1,3-thiazole-4-carboxamide hydrochloride.

Example 821

A solution of 100 mg of N-{2-[4-(2-amino-2-oxoethyl)-1-piperazinyl]phenyl}-2-bromo-1,3-thiazole-4-carboxamide and 180 mg of 3-(methoxymethyl)azetidine in 2 ml of DMA was stirred at 100° C. for 48 hours, to the mixture was added water, and then the aqueous layer was extracted with chloroform. The organic layer was washed with saturated brine, and then dried over sodium sulfate. After filtration and concentration, the residue was purified by silica gel column chromatography (chloroform:methanol=99:1 to 20:1), the obtained residue was dissolved in methanol, diethyl ether was added thereto, and the precipitated solid was collected by filtration, and dried under reduced pressure to prepare 55 mg of N-{2-

[4-(2-amino-2-oxoethyl)piperazin-1-yl]phenyl}-2-{[3-methoxy-2-(methoxymethyl)propyl]amino}-1,3-thiazole-4-carboxamide.

Example 835

A solution of 370 mg of N-{2-[4-(2-amino-2-oxoethyl)-1-piperazinyl]phenyl}-2-bromo-1,3-thiazole-4-carboxamide, 524 mg of 3-(methylamino)pyrrolidine-1-carboxylic acid tert-butyl ester, and 0.76 ml of ethyldiisopropylamine in 1.85 ml of DMA was stirred overnight at 100° C. To the reaction liquid was added 200 ml of water, followed by extraction with chloroform. The organic layer was washed with water and saturated brine, dried over magnesium sulfate, concentrated under reduced pressure, and purified by preparative TLC to obtain an oily substance. To a solution of this oily substance in 2 ml of methanol was added 8 ml of a 4 M aqueous hydrogen chloride/dioxane solution for reaction overnight at room temperature, and a saturated aqueous sodium hydrogen carbonate solution was added thereto, followed by extraction with chloroform. The organic layer was washed with saturated brine, dried over anhydrous magnesium sulfate, concentrated under reduced pressure, and purified by preparative TLC to obtain an oily substance. To a solution of this oily substance in 0.33 ml of methanol was added 3.3 ml of aqueous ammonia for overnight reaction. The obtained mixture was concentrated under reduced pressure, and purified by preparative TLC, and then a 4 M hydrogen chloride/EtOAc solution was added thereto to prepare 135 mg of N-{2-[4-(2-amino-2-oxoethyl)piperazin-1-yl]phenyl}-2-[methyl(pyrrolidin-3-yl)amino]-1,3-thiazole-4-carboxamide dihydrochloride.

Example 837

To a solution of 50 mg of N-{2-[4-(2-amino-2-oxoethyl)-1-piperazinyl]phenyl}-2-bromo-1,3-thiazole-4-carboxamide, 47.2 mg of 3-(methylamino)pyrrolidine-1-carboxylic acid tert-butyl ester, and 0.041 ml of ethyldiisopropylamine in 0.5 ml of 1-methyl-2-pyrrolidone was radiated with microwave at 200° C. for 30 min. To the mixture was added 100 ml of water, followed by extraction with chloroform, and the organic layer was dried over magnesium sulfate, and concentrated under reduced pressure. The residue was purified using preparative TLC, and a 4 M hydrogen chloride/EtOAc solution was added thereto to prepare 18.4 mg of N-{2-[4-(2-amino-2-oxoethyl)piperazin-1-yl]phenyl}-2-[3-(methylamino)pyrrolidin-1-yl]-1,3-thiazole-4-carboxamide dihydrochloride.

Example 850

A solution of 147 mg of N-{2-[4-(2-amino-2-oxoethyl)-1-piperazinyl]phenyl}-2-(2-chloro-4-pyridinyl)-1,3-thiazole-4-carboxamide, 434 mg of methylamine hydrochloride, and 0.9 ml of triethylamine in 2 ml of DMSO was radiated with microwave at 200° C. for 70 min. To the obtained mixture was added water, followed by extraction with chloroform. The organic layer was combined, washed with water and saturated brine in this order, dried over magnesium sulfate, and concentrated under reduced pressure. The residue was purified using preparative TLC, and a 4 M hydrogen chloride/EtOAc solution was added thereto to prepare 32.1 mg of N-{2-[4-(2-(methylamino)-2-oxoethyl)-1-piperazinyl]phenyl}-2-[2-(methylamino)-4-pyridinyl]-1,3-thiazole-4-carboxamide hydrochloride.

Example 864

To a solution of 84 mg of 2-[1-(tert-butoxycarbonyl)-1H-pyrrol-2-yl]-1,3-oxazole-4-carboxylic acid ethyl ester in 2.1 ml of ethanol was added 0.17 ml of a 4 M aqueous lithium hydroxide solution, followed by stirring at room temperature for 3 hours. To the mixture was added 0.68 ml of a 1 M aqueous hydrochloric acid solution, followed by adjustment of its pH to 5 to 6 with a 1 M aqueous sodium hydroxide solution, and then concentration under reduced pressure. A solution of the concentrated residue, 64.25 mg of 2-[4-(2-aminophenyl)-1-piperazinyl]acetoamide, 236.7 mg of WSC·HCl, and 166.7 mg of HOBt in 2.52 ml of DMF was stirred overnight at room temperature. To the mixture was added 30 ml of a solution of a saturated aqueous sodium hydrogen carbonate solution, followed by extraction with EtOAc. The organic layer was saturated brine, dried over magnesium sulfate, and concentrated under reduced pressure. The residue was purified by preparative TLC to prepare 32 mg of N-{2-[4-(2-amino-2-oxomethyl)-1-piperazinyl]phenyl}-2-(1H-pyrrolo-2-yl)-1,3-oxazole-4-carboxamide.

Example 952

To a solution of 120 mg of sodium 2-(4-ethoxypiperidin-1-yl)-1,3-oxazole-4-carboxylate in 3 ml of DMF were added 209 mg of O-(7-azabenzotriazol-1-yl)-N,N,N',N'-tetramethyluronium hexafluorophosphate and 104 mg of 1-(3-aminopyridin-2-yl)piperidine-4-carboxamide, followed by stirring at room temperature for 3 days. Water was added thereto, and the precipitated solid was washed with water and then collected by filtration, followed by dryness to prepare 48 mg of 1-[3-({[2-(4-ethoxypiperidin-1-yl)-1,3-oxazol-4-yl]carbonyl}amino)pyridin-2-yl]piperidine-4-carboxamide.

Example 980

To a solution of 4.4 mg of 2-piperidin-1-ylaniline, 5.1 mg of 2-phenyl-1,3-thiazole-4-carboxylic acid, and 3.4 mg of HOBt in 1.00 ml of N,N-dimethylformamide were added 100 mg of PS-Carbodiimide (Argonaut Technologies, Inc.) at room temperature, followed by stirring overnight. To the reaction liquid was added 50 mg of MP-Carbonate (Argonaut Technologies, Inc.) and 50 mg of PS-Isocyanate (Argonaut Technologies, Inc.) at room temperature, followed by stirring for 4 hours, the insolubles were filtered, and the filtrate was concentrated under reduced pressure to prepare 7.3 mg of 2-phenyl-N-(2-piperidin-1-ylphenyl)-1,3-thiazole-4-carboxamide. In the same manner as in Example 980, the compounds of Examples 978 to 1000 and Examples 1092 to 1112 were prepared using the corresponding substituted aniline and carboxylic acid as starting materials.

Example 1029

To a solution of 14.1 mg of 1-fluoro-2-nitrobenzene in 100 μl of acetonitrile was added a solution of 21.91 mg of 4-(piperazin-1-ylcarbonyl)morpholine in 220 μl of 1-methylpyrrolidin-2-one at room temperature, followed by stirring at 80° C. for 4 hours. To the reaction liquid were added 700 μl of N,N-dimethylformamide and 100 mg of PS-Isocyanate (Argonaut Technologies, Inc.) at room temperature, followed by stirring overnight, the insolubles were filtered, the filtrate was concentrated under reduced pressure, and to the obtained residue was added a solution of 112.8 mg of tin chloride (II) dihydrate in 500 μl of ethanol and 50 μl of concentrated hydrochloric acid, followed by stirring at 70° C. for 4 hours.

The reaction liquid was concentrated under reduced pressure, and 1.5 ml of a 2 M aqueous sodium hydroxide solution was added thereto, followed by extraction with chloroform. A solvent was evaporated under reduced pressure, and to the residue was added a solution of 10.3 mg of 2-phenyl-1,3-thiazole-4-carboxylic acid and 6.8 mg of HOBt in 1.00 ml of N,N-dimethylformamide, and 75 mg of PL-DCC Resin (Polymer Laboratories Ltd.) at room temperature, followed by stirring overnight. To the reaction liquid were added 50 mg of MP-Carbonate (Argonaut Technologies, Inc.) and 50 mg of PS-Isocyanate (Argonaut Technologies, Inc.) at room temperature, followed by stirring overnight, the insolubles were filtered, the filtrate was concentrated under reduced pressure, and the obtained residue was purified by preparative high performance liquid chromatography (methanol-0.1% aqueous formic acid solution) to prepare 3.0 mg of N-{2-[4-(morpholin-4-ylcarbonyl)piperazin-1-yl]phenyl}-2-phenyl-1,3-thiazole-4-carboxamide.

From 1-fluoro-2-nitrobenzene, 2-phenyl-1,3-thiazole-4-carboxylic acid, and each corresponding starting material, in the same manner as in Example 1029, the compounds of Examples 1001 to 1044 were prepared.

Example 1048

To a solution of 7.4 mg of 1-(2-aminophenyl)piperidine-4-carboxylic acid ethyl ester, 7.4 mg of 2-(2-thienyl)-1,3-thiazole-4-carboxylic acid, and 4.1 mg of HOBt in 1.00 ml of N,N-dimethylformamide solution was added 100 mg of PS-Carbodiimide (Argonaut Technologies, Inc.) at room temperature, followed by stirring overnight. To the reaction liquid were added 50 mg of MP-Carbonate (Argonaut Technologies, Inc.) and 50 mg of PS-Isocyanate (Argonaut Technologies, Inc.) at room temperature, followed by stirring for 4 hours, and the insolubles were filtered. The filtrate was concentrated under reduced pressure, the obtained residue was dissolved in 0.5 ml of ethanol and 0.5 ml of tetrahydrofuran, and 0.5 ml of a 2 M aqueous sodium hydroxide solution was added dropwise thereto at room temperature, followed by stirring at 60° C. for one day. To the reaction liquid was added dropwise 1.0 ml of a 1M aqueous hydrochloric acid solution, followed by extraction with chloroform. A solvent was evaporated under reduced pressure, and the residue was purified by preparative high performance liquid chromatography (methanol-0.1% aqueous formic acid solution) to prepare 2.4 mg of 1-[2-({[2-(2-thienyl)-1,3-thiazol-4-yl]carbonyl}amino)phenyl]piperidine-4-carboxylic acid.

From 1-(2-aminophenyl)piperidine-4-carboxylic acid ethyl ester and each corresponding starting material, in the same manner as in Example 1048, the compounds of Examples 1045 to 1052 were prepared.

Example 1065

To a solution of 10.9 mg of 2-phenyl-N-(2-piperidin-4-ylphenyl)-1,3-thiazole-4-carboxamide in 0.5 ml of N,N-dimethylformamide were added 4.0 mg of 3-bromopropanenitrile and 12.4 mg of potassium carbonate, followed by stirring overnight at 60° C. To the reaction liquid was added water, followed by extraction with chloroform. A solvent was evaporated under reduced pressure, and the residue was purified by preparative high performance liquid chromatography (methanol-0.1% aqueous formic acid solution) to prepare 3.6 mg of N-{2-[1-(2-cyanoethyl)piperidin-4-yl]phenyl}-2-phenyl-1,3-thiazole-4-carboxamide.

From 2-phenyl-N-(2-piperidin-4-ylphenyl)-1,3-thiazole-4-carboxamide and each corresponding starting material, in the same manner as in Example 1065, the compounds of Examples 1053 to 1091 were prepared.

Example 1116

To a solution of 2.2 mg of propionic acid in 60 µl of 1-methylpyrrolidin-2-one were added 12.5 mg of N-{2-[4-(2-amino-2-oxoethyl)piperazin-1-yl]phenyl}-2-piperidin-4-yl-1,3-thiazole-4-carboxamide dihydrochloride, 10.4 µl of triethylamine, a solution of 3.4 mg of HOBt in 1.00 ml of N,N-dimethylformamide, and 100 mg of PS-Carbodiimide (Argonaut Technologies, Inc.) at room temperature, followed by stirring overnight. To the reaction liquid were added 50 mg of MP-Carbonate (Argonaut Technologies, Inc.) and 50 mg of PS-Isocyanate (Argonaut Technologies, Inc.) at room temperature, followed by stirring for 4 hours, and the insolubles were filtered. The filtrate was concentrated under reduced pressure to prepare 10.4 mg of N-{2-[4-(2-amino-2-oxoethyl)piperazin-1-yl]phenyl-}2-(1-propionylpiperidin-4-yl)-1,3-thiazole-4-carboxamide.

In the same manner as in Example 1116, the compounds of Examples 1116 to 1161 were prepared using the corresponding carboxylic acid as a starting material.

Example 1162

To a solution of 1.7 mg of propionaldehyde, 12.5 mg of N-{2-[4-(2-amino-2-oxoethyl)piperazin-1-yl]phenyl}-2-piperidin-4-yl-1,3-thiazole-4-carboxamide dihydrochloride, and 6.9 µl of triethylamine in 0.50 ml of N,N-dimethylformamide were added 50 µl of acetic acid and 75 mg MP-Triacetoxyborohydride (Argonaut Technologies, Inc.) at room temperature, followed by stirring overnight. To the reaction liquid was added 50 mg of PS-Isocyanate (Argonaut Technologies, Inc.) at room temperature, followed by stirring for 4 hours, and the insolubles were filtered. The filtrate was purified by solid phase extraction using BondElut® SCX (Varian, Inc., USA) (eluent, concentrated aqueous ammonia:methanol=1:9) to prepare 0.9 mg of N-{2-[4-(2-amino-2-oxoethyl)piperazin-1-yl]phenyl}-2-(1-propylpiperidin-4-yl)-1,3-thiazole-4-carboxamide.

In the same manner as in Example 1162, the compounds of Examples 1162 to 1177 were prepared using the corresponding aldehyde as a starting material.

Example 1178

To 3.4 mg of methanesulfonylchloride was added a mixed solution of 12.5 mg of N-{2-[4-(2-amino-2-oxoethyl)piperazin-1-yl]phenyl}-2-piperidin-4-yl-1,3-thiazole-4-carboxamide dihydrochloride and 10.4 µl of triethylamine in 0.50 ml dichloroethane and 0.50 ml of N,N-dimethylformamide at room temperature, followed by stirring overnight. To the reaction liquid were added 50 mg of PS-Isocyanate (Argonaut Technologies, Inc.) and 50 mg of PS-Trisamine (Argonaut Technologies, Inc.) at room temperature, followed by stirring for 4 hours, and the insolubles were filtered. The filtrate was purified by solid phase extraction using BondElut® SCX (Varian, Inc., USA) (eluent, concentrated aqueous ammonia: methanol=1:9) to prepare 11.4 mg of N-{2-[4-(2-amino-2-oxoethyl)piperazin-1-yl]phenyl}-2-(1-(methylsulfonyl)piperidin-4-yl)-1,3-thiazole-4-carboxamide.

In the same manner as in Example 1178, the compounds of Examples 1178 to 1195 were prepared using the corresponding sulfonyl chloride as a starting material.

Example 1196

To 2.6 mg of isopropylisocyanate was added a solution of 12.5 mg of N-{2-[4-(2-amino-2-oxoethyl)piperazin-1-yl]

phenyl}-2-piperidin-4-yl-1,3-thiazole-4-carboxamide dihydrochloride and 10.4 μl of triethylamine in 0.50 ml of N,N-dimethylformamide at room temperature, followed by stirring overnight. To the reaction liquid were added 50 mg of PS-Isocyanate (Argonaut Technologies, Inc.) and 50 mg of PS-Trisamine (Argonaut Technologies, Inc.) at room temperature, followed by stirring for 4 hours, and the insolubles were filtered. The filtrate was purified by solid phase extraction using BondElut® SCX (Varian, Inc., USA) (eluent, concentrated aqueous ammonia:methanol=1:9) to prepare 11.9 mg of 4-{4-[({2-[4-(2-amino-2-oxoethyl)piperazin-1-yl]phenyl}amino)carbonyl]-1,3-thiazol-2-yl}-N-isopropylpiperidine-1-carboxamide.

In the same manner as in Example 1196, the compounds of Examples 1196 to 1202 were prepared using the corresponding isocyanate or isothiocyanate as a starting material.

The structures and the physiochemical data of the compounds of Examples 1 to 1202 are shown in Tables 6 to 68. In addition to the description on the preparation methods in Examples as above, the compounds of the Example Nos. were prepared in the same manner as the methods of Examples of the numbers shown in Syn of Tables, using each corresponding starting material.

In the tables as described below in Examples, the following abbreviations are used.

Ex in the left-hand columns in the Tables represents Example Nos., and the cells in the middle columns except for the top cell of each table show the structural formulae corresponding to the substituents of the compounds of the present invention represented by the general formulae. The structural formulae marked with * in the cells of the tables indicate that the compounds are optically active. Example Nos. with reference to the preparation methods with Syn are shown at the tops of the right-hand columns. The materials horizontally described in the right hand of Syn, that is, (Sal) indicate salts, and the materials without such a description represents free compounds.

(HCl) represents hydrochloride, and (Na) represents a sodium salt. The values by mass analysis as Dat (physiochemical data) are shown at the bottoms in the right-hand columns.

TABLE 6

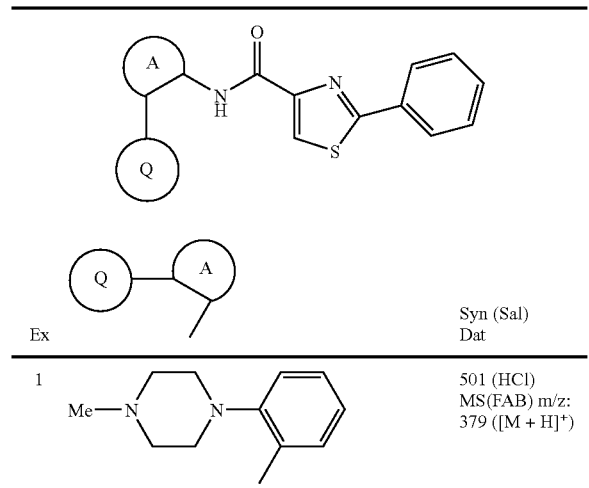

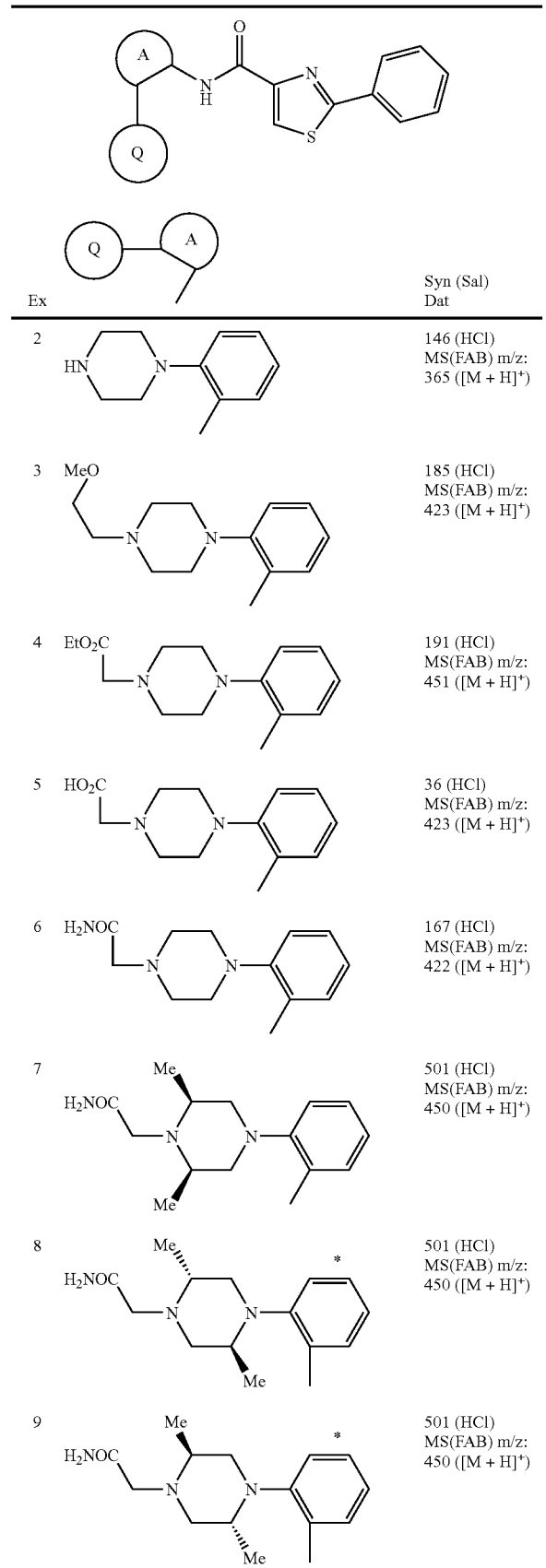

TABLE 6-continued

| Ex | Structure (A/Q) | Syn (Sal) Dat |
|---|---|---|
| 10 | HO-CH2, Me-N-piperazine-N-(2-methylphenyl) | 501 (HCl) MS(FAB) m/z: 409 ([M + H]⁺) |
| 11 | H2NOC-CH2-N-piperazine-N-aryl(MeO2C-CH2, Me) | 234 MS(API) m/z: 494 ([M + H]⁺) |
| 12 | H2NOC-CH2-N-piperazine-N-aryl(HO2C-CH2, Me) | 36 (Na) MS(FAB) m/z: 480 ([M + H]⁺) |
| 13 | H2NOC-CH2-N-piperazine-N-aryl(H2NOC-CH2, Me) | 167 (HCl) MS(ESI) m/z: 479 ([M + H]⁺) |
| 14 | H2NOC-CH2-N-piperazine-N-aryl(EtO2C-CH2CH2, Me) | 501 MS(ESI) m/z: 522 ([M + H]⁺) |
| 15 | H2NOC-CH2-N-piperazine-N-aryl(HO2C-CH2CH2, Me) | 36 (Na) MS(FAB) m/z: 494 ([M + H]⁺) |
| 16 | H2NOC-CH2-N-piperazine-N-aryl(H2NOC-CH2CH2, Me) | 167 (HCl) MS(ESI) m/z: 493 ([M + H]⁺) |
| 17 | Me-N-piperazine-N-aryl(CO2H, Me) | 17 MS(ESI) m/z: 423 ([M + H]⁺) |
| 18 | Me-N-piperazine-N-aryl(CONH2, Me) | 234 (HCl) MS(ESI) m/z: 422 ([M + H]⁺) |
| 19 | H2NOC-CH2-N-piperazine-N-aryl(F, Me) | 234 (HCl) MS(FAB) m/z: 440 ([M + H]⁺) |
| 20 | H2NOC-CH2-N-piperazine-N-aryl(F, Me) | 234 (HCl) MS(FAB) m/z: 440 ([M + H]⁺) |
| 21 | H2NOC-CH2-N-piperazine-N-aryl(F, Me) | 234 (HCl) MS(FAB) m/z: 440 ([M + H]⁺) |
| 22 | H2NOC-CH2-N-piperazine-N-aryl(F, Me) | 234 (HCl) MS(FAB) m/z: 440 ([M + H]⁺) |
| 23 | H2NOC-CH2-N-piperazine-N-aryl(Cl, Me) | 234 (HCl) MS(FAB) m/z: 456 ([M + H]⁺) |
| 24 | H2NOC-CH2-N-piperazine-N-aryl(Cl, Me) | 234 (HCl) MS(FAB) m/z: 456 ([M + H]⁺) |

TABLE 6-continued

| Ex | Structure | Syn (Sal) Dat |
|---|---|---|
| 25 | H₂NOC-CH₂-N(piperazine)N-(2,5-dimethylphenyl) | 234 (HCl) MS(FAB) m/z: 436 ([M + H]⁺) |
| 26 | H₂NOC-CH₂-N(piperazine)N-(2,4-dimethylphenyl) | 234 (HCl) MS(FAB) m/z: 436 ([M + H]⁺) |
| 27 | H₂NOC-CH₂-N(piperazine)N-(2-methyl-5-methoxyphenyl) | 234 (HCl) MS(FAB) m/z: 452 ([M + H]⁺) |
| 28 | Me-C(O)-N(piperazine)N-(2-methylphenyl) | 28 MS(FAB) m/z: 407 ([M + H]⁺) |
| 29 | EtO-C(O)-N(piperazine)N-(2-methylphenyl) | 29 MS(FAB) m/z: 437 ([M + H]⁺) |
| 30 | Boc-N(piperazine)N-(2-methylphenyl) | 501 MS(FAB) m/z: 465 ([M + H]⁺) |
| 31 | MeSO₂-N(piperazine)N-(2-methylphenyl) | 31 MS(FAB) m/z: 443 ([M + H]⁺) |
| 32 | 3-oxopiperazin-1-yl-(2-methylphenyl) | 501 MS(ESI) m/z: 379 ([M + H]⁺) |
| 33 | 4-methyl-3-oxopiperazin-1-yl-(2-methylphenyl) | 234 (HCl) MS(FAB) m/z: 393 ([M + H]⁺) |
| 34 | H₂NOC-(diazabicyclo)-N-(2-methylphenyl) | 501 (HCl) MS(FAB) m/z: 434 ([M + H]⁺) |
| 35 | EtO₂C-piperidine-N-(2-methylphenyl) | 501 MS(FAB) m/z: 436 ([M + H]⁺) |
| 36 | HO₂C-piperidine-N-(2-methylphenyl) | 36 (Na) MS(FAB) m/z: 408 ([M + H]⁺) |
| 37 | H₂NOC-piperidine-N-(2-methylphenyl) | 501 MS(ESI) m/z: 407 ([M + H]⁺) |
| 38 | MeHN-C(O)-piperidine-N-(2-methylphenyl) | 167 MS(FAB) m/z: 421 ([M + H]⁺) |
| 39 | Me₂N-C(O)-piperidine-N-(2-methylphenyl) | 167 MS(FAB) m/z: 435 ([M + H]⁺) |
| 40 | HO-CH₂CH₂-NH-C(O)-piperidine-N-(2-methylphenyl) | 167 MS(ESI) m/z: 451 ([M + H]⁺) |

TABLE 6-continued

| Ex | | Syn (Sal) Dat |
|---|---|---|
| 41 | MeO—CH₂CH₂—NH—C(O)—[piperidine-4-yl]—N-(2-methylphenyl) | 167 MS(ESI) m/z: 465 ([M + H]⁺) |
| 42 | piperidine-C(O)—[piperidine-4-yl]—N-(2-methylphenyl) | 167 MS(FAB) m/z: 475 ([M + H]⁺) |
| 43 | morpholine-C(O)—[piperidine-4-yl]—N-(2-methylphenyl) | 167 MS(FAB) m/z: 477 ([M + H]⁺) |
| 44 | Me-piperazine-C(O)—[piperidine-4-yl]—N-(2-methylphenyl) | 167 (HCl) MS(FAB) m/z: 490 ([M + H]⁺) |
| 45 | HO—[piperidine-4-yl]—N-(2-methylphenyl) | 501 MS(FAB) m/z: 380 ([M + H]⁺) |
| 46 | HO, HO—[piperidine-3,4-diyl]—N-(2-methylphenyl) | 501 MS(FAB) m/z: 396 ([M + H]⁺) |
| 47 | OH, HOCH₂—[piperidine-4-yl]—N-(2-methylphenyl) | 501 MS(FAB) m/z: 410 ([M + H]⁺) |
| 48 | EtO₂C—[piperidine-3-yl]—N-(2-methylphenyl) | 501 MS(ESI) m/z: 436 ([M + H]⁺) |
| 49 | HO₂C—[piperidine-3-yl]—N-(2-methylphenyl) | 36 MS(FAB) m/z: 408 ([M + H]⁺) |
| 50 | H₂NOC—[piperidine-3-yl]—N-(2-methylphenyl) | 167 MS(FAB) m/z: 407 ([M + H]⁺) |
| 51 | HO—[piperidine-3-yl]—N-(2-methylphenyl) | 501 MS(ESI) m/z: 380 ([M + H]⁺) |
| 52 | EtO₂C—CH₂—[piperidine-4-yl]—N-(3-methylphenyl) | 501 MS(FAB) m/z: 450 ([M + H]⁺) |
| 53 | HO₂C—CH₂—[piperidine-4-yl]—N-(2-methylphenyl) | 36 MS(FAB) m/z: 422 ([M + H]⁺) |
| 54 | H₂NOC—CH₂—[piperidine-4-yl]—N-(2-methylphenyl) | 167 MS(FAB) m/z: 421 ([M + H]⁺) |

TABLE 6-continued

| Ex | Structure | Syn (Sal) Dat |
|---|---|---|
| 55 | 4-(4-carbamoylpiperidin-1-yl)-3-methylphenyl with CO2Me | 501 MS(FAB) m/z: 465 ([M + H]+) |
| 56 | 4-(4-carbamoylpiperidin-1-yl)-3-methylphenyl with CONH2 | 501 MS(FAB) m/z: 450 ([M + H]+) |
| 57 | 4-(4-carbamoylpiperidin-1-yl)-3-methylphenyl with CO2H | 36 (Na) MS(FAB) m/z: 451 ([M + H]+) |
| 58 | 4-(4-cyanopiperidin-1-yl)-3-methylphenyl with CO2H | 63 MS(FAB) m/z: 432 ([M + H]+) |
| 59 | 4-cyano-2-methyl-phenyl-(4-cyanopiperidin-1-yl) | 63 MS(FAB) m/z: 414 ([M + H]+) |
| 60 | 3-(4-carbamoylpiperidin-1-yl)-4-methylphenyl with CH2CO2Me | 501 MS(FAB) m/z: 479 ([M + H]+) |
| 61 | 4-(4-carbamoylpiperidin-1-yl)-3-methylphenyl with CH2CONH2 | 501 MS(FAB) m/z: 464 ([M + H]+) |
| 62 | 4-(4-carbamoylpiperidin-1-yl)-3-methylphenyl with CH2CO2H | 36 (Na) MS(FAB) m/z: 465 ([M + H]+) |
| 63 | 4-(4-cyanopiperidin-1-yl)-3-methylphenyl with CH2CN | 63 MS(FAB) m/z: 428 ([M + H]+) |
| 64 | 3-hydroxypyrrolidin-1-yl-(2-methylphenyl) | 501 MS(FAB) m/z: 366 ([M + H]+) |

TABLE 6-continued

| Ex | (structure) | Syn (Sal) Dat |
|---|---|---|
| 65 | pyrrolidine-3,4-diol, N-(2-methylphenyl) | 501 MS(FAB) m/z: 382 ([M + H]+) |
| 66 | pyrrolidine-3,4-diol (stereo*), N-(2-methylphenyl) | 501 MS(ESI) m/z: 382 ([M + H]+) |
| 67 | pyrrolidine-3,4-diol (stereo*), N-(2-methylphenyl) | 501 MS(FAB) m/z: 382 ([M + H]+) |
| 68 | 3-HO2C-pyrrolidine, N-(2-methylphenyl) | 68 MS(FAB) m/z: 394 ([M + H]+) |
| 69 | 3-H2NOC-pyrrolidine, N-(2-methylphenyl) | 167 MS(FAB) m/z: 393 ([M + H]+) |
| 70 | MeO2C-azetidine, N-(2-methylphenyl) | 501 MS(FAB) m/z: 394 ([M + H]+) |
| 71 | HO2C-azetidine, N-(2-methylphenyl) | 36 (Na) MS(ESI) m/z: 380 ([M + H]+) |
| 72 | HO-azepane, N-(2-methylphenyl) | 501 MS(FAB) m/z: 394 ([M + H]+) |
| 73 | diazepane-CONH2, N-(2-methylphenyl) | 501 (HCl) MS(FAB) m/z: 436 ([M + H]+) |
| 74 | morpholine, N-(2-methylphenyl) | 501 MS(FAB) m/z: 366 ([M + H]+) |
| 75 | thiomorpholine, N-(2-methylphenyl) | 501 MS(ESI) m/z: 382 ([M + H]+) |
| 76 | thiomorpholine S-oxide, N-(2-methylphenyl) | 76 MS(FAB) m/z: 398 ([M + H]+) |
| 77 | thiomorpholine S,S-dioxide, N-(2-methylphenyl) | 77 MS(FAB) m/z: 414 ([M + H]+) |
| 78 | thiomorpholine S-oxide N-oxide, N-(2-methylphenyl) | 77 MS(FAB) m/z: 414 ([M + H]+) |
| 79 | N-Boc-piperidine, 4-(2-methylphenyl) | 501 MS(FAB) m/z: 464 ([M + H]+) |
| 80 | piperidine, 4-(2-methylphenyl) | 146 (HCl) MS(FAB) m/z: 364 ([M + H]+) |
| 81 | piperidine-1-CONH2, 4-(2-methylphenyl) | 99 MS(FAB) m/z: 407 ([M + H]+) |

TABLE 6-continued
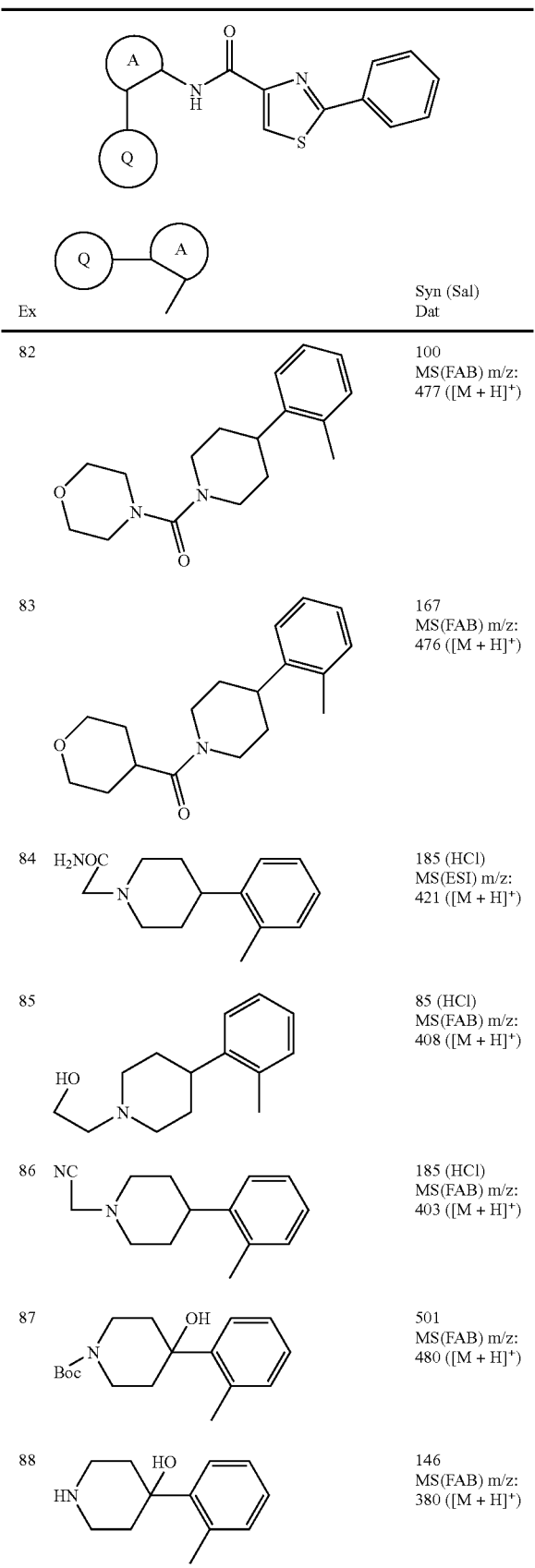
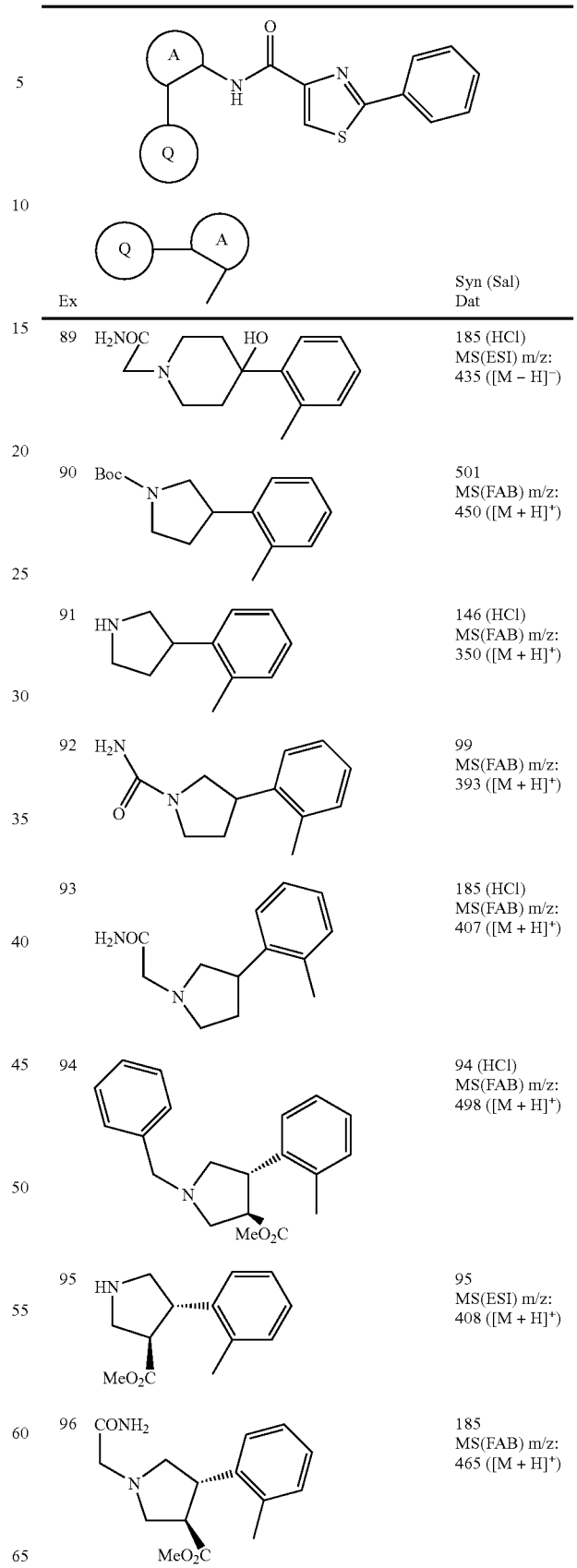

TABLE 6-continued

| Ex | Q substituent | Syn (Sal) Dat |
|----|---|---|
| 97 | Boc-piperidinyl-(2-methylphenyl) | 501 MS(FAB) m/z: 462 ([M + H]+) |
| 98 | HN-tetrahydropyridinyl-(2-methylphenyl) | 146 (HCl) MS(FAB) m/z: 362 ([M + H]+) |
| 99 | H2N-C(O)-tetrahydropyridinyl-(2-methylphenyl) | 99 MS(FAB) m/z: 405 ([M + H]+) |
| 100 | morpholine-C(O)-tetrahydropyridinyl-(2-methylphenyl) | 100 MS(FAB) m/z: 475 ([M + H]+) |
| 101 | H2NOC-CH2-tetrahydropyridinyl-(2-methylphenyl) | 185 (HCl) MS(FAB) m/z: 419 ([M + H]+) |
| 102 | NC-CH2-tetrahydropyridinyl-(2-methylphenyl) | 185 (HCl) MS(FAB) m/z: 401 ([M + H]+) |
| 103 | H2NOC-piperidinyl-(3-methylpyridin-2-yl) | 234 (HCl) MS(ESI) m/z: 408 ([M + H]+) |

TABLE 6-continued

| Ex | Q substituent | Syn (Sal) Dat |
|----|---|---|
| 104 | H2NOC-piperidinyl-(3-methylpyridin-3-yl) | 234 (HCl) MS(ESI) m/z: 408 ([M + H]+) |
| 105 | H2NOC-piperidinyl-(3-methylpyridin-4-yl) | 234 (HCl) MS(ESI) m/z: 408 ([M + H]+) |
| 106 | Ac-N-piperidinyl-OAc-(2-methylphenyl) | 28 MS(FAB) m/z: 464 ([M + H+]) |

TABLE 7

| Ex | Q substituent | Syn (Sal) Dat |
|----|---|---|
| 107 | Me-N-piperazinyl-(2-methylphenyl) | 119 (2HCl) MS(FAB) m/z: 380 ([M + H]+) |
| 108 | oxopiperazinyl-(2-methylphenyl) | 501 (HCl) MS(FAB) m/z: 380 ([M + H]+) |
| 109 | H2NOC-CH2-piperazinyl-(2-methylphenyl) | 501 (2HCl) MS(FAB) m/z: 423 ([M + H]+) |

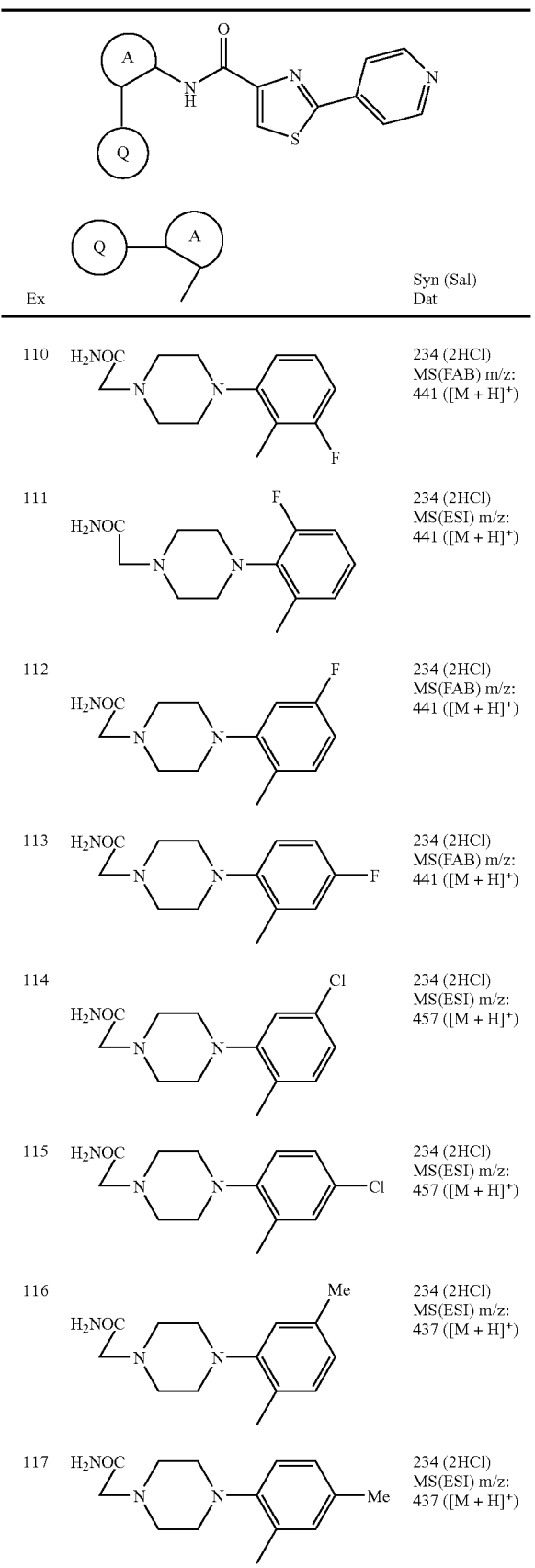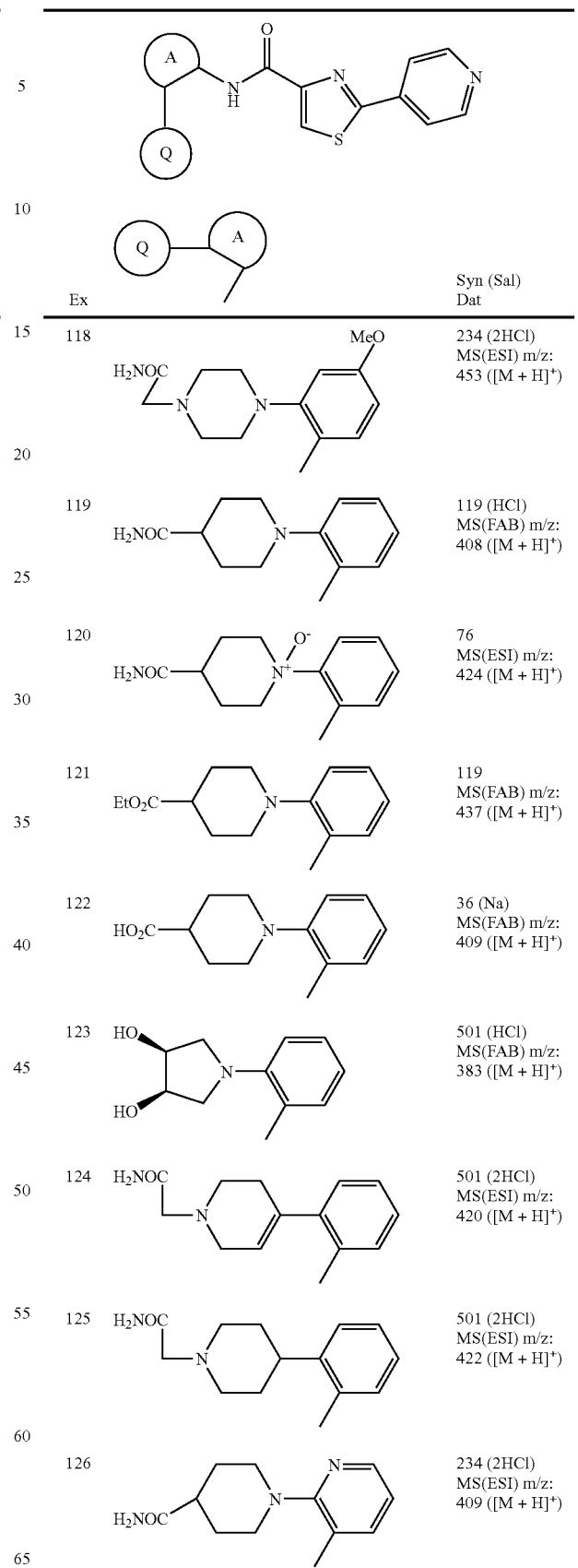

TABLE 7-continued
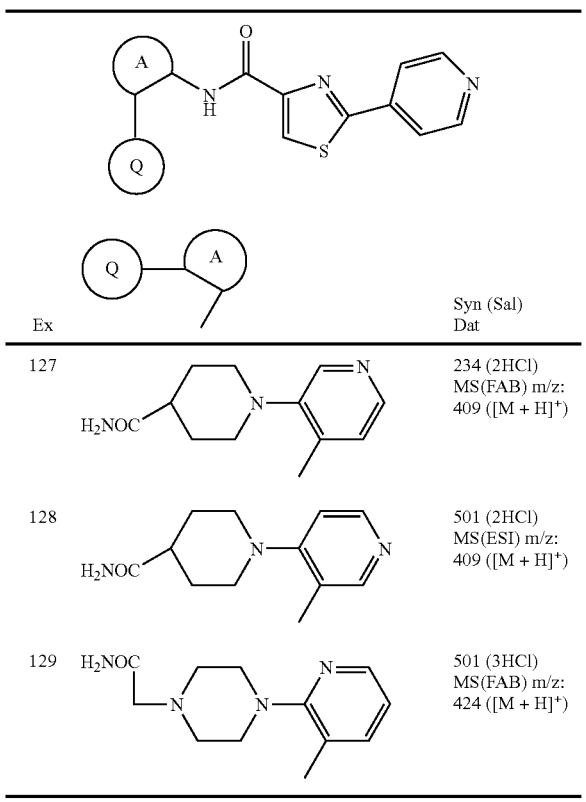
TABLE 8
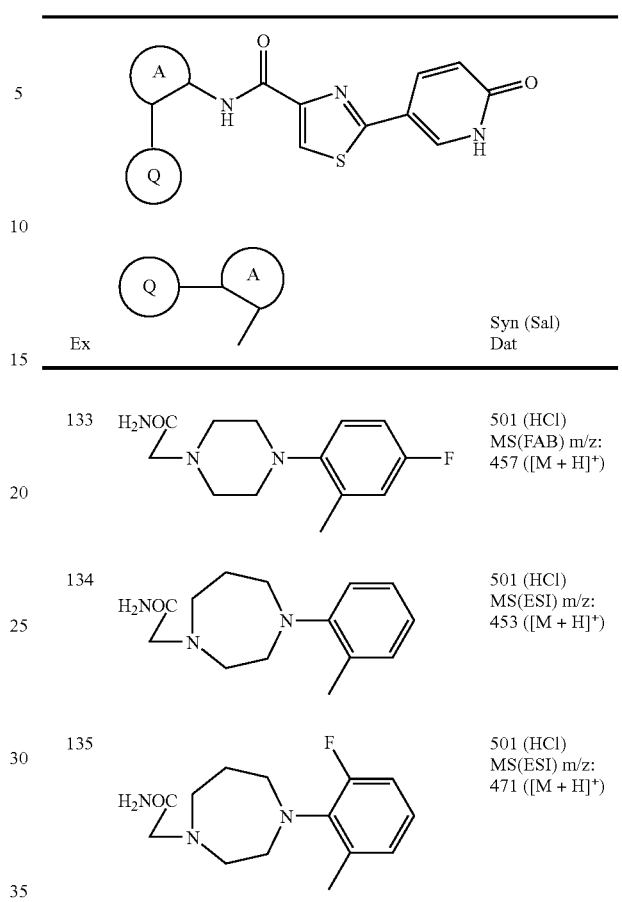

TABLE 9
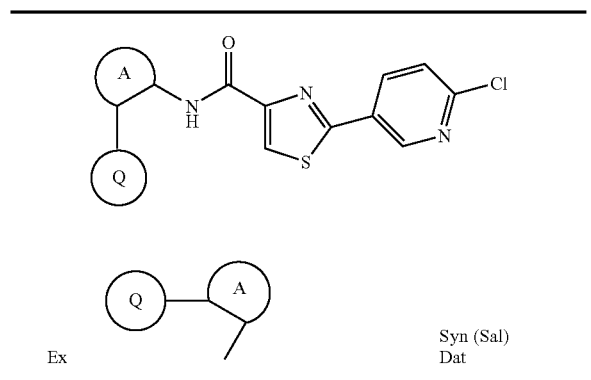
| Ex | 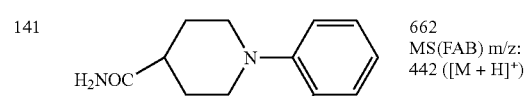 | Syn (Sal) Dat |
|---|---|---|
| 141 | 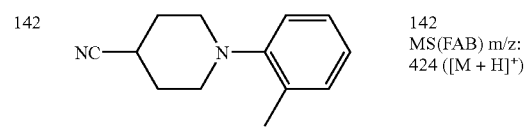 H$_2$NOC— | 662 MS(FAB) m/z: 442 ([M + H]$^+$) |
| 142 | NC— | 142 MS(FAB) m/z: 424 ([M + H]$^+$) |
TABLE 10
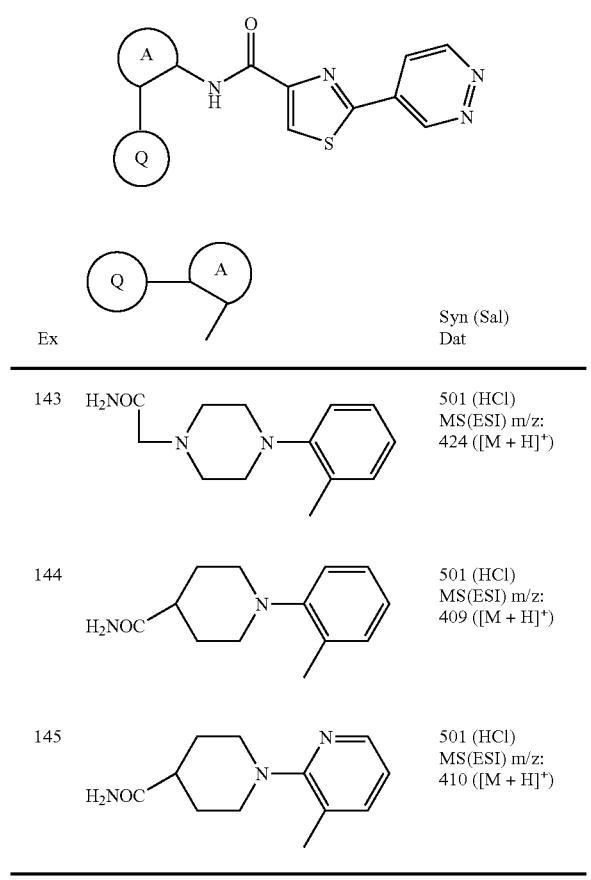
| Ex | | Syn (Sal) Dat |
|---|---|---|
| 143 | H$_2$NOC— | 501 (HCl) MS(ESI) m/z: 424 ([M + H]$^+$) |
| 144 | H$_2$NOC— | 501 (HCl) MS(ESI) m/z: 409 ([M + H]$^+$) |
| 145 | H$_2$NOC— | 501 (HCl) MS(ESI) m/z: 410 ([M + H]$^+$) |
TABLE 11
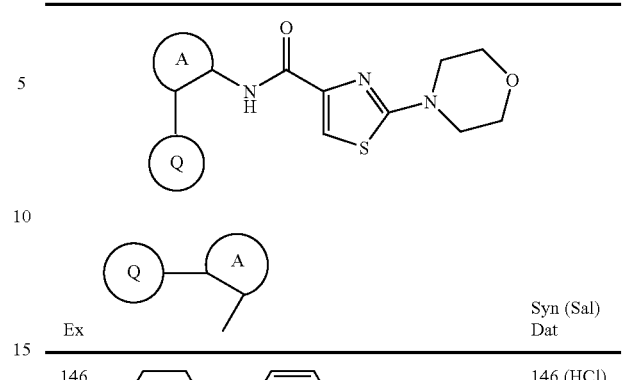
| Ex | | Syn (Sal) Dat |
|---|---|---|
| 146 | 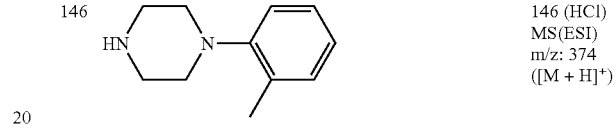 | 146 (HCl) MS(ESI) m/z: 374 ([M + H]$^+$) |
| 147 | 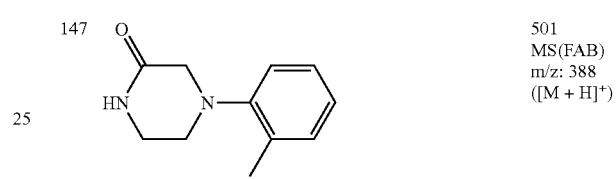 | 501 MS(FAB) m/z: 388 ([M + H]$^+$) |
| 148 | 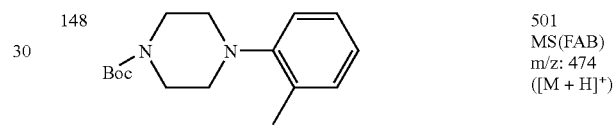 | 501 MS(FAB) m/z: 474 ([M + H]$^+$) |
| 149 | 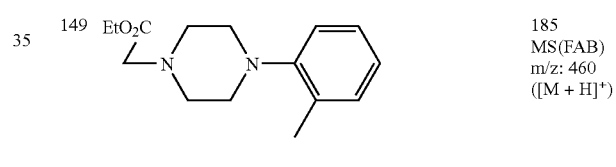 | 185 MS(FAB) m/z: 460 ([M + H]$^+$) |
| 150 | 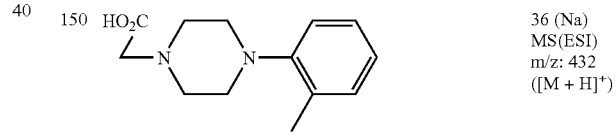 | 36 (Na) MS(ESI) m/z: 432 ([M + H]$^+$) |
| 151 | 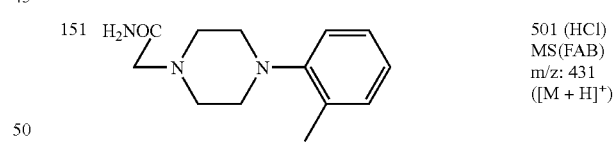 | 501 (HCl) MS(FAB) m/z: 431 ([M + H]$^+$) |
| 152 | 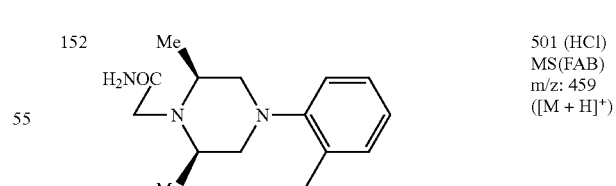 | 501 (HCl) MS(FAB) m/z: 459 ([M + H]$^+$) |
| 153 | 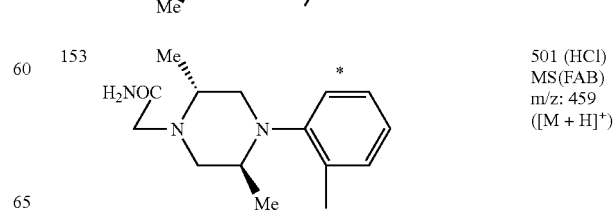 | 501 (HCl) MS(FAB) m/z: 459 ([M + H]$^+$) |

TABLE 11-continued

| Ex | Structure | Syn (Sal) Dat |
|---|---|---|
| 154 | H2NOC-, Me, piperazine with 2-methylphenyl, Me (trans dimethyl piperazine) | 501 (HCl) MS(FAB) m/z: 459 ([M+H]+) |
| 155 | MeO2C, Boc-piperazine with 2-methylphenyl | 501 MS(FAB) m/z: 532 ([M+H]+) |
| 156 | MeO2C, Boc-piperazine with 2-methylphenyl (enantiomer) | 501 MS(FAB) m/z: 532 ([M+H]+) |
| 157 | MeO2C, HN-piperazine with 2-methylphenyl | 146 (HCl) MS(FAB) m/z: 432 ([M+H]+) |
| 158 | MeO2C, HN-piperazine with 2-methylphenyl (enantiomer) | 146 MS(ESI) m/z: 432 ([M+H]+) |
| 159 | MeO2C, Me-N-piperazine with 2-methylphenyl | 191 (HCl) MS(FAB) m/z: 446 ([M+H]+) |
| 160 | HO2C, Me-N-piperazine with 2-methylphenyl | 36 MS(ESI) m/z: 432 ([M+H]+) |
| 161 | H2NOC-CH2, piperazinone with 2-methylphenyl | 501 MS(ESI) m/z: 445 ([M+H]+) |
| 162 | NH2-C(O)-CH(Me)-piperazine with 2-methylphenyl | 185 (HCl) MS(ESI) m/z: 445 ([M+H]+) |
| 163 | Me-NH-C(O)-CH2-piperazine with 2-methylphenyl | 167 (HCl) MS(FAB) m/z: 445 ([M+H]+) |
| 164 | Me2N-C(O)-CH2-piperazine with 2-methylphenyl | 167 (HCl) MS(FAB) m/z: 459 ([M+H]+) |
| 165 | pyrrolidinyl-C(O)-CH2-piperazine with 2-methylphenyl | 167 (HCl) MS(FAB) m/z: 485 ([M+H]+) |
| 166 | 2,5-dihydropyrrolyl-C(O)-CH2-piperazine with 2-methylphenyl | 167 MS(FAB) m/z: 483 ([M+H]+) |
| 167 | morpholinyl-C(O)-CH2-piperazine with 2-methylphenyl | 167 (HCl) MS(FAB) m/z: 501 ([M+H]+) |

TABLE 11-continued

| Ex | Structure | Syn (Sal) Dat |
|---|---|---|
| 168 | N-methylpiperazine-CH2-C(O)-N(piperazine)-2-methylphenyl | 167 (2HCl) MS(FAB) m/z: 514 ([M+H]+) |
| 169 | (3,4-dihydroxypyrrolidin-1-yl)-CH2-C(O)-N(piperazine)-2-methylphenyl | 169 (HCl) MS(FAB) m/z: 517 ([M+H]+) |
| 170 | tetrahydropyran-4-yl-NH-C(O)-CH2-N(piperazine)-2-methylphenyl | 167 (HCl) MS(FAB) m/z: 515 ([M+H]+) |
| 171 | pyrrolidin-1-yl-CH2CH2-C(O)-N(piperazine)-2-methylphenyl | 167 (HCl) MS(FAB) m/z: 499 ([M+H]+) |
| 172 | morpholino-CH2CH2-NH-C(O)-CH2-N(piperazine)-2-methylphenyl | 167 (2HCl) MS(FAB) m/z: 544 ([M+H]+) |
| 173 | morpholino-C(O)-N(piperazine)-2-methylphenyl | 100 MS(FAB) m/z: 487 ([M+H]+) |
| 174 | AcO-CH2-C(O)-N(piperazine)-2-methylphenyl | 28 MS(FAB) m/z: 474 ([M+H]+) |
| 175 | MeO-CH2-C(O)-N(piperazine)-2-methylphenyl | 28 MS(FAB) m/z: 446 ([M+H]+) |
| 176 | morpholino-CH2-C(O)-N(piperazine)-2-methylphenyl | 167 (HCl) MS(FAB) m/z: 501 ([M+H]+) |
| 177 | N-methylpiperazine-CH2-C(O)-N(piperazine)-2-methylphenyl | 167 (2HCl) MS(FAB) m/z: 514 ([M+H]+) |
| 178 | 1,1-dioxothiomorpholino-CH2-C(O)-N(piperazine)-2-methylphenyl | 167 (HCl) MS(ESI) m/z: 549 ([M+H]+) |
| 179 | NC-CH2-N(piperazine)-2-methylphenyl | 185 (HCl) MS(ESI) m/z: 413 ([M+H]+) |

TABLE 11-continued

| Ex | Q / A structure | Syn (Sal) Dat |
|---|---|---|
| 180 | CN-ethyl-piperazine-(2-methylphenyl) | 185 (HCl) MS(FAB) m/z: 427 ([M + H]+) |
| 181 | CONH2-ethyl-piperazine-(2-methylphenyl) | 185 (HCl) MS(ESI) m/z: 445 ([M + H]+) |
| 182 | 4-pyridyl-methyl-piperazine-(2-methylphenyl) | 185 (2HCl) MS(FAB) m/z: 465 ([M + H]+) |
| 183 | oxazol-2-yl-methyl-piperazine-(2-methylphenyl) | 191 (HCl) MS(FAB) m/z: 455 ([M + H]+) |
| 184 | thiazol-4-yl-methyl-piperazine-(2-methylphenyl) | 185 (HCl) MS(FAB) m/z: 471 ([M + H]+) |
| 185 | 1,2,4-oxadiazol-3-yl-methyl-piperazine-(2-methylphenyl) | 185 (HCl) MS(FAB) m/z: 456 ([M + H]+) |
| 186 | 5-oxo-1,2,4-triazol-3-yl-methyl-piperazine-(2-methylphenyl) | 185 (HCl) MS(FAB) m/z: 471 ([M + H]+) |
| 187 | 4-methyl-imidazol-5-yl-methyl-piperazine-(2-methylphenyl) | 185 (2HCl) MS(ESI) m/z: 468 ([M + H]+) |
| 188 | morpholino-ethyl-piperazine-(2-methylphenyl) | 185 (2HCl) MS(FAB) m/z: 487 ([M + H]+) |
| 189 | 1,4-oxazepan-4-yl-ethyl-piperazine-(2-methylphenyl) | 185 (2HCl) MS(FAB) m/z: 501 ([M + H]+) |
| 190 | 1-methyl-pyrrolidin-2-yl-ethyl-piperazine-(2-methylphenyl) | 185 (2HCl) MS(ESI) m/z: 485 ([M + H]+) |
| 191 | tetrahydropyran-4-yl-piperazine-(2-methylphenyl) | 191 (HCl) MS(ESI) m/z: 458 ([M + H]+) |
| 192 | 4-hydroxy-tetrahydrofuran-3-yl-piperazine-(2-methylphenyl) | 192 (HCl) MS(ESI) m/z: 460 ([M + H]+) |
| 193 | H2NOC-methyl-piperazine-(2-fluoro-6-methylphenyl) | 234 (HCl) MS(ESI) m/z: 449 ([M + H]+) |
| 194 | H2NOC-methyl-piperazine-(5-fluoro-2-methylphenyl) | 234 (HCl) MS(FAB) m/z: 449 ([M + H]+) |

TABLE 11-continued

[Structure: A-C(=O)-NH-CH(Q)- attached to thiazole-2-morpholine]

| Ex | Structure | Syn (Sal) Dat |
|---|---|---|
| 195 | H₂NOC-CH₂-piperazine-N-(2-methyl-5-fluorophenyl) | 234 (HCl) MS(FAB) m/z: 449 ([M + H]⁺) |
| 196 | H₂NOC-CH₂-piperazine-N-(2-methyl-3-fluorophenyl) | 501 (HCl) MS(ESI) m/z: 449 ([M + H]⁺) |
| 197 | H₂NOC-CH₂-piperazine-N-(2,3-difluoro-6-methylphenyl) | 501 (HCl) MS(FAB) m/z: 467 ([M + H]⁺) |
| 198 | H₂NOC-CH₂-piperazine-N-(2,4-difluoro-6-methylphenyl) | 501 (HCl) MS(FAB) m/z: 467 ([M + H]⁺) |
| 199 | H₂NOC-CH₂-piperazine-N-(5-chloro-2-methylphenyl) | 234 (HCl) MS(ESI) m/z: 465 ([M + H]⁺) |
| 200 | H₂NOC-CH₂-piperazine-N-(4-chloro-?-methylphenyl) | 234 (HCl) MS(FAB) m/z: 465 ([M + H]⁺) |
| 201 | H₂NOC-CH₂-piperazine-N-(5-bromo-2-methylphenyl) | 501 MS(ESI) m/z: 509 ([M + H]⁺) |
| 202 | H₂NOC-CH₂-piperazine-N-(2,5-dimethylphenyl) | 234 (HCl) MS(FAB) m/z: 445 ([M + H]⁺) |
| 203 | piperazine-N-(2-methyl-4-methylphenyl), other N-CH₂CONH₂ | 501 (HCl) MS(FAB) m/z: 445 ([M + H]⁺) |
| 204 | H₂NOC-CH₂-piperazine-N-(5-methoxy-2-methylphenyl) | 234 (HCl) MS(ESI) m/z: 461 ([M + H]⁺) |
| 205 | H₂NOC-CH₂-piperazine-N-(2-cyano-6-methylphenyl) | 501 (HCl) MS(FAB) m/z: 456 ([M + H]⁺) |
| 206 | H₂NOC-CH₂-piperazine-N-(5-cyano-2-methylphenyl) | 206 (HCl) MS(API) m/z: 456 ([M + H]⁺) |
| 207 | H₂NOC-CH₂-piperazine-N-(3-methyl-5-cyanophenyl) | 501 (HCl) MS(ESI) m/z: 456 ([M + H]⁺) |
| 208 | piperazine-N-(4-methylsulfinyl-2-methylphenyl), other N-CH₂CONH₂ | 501 (HCl) MS(ESI) m/z: 493 ([M + H]⁺) |

TABLE 11-continued

| Ex | Q-A structure | Syn (Sal) Dat |
|---|---|---|
| 209 | 4-[4-(aminocarbonylmethyl)piperazin-1-yl]-3-methylphenyl-SO2Me | 501 (HCl) MS(ESI) m/z: 509 ([M + H]+) |
| 210 | 4-[4-(aminocarbonylmethyl)piperazin-1-yl]-3-methylphenyl-SO2NH2 | 501 (HCl) MS(ESI) m/z: 510 ([M + H]+) |
| 211 | H2NOC-diazabicyclic-N-(2-methylphenyl) | 501 (HCl) MS(FAB) m/z: 443 ([M + H]+) |
| 212 | EtO2C-piperidin-1-yl-(2-methylphenyl) | 501 MS(FAB) m/z: 445 ([M + H]+) |
| 213 | HOOC-piperidin-1-yl-(2-methylphenyl) | 36 (Na) MS(FAB) m/z: 417 ([M + H]+) |
| 214 | H2NOC-piperidin-1-yl-(2-methylphenyl) | 501 MS(FAB) m/z: 416 ([M + H]+) |
| 215 | morpholino-piperidin-1-yl-(2-methylphenyl) | 501 (HCl) MS(FAB) m/z: 458 ([M + H]+) |
| 216 | 3-oxopiperazin-1-yl-piperidin-1-yl-(2-methylphenyl) | 501 (HCl) MS(FAB) m/z: 471 ([M + H]+) |
| 217 | 4-hydroxy-4-(hydroxymethyl)piperidin-1-yl-(2-methylphenyl) | 501 MS(ESI) m/z: 419 ([M + H]+) |
| 218 | 3-carbamoylpyrrolidin-1-yl-(2-methylphenyl) | 501 MS(FAB) m/z: 402 ([M + H]+) |
| 219 | (3,4-dihydroxy)pyrrolidin-1-yl-(2-methylphenyl) | 501 MS(FAB) m/z: 391 ([M + H]+) |
| 220 | (carbamoylmethyl)-1,4-diazepan-1-yl-(2-methylphenyl) | 501 (HCl) MS(ESI) m/z: 445 ([M + H]+) |
| 221 | (carbamoylmethyl)-1,4-diazepan-1-yl-(2-fluoro-6-methylphenyl) | 501 (HCl) MS(ESI) m/z: 463 ([M + H]+) |
| 222 | N-Boc-1,2,3,6-tetrahydropyridin-4-yl-(2-methylphenyl) | 501 MS(ESI) m/z: 471 ([M + H]+) |
| 223 | 1,2,3,6-tetrahydropyridin-4-yl-(3-methylphenyl) | 146 (HCl) MS(ESI) m/z: 371 ([M + H]+) |

TABLE 11-continued
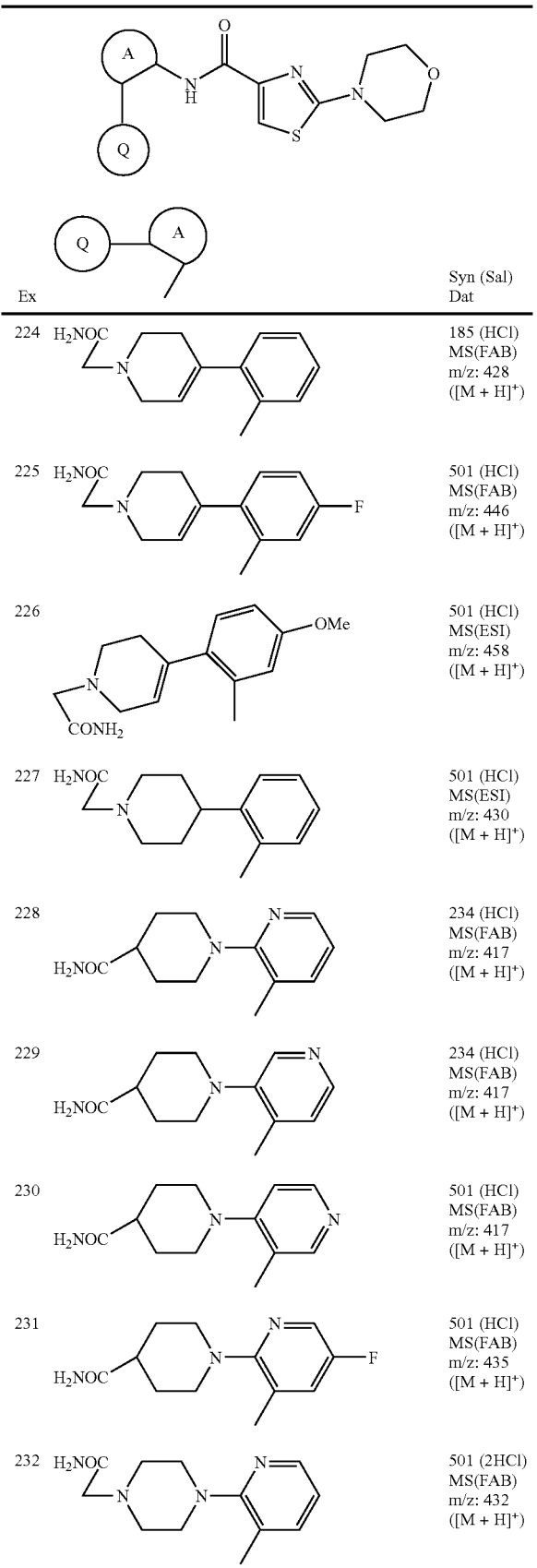
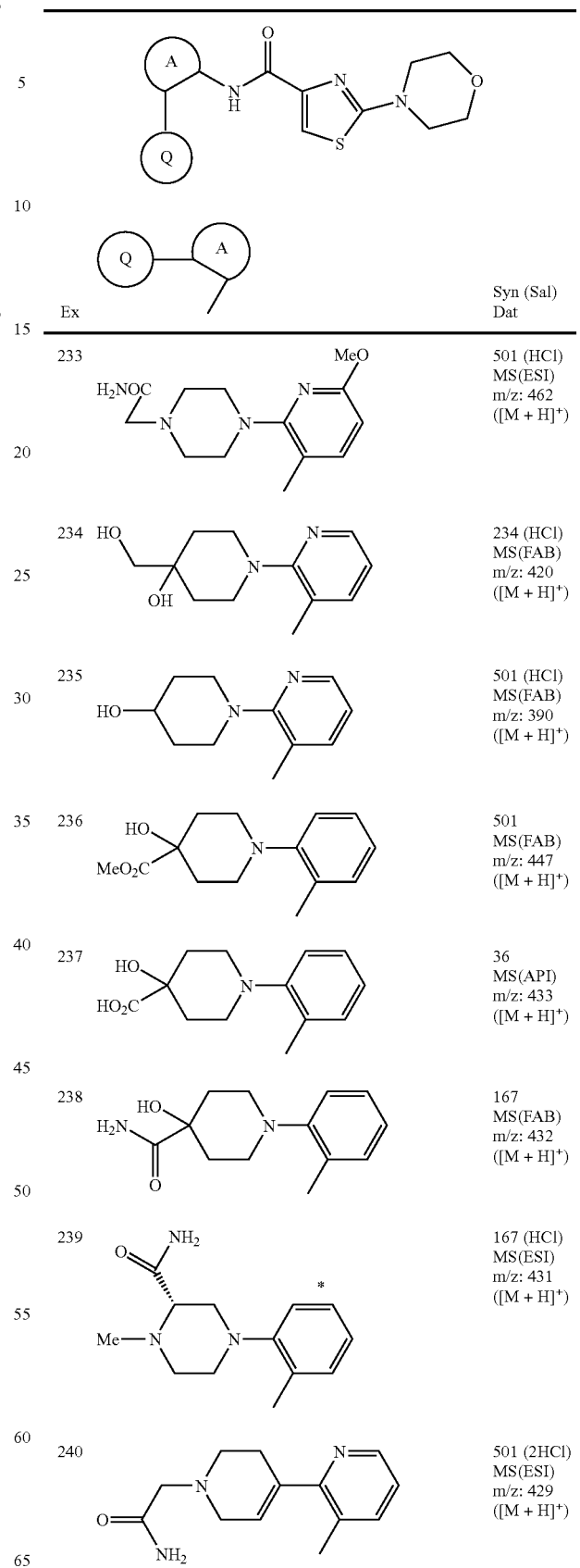

TABLE 11-continued

| Ex | Structure | Syn (Sal) Dat |
|---|---|---|
| 241 | 4-carbamoylpiperidine-N-(6-fluoro-3-methylpyridin-2-yl) | 501 (HCl) MS(FAB) m/z: 435 ([M + H]+) |
| 242 | piperazinyl-acetamide-(6-fluoro-3-methylpyridin-2-yl) | 501 (2HCl) MS(ESI) m/z: 450 ([M + H]+) |
| 243 | piperazinyl-acetamide-(2-cyano-4-fluoro-6-methylphenyl) | 501 (HCl) MS(FAB) m/z: 474 ([M + H]+) |
| 244 | piperazinyl-acetamide-(2-fluoro-4-cyano-6-methylphenyl) | 501 (HCl) MS(ESI) m/z: 474 ([M + H]+) |
| 245 | piperazinyl-acetamide-(5-fluoro-3-methylpyridin-2-yl) | 501 (2HCl) MS(FAB) m/z: 450 ([M + H]+) |
| 246 | azepinyl-acetamide-(2-methylphenyl) | 501 (HCl) MS(FAB) m/z: 442 ([M + H]+) |
| 247 | 4-hydroxy-4-methoxycarbonylpiperidine-(3-methylpyridin-2-yl) | 234 MS(ESI) m/z: 448 ([M + H]+) |
| 248 | 4-hydroxy-4-carbamoylpiperidine-(3-methylpyridin-2-yl) | 36 → 167 (HCl) MS(ESI) m/z: 431 ([M − H]−) |
| 249 | piperazinyl-acetamide-(6-cyanomethyl-3-methylpyridin-2-yl) | 501 MS(ESI) m/z: 471 ([M + H]+) |
| 250 | diazepanyl-acetamide-(3-methylpyridin-2-yl) | 501 MS(FAB) m/z: 446 ([M + H]+) |
| 251 | N-methyl-N-carbamoylmethyl-pyrrolidinyl-(2-methylphenyl) | 723 MS(ESI) m/z: 445 ([M + H]+) |
| 252 | N-methyl-N-carbamoylmethyl-piperidinyl-(2-methylphenyl) | 723 (HCl) MS(ESI) m/z: 459 ([M + H]+) |
| 253 | 4-methoxycarbonyl-4-hydroxy-piperidine-(6-fluoro-3-methylpyridin-2-yl) | 501 MS(ESI) m/z: 466 ([M + H]+) |

TABLE 11-continued

| Ex | Structure | Syn (Sal) Dat |
|---|---|---|
| 254 | CO2Me, HO-piperidine-N-pyridine(3-Me,5-F) | 501 MS(FAB) m/z: 466 ([M + H]+) |
| 255 | Me-N(CH2C(O)NH2)-piperidine-N-phenyl(2-Me) | 723 MS(FAB) m/z: 459 ([M + H]+) |
| 256 | CO2Et-piperidine-N-pyridine(3-Me) | 501 MS(FAB) m/z: 446 ([M + H]+) |
| 257 | CO2Et-piperidine-N-phenyl(2-Me,4-F) | 501 MS(FAB) m/z: 463 ([M + H]+) |
| 258 | O−OC-piperidine-N-pyridine(3-Me) | 36 (Na) MS(FAB) m/z: 418 ([M + H]+) |
| 259 | CO2H-piperidine-N-phenyl(2-Me,4-F) | 36 MS(FAB) m/z: 435 ([M + H]+) |
| 260 | Me-N(CH2C(O)NH2)-azepane-N-phenyl(2-Me) | 723 (HCl) MS(ESI) m/z: 473 ([M + H]+) |
| 261 | H2NC(O)CH2-piperazine-N-phenyl(2-Me,4-OMe) | 501 MS(ESI) m/z: 461 ([M + H]+) |
| 262 | CO2H, OH-piperidine-N-pyridine(3-Me,6-F) | 36 MS(FAB) m/z: 452 ([M + H]+) |
| 263 | CO2H, OH-piperidine-N-pyridine(3-Me,5-F) | 36 MS(ESI) m/z: 450 ([M − H]−) |
| 264 | NH2C(O), HO-piperidine-N-pyridine(3-Me,6-F) | 167 MS(ESI) m/z: 451 ([M + H]+) |
| 265 | NH2C(O), HO-piperidine-N-pyridine(3-Me,5-F) | 167 MS(ESI) m/z: 451 ([M + H]+) |
| 266 | MeSO2NHC(O)-piperidine-N-phenyl(2-Me,4-F) | 266 MS(FAB) m/z: 512 ([M + H]+) |
| 267 | HOCH2, HO-piperidine-N-pyridine(3-Me,6-F) | 267 MS(FAB) m/z: 438 ([M + H]+) |
| 268 | HOCH2, HO-piperidine-N-pyridine(3-Me,5-F) | 267 MS(FAB) m/z: 438 ([M + H]+) |
| 269 | (3S)-HO-pyrrolidine-N-phenyl | 501 MS(FAB) m/z: 375 ([M + H]+) |

TABLE 11-continued

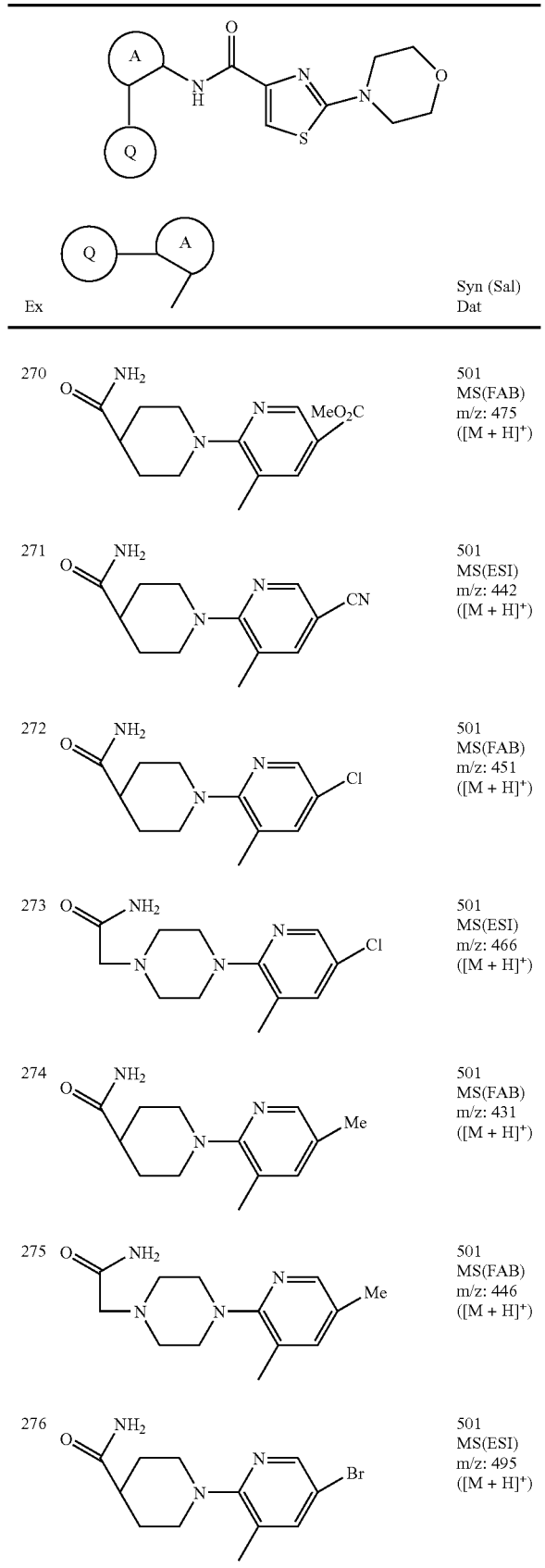
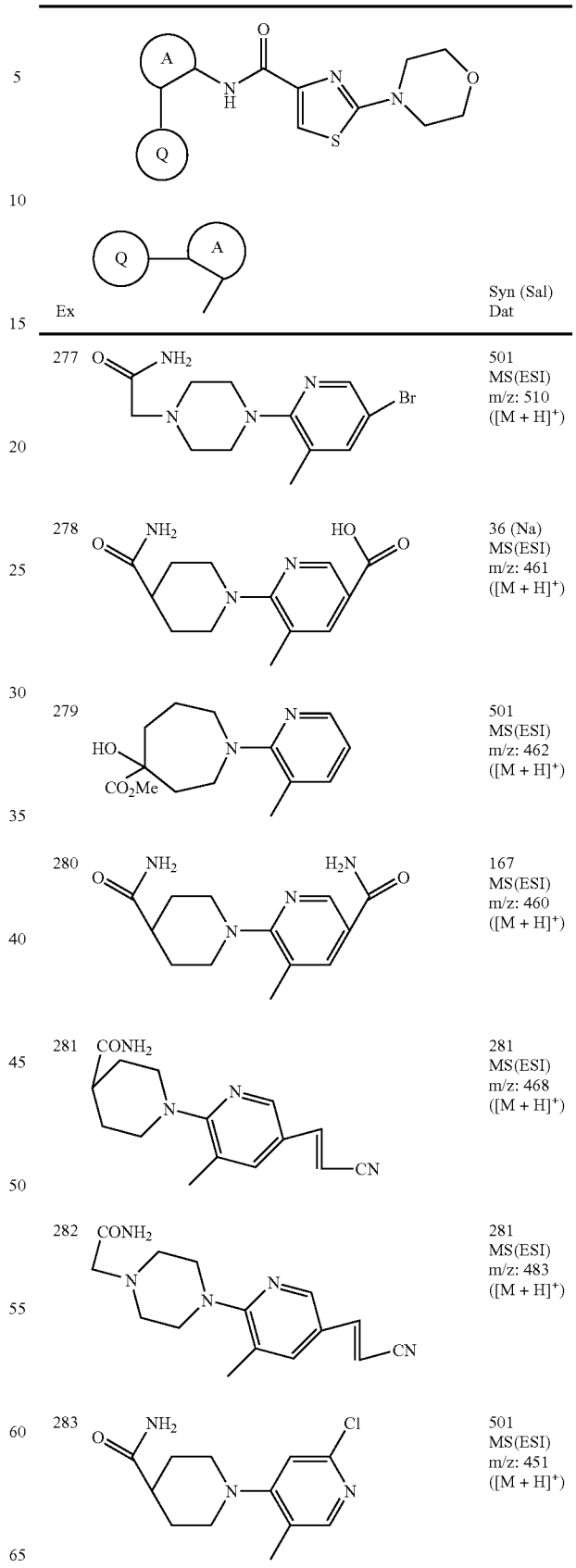

| Ex | | Syn (Sal) Dat |
|---|---|---|
| 270 | 4-carbamoylpiperidine, 5-(methoxycarbonyl)-3-methylpyridine | 501 MS(FAB) m/z: 475 ([M + H]$^+$) |
| 271 | 4-carbamoylpiperidine, 5-cyano-3-methylpyridine | 501 MS(ESI) m/z: 442 ([M + H]$^+$) |
| 272 | 4-carbamoylpiperidine, 5-chloro-3-methylpyridine | 501 MS(FAB) m/z: 451 ([M + H]$^+$) |
| 273 | piperazinyl-acetamide, 5-chloro-3-methylpyridine | 501 MS(ESI) m/z: 466 ([M + H]$^+$) |
| 274 | 4-carbamoylpiperidine, 3,5-dimethylpyridine | 501 MS(FAB) m/z: 431 ([M + H]$^+$) |
| 275 | piperazinyl-acetamide, 3,5-dimethylpyridine | 501 MS(FAB) m/z: 446 ([M + H]$^+$) |
| 276 | 4-carbamoylpiperidine, 5-bromo-3-methylpyridine | 501 MS(ESI) m/z: 495 ([M + H]$^+$) |
| 277 | piperazinyl-acetamide, 5-bromo-3-methylpyridine | 501 MS(ESI) m/z: 510 ([M + H]$^+$) |
| 278 | 4-carbamoylpiperidine, 5-carboxypyridine | 36 (Na) MS(ESI) m/z: 461 ([M + H]$^+$) |
| 279 | 4-hydroxy-4-(methoxycarbonyl)azepane, 3-methylpyridine | 501 MS(ESI) m/z: 462 ([M + H]$^+$) |
| 280 | 4-carbamoylpiperidine, 5-carbamoyl-3-methylpyridine | 167 MS(ESI) m/z: 460 ([M + H]$^+$) |
| 281 | 3-carbamoylpiperidine, 5-(2-cyanovinyl)-3-methylpyridine | 281 MS(ESI) m/z: 468 ([M + H]$^+$) |
| 282 | piperazinyl-acetamide, 5-(2-cyanovinyl)-3-methylpyridine | 281 MS(ESI) m/z: 483 ([M + H]$^+$) |
| 283 | 4-carbamoylpiperidine, 2-chloro-5-methylpyridin-4-yl | 501 MS(ESI) m/z: 451 ([M + H]$^+$) |

TABLE 11-continued

| Ex | | Syn (Sal) Dat |
|---|---|---|
| 284 | piperazine-CH2-C(O)NH2 / 4-bromo-2-methylphenyl | 501 MS(ESI) m/z: 509 ([M + H]+) |
| 285 | 4-carbamoylpiperidine / 2-methoxy-5-methylpyridin-4-yl | 501 MS(ESI) m/z: 447 ([M + H]+) |
| 286 | piperazine-CH2-C(O)NH2 / 5-(2-cyanoethyl)-3-methylpyridin-2-yl | 287 MS(ESI) m/z: 485 ([M + H]+) |
| 287 | 4-carbamoylpiperidine / 5-(2-cyanoethyl)-3-methylpyridin-2-yl | 287 MS(ESI) m/z: 470 ([M + H]+) |
| 288 | piperazine-CH2-C(O)NH2 / 5-vinyl-3-methylphenyl | 288 MS(ESI) m/z: 457 ([M + H]+) |
| 289 | 4-ethoxycarbonylpiperidine / 4-methoxy-2-methylphenyl | 501 MS(ESI) m/z: 475 ([M + H]+) |
| 290 | 4-ethoxycarbonylpiperidine / 4-chloro-2-methylphenyl | 501 MS(ESI) m/z: 479 ([M + H]+) |

TABLE 11-continued

| Ex | | Syn (Sal) Dat |
|---|---|---|
| 291 | (3,4-dihydroxy pyrrolidinyl with hydroxymethyl) / 3-methylpyridin-2-yl | 234 MS(ESI) m/z: 406 ([M + H]+) |
| 292 | piperazine-CH2-C(O)NH2 / 3-methyl-4-ethylphenyl | 287 MS(ESI) m/z: 459 ([M + H]+) |
| 293 | piperazine-CH2-C(O)NH2 / 4-methoxymethyl-2-methylphenyl | 293 MS(ESI) m/z: 475 ([M + H]+) |
| 294 | 4-carbamoylpiperidine / 1-methyl-5-methyl-2-oxo-pyridin-4-yl | 501 MS(ESI) m/z: 447 ([M + H]+) |
| 295 | (hydroxymethyl-hydroxy-cycloheptyl) / 3-methylpyridin-2-yl | 267 MS(ESI) m/z: 434 ([M + H]+) |
| 296 | 3-carbamoylpiperidine / 5-hydroxymethyl-3-methylpyridin-2-yl | 267 MS(ESI) m/z: 447 ([M + H]+) |
| 297 | piperazine-CH2-C(O)NH2 / 2-cyanomethyl-4-chloro-6-methyl-3-fluorophenyl | 501 MS(ESI) m/z: 522 ([M + H]+) |

TABLE 11-continued

| Ex | Q | A | Syn (Sal) Dat |
|---|---|---|---|
| 298 | (N-methylpiperazine carbonyl) | piperidine-N-(3-methylpyridin-2-yl) | 167 MS(ESI) m/z: 500 ([M + H]⁺) |
| 299 | 4-CO₂H piperidine | N-(4-methoxy-2-methylphenyl) | 36 MS(ESI) m/z: 445 ([M + H]⁺) |
| 300 | 4-CO₂H piperidine | N-(4-chloro-2-methylphenyl) | 36 MS(ESI) m/z: 451 ([M + H]⁺) |
| 301 | 1-(carbamoylmethyl)piperazin-4-yl | 6-methyl-2,3-dihydrobenzofuran-5-yl | 501 MS(ESI) m/z: 473 ([M + H]⁺) |
| 302 | 1-(carbamoylmethyl)piperazin-4-yl | 4-trifluoromethoxy-2-methylphenyl | 501 MS(FAB) m/z: 515 ([M + H]⁺) |

TABLE 11-continued

| Ex | Q-A | Syn (Sal) Dat |
|---|---|---|
| 303 | 4-hydroxy-4-carboxy-azepan-1-yl / 3-methylpyridin-2-yl | 36 MS(ESI) m/z: 448 ([M + H]⁺) |

TABLE 12

| Ex | Q | A | Syn (Sal) Dat |
|---|---|---|---|
| 304 | 4-methylpiperazin-1-yl | 2-methylphenyl | 501 (HCl) MS(FAB) m/z: 3386 ([M + H]⁺) |
| 305 | 3-oxopiperazin-1-yl | 2-methylphenyl | 501 MS(FAB) m/z: 386 ([M + H]⁺) |
| 306 | 4-(carbamoylmethyl)piperazin-1-yl | 2-methylphenyl | 356 (HCl) MS(FAB) m/z: 429 ([M + H]⁺) |
| 307 | 4-carbamoylpiperidin-1-yl | 2-methylphenyl | 501 (HCl) MS(FAB) m/z: 414 ([M + H]⁺) |
| 308 | 4-ethoxycarbonylpiperidin-1-yl | 2-methylphenyl | 501 MS(FAB) m/z: 443 ([M + H]⁺) |

TABLE 12-continued

| Ex | | Syn (Sal) Dat |
|---|---|---|
| 309 | HO₂C—[piperidine]—N—[2-methylphenyl] | 36 (Na) MS(FAB) m/z: 415 ([M + H]⁺) |

TABLE 13

| Ex | | Syn (Sal) Dat |
|---|---|---|
| 310 | H₂NOC—CH₂—[piperazine]—N—[2-methylphenyl] | 501 (HCl) MS(ESI) m/z: 445 ([M + H]⁺) |
| 311 | H₂NOC—CH₂—[piperazine]—[2-F, 3-methylphenyl] | 501 (HCl) MS(FAB) m/z: 463 ([M + H]⁺) |
| 312 | H₂NOC—CH₂—[piperazine]—[5-F, 2-methylphenyl] | 501 (HCl) MS(FAB) m/z: 463 ([M + H]⁺) |
| 313 | H₂NOC—CH₂—[piperazine]—[4-F, 2-methylphenyl] | 501 (HCl) MS(FAB) m/z: 463 ([M + H]⁺) |

TABLE 13-continued

| Ex | | Syn (Sal) Dat |
|---|---|---|
| 314 | H₂NOC—CH₂—[piperazine]—[2,4-diF, 6-methylphenyl] | 501 (HCl) MS(FAB) m/z: 481 ([M + H]⁺) |
| 315 | H₂NOC—CH₂—[piperazine]—[2,3-diF, 6-methylphenyl] | 501 (HCl) MS(FAB) m/z: 481 ([M + H]⁺) |
| 316 | H₂NOC—CH₂—[piperazine]—[4-CN, 2-methylphenyl] | 501 (HCl) MS(ESI) m/z: 470 ([M + H]⁺) |
| 317 | [piperazine]—[4-S(O)Me, 2-methylphenyl]—CH₂CONH₂ | 501 (HCl) MS(ESI) m/z: 507 ([M + H]⁺) |
| 318 | [piperazine]—[4-SO₂Me, 3-methylphenyl]—CH₂CONH₂ | 501 (HCl) MS(ESI) m/z: 523 ([M + H]⁺) |
| 319 | [piperazine]—[4-SO₂NH₂, 3-methylphenyl]—CH₂CONH₂ | 501 (HCl) MS(ESI) m/z: 524 ([M + H]⁺) |

TABLE 13-continued

| Ex | Structure (Q-A) | Syn (Sal) Dat |
|---|---|---|
| 320 | 1,2,4-oxadiazol-3-ylmethyl-piperazine-(2-methylphenyl) | 501 (HCl) MS(ESI) m/z: 470 ([M+H]⁺) |
| 321 | (carbamoylmethyl)-1,4-diazepane-(2-methylphenyl) | 501 (HCl) MS(FAB) m/z: 459 ([M+H]⁺) |
| 322 | (carbamoylmethyl)-1,4-diazepane-(2-fluoro-6-methylphenyl) | 501 (HCl) MS(ESI) m/z: 477 ([M+H]⁺) |
| 323 | 4-carbamoylpiperidine-(2-methylphenyl) | 501 MS(FAB) m/z: 430 ([M+H]⁺) |
| 324 | 4-carbamoyl-1,2,3,6-tetrahydropyridine-(2-methylphenyl) | 501 (2HCl) MS(FAB) m/z: 442 ([M+H]⁺) |
| 325 | 4-carbamoylpiperidine-(2-methylphenyl) | 501 (2HCl) MS(FAB) m/z: 444 ([M+H]⁺) |
| 326 | 4-carbamoyl-1,2,3,6-tetrahydropyridine-(4-fluoro-2-methylphenyl) | 501 (HCl) MS(ESI) m/z: 460 ([M+H]⁺) |
| 327 | morpholinocarbonyl-tetrahydropyridine-(4-fluoro-2-methylphenyl) | 501 (HCl) MS(FAB) m/z: 516 ([M+H]⁺) |
| 328 | 4-carbamoylpiperidine-(3-methylpyridin-2-yl) | 501 (2HCl) MS(FAB) m/z: 431 ([M+H]⁺) |
| 329 | 4-carbamoylpiperidine-(3-methylpyridin-4-yl) | 501 MS(ESI) m/z: 431 ([M+H]⁺) |
| 330 | 4-carbamoylpiperidine-(5-fluoro-3-methylpyridin-2-yl) | 501 (HCl) MS(ESI) m/z: 449 ([M+H]⁺) |
| 331 | carbamoylmethyl-piperazine-(3-methylpyridin-2-yl) | 501 (2HCl) MS(FAB) m/z: 446 ([M+H]⁺) |
| 332 | carbamoylmethyl-piperazine-(6-methoxy-3-methylpyridin-2-yl) | 501 (HCl) MS(ESI) m/z: 476 ([M+H]⁺) |
| 333 | 4-hydroxy-4-(hydroxymethyl)piperidine-(3-methylpyridin-2-yl) | 501 MS(FAB) m/z: 434 ([M+H]⁺) |
| 334 | 3-(ethoxycarbonyl)piperidine-(2-methylphenyl) | 501 MS(FAB) m/z: 459 ([M+H]⁺) |

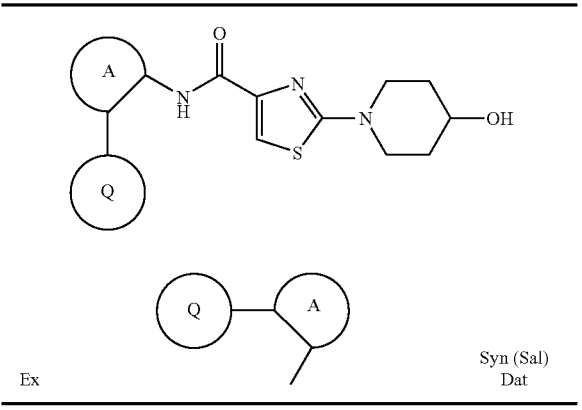

TABLE 15

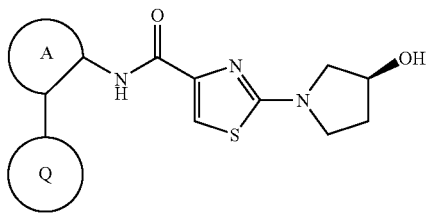

| Ex | Q-A | Syn (Sal) Dat |
|---|---|---|
| 350 | H2NOC-CH2-N(piperazine)N-(2-methylphenyl) | 501 (2HCl) MS(ESI) m/z: 431 ([M + H]+) |
| 351 | H2NOC-CH2-N(piperazine)N-(2-fluoro-6-methylphenyl) | 501 (2HCl) MS(ESI) m/z: 449 ([M + H]+) |
| 352 | H2NOC-CH2-N(tetrahydropyridine)-(2-methylphenyl) | 501 (HCl) MS(ESI) m/z: 428 ([M + H]+) |

TABLE 16

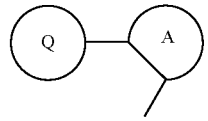

| Ex | Q-A | Syn (Sal) Dat |
|---|---|---|
| 353 | H2NOC-CH2-N(piperazine)N-(2-fluoro-6-methylphenyl) | 501 (HCl) MS(FAB) m/z: 505 ([M + H]+) |
| 354 | H2NOC-CH2-N(tetrahydropyridine)-(2-methylphenyl) | 501 (HCl) MS(FAB) m/z: 484 ([M + H]+) |

TABLE 17

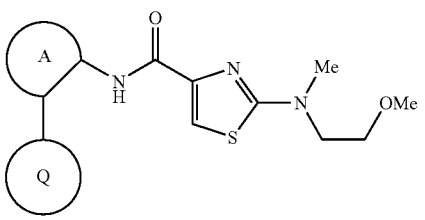

| Ex | Q-A | Syn (Sal) Dat |
|---|---|---|
| 355 | 3-oxopiperazinyl-(2-methylphenyl) | 501 MS(FAB) m/z: 390 ([M + H]+) |
| 356 | H2NOC-CH2-N(piperazine)N-(2-methylphenyl) | 356 (HCl) MS(FAB) m/z: 433 ([M + H]+) |
| 357 | H2NOC-CH2-N(piperazine)N-(2-fluoro-6-methylphenyl) | 501 (HCl) MS(FAB) m/z: 451 ([M + H]+) |
| 358 | H2NOC-CH2-N(piperazine)N-(5-fluoro-2-methylphenyl) | 501 (HCl) MS(ESI) m/z: 451 ([M + H]+) |
| 359 | H2NOC-CH2-N(piperazine)N-(4-fluoro-2-methylphenyl) | 501 (HCl) MS(ESI) m/z: 451 ([M + H]+) |
| 360 | H2NOC-CH2-N(piperazine)N-(2,4-difluoro-6-methylphenyl) | 501 (HCl) MS(FAB) m/z: 469 ([M + H]+) |
| 361 | H2NOC-CH2-N(piperazine)N-(2,3-difluoro-6-methylphenyl) | 501 (HCl) MS(FAB) m/z: 469 ([M + H]+) |

TABLE 17-continued
| Ex | | Syn (Sal) Dat |
|---|---|---|
| 362 | 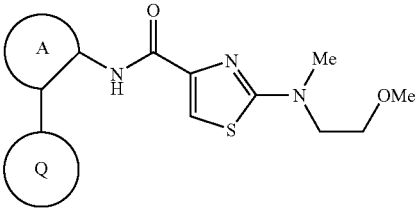 | 501 MS(FAB) m/z: 513 ([M + H]+) |
| 363 | 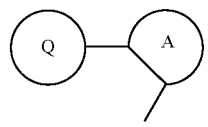 | 501 (HCl) MS(FAB) m/z: 458 ([M + H]+) |
| 364 | 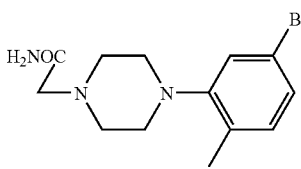 | 206 (HCl) MS(FAB) m/z: 458 ([M + H]+) |
| 365 | 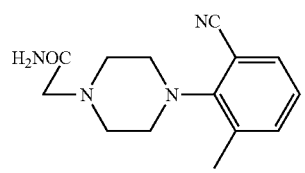 | 501 (HCl) MS(FAB) m/z: 458 ([M + H]+) |
| 366 | 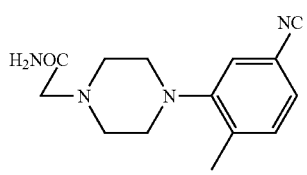 | 501 (HCl) MS(FAB) m/z: 476 ([M + H]+) |
| 367 | 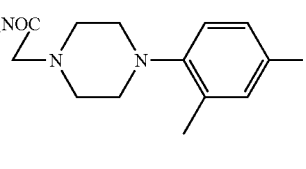 | 234 MS(FAB) m/z: 491 ([M + H]+) |
| 368 | 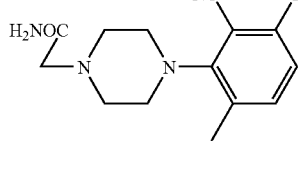 | 36 MS(ESI) m/z: 478 ([M + H]+) |
| 369 | 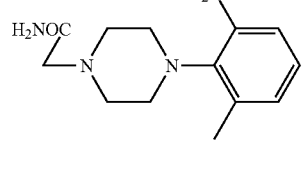 | 501 (HCl) MS(FAB) m/z: 458 ([M + H]+) |
| 370 | 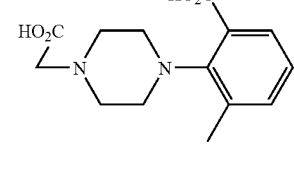 | 501 MS(ESI) m/z: 418 ([M + H]+) |
| 371 | 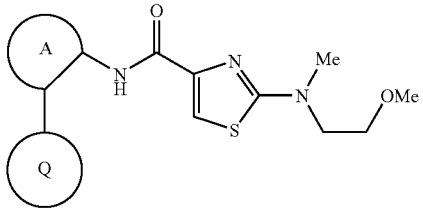 | 501 MS(FAB) m/z: 447 ([M + H]+) |
| 372 | 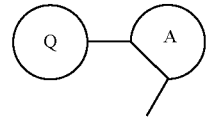 | 36 MS(FAB) m/z: 419 ([M + H]+) |
| 373 | 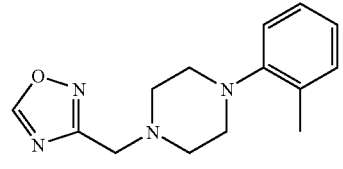 | 501 (HCl) MS(FAB) m/z: 430 ([M + H]+) |
| 374 | 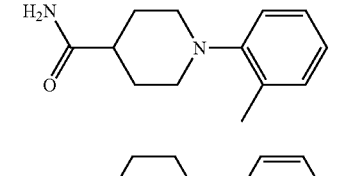 | 501 (HCl) MS(ESI) m/z: 448 ([M + H]+) |
| 375 | 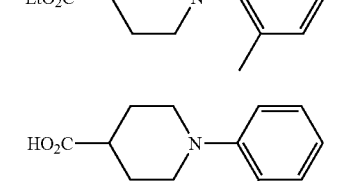 | 501 (HCl) MS(FAB) m/z: 448 ([M + H]+) |
| 376 | 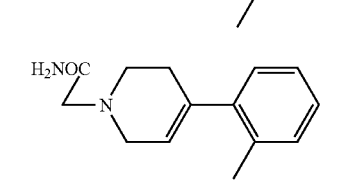 | 501 (HCl) MS(FAB) m/z: 460 ([M + H]+) |

TABLE 17-continued

| Ex | | Syn (Sal) Dat |
|---|---|---|
| 377 | [structure: 4-methoxy-2-methylphenyl tetrahydropyridine N-CH2CONH2] | 501 (HCl) MS(FAB) m/z: 460 ([M + H]+) |
| 378 | [structure: H2NOC-CH2-piperidine-4-(2-methylphenyl)] | 501 (HCl) MS(FAB) m/z: 432 ([M + H]+) |
| 379 | [structure: H2NOC-CH2-piperidine-4-(4-fluoro-2-methylphenyl)] | 501 (HCl) MS(FAB) m/z: 450 ([M + H]+) |
| 380 | [structure: H2NOC-piperidine-N-(3-methylpyridin-2-yl)] | 501 (HCl) MS(FAB) m/z: 419 ([M + H]+) |
| 381 | [structure: H2NOC-piperidine-N-(5-fluoro-3-methylpyridin-2-yl)] | 501 (HCl) MS(FAB) m/z: 437 ([M + H]+) |
| 382 | [structure: H2NOC-CH2-piperazine-N-(3-methylpyridin-2-yl)] | 501 (HCl) MS(FAB) m/z: 434 ([M + H]+) |
| 383 | [structure: H2NOC-CH2-piperazine-N-(6-methoxy-3-methylpyridin-2-yl)] | 501 (HCl) MS(FAB) m/z: 464 ([M + H]+) |
| 384 | [structure: H2NOC-piperidine-N-(5-methylpyrimidin-4-yl)] | 234 (HCl) MS(FAB) m/z: 420 ([M + H]+) |

TABLE 17-continued

| Ex | | Syn (Sal) Dat |
|---|---|---|
| 385 | [structure: HO-piperidine-N-(3-methylpyridin-2-yl)] | 501 (HCl) MS(FAB) m/z: 392 ([M + H]+) |
| 386 | [structure: H2NCOCH2-piperidine-4-OH-(3-methylpyridin-2-yl)] | 234 MS(ESI) m/z: 449 ([M + H]+) |
| 387 | [structure: H2NCOCH2-piperazine-N-(5-fluoro-3-methylpyridin-2-yl)] | 234 (2HCl) MS(FAB) m/z: 452 ([M + H]+) |
| 388 | [structure: H2NCOCH2-tetrahydropyridine-(3-methylpyridin-2-yl)] | 234 (2HCl) MS(ESI) m/z: 431 ([M + H]+) |
| 389 | [structure: (S)-2-(hydroxymethyl)pyrrolidine-N-(2-methylphenyl)] * | 501 (HCl) MS(FAB) m/z: 391 ([M + H]+) |
| 390 | [structure: H2NOC-piperidine-N-(methoxycarbonyl-methylphenyl)] | 501 MS(FAB) m/z: 476 ([M + H]+) |
| 391 | [structure: H2NOC-piperidine-N-(carboxy-methylphenyl)] | 36 MS(ESI) m/z: 462 ([M + H]+) |

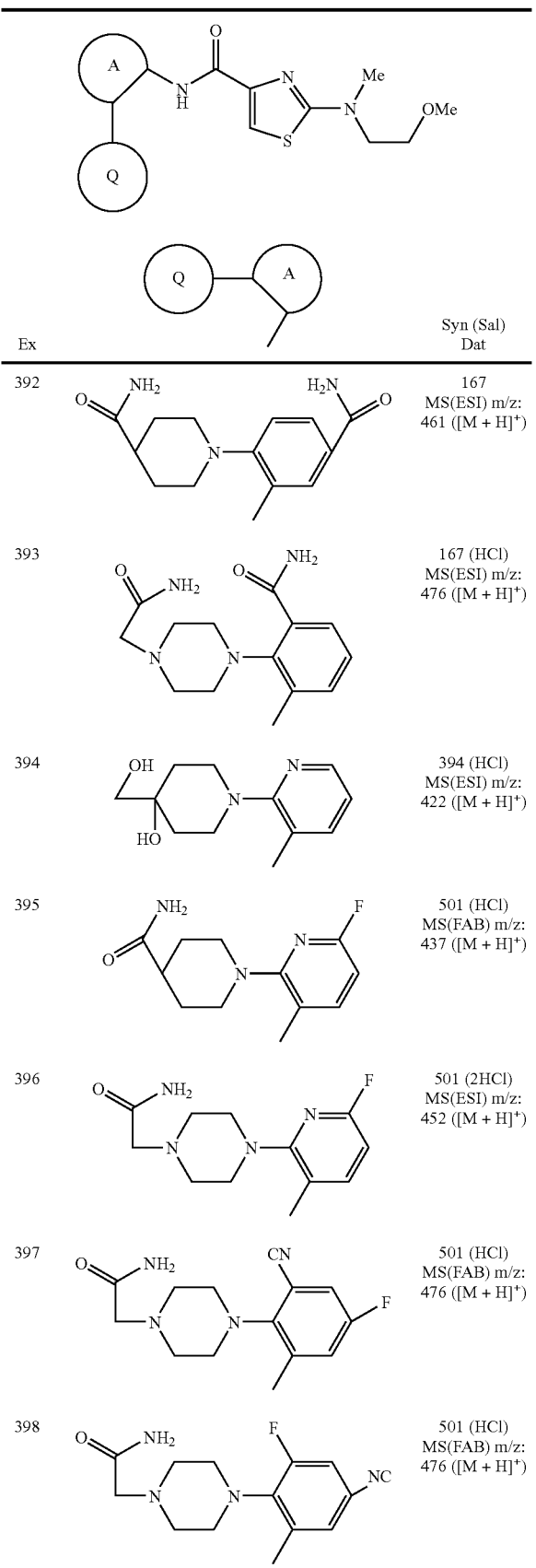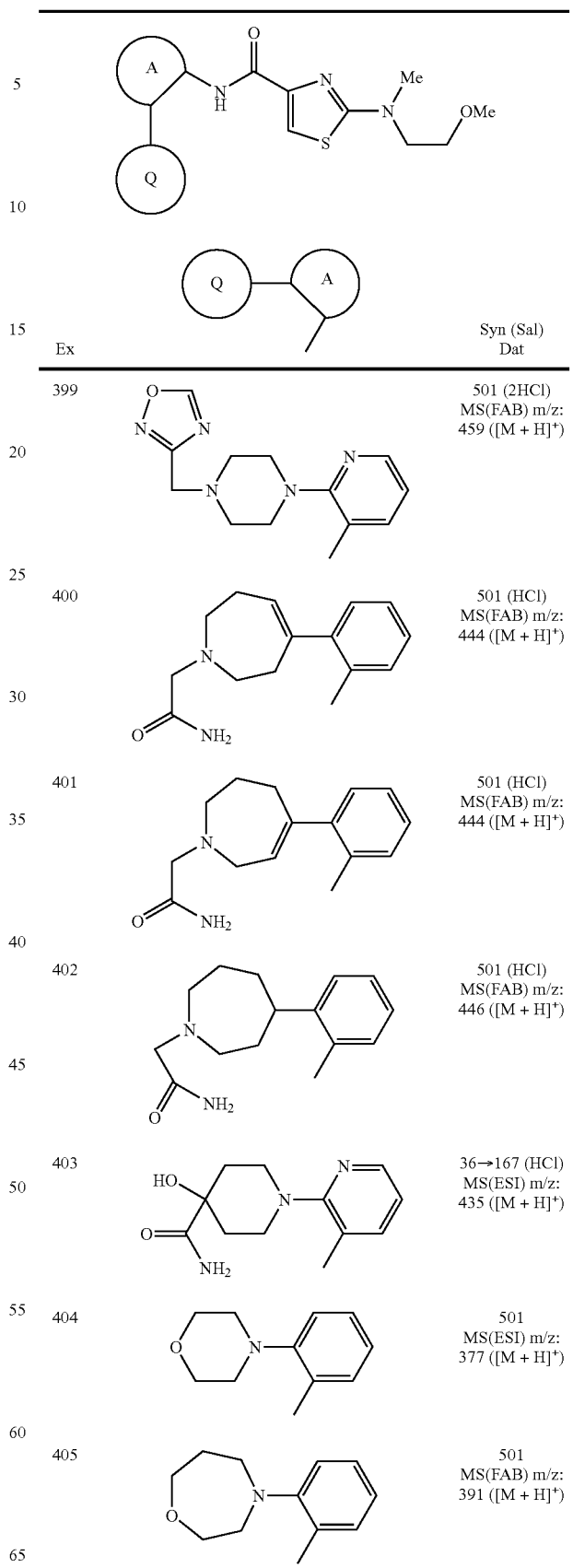

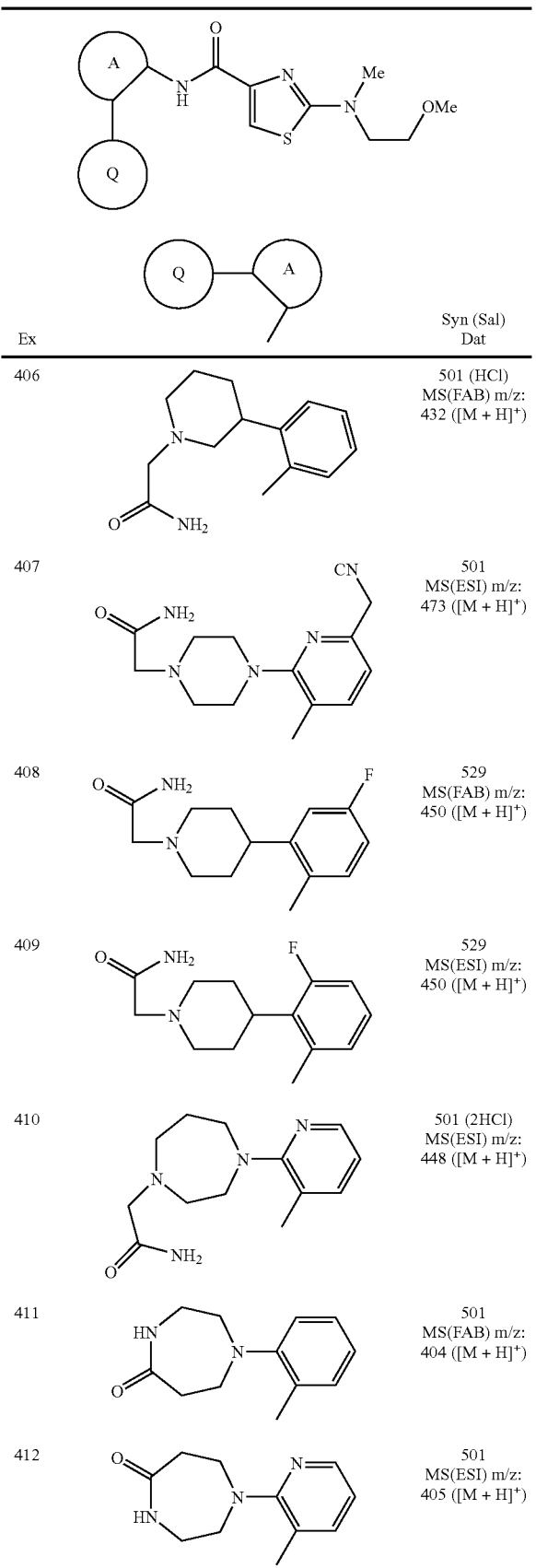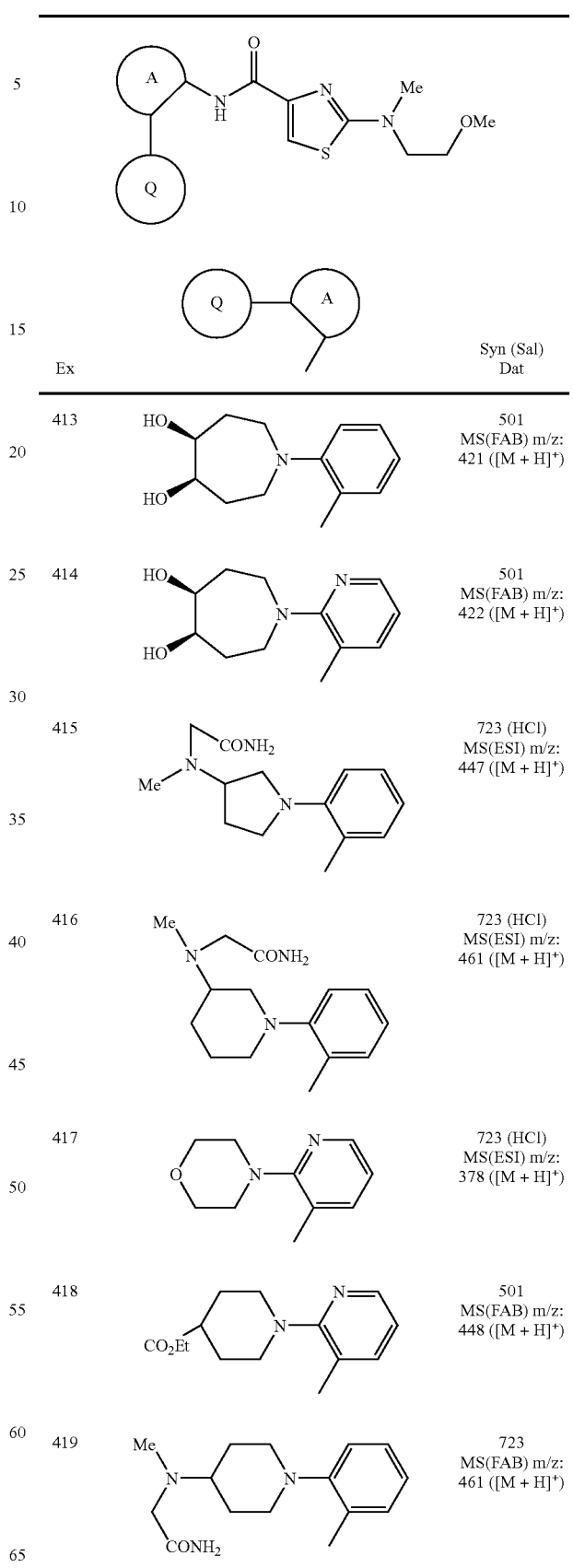

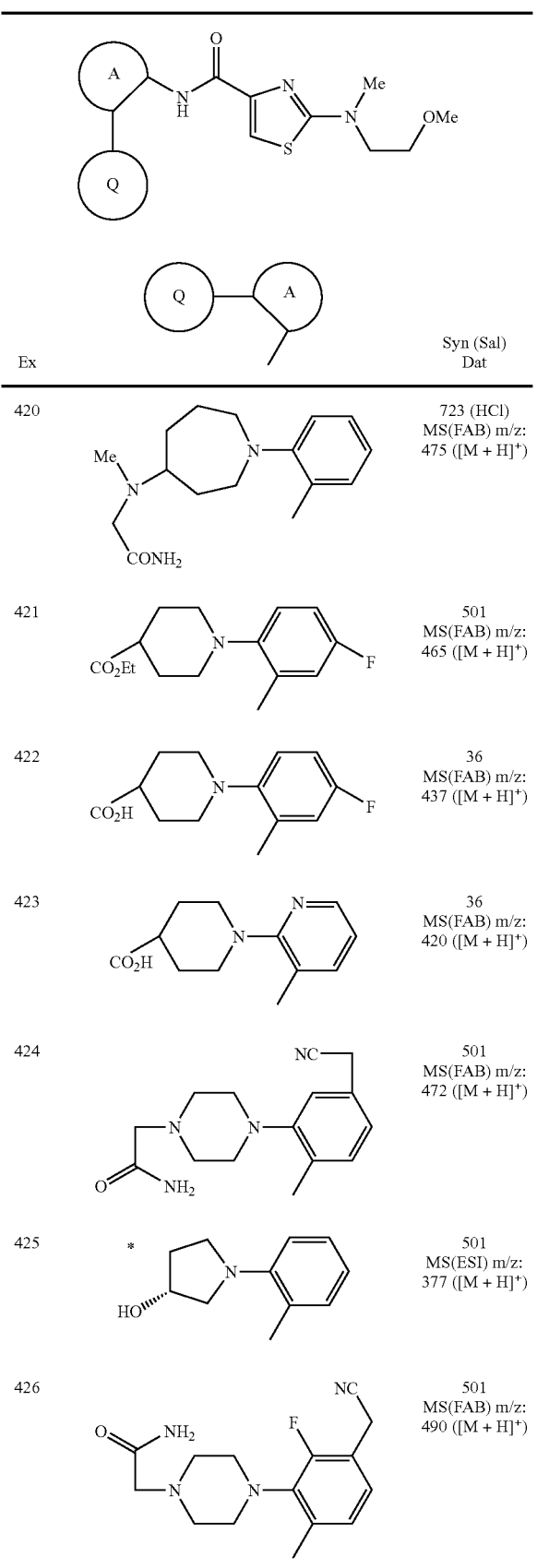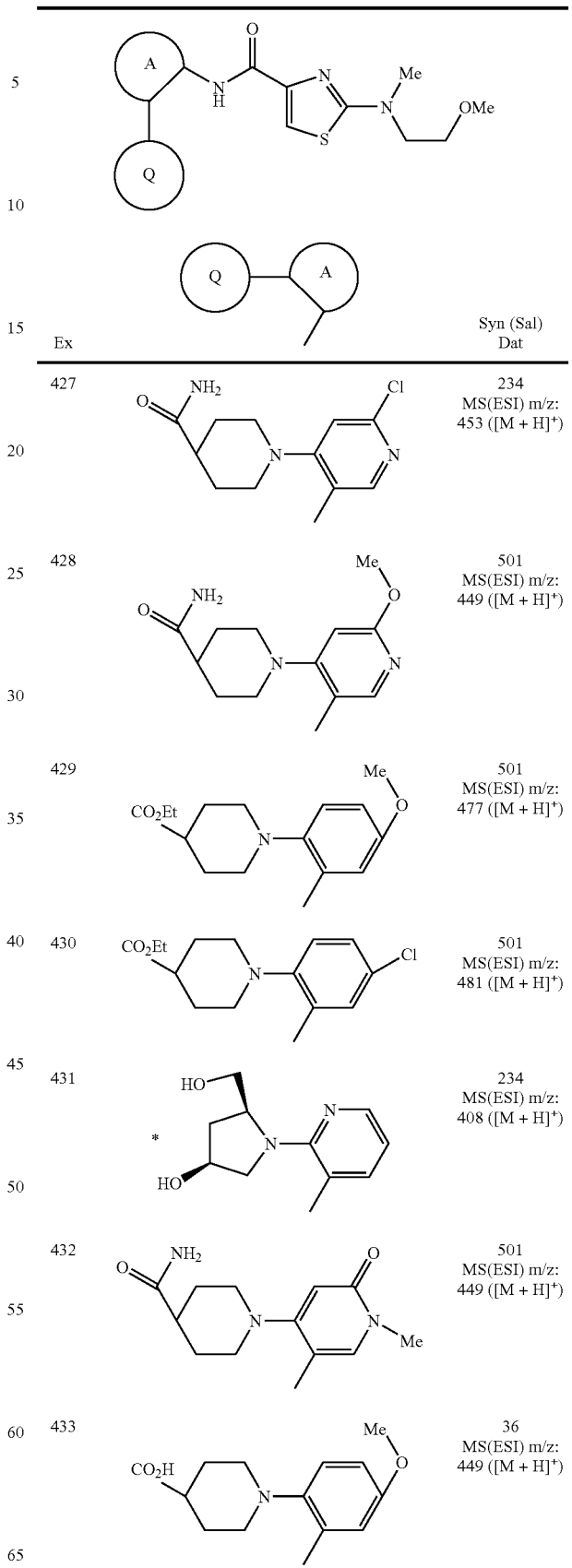

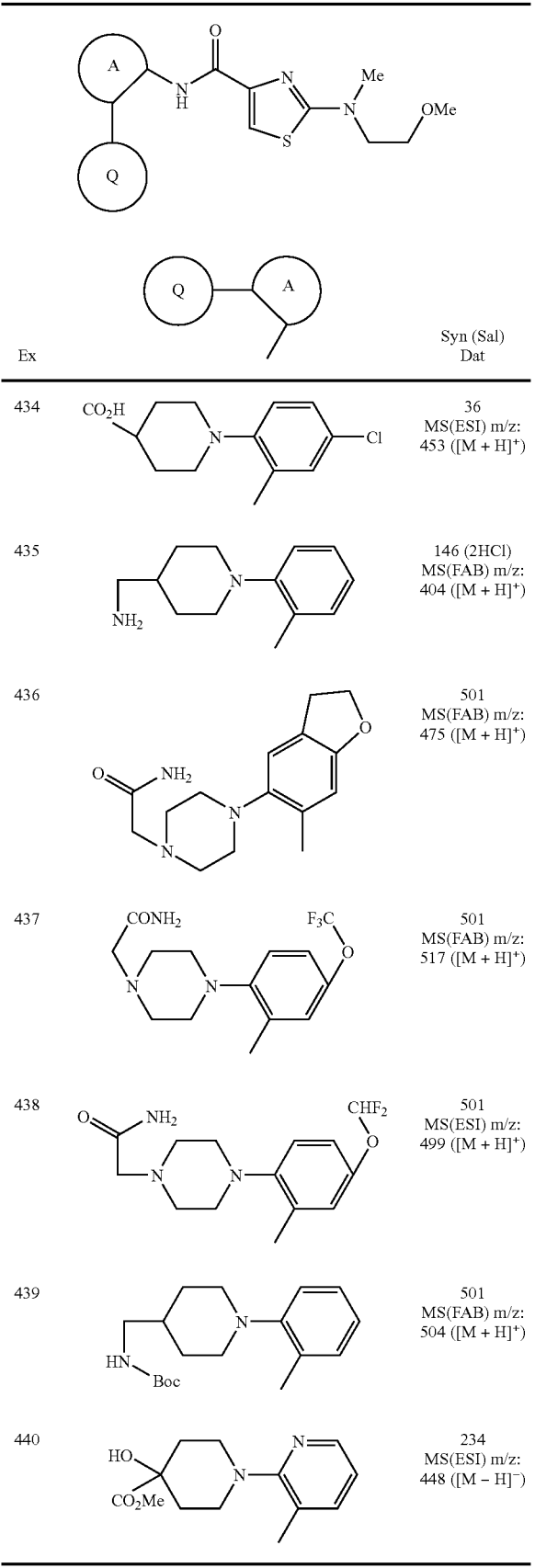
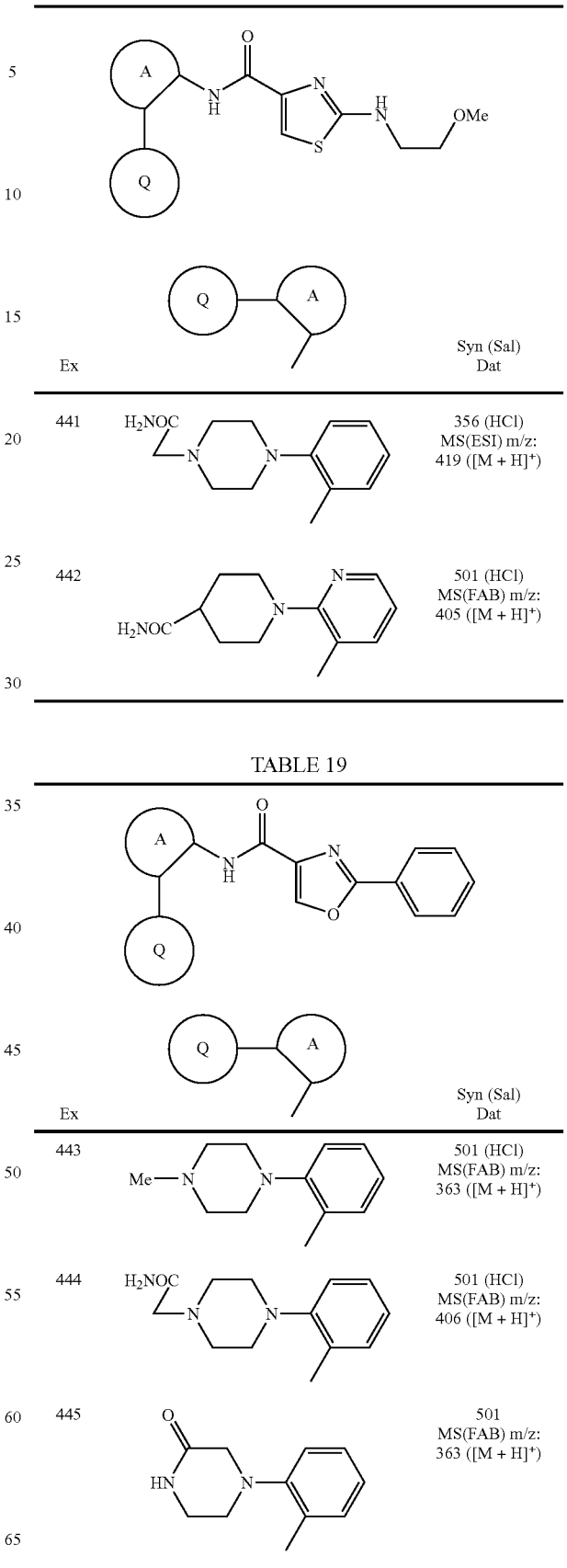

TABLE 19-continued

| Ex | Q-A structure | Syn (Sal) Dat |
|---|---|---|
| 446 | EtO₂C-piperidine-N-(2-methylphenyl) | 501 MS(FAB) m/z: 420 ([M + H]⁺) |
| 447 | HO₂C-piperidine-N-(2-methylphenyl) | 36 (Na) MS(FAB) m/z: 392 ([M + H]⁺) |
| 448 | H₂NOC-piperidine-N-(2-methylphenyl) | 167 MS(FAB) m/z: 391 ([M + H]⁺) |
| 449 | HO-piperidine-N-(2-methylphenyl) | 501 MS(FAB) m/z: 364 ([M + H]⁺) |
| 450 | HO,HO-pyrrolidine-N-(2-methylphenyl) | 501 MS(FAB) m/z: 366 ([M + H]⁺) |
| 451 | H₂NOC-tetrahydropyridine-(2-methylphenyl) | 501 (HCl) MS(FAB) m/z: 405 ([M + H]⁺) |
| 452 | H₂NOC-piperidine-(2-methylphenyl) | 501 (HCl) MS(FAB) m/z: 403 ([M + H]⁺) |

TABLE 20

| Ex | Q-A structure | Syn (Sal) Dat |
|---|---|---|
| 453 | H₂NOC-piperazine-N-(2-methylphenyl) | 501 (2HCl) MS(FAB) m/z: 407 ([M + H]⁺) |
| 454 | H₂NOC-piperazine-N-(2-methyl-6-fluorophenyl) | 501 (2HCl) MS(FAB) m/z: 425 ([M + H]⁺) |
| 455 | H₂NOC-piperidine-N-(2-methylphenyl) | 501 (HCl) MS(FAB) m/z: 392 ([M + H]⁺) |
| 456 | H₂NOC-piperidine-N-(3-methylpyridin-2-yl) | 501 (2HCl) MS(FAB) m/z: 393 ([M + H]⁺) |

TABLE 21

| Ex | Q-A structure | Syn (Sal) Dat |
|---|---|---|
| 457 | H₂NOC-piperazine-N-(2-methylphenyl) | 501 (HCl) MS(FAB) m/z: 408 ([M + H]⁺) |

TABLE 21-continued

Structure: A-NH-C(O)-[oxazole]-pyrimidine with Q attached to A; sub-structure Q-A-methyl

| Ex | Structure | Syn (Sal) Dat |
|---|---|---|
| 458 | H₂NOC-piperazine-N-(2-fluoro-6-methylphenyl) | 501 (HCl) MS(FAB) m/z: 426 ([M + H]⁺) |
| 459 | H₂NOC-piperidine-N-(2-methylphenyl) | 501 MS(FAB) m/z: 393 ([M + H]⁺) |
| 460 | H₂NOC-piperidine-N-(3-methylpyridin-2-yl) | 501 (HCl) MS(FAB) m/z: 394 ([M + H]⁺) |

TABLE 22

Structure: A-NH-C(O)-[oxazole]-pyridazine with Q attached to A

| Ex | Structure | Syn (Sal) Dat |
|---|---|---|
| 461 | H₂NOC-piperazine-N-(2-methylphenyl) | 501 (HCl) MS(FAB) m/z: 408 ([M + H]⁺) |
| 462 | H₂NOC-piperazine-N-(2-fluoro-6-methylphenyl) | 501 (HCl) MS(FAB) m/z: 426 ([M + H]⁺) |

TABLE 22-continued

| Ex | Structure | Syn (Sal) Dat |
|---|---|---|
| 463 | H₂NOC-piperidine-N-(2-methylphenyl) | 501 MS(FAB) m/z: 393 ([M + H]⁺) |
| 464 | H₂NOC-piperidine-N-(3-methylpyridin-2-yl) | 501 (HCl) MS(FAB) m/z: 394 ([M + H]⁺) |
| 465 | H₂NOC-piperazine-N-(3-methylpyridin-2-yl) | 501 (HCl) MS(FAB) m/z: 409 ([M + H]⁺) |

TABLE 23

Structure: A-NH-C(O)-[oxazole]-(6-oxo-1,6-dihydropyridin-3-yl) with Q attached to A

| Ex | Structure | Syn (Sal) Dat |
|---|---|---|
| 466 | H₂NOC-piperazine-N-(2-methylphenyl) | 501 (HCl) MS(FAB) m/z: 423 ([M + H]⁺) |
| 467 | H₂NOC-piperazine-N-(2-fluoro-6-methylphenyl) | 501 (HCl) MS(FAB) m/z: 441 ([M + H]⁺) |

TABLE 23-continued

[Structure with A and Q groups connected via NH-C(O)-oxazole-pyridinone]

[Q-A fragment structure]

| Ex | [Structure] | Syn (Sal) Dat |
|---|---|---|
| 468 | H₂NOC-piperidine-N-(2-methylphenyl) | 501 (HCl) MS(FAB) m/z: 408 ([M + H]⁺) |
| 469 | H₂NOC-piperidine-N-(3-methylpyridin-2-yl) | 501 (HCl) MS(FAB) m/z: 409 ([M + H]⁺) |

TABLE 24

[Structure with A and Q groups connected via NH-C(O)-oxazole-pyridine-NHBoc]

[Q-A fragment structure]

| Ex | [Structure] | Syn (Sal) Dat |
|---|---|---|
| 470 | H₂NOC-CH₂-piperazine-N-(2-methylphenyl) | 501 MS(ESI) m/z: 522 ([M + H]⁺) |
| 471 | H₂NOC-CH₂-piperazine-N-(2-fluoro-6-methylphenyl) | 501 MS(FAB) m/z: 540 ([M + H]⁺) |
| 472 | H₂NOC-piperidine-N-(2-methylphenyl) | 501 MS(FAB) m/z: 507 ([M + H]⁺) |

TABLE 24-continued

[Structure with A and Q groups connected via NH-C(O)-oxazole-pyridine-NHBoc]

[Q-A fragment structure]

| Ex | [Structure] | Syn (Sal) Dat |
|---|---|---|
| 473 | H₂NOC-piperidine-N-(3-methylpyridin-2-yl) | 501 MS(FAB) m/z: 508 ([M + H]⁺) |

TABLE 25

[Structure with A and Q groups connected via NH-C(O)-oxazole-pyridine-NH₂]

[Q-A fragment structure]

| Ex | [Structure] | Syn (Sal) Dat |
|---|---|---|
| 474 | H₂NOC-CH₂-piperazine-N-(2-methylphenyl) | 146 (2HCl) MS(FAB) m/z: 422 ([M + H]⁺) |
| 475 | H₂NOC-CH₂-piperazine-N-(2-fluoro-6-methylphenyl) | 146 (2HCl) MS(FAB) m/z: 440 ([M + H]⁺) |
| 476 | H₂NOC-piperidine-N-(2-methylphenyl) | 146 (HCl) MS(FAB) m/z: 407 ([M + H]⁺) |
| 477 | H₂NOC-piperidine-N-(3-methylpyridin-2-yl) | 146 (2HCl) MS(FAB) m/z: 408 ([M + H]⁺) |

TABLE 26

(structure with A-NH-C(O)-oxazole-pyridine-Cl and Q-A substructure)

| Ex | | Syn (Sal) Dat |
|---|---|---|
| 478 | H₂NOC-piperidine-N-(2-methylphenyl) | 501 MS(FAB) m/z: 426 ([M + H]⁺) |
| 479 | H₂NOC-piperidine-N-(3-methylpyridin-2-yl) | 501 (HCl) MS(FAB) m/z: 427 ([M + H]⁺) |

TABLE 27

(structure with A-NH-C(O)-oxazole-morpholine and Q-A substructure)

| Ex | | Syn (Sal) Dat |
|---|---|---|
| 480 | H₂NOC-piperazine-N-(2-methylphenyl) | 234 (HCl) MS(FAB) m/z: 415 ([M + H]⁺) |
| 481 | H₂NOC-piperazine-N-(2-fluoro-6-methylphenyl) | 501 (HCl) MS(FAB) m/z: 433 ([M + H]⁺) |
| 482 | H₂NOC-piperazine-N-(3-fluoro-6-methylphenyl) | 501 (HCl) MS(FAB) m/z: 433 ([M + H]⁺) |

TABLE 27-continued

| Ex | | Syn (Sal) Dat |
|---|---|---|
| 483 | H₂NOC-piperazine-N-(4-fluoro-2-methylphenyl) | 501 (HCl) MS(FAB) m/z: 433 ([M + H]⁺) |
| 484 | H₂NOC-piperazine-N-(2,4-difluoro-6-methylphenyl) | 501 (HCl) MS(FAB) m/z: 451 ([M + H]⁺) |
| 485 | H₂NOC-piperazine-N-(2,3-difluoro-6-methylphenyl) | 501 (HCl) MS(FAB) m/z: 451 ([M + H]⁺) |
| 486 | H₂NOC-piperazine-N-(5-bromo-2-methylphenyl) | 502 MS(ESI) m/z: 493 ([M + H]⁺) |
| 487 | H₂NOC-piperazine-N-(2-cyano-6-methylphenyl) | 501 (HCl) MS(ESI) m/z: 440 ([M + H]⁺) |
| 488 | H₂NOC-piperazine-N-(4-cyano-2-methylphenyl) | 206 (HCl) MS(FAB) m/z: 440 ([M + H]⁺) |
| 489 | H₂NOC-piperazine-N-(4-cyano-2-methylphenyl) | 501 (HCl) MS(ESI) m/z: 440 ([M + H]⁺) |

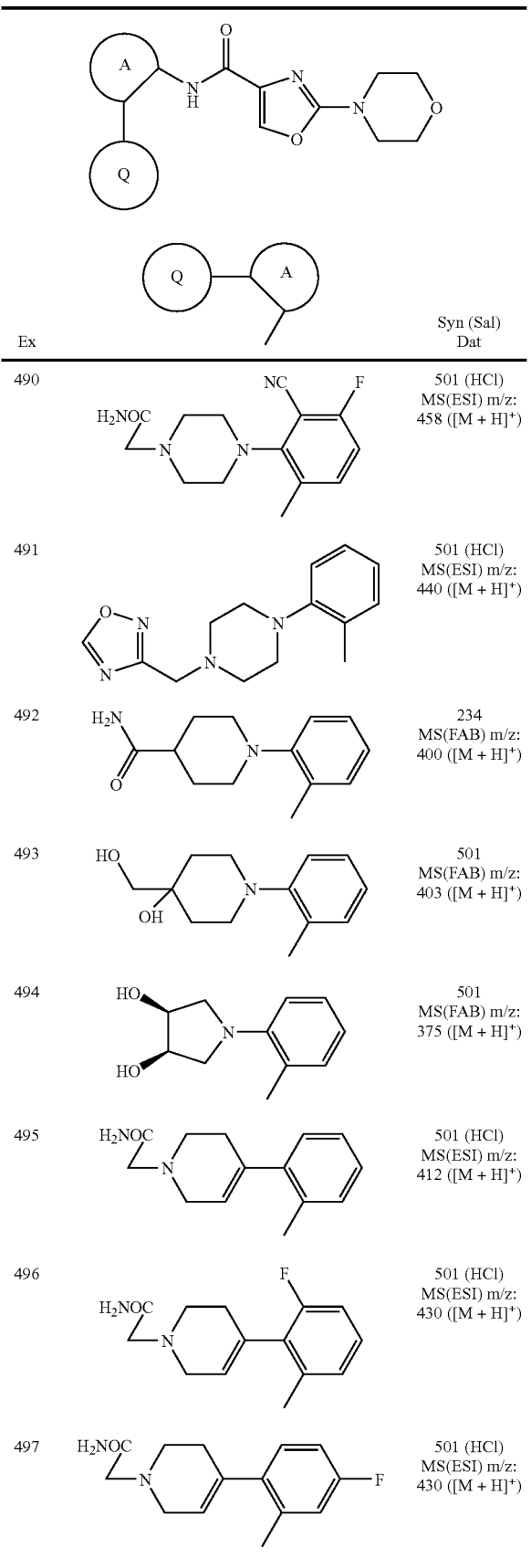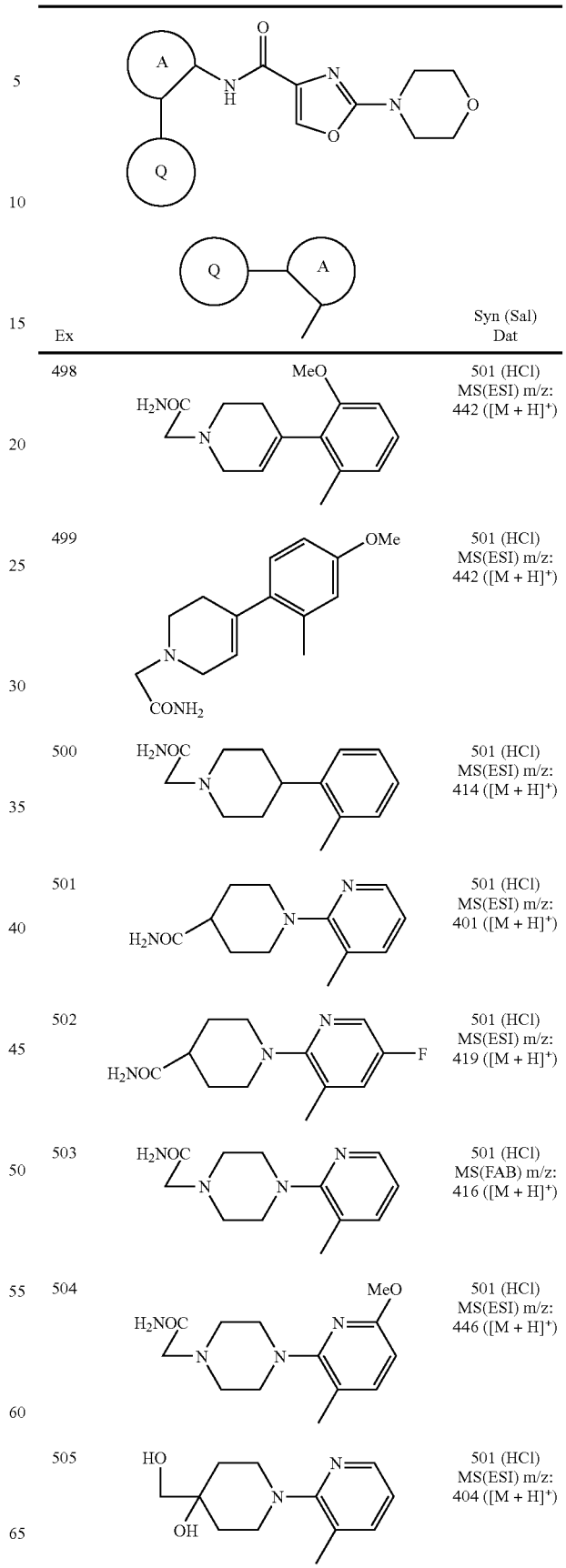

TABLE 27-continued

| Ex | Structure | Syn (Sal) Dat |
|---|---|---|
| 506 | 4-hydroxypiperidin-1-yl linked to 3-methylpyridin-2-yl | 394 (HCl) MS(ESI) m/z: 374 ([M + H]+) |
| 507 | piperazine with CH2C(O)NH2, linked to 5-fluoro-3-methylpyridin-2-yl | 234 (2HCl) MS(ESI) m/z: 434 ([M + H]+) |
| 508 | tetrahydropyridine with CH2C(O)NH2, linked to 3-methylpyridin-2-yl | 501 (2HCl) MS(ESI) m/z: 413 ([M + H]+) |
| 509 | piperidine-4-carboxamide linked to 6-fluoro-3-methylpyridin-2-yl | 501 (HCl) MS(ESI) m/z: 419 ([M + H]+) |
| 510 | piperazine with CH2C(O)NH2, linked to 6-fluoro-3-methylpyridin-2-yl | 501 (2HCl) MS(ESI) m/z: 434 ([M + H]+) |
| 511 | piperazine with CH2C(O)NH2, linked to 2-cyano-4-fluoro-6-methylphenyl | 501 (HCl) MS(FAB) m/z: 458 ([M + H]+) |
| 512 | piperazine with CH2C(O)NH2, linked to 2-fluoro-4-isocyano-6-methylphenyl | 501 (HCl) MS(FAB) m/z: 458 ([M + H]+) |
| 513 | oxadiazolylmethyl-piperazine linked to 3-methylpyridin-2-yl | 501 (2HCl) MS(FAB) m/z: 441 ([M + H]+) |
| 514 | azepene with CH2C(O)NH2, linked to 2-methylphenyl | 501 (HCl) MS(ESI) m/z: 426 ([M + H]+) |
| 515 | azepene with CH2C(O)NH2, linked to 2-methylphenyl | 501 (HCl) MS(FAB) m/z: 426 ([M + H]+) |
| 516 | azepane with CH2C(O)NH2, linked to 2-methylphenyl | 501 (HCl) MS(ESI) m/z: 428 ([M + H]+) |
| 517 | 4-hydroxy-4-methoxycarbonylpiperidine linked to 3-methylpyridin-2-yl | 234 MS(ESI) m/z: 432 ([M + H]+) |
| 518 | 4-hydroxy-4-carbamoylpiperidine linked to 3-methylpyridin-2-yl | 36→167 (HCl) MS(ESI) m/z: 417 ([M + H]+) |
| 519 | tetrahydropyridine with CH2C(O)NH2, linked to 3-cyano-6-methylphenyl | 529 (HCl) MS(FAB) m/z: 437 ([M + H]+) |

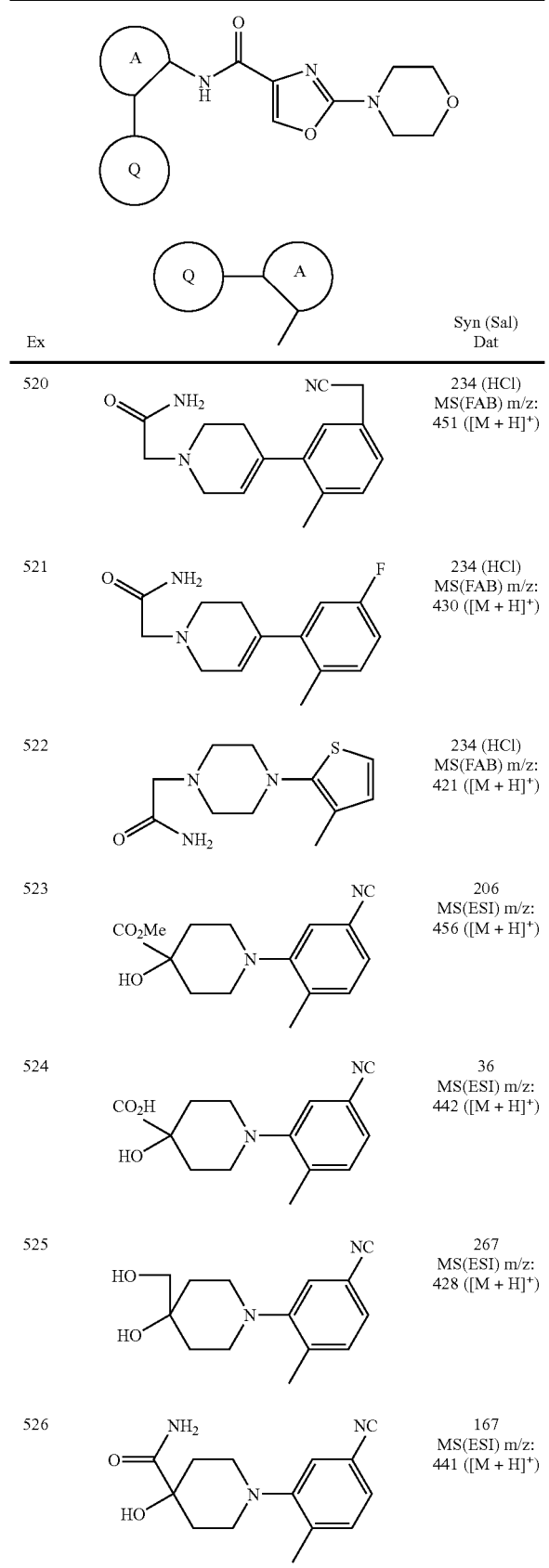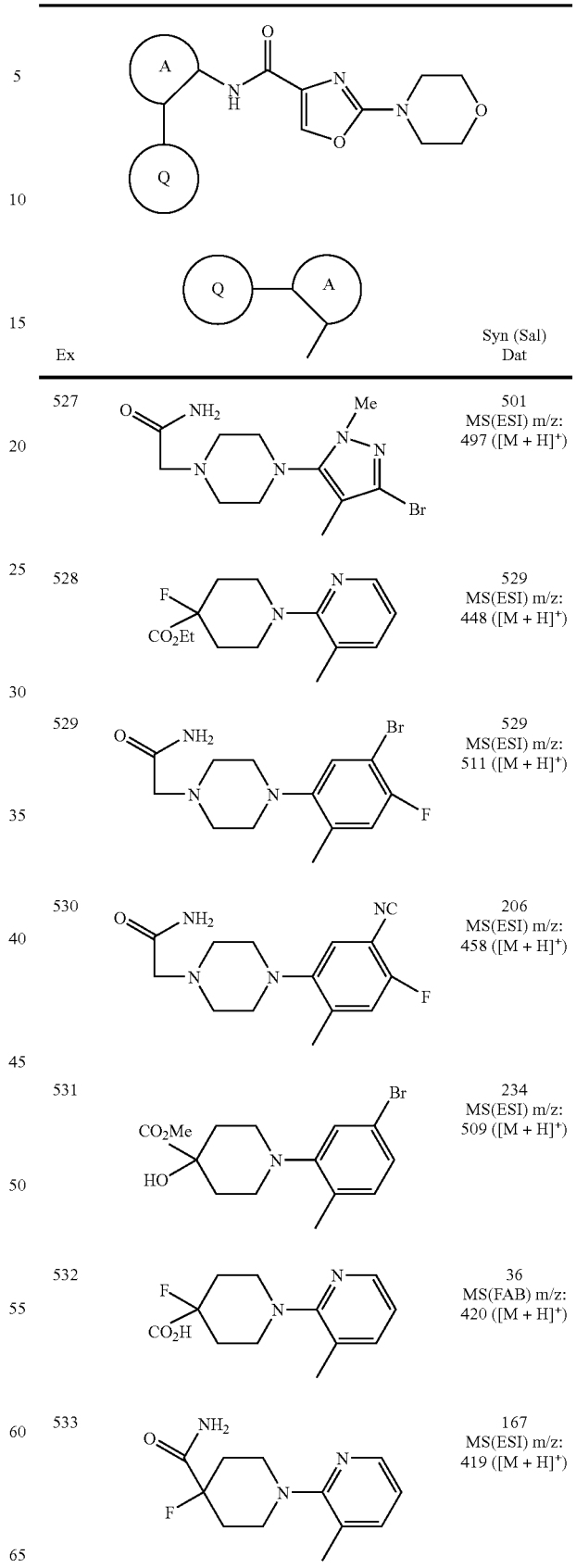

TABLE 27-continued

| Ex | Structure | Syn (Sal) Dat |
|---|---|---|
| 534 | 4-(hydroxymethyl)-4-fluoropiperidine-N-(3-methylpyridin-2-yl) | 267 MS(ESI) m/z: 406 ([M + H]⁺) |
| 535 | 4-CO₂Me-tetrahydropyridine-N-(5-bromo-2-methylphenyl) | 529 MS(ESI) m/z: 491 ([M + H]⁺) |
| 536 | 3-(2-methylphenyl)piperidine-N-CH₂CONH₂ | 501 (HCl) MS(FAB) m/z: 414 ([M + H]⁺) |
| 537 | piperazine-N-CH₂CONH₂, N'-(1,4-dimethylpyrazol-5-yl) | 537 MS(ESI) m/z: 419 ([M + H]⁺) |
| 538 | 4-CO₂Me-tetrahydropyridine-N-(5-cyano-2-methylphenyl) | 206 MS(ESI) m/z: 438 ([M + H]⁺) |
| 539 | piperazine-N-CH₂CONH₂, N'-(6-cyanomethyl-3-methylpyridin-2-yl) | 501 MS(ESI) m/z: 455 ([M + H]⁺) |
| 540 | 1,4-diazepane-N-CH₂CONH₂, N'-(3-methylpyridin-2-yl) | 501 MS(ESI) m/z: 430 ([M + H]⁺) |
| 541 | 4-(2,3-difluoro-6-methylphenyl)-tetrahydropyridine-N-CH₂CONH₂ | 529 MS(ESI) m/z: 448 ([M + H]⁺) |
| 542 | 4-(2,4-difluoro-6-methylphenyl)-tetrahydropyridine-N-CH₂CONH₂ | 529 MS(ESI) m/z: 448 ([M + H]⁺) |
| 543 | piperazine-N-CH₂C(O)NH-tBu, N'-(6-methyl-3-methylpyridin-2-yl) | 501 MS(ESI) m/z: 529 ([M + H]⁺) |
| 544 | 1,4-diazepan-5-one, N-(2-methylphenyl) | 501 MS(FAB) m/z: 386 ([M + H]⁺) |
| 545 | 1,4-diazepan-5-one, N-(3-methylpyridin-2-yl) | 501 MS(FAB) m/z: 387 ([M + H]⁺) |
| 546 | 4,5-dihydroxyazepane-N-(3-methylpyridin-2-yl) | 501 MS(FAB) m/z: 404 ([M + H]⁺) |
| 547 | 4,5-dihydroxyazepane-N-(2-methylphenyl) | 501 MS(FAB) m/z: 403 ([M + H]⁺) |

TABLE 27-continued

| Ex | Structure | Syn (Sal) Dat |
|---|---|---|
| 548 | [piperidine-CO2Et, N-(2-methylphenyl)] | 501 MS(FAB) m/z: 429 ([M + H]$^+$) |
| 549 | [piperidine-COOH, N-(2-methylphenyl)] | 36 MS(FAB) m/z: 401 ([M + H]$^+$) |
| 550 | [piperidine-CONH2, N-(2-methoxy-5-methylpyridin-4-yl)] | 501 MS(ESI) m/z: 431 ([M + H]$^+$) |
| 551 | [piperidine-CONH2, N-(2-chloro-5-methylpyridin-4-yl)] | 501 MS(ESI) m/z: 435 ([M + H]$^+$) |
| 552 | [piperidine-CO2Et, N-(3-methylpyridin-2-yl)] | 501 MS(FAB) m/z: 430 ([M + H]$^+$) |
| 553 | [piperidine-COOH, N-(3-methylpyridin-2-yl)] | 36 MS(FAB) m/z: 402 ([M + H]$^+$) |
| 554 | [4-methylpiperazine-CO-piperidine-N-(3-methylpyridin-2-yl)] | 167 MS(ESI) m/z: 484 ([M + H]$^+$) |
| 555 | [Me2N-CH2CH2-NH-CO-piperidine-N-(3-methylpyridin-2-yl)] | 167 MS(FAB) m/z: 472 ([M + H]$^+$) |
| 556 | [Me2N-CH2CH2-N(Me)-CO-piperidine-N-(3-methylpyridin-2-yl)] | 167 MS(FAB) m/z: 486 ([M + H]$^+$) |
| 557 | [Me2N-CH2CH2CH2-NH-CO-piperidine-N-(3-methylpyridin-2-yl)] | 167 MS(FAB) m/z: 486 ([M + H]$^+$) |
| 558 | [3-dimethylaminopyrrolidine-CO-piperidine-N-(3-methylpyridin-2-yl)] | 167 MS(FAB) m/z: 498 ([M + H]$^+$) |
| 559 | [ethoxycarbonyl-piperidine-CO-piperidine-N-(3-methylpyridin-2-yl)] | 167 MS(FAB) m/z: 541 ([M + H]$^+$) |

TABLE 27-continued

| Ex | | Syn (Sal) Dat |
|---|---|---|
| 560 | [structure: Boc-piperazine-pyridine-Me] | 501 MS(ESI) m/z: 459 ([M + H]+) |
| 561 | [structure: HN-piperazine-pyridine-Me] | 146 (2HCl) MS(ESI) m/z: 359 ([M + H]+) |
| 562 | [structure: N-Me-diazepane-C(O)-piperidine-pyridine-Me] | 167 MS(ESI) m/z: 498 ([M + H]+) |
| 563 | [structure: pyrrolidine-CH2-pyrrolidine-C(O)-piperidine-pyridine-Me] * | 167 MS(FAB) m/z: 538 ([M + H]+) |
| 564 | [structure: CO2H-piperidine-C(O)-piperidine-pyridine-Me] | 36 MS(ESI) m/z: 513 ([M + H]+) |
| 565 | [structure: N-Me-pyrrolidine-N(Me)-C(O)-piperidine-pyridine-Me] | 167 MS(ESI) m/z: 498 ([M + H]+) |
| 566 | [structure: Et-piperazine-C(O)-piperidine-pyridine-Me] | 167 MS(FAB) m/z: 512 ([M + H]+) |
| 567 | [structure: H2N-cyclohexyl-NH-C(O)-piperidine-pyridine-Me] | 167 MS(FAB) m/z: 498 ([M + H]+) |
| 568 | [structure: morpholine-C(O)-piperidine-pyridine-Me] | 167 MS(FAB) m/z: 471 ([M + H]+) |
| 569 | [structure: N-Me-piperidine-C(O)-piperazine-pyridine-Me] | 167 (2HCl) MS(ESI) m/z: 484 ([M + H]+) |
| 570 | [structure: pyridine-NH-C(O)-piperidine-pyridine-Me] | 167 (2HCl) MS(FAB) m/z: 478 ([M + H]+) |

TABLE 27-continued

| Ex | Structure | Syn (Sal) Dat |
|---|---|---|
| 571 | pyrrolidin-1-yl-piperidin-1-yl carbonyl piperidin-1-yl (3-methylpyridin-2-yl) | 167 (2HCl) MS(FAB) m/z: 538 ([M + H]⁺) |
| 572 | 1-methylpiperidin-4-yl-NH-C(O)-piperidin-4-yl (3-methylpyridin-2-yl) | 167 MS(ESI) m/z: 498 ([M + H]⁺) |
| 573 | CONH₂-CH₂-piperazinyl-(6-methyl-2,3-dihydrobenzofuran-5-yl) | 501 MS(FAB) m/z: 457 ([M + H]⁺) |
| 574 | H₂N-C(O)-CH₂-piperazinyl-(2-methyl-4-trifluoromethoxyphenyl) | 501 MS(FAB) m/z: 499 ([M + H]⁺) |
| 575 | CO₂Et-piperidin-4-yl-(3-methyl-5-methylpyridin-2-yl) | 501 MS(ESI) m/z: 444 ([M + H]⁺) |
| 576 | CO₂Et-piperidin-4-yl-(3-methyl-5-fluoropyridin-2-yl) | 501 MS(FAB) m/z: 448 ([M + H]⁺) |
| 577 | CO₂H-piperidin-4-yl-(3-methyl-5-methylpyridin-2-yl) | 36 MS(ESI) m/z: 416 ([M + H]⁺) |
| 578 | CO₂H-piperidin-4-yl-(3-methyl-5-fluoropyridin-2-yl) | 36 MS(ESI) m/z: 420 ([M + H]⁺) |
| 579 | 1-methylpyrrolidin-2-yl-C(O)-piperazinyl-(3-methylpyridin-2-yl) * | 167 (2HCl) MS(ESI) m/z: 470 ([M + H]⁺) |
| 580 | 1-benzyl-3-(N-Me)-pyrrolidinyl-N-C(O)-piperidin-4-yl-(3-methyl-5-methylpyridin-2-yl) * | 167 MS(ESI) m/z: 588 ([M + H]⁺) |
| 581 | 1-benzyl-3-(N-Me)-pyrrolidinyl-N-C(O)-piperidin-4-yl-(3-methyl-5-methylpyridin-2-yl) * | 167 MS(ESI) m/z: 588 ([M + H]⁺) |
| 582 | 1-benzyl-3-(N-Me)-pyrrolidinyl-piperidin-4-yl-(3-methyl-5-fluoropyridin-2-yl) * | 167 MS(ESI) m/z: 592 ([M + H]⁺) |

TABLE 27-continued

| Ex | Q-A structure | Syn (Sal) Dat |
|---|---|---|
| 583 | (N-benzyl pyrrolidin-3-yl)(Me)N-piperidine-pyridine(3-Me, 5-F) | 167 MS(ESI) m/z: 592 ([M + H]⁺) * |

TABLE 28

| Ex | Q-A structure | Syn (Sal) Dat |
|---|---|---|
| 584 | H₂NOC-piperazine-N-phenyl(2-Me) | 501 MS (FAB) m/z: 429 ([M + H]⁺) |
| 585 | H₂NOC-piperazine-N-phenyl(2-F, 6-Me) | 501 (HCl) MS (FAB) m/z: 447 ([M + H]⁺) |
| 586 | H₂NOC-piperidine-N-phenyl(2-Me) | 501 (HCl) MS (ESI) m/z: 414 ([M + H]⁺) |
| 587 | H₂NOC-tetrahydropyridine-phenyl(2-Me) | 501 MS (FAB) m/z: 426 ([M + H]⁺) |

TABLE 29

| Ex | Q-A structure | Syn (Sal) Dat |
|---|---|---|
| 588 | H₂NOC-piperazine-N-phenyl(2-Me) | 501 (2HCl) MS (ESI) m/z: 413 ([M + H]⁺) |
| 589 | H₂NOC-piperazine-N-phenyl(2-F, 6-Me) | 501 (2HCl) MS (FAB) m/z: 431 ([M + H]⁺) |
| 590 | H₂NOC-piperidine-N-pyridine(3-Me) | 501 (2HCl) MS (FAB) m/z: 399 ([M + H]⁺) |

TABLE 30

| Ex | Q-A structure | Syn (Sal) Dat |
|---|---|---|
| 591 | H₂NOC-piperazine-N-phenyl(2-Me) | 501 MS (FAB) m/z: 417 ([M + H]⁺) |
| 592 | H₂NOC-piperazine-N-phenyl(2-F, 6-Me) | 501 (HCl) MS (FAB) m/z: 435 ([M + H]⁺) |

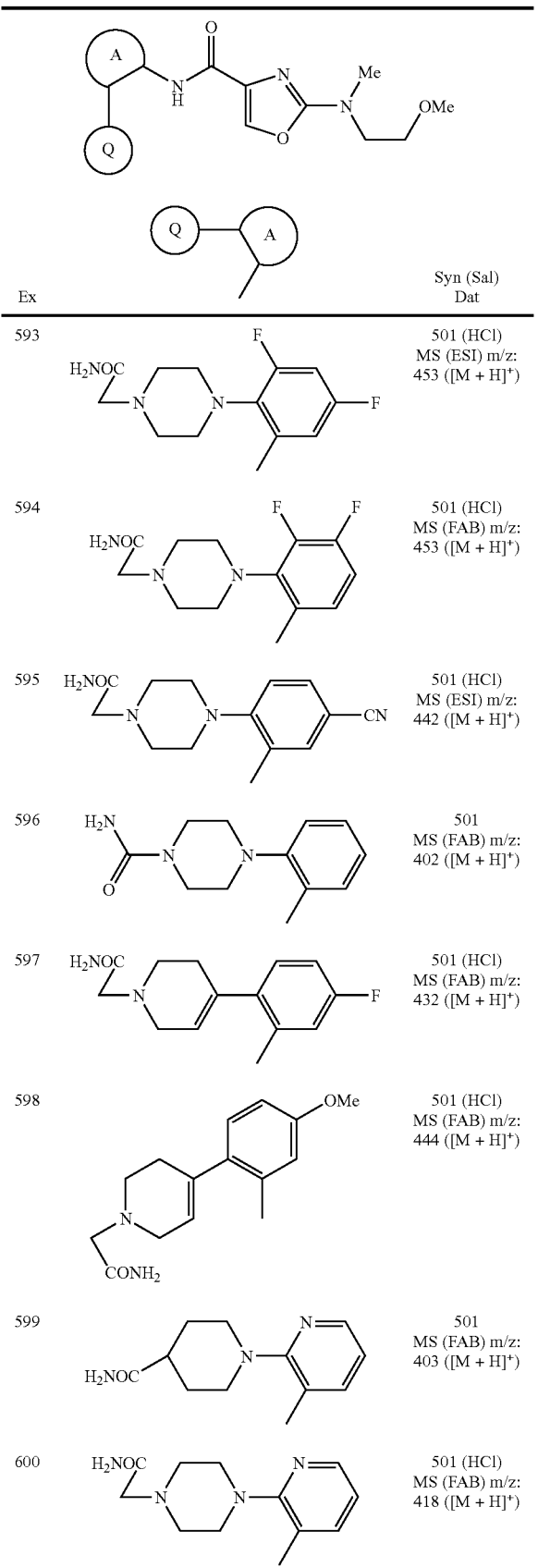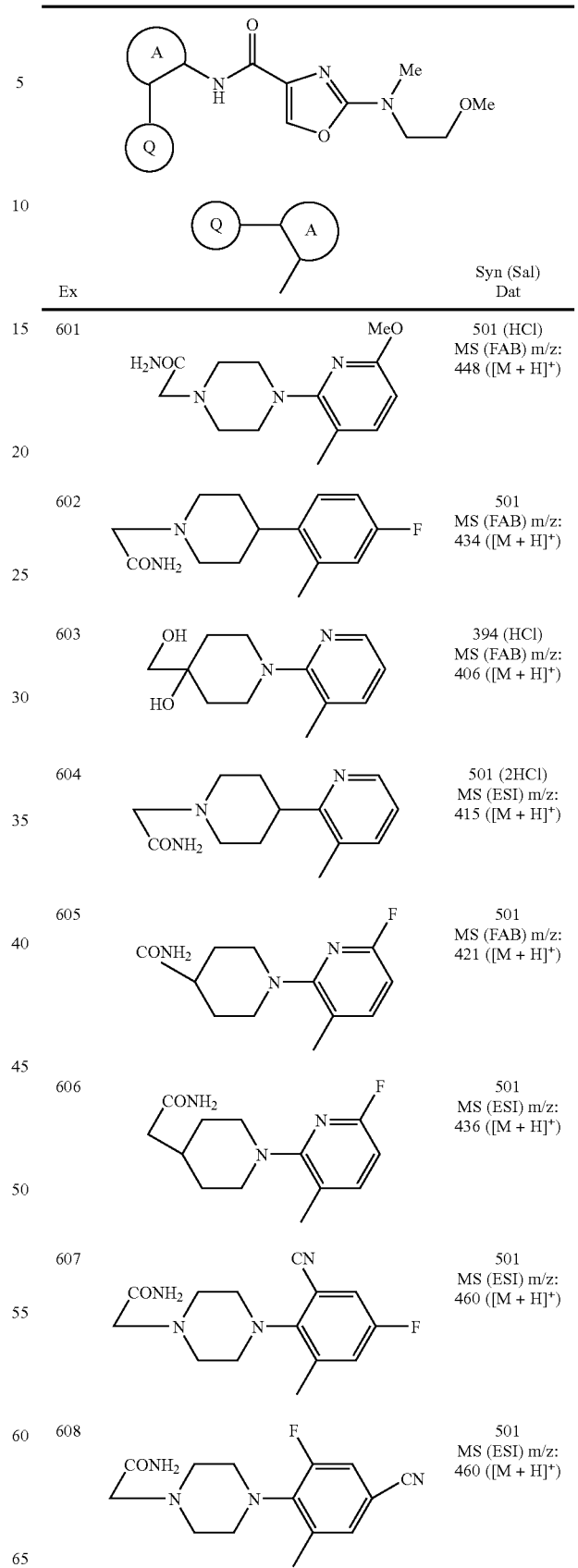

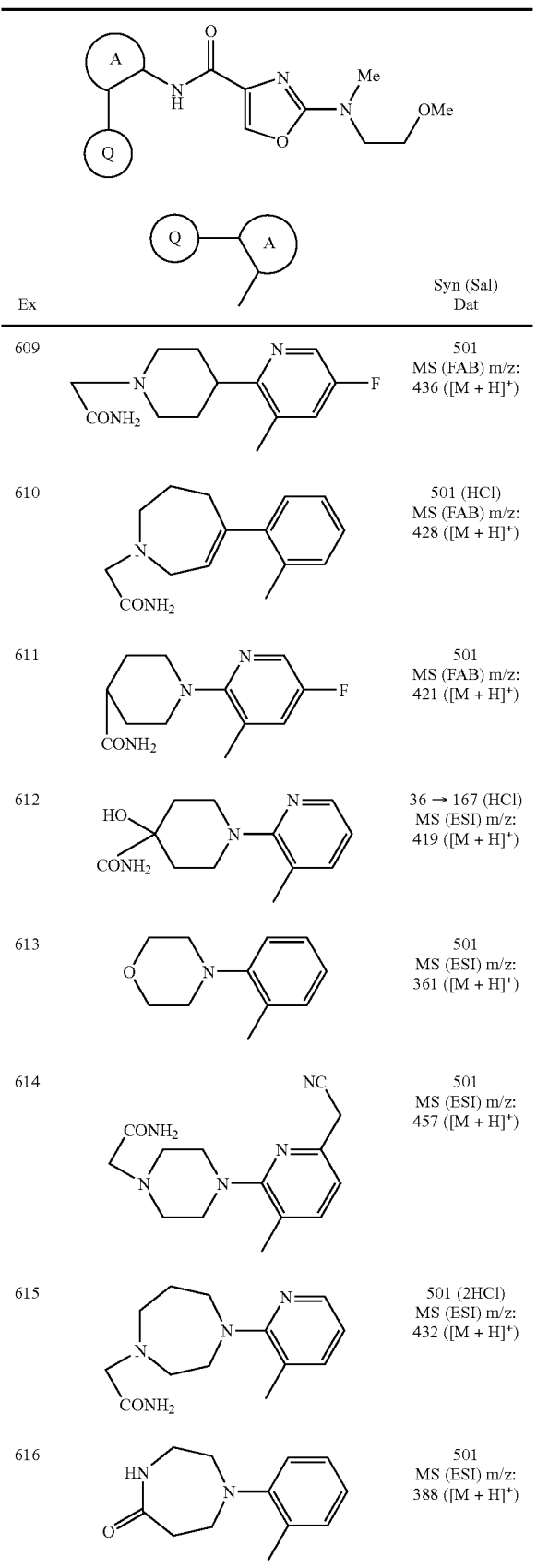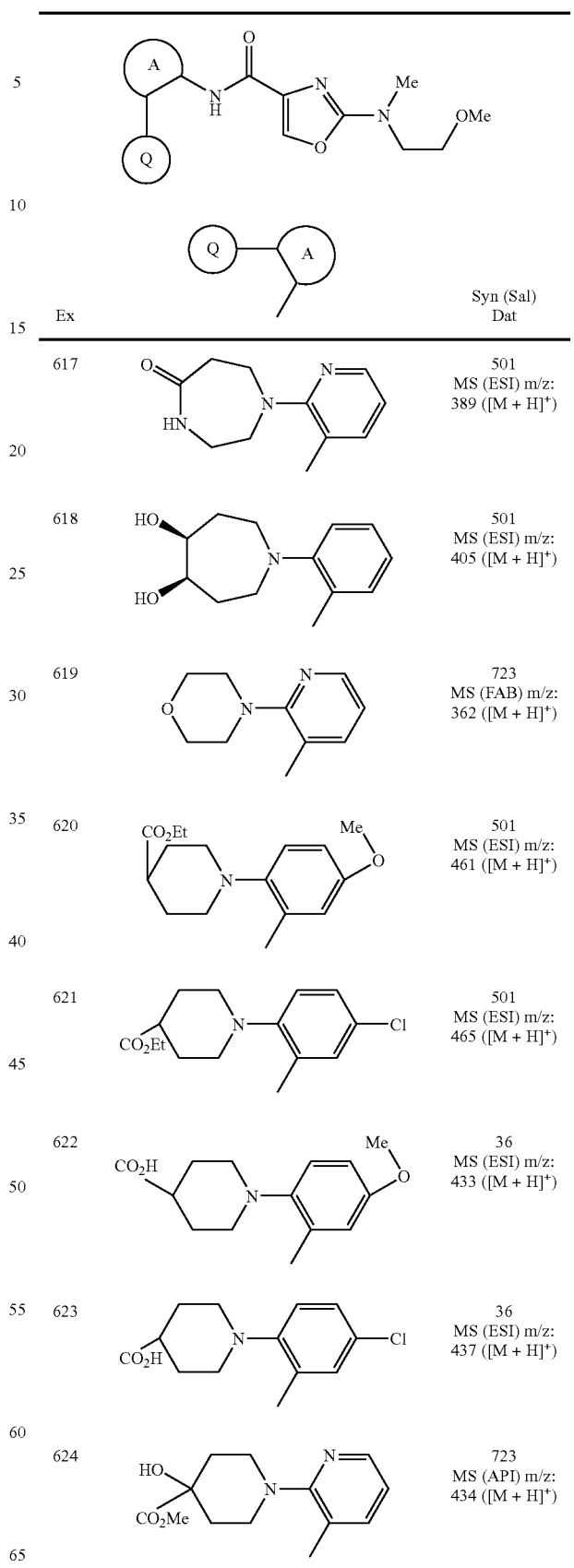

TABLE 31

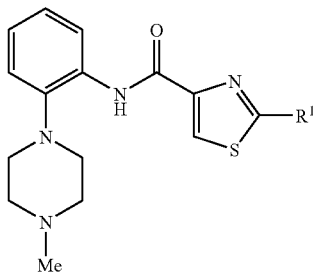

| Ex | R¹ | Syn (Sal) Dat |
|---|---|---|
| 625 | 4-F-phenyl | 501 (HCl) MS (FAB) m/z: 397 ([M + H]⁺) |
| 626 | 2-Cl-phenyl | 501 (HCl) MS (FAB) m/z: 413 ([M + H]⁺) |
| 627 | 4-Cl-phenyl | 501 (HCl) MS (FAB) m/z: 413 ([M + H]⁺) |
| 628 | 2-Br-phenyl | 501 MS (FAB) m/z: 457 ([M + H]⁺) |
| 629 | 3-Br-phenyl | 501 MS (FAB) m/z: 457 ([M + H]⁺) |
| 630 | 2-HO-phenyl | 691 (HCl) MS (FAB) m/z: 395 ([M + H]⁺) |
| 631 | 2-MeO-phenyl | 501 (HCl) MS (FAB) m/z: 409 ([M + H]⁺) |
| 632 | 3-MeO-phenyl | 501 (HCl) MS (FAB) m/z: 409 ([M + H]⁺) |
| 633 | 3-NMe₂-phenyl | 662 (2HCl) MS (FAB) m/z: 422 ([M + H]⁺) |
| 634 | 4-NMe₂-phenyl | 501 (2HCl) MS (FAB) m/z: 422 ([M + H]⁺) |

TABLE 31-continued

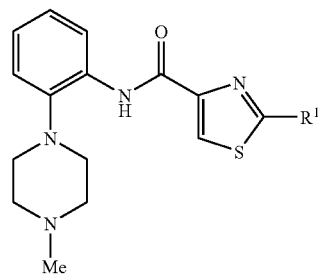

| Ex | R¹ | Syn (Sal) Dat |
|---|---|---|
| 635 | 2-HO₂C-phenyl | 635 (HCl) MS (ESI) m/z: 423 ([M + H]⁺) |
| 636 | 2-CONH₂-phenyl | 167 (HCl) MS (FAB) m/z: 422 ([M + H]⁺) |
| 637 | 3-pyridyl | 501 (2HCl) MS (FAB) m/z: 380 ([M + H]⁺) |
| 638 | 2-pyridyl | 501 (3HCl) MS (FAB) m/z: 380 ([M + H]⁺) |
| 639 | 4-Me-1,4-diazepan-1-yl | 501 (2HCl) MS (FAB) m/z: 415 ([M + H]⁺) |
| 640 | 1-Boc-piperidin-4-yl | 501 MS (FAB) m/z: 486 ([M + H]⁺) |
| 641 | piperidin-4-yl | 146 (2HCl) MS (ESI) m/z: 386 ([M + H]⁺) |
| 642 | 1-acetyl-piperidin-4-yl | 28 (HCl) MS (FAB) m/z: 428 ([M + H]⁺) |
| 643 | 1-Me-piperidin-4-yl | 793 (2HCl) MS (FAB) m/z: 400 ([M + H]⁺) |

TABLE 31-continued

Structure: 2-(4-methylpiperazin-1-yl)phenyl N-linked amide to thiazole-4-carboxamide bearing R¹ at 2-position

| Ex | R¹ | Syn (Sal) Dat |
|---|---|---|
| 644 | 4-methylpiperidine N-SO₂Me | 31 (HCl) MS (FAB) m/z: 464 ([M + H]⁺) |
| 645 | 4-methylpiperidine N-C(O)Ph | 28 (HCl) MS (FAB) m/z: 490 ([M + H]⁺) |

TABLE 32

Structure: 2-(3-oxopiperazin-1-yl)phenyl N-linked amide to thiazole-4-carboxamide bearing R¹ at 2-position

| Ex | R¹ | Syn (Sal) Dat |
|---|---|---|
| 646 | 4-fluorobenzyl (methyl-phenyl-F) | 501 MS (FAB) m/z: 397 ([M + H]⁺) |
| 647 | 3-methylpyridyl | 501 (2HCl) MS (FAB) m/z: 380 ([M + H]⁺) |
| 648 | 3-methylfuryl | 501 MS (ESI) m/z: 369 ([M + H]⁺) |

TABLE 33

Structure: 2-(4-ethoxycarbonylpiperidin-1-yl)phenyl N-linked amide to thiazole-4-carboxamide bearing R¹ at 2-position

| Ex | R¹ | Syn (Sal) Dat |
|---|---|---|
| 649 | 3-methylpyridyl | 501 MS (FAB) m/z: 437 ([M + H]⁺) |
| 650 | 1-methylpyrrolidinyl | 501 MS (FAB) m/z: 429 ([M + H]⁺) |

TABLE 34

Structure: 2-(4-carboxypiperidin-1-yl)phenyl N-linked amide to thiazole-4-carboxamide bearing R¹ at 2-position

| Ex | R¹ | Syn (Sal) Dat |
|---|---|---|
| 651 | 3-methylpyridyl | 36 (Na) MS (FAB) m/z: 409 ([M + H]⁺) |
| 652 | 1-methylpyrrolidinyl | 36 (Na) MS (FAB) m/z: 401 ([M + H]⁺) |

TABLE 35

[Structure: 2-(piperidin-1-yl with 4-CONH2)phenyl NH-C(O)-thiazole-R¹]

| Ex | R¹ | Syn (Sal) Dat |
|---|---|---|
| 653 | 3-pyridyl | 501 (HCl) MS (FAB) m/z: 408 ([M + H]⁺) |
| 654 | 2-pyrazinyl | 501 MS (FAB) m/z: 409 ([M + H]⁺) |
| 655 | 5-pyrimidinyl | 501 (HCl) MS (ESI) m/z: 409 ([M + H]⁺) |
| 656 | 6-OMe-pyridin-3-yl | 692 MS (FAB) m/z: 438 ([M + H]⁺) |
| 657 | 2-Cl-pyridin-3-yl | 662 MS (FAB) m/z: 442 ([M + H]⁺) |
| 658 | 2-HO-pyridin-3-yl | 501 MS (FAB) m/z: 424 ([M + H]⁺) |
| 659 | 2-MeO-pyridin-3-yl | 692 MS (FAB) m/z: 438 ([M + H]⁺) |
| 660 | pyridin-4-yl N-oxide | 501 MS (ESI) m/z: 424 ([M + H]⁺) |
| 661 | pyridin-3-yl N-oxide | 501 MS (ESI) m/z: 424 ([M + H]⁺) |
| 662 | 3-furyl | 662 MS (FAB) m/z: 397 ([M + H]⁺) |
| 663 | 2-furyl | 501 MS (FAB) m/z: 397 ([M + H]⁺) |

TABLE 35-continued

| Ex | R¹ | Syn (Sal) Dat |
|---|---|---|
| 664 | N-methylpyrrolidinyl | 664 MS (FAB) m/z: 400 ([M + H]⁺) |
| 665 | 1-methyl-4-(hydroxymethyl)piperidinyl | 501 MS (ESI) m/z: 444 ([M + H]⁺) |
| 666 | 1-methylpiperidine-4-carboxylic acid ethyl ester | 501 MS (ESI) m/z: 486 ([M + H]⁺) |
| 667 | 1-methylpiperidine-4-carboxylic acid | 36 (Na) MS (FAB) m/z: 458 ([M + H]⁺) |
| 668 | 4-methylthiomorpholinyl | 234 (HCl) MS (FAB) m/z: 432 ([M + H]⁺) |
| 669 | 4-methylthiomorpholine S-oxide | 76 MS (FAB) m/z: 448 ([M + H]⁺) |
| 670 | 4-methylthiomorpholine S,S-dioxide | 723 MS (FAB) m/z: 464 ([M + H]⁺) |
| 671 | 4-methyl-3-oxopiperazinyl | 501 MS (FAB) m/z: 429 ([M + H]⁺) |
| 672 | 4-methyl-1-acetylpiperazinyl | 662 MS (FAB) m/z: 457 ([M + H]⁺) |
| 673 | 1-methyl-4-acetyl-1,4-diazepanyl | 501 MS (FAB) m/z: 471 ([M + H]⁺) |

TABLE 35-continued

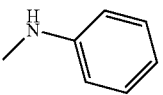

| Ex | R¹ | Syn (Sal) Dat |
|---|---|---|
| 674 | 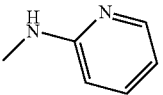 | 501<br>MS (FAB) m/z:<br>422 ([M + H]⁺) |
| 675 | 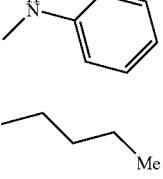 | 501 (HCl)<br>MS (FAB) m/z:<br>423 ([M + H]⁺) |
| 676 | 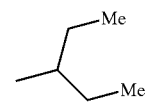 | 501<br>MS (FAB) m/z:<br>387 ([M + H]⁺) |
| 677 | 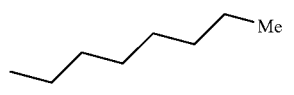 | 234<br>MS (FAB) m/z:<br>401 ([M + H]⁺) |
| 678 | 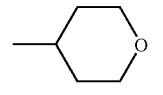 | 234<br>MS (FAB) m/z:<br>429 ([M + H]⁺) |
| 679 | 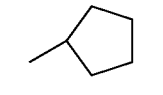 | 234<br>MS (FAB) m/z:<br>415 ([M + H]⁺) |
| 680 | 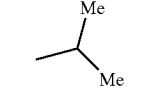 | 234<br>MS (ESI) m/z:<br>399 ([M + H]⁺) |
| 681 | 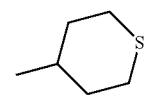 | 234<br>MS (ESI) m/z:<br>373 ([M + H]⁺) |
| 682 | 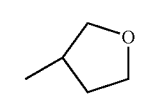 | 234<br>MS (ESI) m/z:<br>431 ([M + H]⁺) |
| 683 | 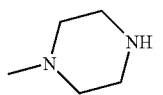 | 234<br>MS (FAB) m/z:<br>401 ([M + H]⁺) |
| 684 | 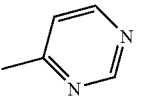 | 356 (HCl)<br>MS (FAB) m/z:<br>415 ([M + H]⁺) |

TABLE 36

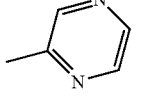

| Ex | R¹ | Syn (Sal) Dat |
|---|---|---|
| 685 | 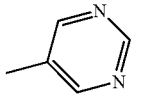 | 501 (2HCl)<br>MS (FAB) m/z:<br>424 ([M + H]⁺) |
| 686 | 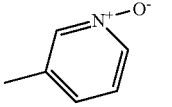 | 501 (HCl)<br>MS (FAB) m/z:<br>424 ([M + H]⁺) |
| 687 | 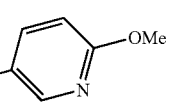 | 501 (HCl)<br>MS (ESI) m/z:<br>424 ([M + H]⁺) |
| 688 | 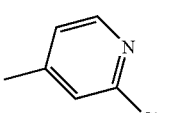 | 501 (HCl)<br>MS (ESI) m/z:<br>439 ([M + H]⁺) |
| 689 | 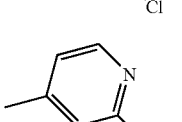 | 501<br>MS (FAB) m/z:<br>453 ([M + H]⁺) |
| 690 | 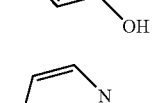 | 501 (HCl)<br>MS (FAB) m/z:<br>457 ([M + H]⁺) |
| 691 | 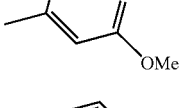 | 691 (HCl)<br>MS (ESI) m/z:<br>439 ([M + H]⁺) |
| 692 | 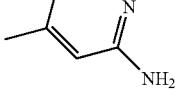 | 692<br>MS (ESI) m/z:<br>453 ([M + H]⁺) |
| 693 |  | 693 (2HCl)<br>MS (ESI) m/z:<br>438 ([M + H]⁺) |
| 694 |  | 850 (2HCl)<br>MS (ESI) m/z:<br>452 ([M + H]⁺) |

TABLE 36-continued

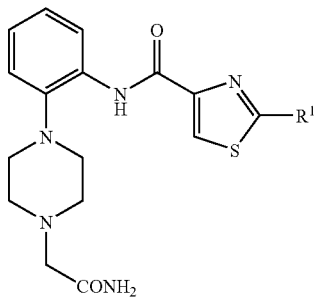

| Ex | R¹ | Syn (Sal) Dat |
|---|---|---|
| 695 | 4-methyl-2-(NMe₂)pyridyl | 695 (2HCl) MS (ESI) m/z: 466 ([M + H]⁺) |
| 696 | 4-methyl-2-(N(Me)CH₂CH₂OMe)pyridyl | 695 (2HCl) MS (ESI) m/z: 510 ([M + H]⁺) |
| 697 | 4-methyl-2-CN-pyridyl | 206 (HCl) MS (ESI) m/z: 448 ([M + H]⁺) |
| 698 | 4-methyl-2-CONH₂-pyridyl | 698 (HCl) MS (ESI) m/z: 466 ([M + H]⁺) |
| 699 | 3-methylfuran | 501 (HCl) MS (FAB) m/z: 412 ([M + H]⁺) |
| 700 | 2-methylfuran | 501 (HCl) MS (FAB) m/z: 412 ([M + H]⁺) |
| 701 | 1-methyl-4-fluoropiperidyl | 356 (HCl) MS (ESI) m/z: 447 ([M + H]⁺) |
| 702 | 1-methyl-3-fluoropiperidyl | 346 (HCl) MS (FAB) m/z: 447 ([M + H]⁺) |
| 703 | 1-methyl-4-oxopiperidyl | 703 (HCl) MS (ESI) m/z: 443 ([M + H]⁺) |
| 704 | (3R)-1-methyl-3-hydroxypiperidyl * | 501 (HCl) MS (ESI) m/z: 445 ([M + H]⁺) |

TABLE 36-continued

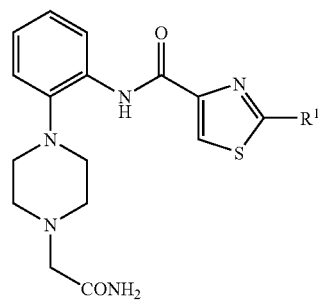

| Ex | R¹ | Syn (Sal) Dat |
|---|---|---|
| 705 | (3S)-1-methyl-3-hydroxypiperidyl * | 501 (HCl) MS (ESI) m/z: 445 ([M + H]⁺) |
| 706 | 1-methyl-4-methoxypiperidyl | 356 (HCl) MS (ESI) m/z: 459 ([M + H]⁺) |
| 707 | 1-methyl-4-carbamoylpiperidyl | 501 (2HCl) MS (ESI) m/z: 472 ([M + H]⁺) |
| 708 | 1-methylpiperidin-4-yl-C(O)NH-(CH₂)₃-OH | 501 (2HCl) MS (FAB) m/z: 530 ([M + H]⁺) |
| 709 | 1-methylpiperidin-4-yl-C(O)NH-CH₂-(tetrahydrofuran-2-yl) | 501 (2HCl) MS (FAB) m/z: 556 ([M + H]⁺) |
| 710 | 1-methylpyrrolidinyl | 356 (HCl) MS (FAB) m/z: 415 ([M + H]⁺) |
| 711 | (3R,4R)-1-methyl-3,4-dihydroxypyrrolidyl * | 356 (HCl) MS (ESI) m/z: 447 ([M + H]⁺) |
| 712 | (3S,4S)-1-methyl-3,4-dihydroxypyrrolidyl | 501 (2HCl) MS (ESI) m/z: 447 ([M + H]⁺) |
| 713 | 1-methyl-4-hydroxy-4-(hydroxymethyl)piperidyl | 501 (HCl) MS (ESI) m/z: 475 ([M + H]⁺) |

TABLE 36-continued

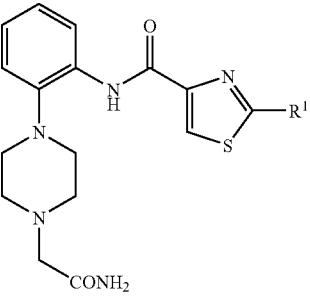

| Ex | R¹ | Syn (Sal) Dat |
|---|---|---|
| 714 | 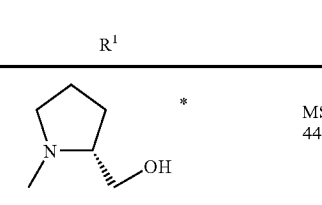 | 356 (HCl) MS (FAB) m/z: 445 ([M + H]⁺) |
| 715 | 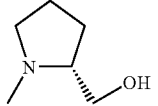 | 356 (HCl) MS (ESI) m/z: 445 ([M + H]⁺) |
| 716 | 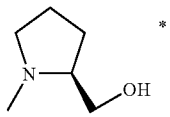 | 356 (HCl) MS (FAB) m/z: 459 ([M + H]⁺) |
| 717 | 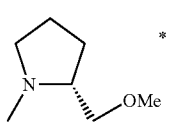 | 356 (HCl) MS (FAB) m/z: 459 ([M + H]⁺) |
| 718 | 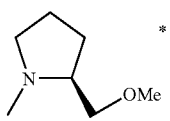 | 718 (HCl) MS (ESI) m/z: 401 ([M + H]⁺) |
| 719 |  | 356 MS (ESI) m/z: 417 ([M + H]⁺) |
| 720 |  | 356 (HCl) MS (FAB) m/z: 445 ([M + H]⁺) |
| 721 | 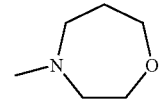 | 356 (HCl) MS (FAB) m/z: 475 ([M + H]⁺) |
| 722 | 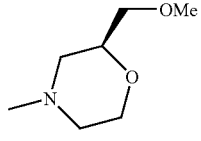 | 234 (HCl) MS (FAB) m/z: 447 ([M + H]⁺) |
| 723 | 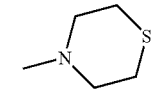 | 723 (HCl) MS (ESI) m/z: 463 ([M + H]⁺) |

TABLE 36-continued

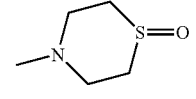

| Ex | R¹ | Syn (Sal) Dat |
|---|---|---|
| 724 | 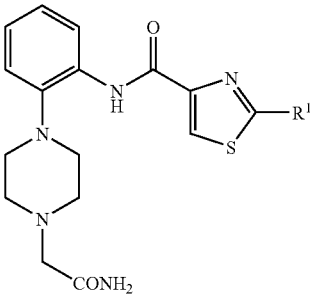 | 723 MS (FAB) m/z: 479 ([M + H]⁺) |
| 725 | 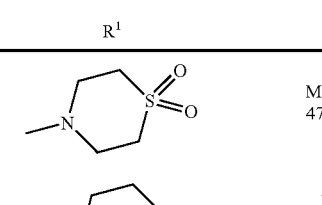 | 356 (2HCl) MS (FAB) m/z: 430 ([M + H]⁺) |
| 726 | 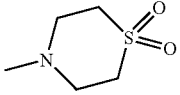 | 501 (HCl) MS (ESI) m/z: 444 ([M + H]⁺) |
| 727 | 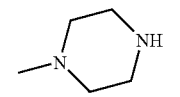 | 356 (HCl) MS (ESI) m/z: 458 ([M + H]⁺) |
| 728 | 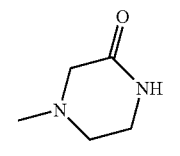 | 501 MS (ESI) m/z: 461 ([M + H]⁺) |
| 729 | —NH₂ | 146 MS (ESI) m/z: 361 ([M + H]⁺) |
| 730 | 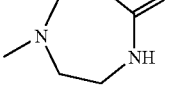 | 356 (HCl) MS (FAB) m/z: 389 ([M + H]⁺) |
| 731 | 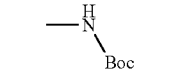 | 356 (HCl) MS (ESI) m/z: 429 ([M + H]⁺) |
| 732 | 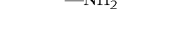 | 356 (HCl) MS (FAB) m/z: 407 ([M + H]⁺) |
| 733 | 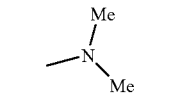 | 356 (HCl) MS (FAB) m/z: 457 ([M + H]⁺) |
| 734 | 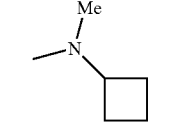 | 734 (HCl) MS (ESI) m/z: 437 ([M + H]⁺) |
| 735 | 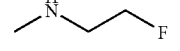 | 356 (HCl) MS (ESI) m/z: 419 ([M + H]⁺) |

TABLE 36-continued

[Common structure for Ex 736–745 and 746–757: 2-(piperazin-1-yl)phenyl amide of 2-R¹-thiazole-4-carboxamide, with piperazine N substituted by –CH₂CONH₂]

| Ex | R¹ | Syn (Sal) Dat |
|---|---|---|
| 736 | MeNH–CH₂CH₂–OH | 356 (HCl) MS (ESI) m/z: 405 ([M + H]⁺) |
| 737 | Et(Me)N–CH₂CH₂–OMe | 356 (HCl) MS (FAB) m/z: 447 ([M + H]⁺) |
| 738 | (Me)(MeCH–)N–CH₂CH₂–OMe | 356 (HCl) MS (ESI) m/z: 461 ([M + H]⁺) |
| 739 | (Me)(iPr)N–CH₂CH₂–OMe | 501 (HCl) MS (ESI) m/z: 461 ([M + H]⁺) |
| 740 | (cyclobutyl)(Me)N–CH₂CH₂–OMe | 501 (HCl) MS (FAB) m/z: 473 ([M + H]⁺) |
| 741 | (CF₃CH₂)(Me)N–CH₂CH₂–OMe | 501 (HCl) MS (FAB) m/z: 501 ([M + H]⁺) |
| 742 | (MeOCH₂CH₂)₂N– | 356 (HCl) MS (FAB) m/z: 477 ([M + H]⁺) |
| 743 | Me₂N–CH₂CH₂CH₂–OMe | 356 (HCl) MS (ESI) m/z: 447 ([M + H]⁺) |
| 744 | Me-N(tetrahydrofuran-3-yl)Me | 356 (HCl) MS (ESI) m/z: 445 ([M + H]⁺) |
| 745 | Me₂N–CH₂–(tetrahydrofuran-2-yl) | 356 (HCl) MS (ESI) m/z: 459 ([M + H]⁺) |
| 746 | Me₂N–CH₂CH₂–NH₂ | 146 (2HCl) MS (FAB) m/z: 418 ([M + H]⁺) |
| 747 | Me₂N–CH₂CH₂–NMe₂ | 356 (2HCl) MS (FAB) m/z: 446 ([M + H]⁺) |
| 748 | Me₂N–CH₂CH₂–NHAc | 28 (HCl) MS (FAB) m/z: 460 ([M + H]⁺) |
| 749 | Me₂N–CH₂CH₂–NHMs | 31 (HCl) MS (FAB) m/z: 496 ([M + H]⁺) |
| 750 | Me₂N–CH₂CH₂–NHBoc | 356 MS (FAB) m/z: 518 ([M + H]⁺) |
| 751 | Me₂N–(azetidin-3-yl)-N–CHPh₂ | 356 MS (FAB) m/z: 596 ([M + H]⁺) |
| 752 | Me₂N–CH₂CH₂–CN | 356 (HCl) MS (FAB) m/z: 428 ([M + H]⁺) |
| 753 | Me₂N–CH₂–CO₂Me | 356 (HCl) MS (FAB) m/z: 447 ([M + H]⁺) |
| 754 | Me₂N–CH₂–CO₂H | 36 (HCl) MS (FAB) m/z: 433 ([M + H]⁺) |
| 755 | Me₂N–CH₂–CONH₂ | 356 (HCl) MS (FAB) m/z: 432 ([M + H]⁺) |
| 756 | Me₂N–CH₂–CONMe₂ | 356 (HCl) MS (FAB) m/z: 460 ([M + H]⁺) |
| 757 | Me₂N–CH₂–Ph | 356 (HCl) MS (ESI) m/z: 465 ([M + H]⁺) |

TABLE 36-continued

Structure (Ex 758–769): 2-(piperazin-1-yl)phenyl connected via NH-C(O) to thiazole bearing R¹; piperazine N substituted with CH₂CONH₂.

| Ex | R¹ | Syn (Sal) Dat |
|---|---|---|
| 758 | N(Me)CH₂-(2-furyl) | 356 (HCl) MS (FAB) m/z: 455 ([M + H]⁺) |
| 759 | N(Me)CH₂CH₂-(2-pyridyl) | 356 (2HCl) MS (ESI) m/z: 480 ([M + H]⁺) |
| 760 | —Br | 501 MS (ESI) m/z: 426 ([M + H]⁺) |
| 761 | 4-methylpiperidin-1-yl | 146 (2HCl) MS (FAB) m/z: 429 ([M + H]⁺) |
| 762 | 1-acetyl-4-methylpiperidin-4-yl | 28 (2HCl) MS (FAB) m/z: 471 ([M + H]⁺) |
| 763 | 1-(carboxymethyl)-4-methylpiperidin-4-yl | 185 MS (FAB) m/z: 487 ([M + H]⁺) |
| 764 | isobutyl (CH₂CH(Me)₂) | 234 (HCl) MS (FAB) m/z: 416 ([M + H]⁺) |
| 765 | n-hexyl | 234 (HCl) MS (FAB) m/z: 444 ([M + H]⁺) |
| 766 | 4-methyltetrahydropyran-4-yl | 234 (HCl) MS (FAB) m/z: 430 ([M + H]⁺) |
| 767 | 3-methyltetrahydrofuran-3-yl | 234 (HCl) MS (FAB) m/z: 416 ([M + H]⁺) |
| 768 | methylcyclopentyl | 234 (HCl) MS (ESI) m/z: 414 ([M + H]⁺) |
| 769 | isopropyl-methyl (CMe₂-) | 234 (HCl) MS (ESI) m/z: 388 ([M + H]⁺) |

TABLE 36-continued

Structure (Ex 770–780): same scaffold as above.

| Ex | R¹ | Syn (Sal) Dat |
|---|---|---|
| 770 | 1-acetyl-3-methylpiperidin-3-yl | 28 (HCl) MS (FAB) m/z: 471 ([M + H]⁺) |
| 771 | n-pentyl (CH(Me)CH₂CH₂CH₃-like) | 234 (HCl) MS (FAB) m/z: 402 ([M + H]⁺) |
| 772 | 3-methylpiperidin-3-yl | 146 (HCl) MS (FAB) m/z: 429 ([M + H]⁺) |
| 773 | 1-Boc-3-methylpiperidin-3-yl | 501 MS (FAB) m/z: 529 ([M + H]⁺) |
| 774 | 4-methylthian-4-yl | 234 (HCl) MS (ESI) m/z: 446 ([M + H]⁺) |
| 775 | 4-methyl-1,1-dioxothian-4-yl | 723 (HCl) MS (ESI) m/z: 478 ([M + H]⁺) |
| 776 | ethyl-methyl (CH(Me)Et) | 234 (HCl) MS (ESI) m/z: 374 ([M + H]⁺) |
| 777 | 1-(carbamoylmethyl)-4-methylpiperidin-4-yl | 185 (HCl) MS (ESI) m/z: 486 ([M + H]⁺) |
| 778 | 1-carbamoyl-4-methylpiperidin-4-yl | 99 (HCl) MS (ESI) m/z: 472 ([M + H]⁺) |
| 779 | 4-hydroxybutyl | 501 (HCl) MS (ESI) m/z: 404 ([M + H]⁺) |
| 780 | 4-methoxybutyl | 501 (HCl) MS (FAB) m/z: 418 ([M + H]⁺) |

TABLE 36-continued

Structure (both 245 and 246): 2-(piperazin-1-yl)phenyl thiazole-4-carboxamide with N-CH2-CONH2 on piperazine, R1 on thiazole C-2.

| Ex | R¹ | Syn (Sal) Dat |
|---|---|---|
| 781 | CH(Me)OH | 501 (HCl) MS (FAB) m/z: 390 ([M + H]⁺) |
| 782 | C(=O)Me | 501 (HCl) MS (FAB) m/z: 388 ([M + H]⁺) |
| 783 | CH(Me)OMe | 501 (HCl) MS (FAB) m/z: 404 ([M + H]⁺) |
| 784 | N(cyclopropyl)(CH2CH2OMe)-CH2– | 501 (HCl) MS (FAB) m/z: 459 ([M + H]⁺) |
| 785 | MeN(H)CH2CH2N(Me)– | 356 (2HCl) MS (FAB) m/z: 432 ([M + H]⁺) |
| 786 | 4-methylpiperazin-1-yl | 356 (2HCl) MS (FAB) m/z: 444 ([M + H]⁺) |
| 787 | N(Me)(tetrahydropyran-4-yl)– | 356 (HCl) MS (FAB) m/z: 459 ([M + H]⁺) |
| 788 | N(Me)(CH2-4-pyridyl)– | 356 (2HCl) MS (FAB) m/z: 466 ([M + H]⁺) |
| 789 | 1-methylpyrrolidin-3-yl-CH2OH | 356 (HCl) MS (ESI) m/z: 445 ([M + H]⁺) |
| 790 | (2-methyl-1-methylpyrrolidinyl)* | 356 (HCl) MS (ESI) m/z: 429 ([M + H]⁺) |
| 791 | (2-methyl-1-methylpyrrolidinyl)* | 356 (HCl) MS (ESI) m/z: 429 ([M + H]⁺) |
| 792 | MeOCH2CH2OCH2– | 792 (HCl) MS (FAB) m/z: 420 ([M + H]⁺) |
| 793 | 4-methylpiperazin-1-yl-CH2CH2– | 793 (2HCl) MS (FAB) m/z: 472 ([M + H]⁺) |
| 794 | N(Me)(CH2CH2OH)CH2– | 356 (HCl) MS (ESI) m/z: 433 ([M + H]⁺) |
| 795 | N(Me)(CH2CH2OEt)CH2– | 356 (HCl) MS (FAB) m/z: 447 ([M + H]⁺) |
| 796 | N(Me)(CH2CH2SMe)CH2– | 356 (HCl) MS (FAB) m/z: 449 ([M + H]⁺) |
| 797 | 4,4-difluoro-1-methylpiperidinyl | 356 (HCl) MS (ESI) m/z: 465 ([M + H]⁺) |
| 798 | 3,3-difluoro-1-methylpyrrolidinyl | 356 (HCl) MS (ESI) m/z: 451 ([M + H]⁺) |
| 799 | 3-fluoro-1-methylpyrrolidinyl* | 356 (HCl) MS (ESI) m/z: 433 ([M + H]⁺) |
| 800 | 3-fluoro-1-methylpyrrolidinyl* | 356 (HCl) MS (ESI) m/z: 433 ([M + H]⁺) |
| 801 | C(Me)2CH2OH | 501 (HCl) MS (FAB) m/z: 418 ([M + H]⁺) |
| 802 | C(Me)2CH2OMe | 501 (HCl) MS (FAB) m/z: 432 ([M + H]⁺) |

TABLE 36-continued

| Ex | R¹ | Syn (Sal) Dat |
|---|---|---|
| 803 | —N(Me)CH₂CH₂OCH₂CH₂OMe | 356 (HCl) MS (FAB) m/z: 477 ([M + H]⁺) |
| 804 | —N(Me)CH₂CH₂S(=O)Me | 662 (HCl) MS (ESI) m/z: 465 ([M + H]⁺) |
| 805 | —N(Me)CH₂CH₂S(=O)₂Me | 662 (HCl) MS (ESI) m/z: 481 ([M + H]⁺) |
| 806 | N-ethylmorpholinyl | 501 (2HCl) MS (ESI) m/z: 445 ([M + H]⁺) |
| 807 | N-ethyl-Me,Me-morpholine | 501 (2HCl) MS (FAB) m/z: 447 ([M + H]⁺) |
| 808 | 3-methyl-6-methoxypyridazinyl | 501 (HCl) MS (ESI) m/z: 454 ([M + H]⁺) |
| 809 | —CH(Me)CH₂OH | 501 (HCl) MS (ESI) m/z: 418 ([M + H]⁺) |
| 810 | N-methyl-1-Cbz-pyrrolidin-3-ylamine | 356 (HCl) MS (ESI) m/z: 578 ([M + H]⁺) |
| 811 | (4-methylmorpholin-2-yl)methyl-NMe₂ * | 356 (2HCl) MS (ESI) m/z: 488 ([M + H]⁺) |
| 812 | (3R)-1-methyl-3-methoxypyrrolidinyl * | 356 (HCl) MS (ESI) m/z: 445 ([M + H]⁺) |

TABLE 36-continued

| Ex | R¹ | Syn (Sal) Dat |
|---|---|---|
| 813 | 1-methyl-3-ethylazetidinyl | 356 MS (FAB) m/z: 431 ([M + H]⁺) |
| 814 | 1-methyl-3-hydroxymethylazetidinyl | 356 MS (ESI) m/z: 431 ([M + H]⁺) |
| 815 | (3)-3-(methoxymethyl)piperazin-1-yl-methyl * | 815 (2HCl) MS (FAB) m/z: 474 ([M + H]⁺) |
| 816 | —CH₂CH(Me)CH₂OMe | 501 (HCl) MS (FAB) m/z: 432 ([M + H]⁺) |
| 817 | —CMe₂CH₂OMe | 501 (HCl) MS (FAB) m/z: 446 ([M + H]⁺) |
| 818 | (S)-2-(methoxymethyl)-4-methylpiperazin-1-yl * | 146 (2HCl) MS (FAB) m/z: 474 ([M + H]⁺) |
| 819 | —CMe₂CH₂CH₂OH | 501 (HCl) MS (FAB) m/z: 432 ([M + H]⁺) |
| 820 | —N(Me)CH₂CH(OH)Me | 662 (HCl) MS (ESI) m/z: 433 ([M + H]⁺) |
| 821 | —NHMe CH(CH₂OMe)₂ | 821 MS (ESI) m/z: 477 ([M + H]⁺) |
| 822 | 1-methyl-1,4-diazepanyl | 356 (2HCl) MS (FAB) m/z: 444 ([M + H]⁺) |
| 823 | 1,4-dimethyl-1,4-diazepanyl | 356 (2HCl) MS (FAB) m/z: 458 ([M + H]⁺) |

TABLE 36-continued

Structure (Ex 824–832): 2-(piperazin-1-yl)phenyl core with N-H amide linked to thiazole bearing R¹; piperazine N substituted with CH₂CONH₂.

| Ex | R¹ | Syn (Sal) Dat |
|---|---|---|
| 824 | N(Me)- linked to oxetan-3-yl (N-methyl) | 356 MS (ESI) m/z: 431 ([M + H]⁺) |
| 825 | NH(Me)- oxetan-3-yl | 356 MS (ESI) m/z: 417 ([M + H]⁺) |
| 826 | N(Me)(Et)(Et)- (diethylmethylamine-like) | 356 (HCl) MS (ESI) m/z: 417 ([M + H]⁺) |
| 827 | 4-methylpiperazin-2-yl-methanol (*) | 815 (2HCl) MS (FAB) m/z: 460 ([M + H]⁺) |
| 828 | 2,5-diazabicyclo[2.2.1]heptane, N-methyl | 356 (2HCl) MS (FAB) m/z: 442 ([M + H]⁺) |
| 829 | 4-methylmorpholin-3-yl-methanol | 501 (HCl) MS (ESI) m/z: 461 ([M + H]⁺) |
| 830 | 1-methyl-3,4-dimethoxypyrrolidin-3-yl | 356 (HCl) MS (ESI) m/z: 475 ([M + H]⁺) |
| 831 | 4-methylmorpholin-3-yl-methoxymethyl | 501 (HCl) MS (ESI) m/z: 475 ([M + H]⁺) |
| 832 | 4-methylpiperidin-4-yl (NH) | 146 (2HCl) MS (FAB) m/z: 443 ([M + H]⁺) |

TABLE 36-continued

Structure (Ex 833–841): same core as above.

| Ex | R¹ | Syn (Sal) Dat |
|---|---|---|
| 833 | *CH(CF₃)-N(Me)-tetrahydrofuran-3-yl | 662 (HCl) MS (FAB) m/z: 513 ([M + H]⁺) |
| 834 | 2-bromo-6-ethoxyphenyl | 723 (HCl) MS (FAB) m/z: 530 ([M + H]⁺) |
| 835 | N,N-dimethyl-pyrrolidin-3-amine (NH) | 835 (2HCl) MS (ESI) m/z: 444 ([M + H]⁺) |
| 836 | N,N-dimethyl-(1-methylpyrrolidin-3-yl)amine | 793 (2HCl) MS (ESI) m/z: 458 ([M + H]⁺) |
| 837 | 1-methyl-3-(methylamino)pyrrolidine | 837 (2HCl) MS (ESI) m/z: 444 ([M + H]⁺) |
| 838 | 3-ethyl-5-(trifluoromethyl)phenyl | 723 (HCl) MS (FAB) m/z: 504 ([M + H]⁺) |
| 839 | 1-methyl-3-(methoxymethyl)pyrrolidine (*) | 356 (HCl) MS (ESI) m/z: 459 ([M + H]⁺) |
| 840 | 1-methyl-3-hydroxy-5-(hydroxymethyl)pyrrolidine (*) | 723 MS (ESI) m/z: 461 ([M + H]⁺) |
| 841 | N-ethyl-N,N-dimethyl (ethyldimethylamine) | 723 (2HCl) MS (FAB) m/z: 403 ([M + H]⁺) |

TABLE 36-continued

Structure: 2-(piperazin-1-yl)phenyl-NH-C(O)-thiazole-R¹, with piperazine N-CH₂-CONH₂

| Ex | R¹ | Syn (Sal) Dat |
|---|---|---|
| 842 | 3,5-dichloro-ethylphenyl | 723 (HCl) MS (FAB) m/z: 504 ([M + H]⁺) |
| 843 | (trans)-1-methyl-4-phenyl-3-(hydroxymethyl)pyrrolidine | 356 MS (ESI) m/z: 521 ([M + H]⁺) |
| 844 | 1-methyl-2-oxopyrrolidin-3-yl | 501 (HCl) MS (ESI) m/z: 429 ([M + H]⁺) |
| 845 | 4-methyl-1-Boc-piperidine | 501 MS (ESI) m/z: 529 ([M + H]⁺) |
| 846 | 3-methyl-4-Boc-morpholine | 501 MS (ESI) m/z: 515 ([M + H]⁺) |
| 847 | (methoxymethyl)-1-methyl-4-Boc-piperazine* | 501 MS (FAB) m/z: 574 ([M + H]⁺) |
| 848 | 1-methyl-4-benzyl-2-(hydroxymethyl)piperazine* | 356 MS (FAB) m/z: 550 ([M + H]⁺) |
| 849 | 4,4-dimethyl-1-Boc-piperidine | 501 MS (FAB) m/z: 543 ([M + H]⁺) |

TABLE 37

Structure: 2-(piperidin-1-yl)phenyl-NH-C(O)-thiazole-R¹, with piperidine 4-C(O)NHMe

| Ex | R¹ | Syn (Sal) Dat |
|---|---|---|
| 850 | 4-methyl-2-(NHMe)pyridine | 850 (2HCl) MS (ESI) m/z: 466 ([M + H]⁺) |

TABLE 38

Structure: 3-amino-2-(piperidin-1-yl)pyridine-NH-C(O)-thiazole-R¹, with piperidine 4-CONH₂

| Ex | R¹ | Syn (Sal) Dat |
|---|---|---|
| 851 | cyclobutyl-N(Me)-CH₂CH₂-OMe | 501 (HCl) MS (FAB) m/z: 459 ([M + H]⁺) |
| 852 | 4-methyl-tetrahydropyran | 501 (HCl) MS (ESI) m/z: 416 ([M + H]⁺) |
| 853 | isopropyl (CHMe₂) | 501 (HCl) MS (ESI) m/z: 374 ([M + H]⁺) |
| 854 | n-propyl-OMe | 501 (HCl) MS (FAB) m/z: 404 ([M + H]⁺) |
| 855 | 1-hydroxyethyl (CH(Me)OH) | 501 (HCl) MS (ESI) m/z: 376 ([M + H]⁺) |
| 856 | acetyl (C(O)Me) | 502 (HCl) MS (FAB) m/z: 374 ([M + H]⁺) |

TABLE 38-continued

| Ex | R¹ | Syn (Sal) Dat |
|---|---|---|
| 857 | | 501 (HCl) MS (FAB) m/z: 390 ([M + H]⁺) |
| 858 | | 501 (HCl) MS (FAB) m/z: 445 ([M + H]⁺) |
| 859 | | 662 (HCl) MS (ESI) m/z: 419 ([M + H]⁺) |
| 860 | | 234 (HCl) MS (FAB) m/z: 433 ([M + H]⁺) |

TABLE 39

| Ex | R¹ | Syn (Sal) Dat |
|---|---|---|
| 861 | | 501 (HCl) MS(ESI) m/z: 412([M + H]⁺) |
| 862 | | 501 (HCl) MS(FAB) m/z: 396([M + H]⁺) |
| 863 | | 501 (HCl) MS(FAB) m/z: 396([M + H]⁺) |
| 864 | | 864 MS(ESI) m/z: 395([M + H]⁺) |

TABLE 39-continued

| Ex | R¹ | Syn (Sal) Dat |
|---|---|---|
| 865 | | 501 (HCl) MS(ESI) m/z: 414([M + H]⁺) |
| 866 | | 501 (HCl) MS(ESI) m/z: 428([M + H]+) |
| 867 | | 501 (HCl) MS(ESI) m/z: 428([M + H]⁺) |
| 868 | | 501 (HCl) MS(ESI) m/z: 412([M + H]⁺) |
| 869 | | 501 (HCl) MS(FAB) m/z: 436([M + H]⁺) |
| 870 | | 501 (2HCl) MS(ESI) m/z: 489([M + H]⁺) |
| 871 | | 146 (2HCl) MS(ESI) m/z: 415([M + H]⁺) |
| 872 | | 723 (HCl) MS(ESI) m/z: 441([M + H]⁺) |
| 873 | | 501 (HCl) MS(FAB) m/z: 514([M + H]⁺) |
| 874 | | 723 (HCl) MS(FAB) m/z: 402([M + H]⁺) |
| 875 | | 723 (HCl) MS(FAB) m/z: 374([M + H]⁺) |

TABLE 39-continued

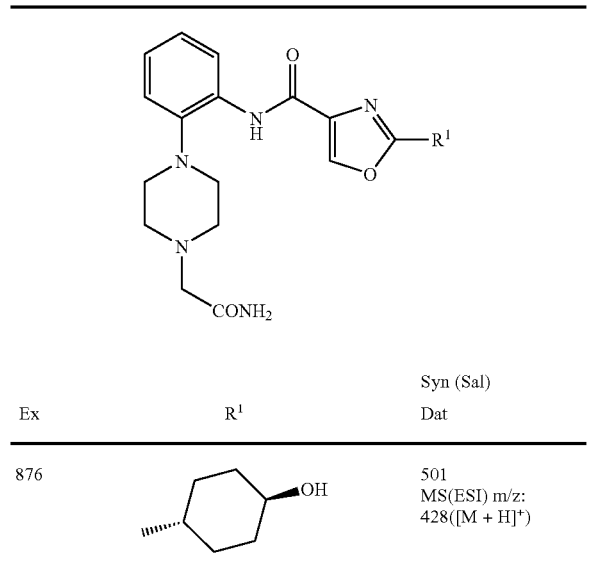

| Ex | R[1] | Syn (Sal) Dat |
|---|---|---|
| 876 | (trans-4-methylcyclohexan-1-ol) | 501 MS(ESI) m/z: 428([M + H]+) |

TABLE 40

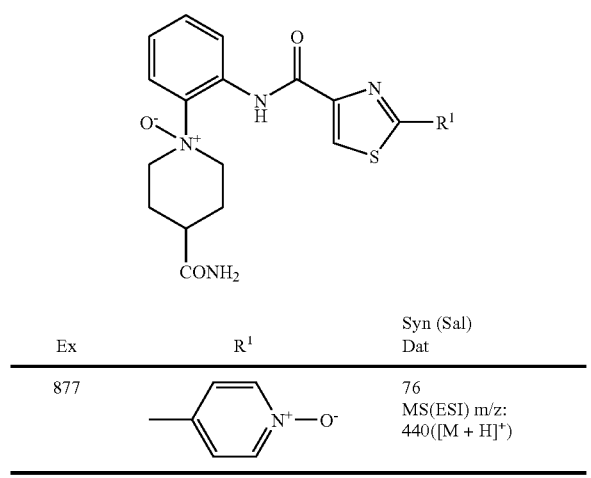

| Ex | R[1] | Syn (Sal) Dat |
|---|---|---|
| 877 | (4-methylpyridine N-oxide) | 76 MS(ESI) m/z: 440([M + H]+) |

TABLE 41

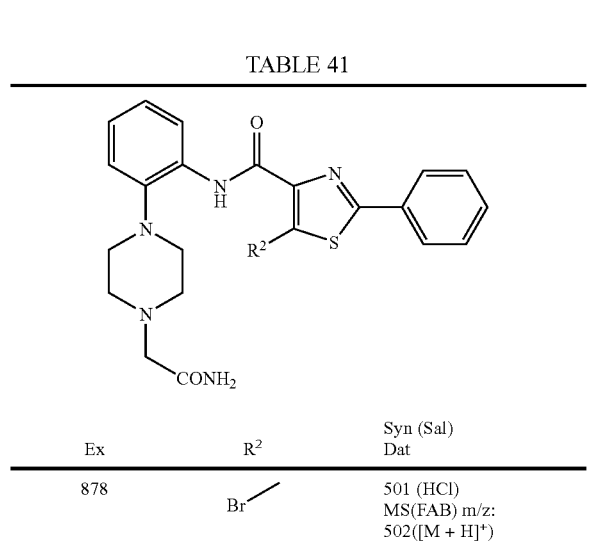

| Ex | R[2] | Syn (Sal) Dat |
|---|---|---|
| 878 | Br— | 501 (HCl) MS(FAB) m/z: 502([M + H]+) |

TABLE 41-continued

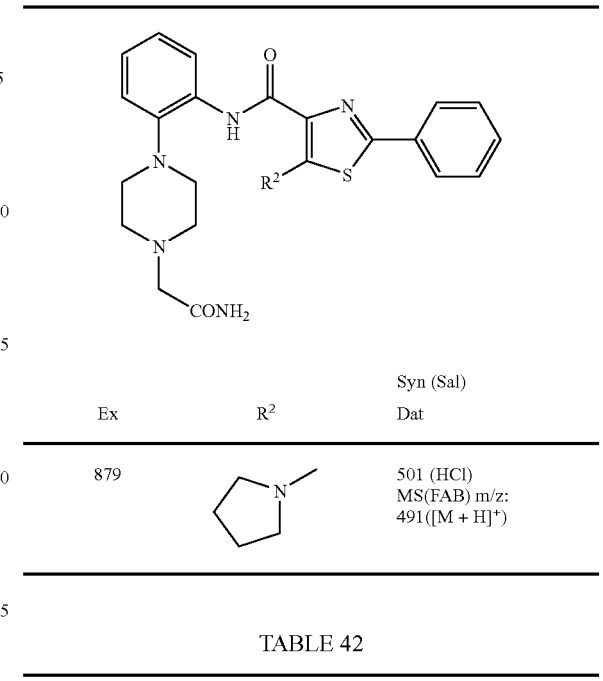

| Ex | R[2] | Syn (Sal) Dat |
|---|---|---|
| 879 | (1-methylpyrrolidine) | 501 (HCl) MS(FAB) m/z: 491([M + H]+) |

TABLE 42

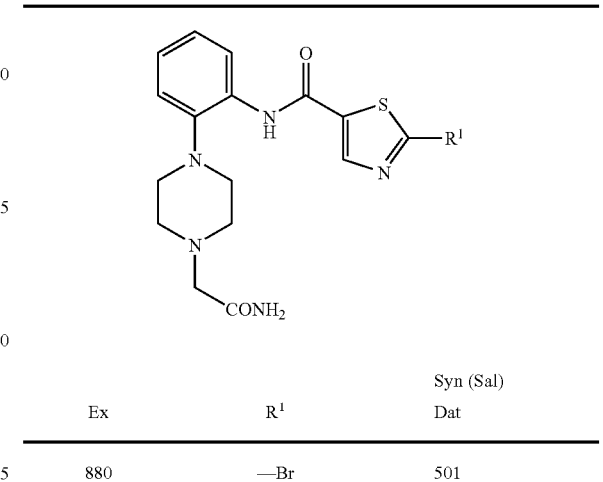

| Ex | R[1] | Syn (Sal) Dat |
|---|---|---|
| 880 | —Br | 501 MS(FAB) m/z: 424([M + H]+) |
| 881 | (morpholine) | 356 (HCl) MS(FAB) m/z: 431([M + H]+) |
| 882 | (N,N-dimethyl-2-methoxyethylamine) | 356 (HCl) MS(FAB) m/z: 433([M + H]+) |
| 883 | (3-(trifluoromethyl)phenyl) | 723 (HCl) MS(FAB) m/z: 504([M + H]) |

TABLE 43

[Structure: A-NH-C(=O)-thiazole-tetrahydropyran, with A-Q substructure shown]

| Ex | Structure | Syn (Sal) Dat |
|---|---|---|
| 884 | HN-piperidine-2-methylphenyl | 146 (HCl) MS(FAB) m/z: 370([M + H]+) |
| 885 | Boc-N-tetrahydropyridine-2-methylphenyl | 501 MS(FAB) m/z: 470([M + H]+) |
| 886 | CONH2-CH2-N-tetrahydropyridine-2-methylphenyl | 185 (HCl) MS(ESI) m/z: 427([M + H]+) |
| 887 | CONH2-CH2-N-piperidine-2-methylphenyl | 234 (HCl) MS(FAB) m/z: 429([M + H]+) |
| 888 | CN-CH2-N-tetrahydropyridine-2-methylphenyl | 63 (HCl) MS(FAB) m/z: 409([M + H]+) |
| 889 | CONH2-CH2-N-piperazine-2-F-6-methylphenyl | 501 (HCl) MS(ESI) m/z: 448([M + H]+) |
| 890 | CONH2-CH2-N-piperazine-5-F-2-methylphenyl | 501 (HCl) MS(ESI) m/z: 448([M + H]+) |
| 891 | CONH2-CH2-N-piperazine-4-F-2-methylphenyl | 501 (HCl) MS(ESI) m/z: 448([M + H]+) |
| 892 | CONH2-CH2-N-piperidine-methylpyridine | 501 (HCl) MS(ESI) m/z: 416([M + H]+) |

TABLE 43-continued

| Ex | Structure | Syn (Sal) Dat |
|---|---|---|
| 893 | CONH2-CH2-N-diazepane-N-2-methylphenyl | 501 (HCl) MS(FAB) m/z: 444([M + H]+) |
| 894 | CONH2-CH2-N-piperazine-N-3-methylpyridin-2-yl | 501 (2HCl) MS(FAB) m/z: 431([M + H]+) |
| 895 | CONH2-piperidine-N-5-F-3-methylpyridin-2-yl | 501 (HCl) MS(FAB) m/z: 434([M + H]+) |
| 896 | CONH2-CH2-N-piperazine-N-6-OMe-3-methylpyridin-2-yl | 501 (HCl) MS(FAB) m/z: 461([M + H]+) |
| 897 | CONH2-CH2-N-piperazine-N-4-CN-3-methylphenyl | 501 (HCl) MS(ESI) m/z: 455([M + H]+) |
| 898 | oxadiazole-CH2-N-piperazine-N-2-methylphenyl | 501 (HCl) MS(ESI) m/z: 455([M + H]+) |
| 899 | CONH2-CH2-N-tetrahydropyridine-4-OMe-2-methylphenyl | 501 (HCl) MS(ESI) m/z: 457([M + H]+) |

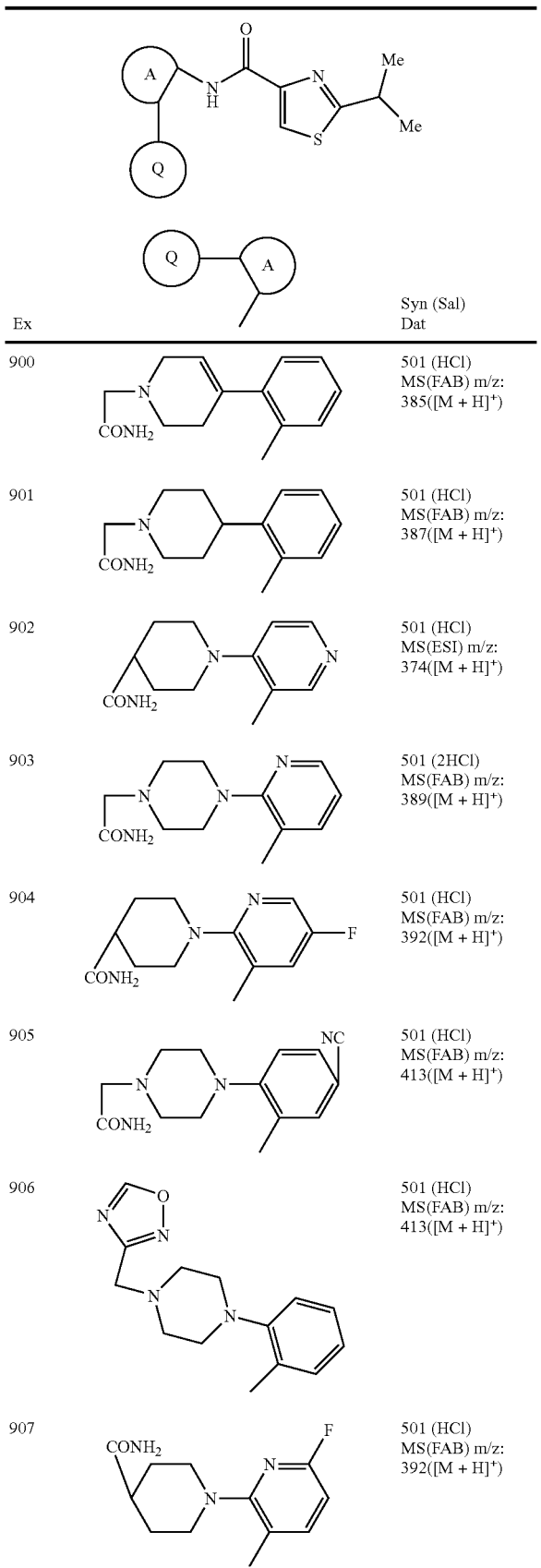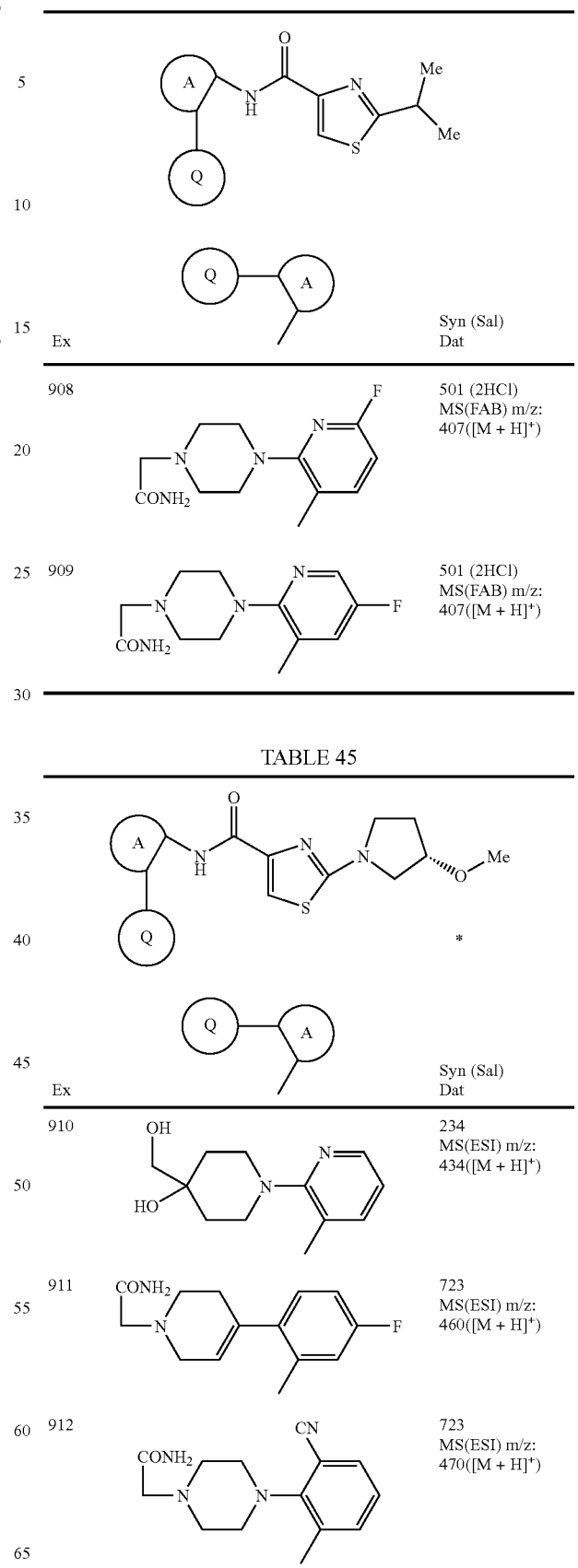

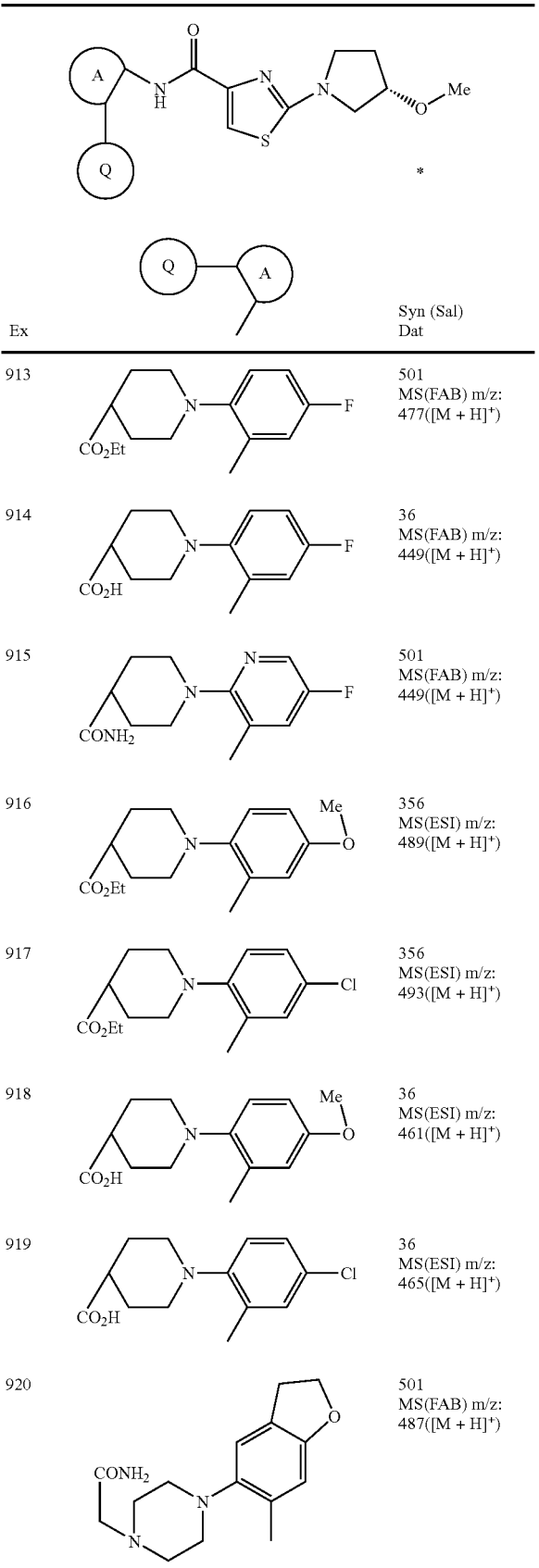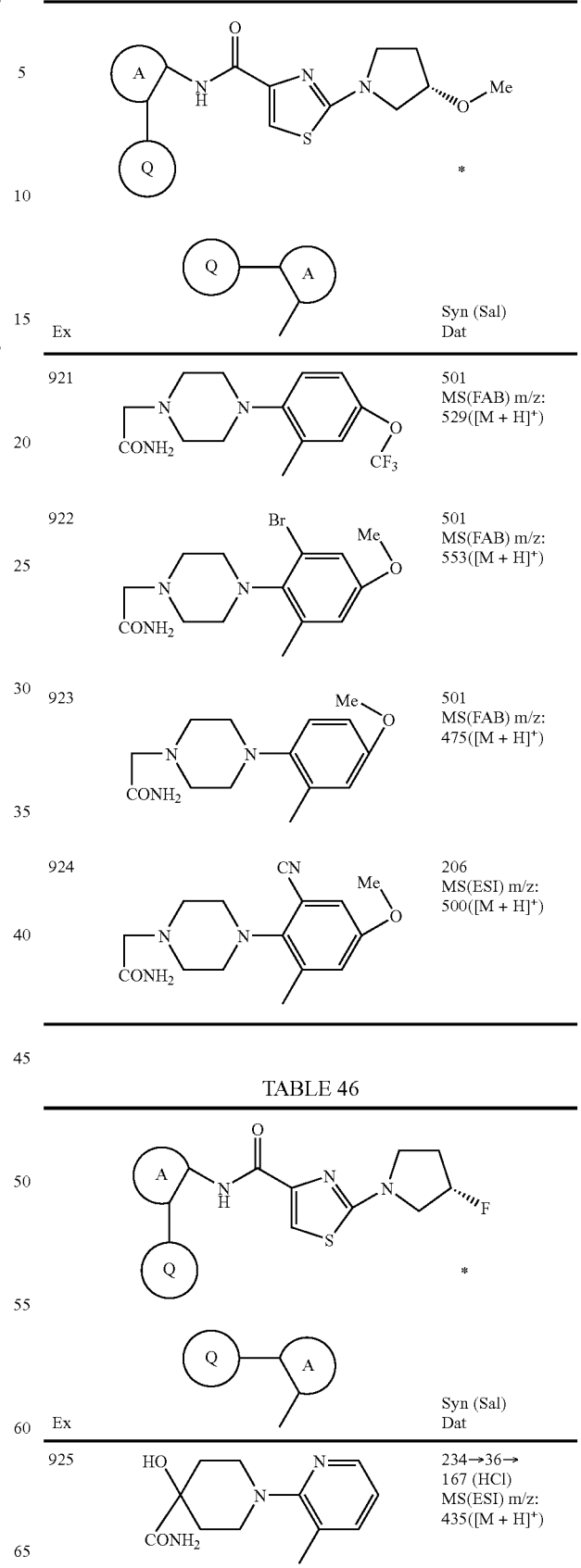

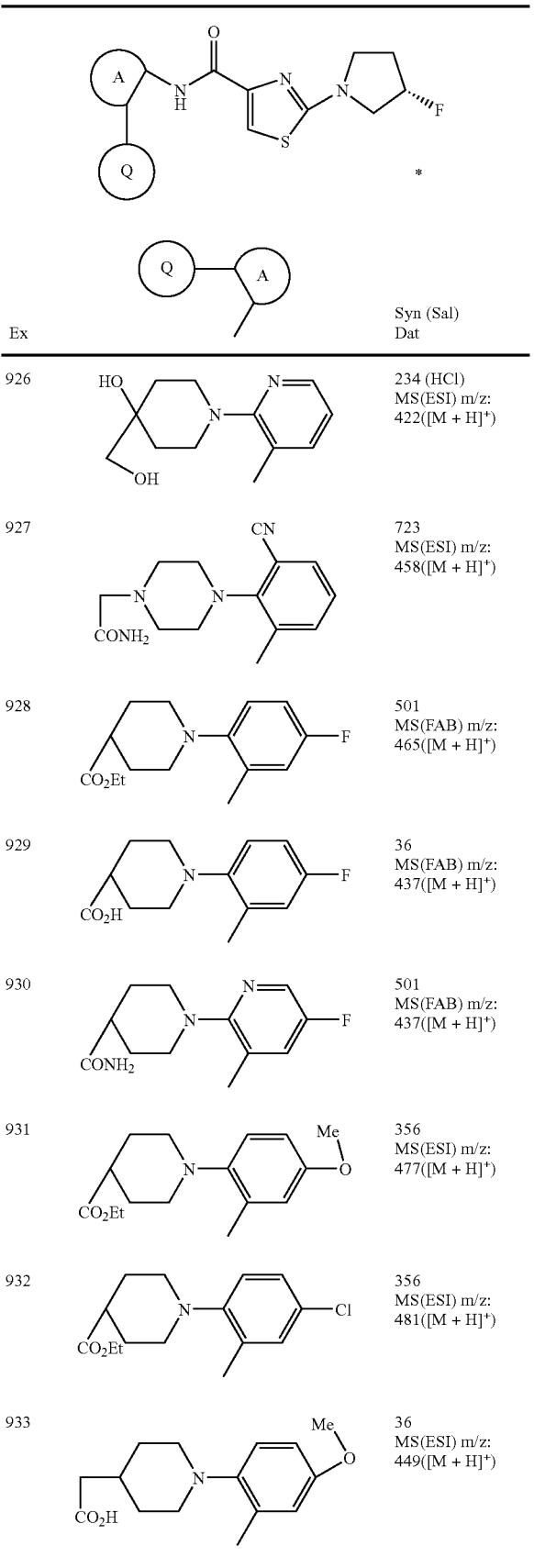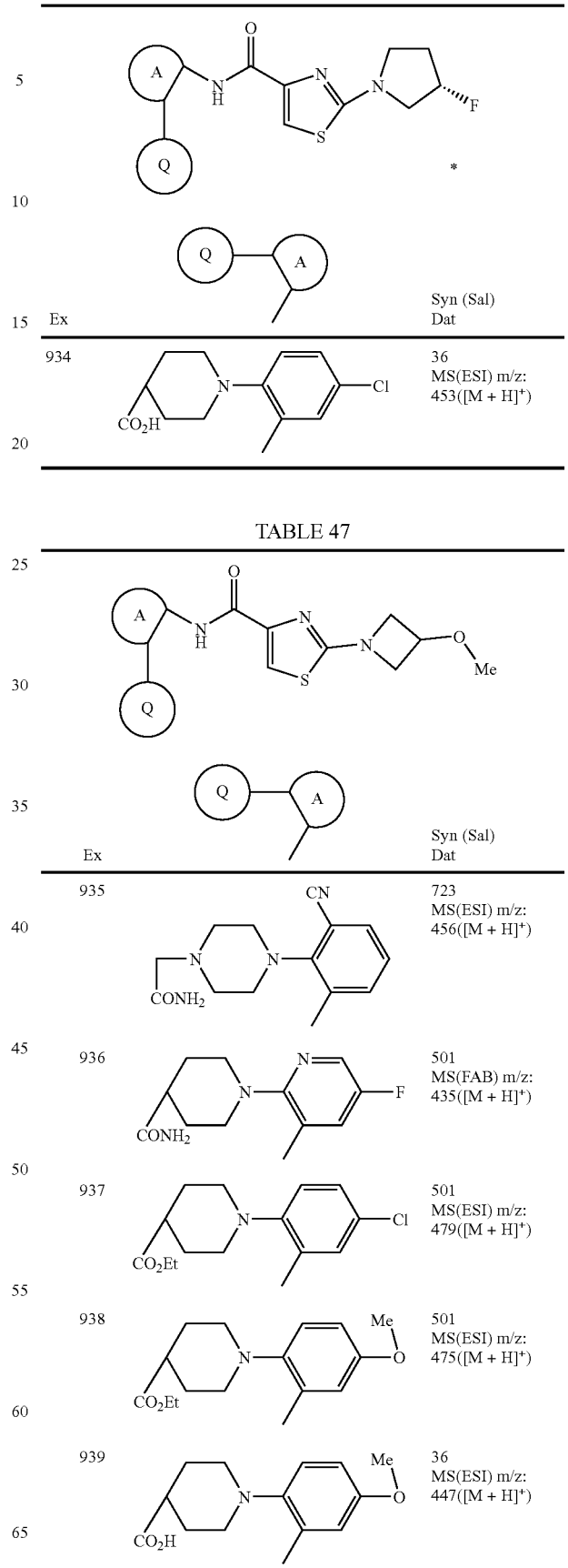

TABLE 47-continued

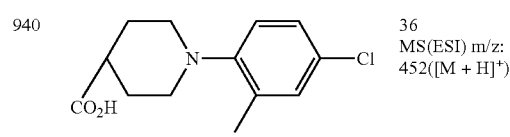

| Ex | Q-A | Syn (Sal) Dat |
|---|---|---|
| 940 | (piperidine-N-(4-Cl-2-Me-phenyl), 4-CO₂H) | 36 MS(ESI) m/z: 452([M + H]⁺) |

TABLE 48

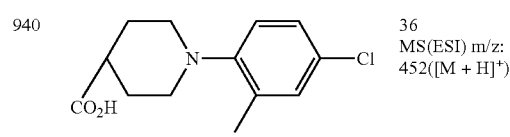

| Ex | Q-A | Syn (Sal) Dat |
|---|---|---|
| 941 | 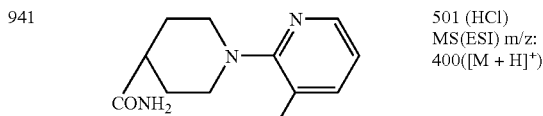 | 501 (HCl) MS(ESI) m/z: 400([M + H]⁺) |
| 942 | 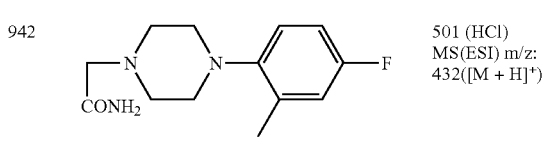 | 501 (HCl) MS(ESI) m/z: 432([M + H]⁺) |
| 943 | 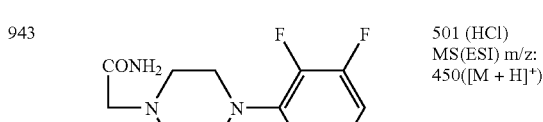 | 501 (HCl) MS(ESI) m/z: 450([M + H]⁺) |

TABLE 49

| Ex | | Syn (Sal) Dat |
|---|---|---|
| 944 | (piperidine-N-(2-Me-phenyl), 4-CONH₂) | 501 MS(ESI) m/z: 357([M + H]⁺) |

TABLE 50

| Ex | R¹ | Syn (Sal) Dat |
|---|---|---|
| 945 | N-Me piperidine-4-OMe | 501 MS(FAB) m/z: 463([M + H]⁺) |
| 946 | (S)-N-Me-2-Me-pyrrolidine * | 501 MS(FAB) m/z: 433([M + H]⁺) |
| 947 | N(Me)(CH₂CH₂OMe)(Et) | 356 MS(FAB) m/z: 451([M + H]⁺) |
| 948 | N(Me)-(tetrahydrofuran-3-yl) | 356 MS(FAB) m/z: 449([M + H]⁺) |
| 949 | —Br | 501 MS(FAB) m/z: 428([M + H]⁺) |

TABLE 51

| Ex | R¹ | Syn (Sal) Dat |
|---|---|---|
| 950 | cyclohexyl-OH (4-Me, trans) | 501 (HCl) MS(ESI) m/z: 414([M + H]⁺) |
| 951 | cyclohexyl-OH (4-Me, cis) | 501 (HCl) MS(ESI) m/z: 414([M + H]⁺) |
| 952 | 1-methylpiperidin-4-yl-O-Et | 952 MS(ESI) m/z: 443([M + H]⁺) |

TABLE 52

| Ex | R¹ | Syn (Sal) Dat |
|---|---|---|
| 953 | (3-methylmorpholin-3-yl)methyl OMe * | 501 MS(FAB) m/z: 507([M + H]⁺) |
| 954 | (3S)-3-methyl-4-methylmorpholine * | 501 MS(FAB) m/z: 477([M + H]⁺) |
| 955 | N,N-dimethyl-1-methoxy-2-propyl * | 501 MS(FAB) m/z: 479([M + H]⁺) |
| 956 | N,N-dimethyl-1-methoxy-2-propyl * | 501 MS(FAB) m/z: 479([M + H]⁺) |
| 957 | N-methyl-oxabicyclic amine * | 501 MS(FAB) m/z: 475([M + H]⁺) |
| 958 | (3-methoxy-1-methylpiperidin-3-yl) * | 501 MS(FAB) m/z: 491([M + H]+) |
| 959 | (1,1-dimethyl)-N-methyl-N-(2-methoxyethyl)amine | 501 MS(FAB) m/z: 493([M + H]⁺) |

TABLE 53

| Ex | R¹ | Syn (Sal) Dat |
|---|---|---|
| 960 | (3-methylmorpholin-3-yl)methyl OMe * | 36 MS(FAB) m/z: 479([M + H]⁺) |

TABLE 53-continued

Core structure: 4-fluoro-2-(piperidin-1-yl)phenyl with 4-CO2H on piperidine, N-(thiazol-4-yl-carboxamide) where thiazole bears R¹ at 2-position.

| Ex | R¹ | Syn (Sal) Dat |
|---|---|---|
| 961 | (3S)-3-methylmorpholin-4-yl (*) | 36 MS(FAB) m/z: 449([M + H]⁺) |
| 962 | N,N,2-trimethyl-1-methoxypropan-2-amine derivative (N(Me)–C(Me)(Me)–CH2–OMe) (*) | 36 MS(FAB) m/z: 451([M + H]⁺) |
| 963 | same as 962, opposite stereochem (*) | 36 MS(FAB) m/z: 451([M + H]⁺) |
| 964 | N-methyl-8-oxa-3-azabicyclo[3.2.1]octane (*) | 36 MS(FAB) m/z: 447([M + H]⁺) |
| 965 | (3R)-3-methoxy-1-methylpiperidin-1-yl (*) | 36 MS(FAB) m/z: 463([M + H]⁺) |
| 966 | N-(1-methylethyl)-N-methyl-2-methoxyethylamine | 36 MS(FAB) m/z: 465([M + H]⁺) |

TABLE 54

Core: 3-fluoro-2-[4-(carbamoylmethyl)piperazin-1-yl]phenyl N-(2-R¹-thiazol-4-yl)carboxamide.

| Ex | R¹ | Syn (Sal) Dat |
|---|---|---|
| 967 | –CH(Me)–O–(CH2)2–Me (butoxy-methyl type: N-Me, O-Me branched) | 501 (HCl) MS (FAB) m/z: 436 ([M + H]⁺) |

TABLE 55

Core: pyridin-3-yl (2-piperidinyl with 4-OH, 4-CONH2) N-(2-R¹-thiazol-4-yl)carboxamide.

| Ex | R¹ | Syn (Sal) Dat |
|---|---|---|
| 968 | –N(Me)–CH2–CH(Me)–O–Me | 36 (HCl) MS (FAB) m/z: 449 ([M + H]⁺) |

TABLE 56

Core: 3-cyano-2-[4-(carbamoylmethyl)piperazin-1-yl]phenyl N-(2-R¹-thiazol-4-yl)carboxamide.

| Ex | R¹ | Syn (Sal) Dat |
|---|---|---|
| 969 | N-methyl-N-(tetrahydrofuran-3-yl)amino | 723 MS(ESI) m/z: 470([M + H]⁺) |

TABLE 56-continued

| Ex | R¹ | Syn (Sal) Dat |
|---|---|---|
| 970 | N-methyl pyrrolidine (Me, *) | 723 MS(ESI) m/z: 454([M + H]⁺) |

TABLE 57

| Ex | (structure) | Syn (Sal) Dat |
|---|---|---|
| 971 | CO₂Et-piperidine-N-phenyl(Me)(O-) | 356 MS(ESI) m/z: 503([M + H]⁺) |
| 972 | CO₂Et-piperidine-N-phenyl(Me)(Cl) | 365 MS(ESI) m/z: 507([M + H]⁺) |
| 973 | CO₂H-piperidine-N-phenyl(Me)(O-) | 36 MS(ESI) m/z: 475([M + H]⁺) |
| 974 | CO₂H-piperidine-N-phenyl(Me)(Cl) | 36 MS(ESI) m/z: 479([M + H]⁺) |

TABLE 58

| Ex | (structure) | Syn (Sal) Dat |
|---|---|---|
| 975 | CO₂Et-piperidine-N-phenyl(Me)(Cl) | 501 MS(ESI) m/z: 472([M + H]⁺) |
| 976 | CO₂Et-piperidine-N-phenyl(Me)(O-Me) | 501 MS(ESI) m/z: 468([M + H]⁺) |

TABLE 59

| Ex | R¹ | Syn (Sal) Dat |
|---|---|---|
| 977 | —N(Me)—CH₂—CH(Me)—O—Me | 234 MS(ESI) m/z: 464([M + H]⁺) |

TABLE 60

| Ex | R¹ | Syn (Sal) Dat |
|---|---|---|
| 978 | 2-methylthiophene | 980 MS(ESI) m/z: 372 ([M + H]⁺) |

TABLE 60-continued

Structure: 2-(morpholin-4-yl)phenyl amide of 2-R¹-thiazole-4-carboxamide

| Ex | R¹ | Syn (Sal) Dat |
|---|---|---|
| 979 | 4-methylpyridin-yl | 980 MS(ESI) m/z: 367 ([M + H]⁺) |

TABLE 61

Structure: 2-(piperidin-1-yl)phenyl amide of 2-R¹-thiazole-4-carboxamide

| Ex | R¹ | Syn (Sal) Dat |
|---|---|---|
| 980 | phenyl | 980 MS(ESI) m/z: 364 ([M + H]⁺) |
| 981 | pyridin-3-yl | 980 MS(ESI) m/z: 365 ([M + H]⁺) |
| 982 | pyridin-4-yl | 980 MS(ESI) m/z: 365 ([M + H]⁺) |
| 983 | 4-methylphenyl | 980 MS(ESI) m/z: 378 ([M + H]⁺) |
| 984 | 4-chlorophenyl | 980 MS(ESI) m/z: 398 ([M + H]⁺) |
| 985 | thiophen-2-yl | 980 MS(ESI) m/z: 370 ([M + H]⁺) |
| 986 | 3-(trifluoromethyl)phenyl | 980 MS(ESI) m/z: 432 ([M + H]⁺) |

TABLE 62

Structure: 2-(4-methylpiperazin-1-yl)phenyl amide of 2-R¹-thiazole-4-carboxamide

| Ex | R¹ | Syn (Sal) Dat |
|---|---|---|
| 987 | thiophen-2-yl | 980 MS(ESI) m/z: 385 ([M + H]⁺) |
| 988 | 3-(trifluoromethyl)phenyl | 980 MS(ESI) m/z: 447 ([M + H]⁺) |
| 989 | 4-chlorophenyl | 980 MS(ESI) m/z: 413 ([M + H]⁺) |
| 990 | 4-methylphenyl | 980 MS(ESI) m/z: 393 ([M + H]⁺) |
| 991 | N-methylacetamido | 980 MS(ESI) m/z: 360 ([M + H]⁺) |
| 992 | 1-methyl-5-(trifluoromethyl)-3-methylpyrazol-yl | 980 MS(ESI) m/z: 451 ([M + H]⁺) |
| 993 | 4-methoxyphenyl | 980 MS(ESI) m/z: 409 ([M + H]⁺) |
| 994 | 2,3-dichlorophenyl | 980 MS(ESI) m/z: 447 ([M + H]⁺) |
| 995 | 2,3-dihydrobenzofuran-5-yl | 980 MS(ESI) m/z: 421 ([M + H]⁺) |
| 996 | 3-chlorophenyl | 980 MS(ESI) m/z: 413 ([M + H]⁺) |

TABLE 62-continued

Structure: 2-(4-methylpiperazin-1-yl)phenyl thiazole-4-carboxamide with R¹ at thiazole 2-position

| Ex | R¹ | Syn (Sal) Dat |
|---|---|---|
| 997 | 4-(trifluoromethyl)benzyl | 980 MS(ESI) m/z: 447 ([M + H]⁺) |
| 998 | benzyl | 980 MS(ESI) m/z: 393 ([M + H]⁺) |
| 999 | 4-chlorobenzyl | 980 MS(ESI) m/z: 427 ([M + H]⁺) |
| 1000 | Me | 980 MS(ESI) m/z: 317 ([M + H]⁺) |

TABLE 63

Structure: N-(2-Q-phenyl)-2-phenylthiazole-4-carboxamide

| Ex | Q | Syn (Sal) Dat |
|---|---|---|
| 1001 | (3S)-1-methyl-3-(dimethylamino)pyrrolidin-3-yl | 1029 MS(ESI) m/z: 393 ([M + H]⁺) |
| 1002 | 1-methyl-3-(methylsulfonyl)pyrrolidin-3-yl | 1029 MS(ESI) m/z: 428 ([M + H]⁺) |
| 1003 | 1-methyl-3-(N-ethyl-N-acetylamino)pyrrolidin-3-yl | 1029 MS(ESI) m/z: 435 ([M + H]⁺) |
| 1004 | (1-methylpiperidin-3-yl)methanol | 1029 MS(ESI) m/z: 394 ([M + H]⁺) |
| 1005 | 1-methyl-3-(N,N-diethylcarbamoyl)piperidin-3-yl | 1029 MS(ESI) m/z: 463 ([M + H]⁺) |
| 1006 | (1-methylpiperidin-4-yl)methanol | 1029 MS(ESI) m/z: 394 ([M + H]⁺) |
| 1007 | 4-methyl-1-(1-methylethyl)piperazin-1-yl | 1029 MS(ESI) m/z: 407 ([M + H]⁺) |
| 1008 | 4-methylpiperazine-1-carboxamide | 1029 MS(ESI) m/z: 408 ([M + H]⁺) |
| 1009 | 1-acetyl-4-methyl-1,4-diazepan-4-yl | 1029 MS(ESI) m/z: 421 ([M + H]⁺) |
| 1010 | 1-methylazocan-1-yl | 1029 MS(ESI) m/z: 392 ([M + H]⁺) |
| 1011 | 2-methyloctahydro-2H-pyrido[1,2-a]pyrazin-yl | 1029 MS(ESI) m/z: 419 ([M + H]⁺) |
| 1012 | 2,8-dimethyl-1-oxo-2,8-diazaspiro[4.5]decane | 1029 MS(ESI) m/z: 447 ([M + H]⁺) |
| 1013 | 1-methyl-2-pyrrolidinyl (on pyridine) | 1029 MS(ESI) m/z: 426 ([M + H]⁺) |
| 1014 | 1,1'-dimethyl-2,2'-bipiperidinyl | 1029 MS(ESI) m/z: 461 ([M + H]⁺) |

TABLE 63-continued
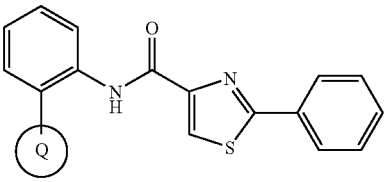
| Ex | Q | Syn (Sal) Dat |
|---|---|---|
| 1015 | 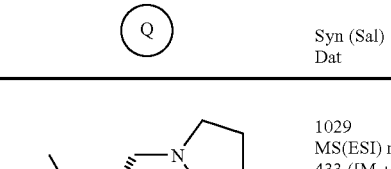 | 1029 MS(ESI) m/z: 433 ([M + H]+) |
| 1016 |  | 1029 MS(ESI) m/z: 440 ([M + H]+) |
| 1017 | 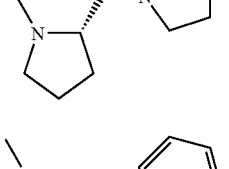 | 1029 MS(ESI) m/z: 490 ([M + H]+) |
| 1018 | 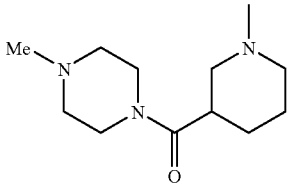 | 1029 MS(ESI) m/z: 440 ([M + H]+) |
| 1019 | 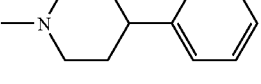 | 1029 MS(ESI) m/z: 447 ([M + H]+) |
| 1020 | 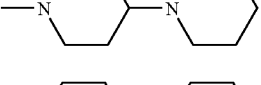 | 1029 MS(ESI) m/z: 449 ([M + H]+) |
| 1021 | 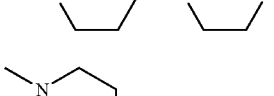 | 1029 MS(ESI) m/z: 462 ([M + H]+) |
| 1022 | 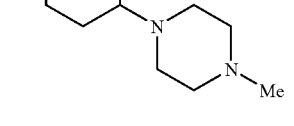 | 1029 MS(ESI) m/z: 462 ([M + H]+) |
| 1023 | 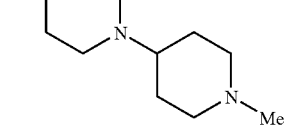 | 1029 MS(ESI) m/z: 454 ([M + H]+) |
TABLE 63-continued
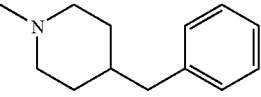
| Ex | Q | Syn (Sal) Dat |
|---|---|---|
| 1024 | 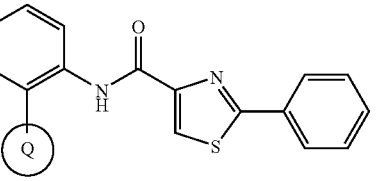 | 1029 MS(ESI) m/z: 470 ([M + H]+) |
| 1025 | 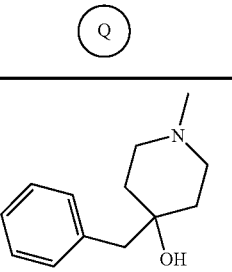 | 1029 MS(ESI) m/z: 456 ([M + H]+) |
| 1026 | 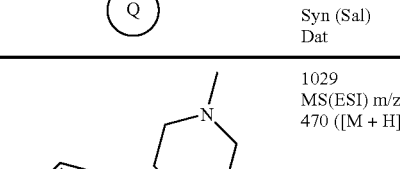 | 1029 MS(ESI) m/z: 461 ([M + H]+) |
| 1027 | 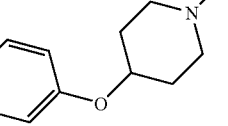 | 1029 MS(ESI) m/z: 476 ([M + H]+) |
| 1028 | 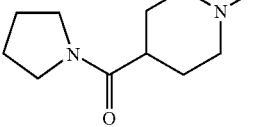 | 1029 MS(ESI) m/z: 476 ([M + H]+) |
| 1029 | 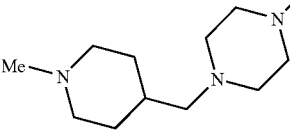 | 1029 MS(ESI) m/z: 478 ([M + H]+) |
| 1030 | 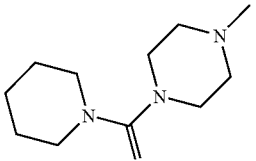 | 1029 MS(ESI) m/z: 469 ([M + H]+) |
| 1031 | 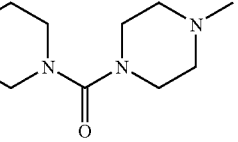 | 1029 MS(ESI) m/z: 461 ([M + H]+) |

TABLE 63-continued

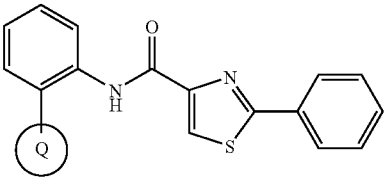

| Ex | Q | Syn (Sal) Dat |
|---|---|---|
| 1032 |  | 1029 MS(ESI) m/z: 476 ([M + H]$^+$) |
| 1033 | 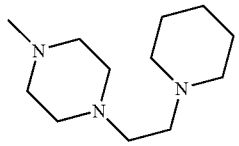 | 1029 MS(ESI) m/z: 478 ([M + H]$^+$) |
| 1034 | 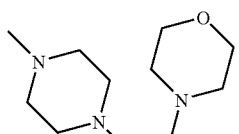 | 1029 MS(ESI) m/z: 476 ([M + H]$^+$) |
| 1035 | 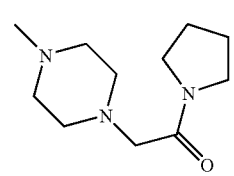 | 1029 MS(ESI) m/z: 490 ([M + H]$^+$) |
| 1036 | 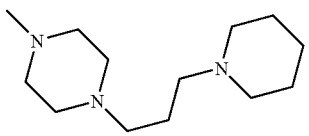 | 1029 MS(ESI) m/z: 492 ([M + H]$^+$) |
| 1037 |  | 1029 MS(ESI) m/z: 379 ([M + H]$^+$) |
| 1038 | 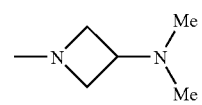 | 1029 MS(ESI) m/z: 419 ([M + H]$^+$) |
| 1039 | 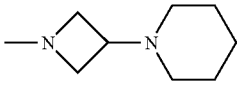 | 1029 MS(ESI) m/z: 434 ([M + H]$^+$) |
| 1040 | 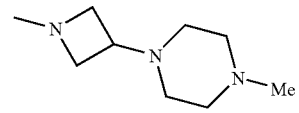 | 1029 MS(ESI) m/z: 350 ([M + H]$^+$) |
| 1041 | 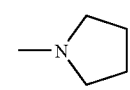 | 1029 MS(ESI) m/z: 380 ([M + H]$^+$) |

TABLE 63-continued

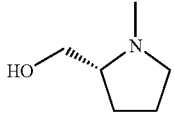

| Ex | Q | Syn (Sal) Dat |
|---|---|---|
| 1042 | 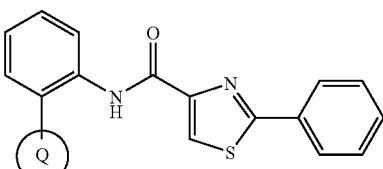 | 1029 MS(ESI) m/z: 407 ([M + H]$^+$) |
| 1043 |  | 1029 MS(ESI) m/z: 407 ([M + H]$^+$) |
| 1044 | 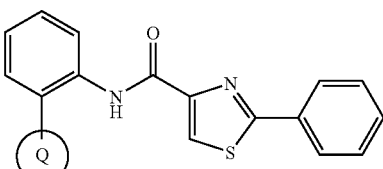 | 1029 MS(ESI) m/z: 393 ([M + H]$^+$) |

TABLE 64

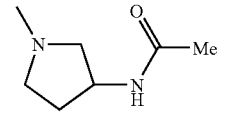

| Ex | R$^1$ | Syn (Sal) Dat |
|---|---|---|
| 1045 | 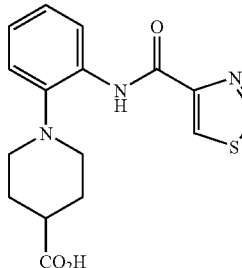 | 1048 MS(ESI) m/z: 389 ([M + H]$^+$) |
| 1046 | 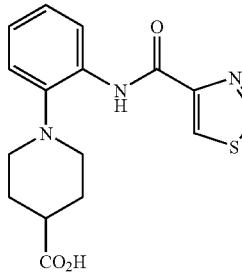 | 1048 MS(ESI) m/z: 476 ([M + H]$^+$) |
| 1047 |  | 1048 MS(ESI) m/z: 422 ([M + H]$^+$) |
| 1048 | 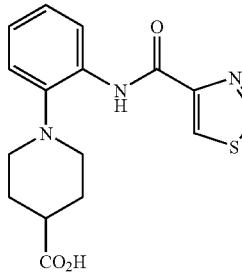 | 1048 MS(ESI) m/z: 414 ([M + H]$^+$) |

TABLE 64-continued

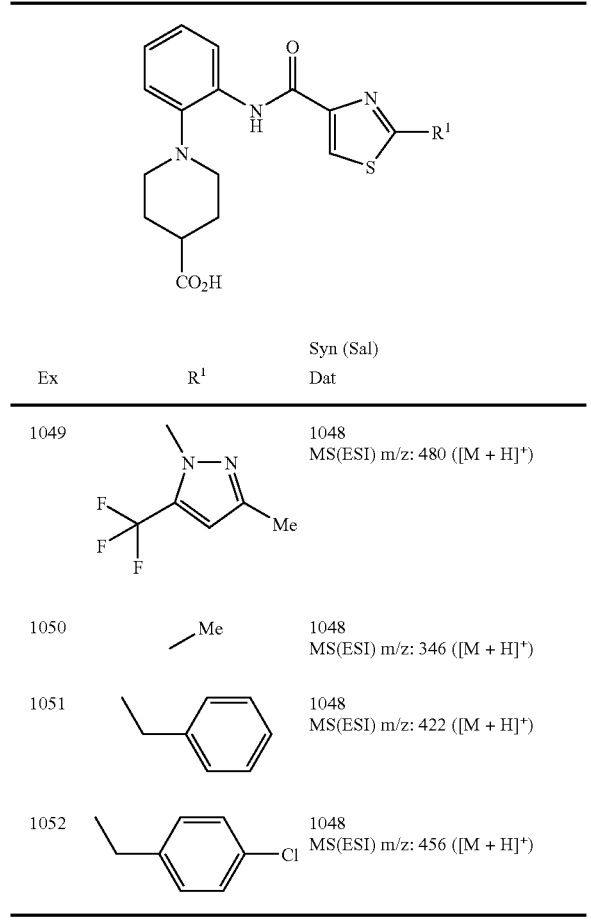

| Ex | R¹ | Syn (Sal) Dat |
|---|---|---|
| 1049 | (1-methyl-5-trifluoromethyl-3-methyl-pyrazol-4-yl) | 1048 MS(ESI) m/z: 480 ([M + H]⁺) |
| 1050 | Me | 1048 MS(ESI) m/z: 346 ([M + H]⁺) |
| 1051 | CH₂-phenyl | 1048 MS(ESI) m/z: 422 ([M + H]⁺) |
| 1052 | CH₂-(4-Cl-phenyl) | 1048 MS(ESI) m/z: 456 ([M + H]⁺) |

TABLE 65

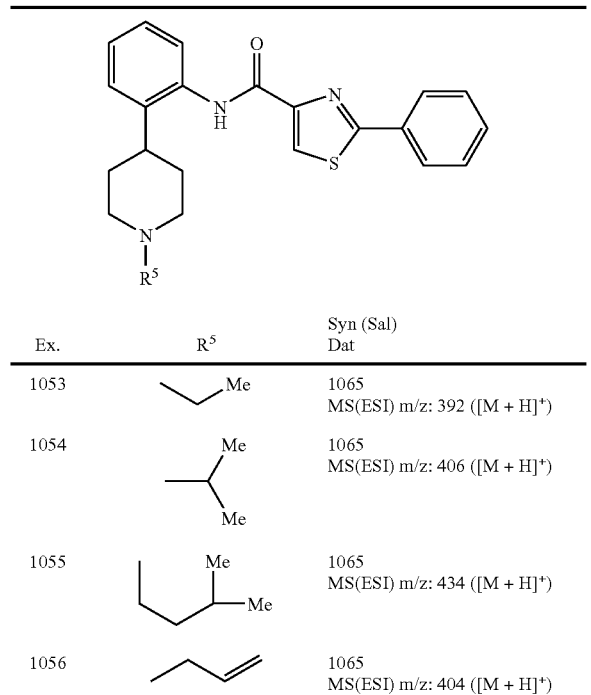

| Ex. | R⁵ | Syn (Sal) Dat |
|---|---|---|
| 1053 | Et | 1065 MS(ESI) m/z: 392 ([M + H]⁺) |
| 1054 | iPr | 1065 MS(ESI) m/z: 406 ([M + H]⁺) |
| 1055 | sec-pentyl | 1065 MS(ESI) m/z: 434 ([M + H]⁺) |
| 1056 | allyl | 1065 MS(ESI) m/z: 404 ([M + H]⁺) |

TABLE 65-continued

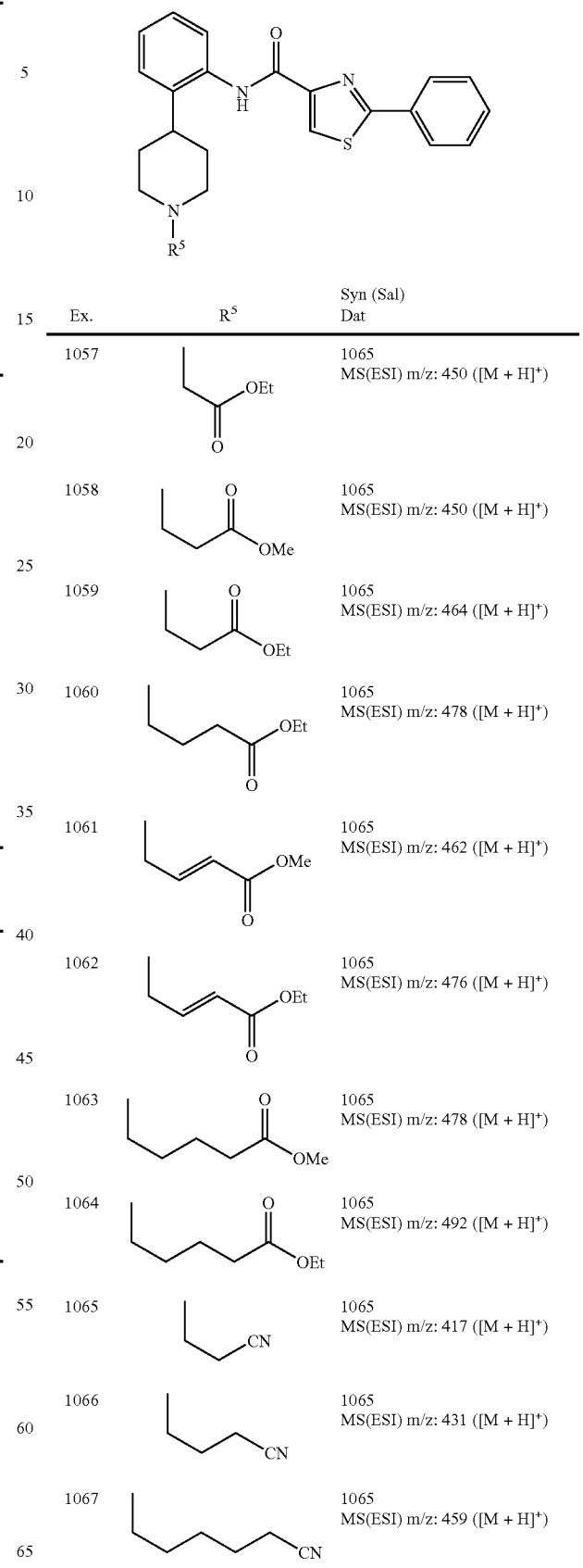

| Ex. | R⁵ | Syn (Sal) Dat |
|---|---|---|
| 1057 | CH₂CH₂C(O)OEt | 1065 MS(ESI) m/z: 450 ([M + H]⁺) |
| 1058 | CH₂CH₂CH₂C(O)OMe | 1065 MS(ESI) m/z: 450 ([M + H]⁺) |
| 1059 | CH₂CH₂CH₂C(O)OEt | 1065 MS(ESI) m/z: 464 ([M + H]⁺) |
| 1060 | CH₂CH₂CH₂CH₂C(O)OEt | 1065 MS(ESI) m/z: 478 ([M + H]⁺) |
| 1061 | CH₂CH=CHC(O)OMe | 1065 MS(ESI) m/z: 462 ([M + H]⁺) |
| 1062 | CH₂CH=CHC(O)OEt | 1065 MS(ESI) m/z: 476 ([M + H]⁺) |
| 1063 | (CH₂)₅C(O)OMe | 1065 MS(ESI) m/z: 478 ([M + H]⁺) |
| 1064 | (CH₂)₅C(O)OEt | 1065 MS(ESI) m/z: 492 ([M + H]⁺) |
| 1065 | CH₂CH₂CN | 1065 MS(ESI) m/z: 417 ([M + H]⁺) |
| 1066 | CH₂CH₂CH₂CN | 1065 MS(ESI) m/z: 431 ([M + H]⁺) |
| 1067 | (CH₂)₅CN | 1065 MS(ESI) m/z: 459 ([M + H]⁺) |

TABLE 65-continued

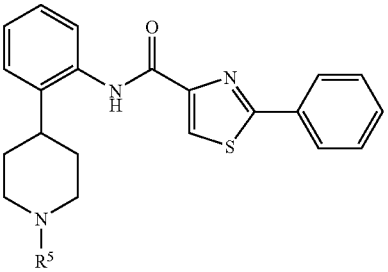

| Ex. | R⁵ | Syn (Sal) Dat |
|---|---|---|
| 1068 |  | 1065 MS(ESI) m/z: 422 ([M + H]⁺) |
| 1069 |  | 1065 MS(ESI) m/z: 436 ([M + H]⁺) |
| 1070 | 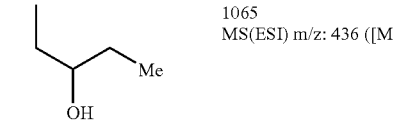 | 1065 MS(ESI) m/z: 438 ([M + H]⁺) |
| 1071 | 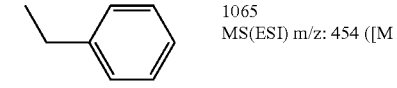 | 1065 MS(ESI) m/z: 436 ([M + H]⁺) |
| 1072 | 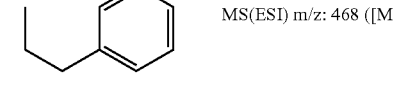 | 1065 MS(ESI) m/z: 454 ([M + H]⁺) |
| 1073 | 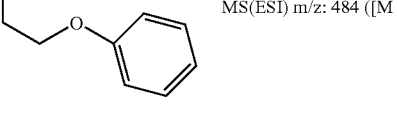 | 1065 MS(ESI) m/z: 468 ([M + H]⁺) |
| 1074 | 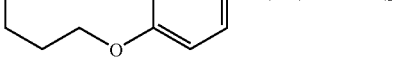 | 1065 MS(ESI) m/z: 484 ([M + H]⁺) |
| 1075 | 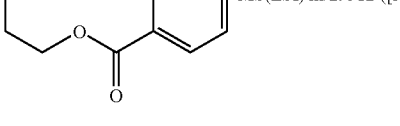 | 1065 MS(ESI) m/z: 498 ([M + H]⁺) |
| 1076 | 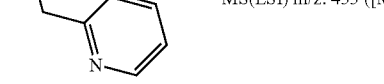 | 1065 MS(ESI) m/z: 512 ([M + H]⁺) |
| 1077 | 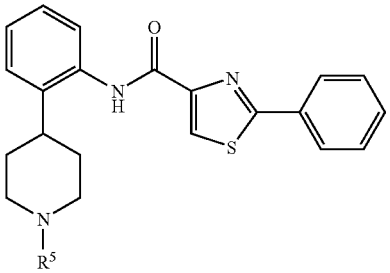 | 1065 MS(ESI) m/z: 455 ([M + H]⁺) |

TABLE 65-continued

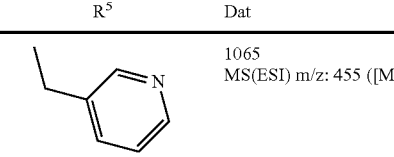

| Ex. | R⁵ | Syn (Sal) Dat |
|---|---|---|
| 1078 | 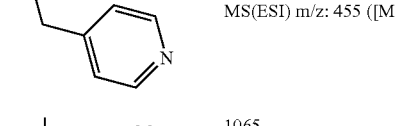 | 1065 MS(ESI) m/z: 455 ([M + H]⁺) |
| 1079 | 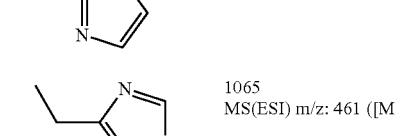 | 1065 MS(ESI) m/z: 455 ([M + H]⁺) |
| 1080 | 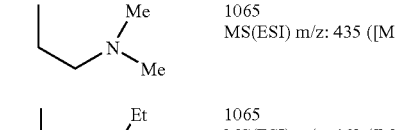 | 1065 MS(ESI) m/z: 458 ([M + H]⁺) |
| 1081 | 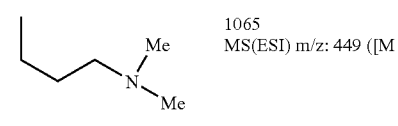 | 1065 MS(ESI) m/z: 461 ([M + H]⁺) |
| 1082 | 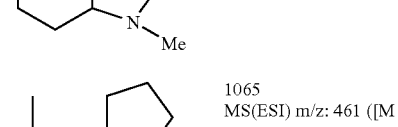 | 1065 MS(ESI) m/z: 435 ([M + H]⁺) |
| 1083 | 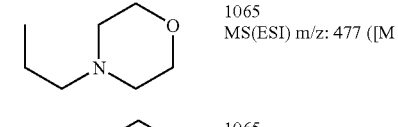 | 1065 MS(ESI) m/z: 463 ([M + H]⁺) |
| 1084 | 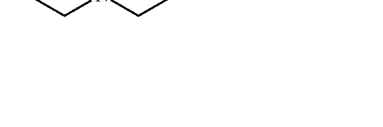 | 1065 MS(ESI) m/z: 449 ([M + H]⁺) |
| 1085 | 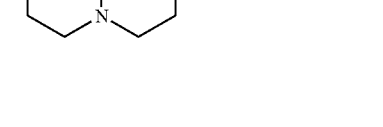 | 1065 MS(ESI) m/z: 475 ([M + H]⁺) |
| 1086 |  | 1065 MS(ESI) m/z: 461 ([M + H]⁺) |
| 1087 |  | 1065 MS(ESI) m/z: 477 ([M + H]⁺) |
| 1088 |  | 1065 MS(ESI) m/z: 475 ([M + H]⁺) |

TABLE 65-continued

Structure: 2-phenyl-thiazole-4-carboxamide with N-(2-(1-R5-piperidin-4-yl)phenyl)

| Ex. | R⁵ | Syn (Sal) Dat |
|---|---|---|
| 1089 | butyl-piperidinyl | 1065; MS(ESI) m/z: 489 ([M + H]⁺) |
| 1090 | -C(O)CH₂CH₂-N(Me)₂ | 1065; MS(ESI) m/z: 489 ([M + H]⁺) |
| 1091 | -C(O)CH₂CH₂-N(Et)₂ | 1065; MS(ESI) m/z: 477 ([M + H]⁺) |

TABLE 6

Structure: N-(2-(3,4-dihydroxypyrrolidin-1-yl)phenyl)-2-R¹-thiazole-4-carboxamide

| Ex | R¹ | Syn (Sal) Dat |
|---|---|---|
| 1092 | 3-pyridyl | 980; MS(ESI) m/z: 383 ([M + H]⁺) |
| 1093 | 3-chlorophenyl | 980; MS(ESI) m/z: 416 ([M + H]⁺) |
| 1094 | 4-chlorophenyl | 980; MS(ESI) m/z: 416 ([M + H]⁺) |
| 1095 | 2,3-dichlorophenyl | 980; MS(ESI) m/z: 450 ([M + H]⁺) |

TABLE 6-continued

| Ex | R¹ | Syn (Sal) Dat |
|---|---|---|
| 1096 | 3-(trifluoromethyl)phenyl | 980; MS(ESI) m/z: 450 ([M + H]⁺) |
| 1097 | 4-methylphenyl | 980; MS(ESI) m/z: 396 ([M + H]⁺) |
| 1098 | 4-methoxyphenyl | 980; MS(ESI) m/z: 412 ([M + H]⁺) |
| 1099 | 2-thienyl | 980; MS(ESI) m/z: 388 ([M + H]⁺) |
| 1100 | 5-methylpyrimidinyl | 980; MS(ESI) m/z: 384 ([M + H]⁺) |
| 1101 | 3-furyl | 980; MS(ESI) m/z: 372 ([M + H]⁺) |
| 1102 | 1-methylpyrrolidinyl | 980; MS(ESI) m/z: 375 ([M + H]⁺) |
| 1103 | 2-ethylphenyl | 980; MS(ESI) m/z: 396 ([M + H]⁺) |
| 1104 | 4-chloro-phenylethyl | 980; MS(ESI) m/z: 430 ([M + H]⁺) |
| 1105 | 3-methyltetrahydrofuranyl | 980; MS(ESI) m/z: 376 ([M + H]⁺) |
| 1106 | ethyl | 980; MS(ESI) m/z: 334 ([M + H]⁺) |
| 1107 | isopropyl | 980; MS(ESI) m/z: 348 ([M + H]⁺) |

TABLE 6-continued

Structure: 2-(pyrrolidinyl with 3,4-diOH)phenyl-NH-C(O)-thiazole-R¹

| Ex | R¹ | Syn (Sal) Dat |
|---|---|---|
| 1108 | n-butyl (CH₂CH₂CH₂Me) | 980 MS(ESI) m/z: 362 ([M + H]⁺) |
| 1109 | isobutyl (CH₂CH(Me)Me) | 980 MS(ESI) m/z: 376 ([M + H]⁺) |
| 1110 | n-heptyl | 980 MS(ESI) m/z: 404 ([M + H]⁺) |
| 1111 | cyclopentyl | 980 MS(ESI) m/z: 374 ([M + H]⁺) |
| 1112 | 4-methyltetrahydropyran-yl | 980 MS(ESI) m/z: 390 ([M + H]⁺) |

TABLE 67

Structure: 2-Q-phenyl-NH-C(O)-thiazole-CH₂-(3-CF₃-phenyl)

| Ex | Q | Syn (Sal) Dat |
|---|---|---|
| 1113 | 4-methylpiperazin-1-yl | 980 MS(ESI) m/z: 461 ([M + H]⁺) |
| 1114 | 1-methylpiperidine-4-carboxylic acid (N-linked) | 1048 MS(ESI) m/z: 490 ([M + H]⁺) |
| 1115 | 1-methyl-3,4-dihydroxypyrrolidinyl | 980 MS(ESI) m/z: 464 ([M + H]⁺) |

TABLE 68

Structure: 2-[4-(carbamoylmethyl)piperazin-1-yl]phenyl-NH-C(O)-thiazole-2-(piperidin-4-yl with N-R¹ᵘ)

| Ex | R¹ᵘ | Syn (Sal) Dat |
|---|---|---|
| 1116 | C(O)CH₂Me (propanoyl) | 1116 MS(ESI) m/z: 485 ([M + H]⁺) |
| 1117 | C(O)CH₂CH₂Me | 1116 MS(ESI) m/z: 499 ([M + H]⁺) |
| 1118 | C(O)CH₂CH₂CH₂Me | 1116 MS(ESI) m/z: 513 ([M + H]⁺) |
| 1119 | C(O)CH₂CH₂CH₂CH₂Me | 1116 MS(ESI) m/z: 527 ([M + H]⁺) |
| 1120 | C(O)CH(Me)Me | 1116 MS(ESI) m/z: 499 ([M + H]⁺) |
| 1121 | C(O)CH(CH₂Me)CH₂Me | 1116 MS(ESI) m/z: 527 ([M + H]⁺) |
| 1122 | C(O)CH₂OMe | 1116 MS(ESI) m/z: 501 ([M + H]⁺) |
| 1123 | C(O)CH₂CH₂OMe | 1116 MS(ESI) m/z: 515 ([M + H]⁺) |
| 1124 | C(O)CH₂OH | 1116 MS(ESI) m/z: 487 ([M + H]⁺) |
| 1125 | C(O)CH₂CH₂OH | 1116 MS(ESI) m/z: 501 ([M + H]⁺) |
| 1126 | C(O)CH₂NMe₂ | 1116 MS(ESI) m/z: 514 ([M + H]⁺) |

TABLE 68-continued

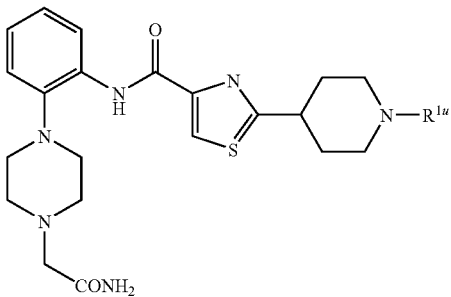

| Ex | R$^{1u}$ | Syn (Sal) Dat |
|---|---|---|
| 1127 | (3-oxobutyl)-N,N-dimethylamino | 1116 MS(ESI) m/z: 528 ([M + H]$^+$) |
| 1128 | acetylcyclobutane | 1116 MS(ESI) m/z: 511 ([M + H]$^+$) |
| 1129 | acetylcyclopentane | 1116 MS(ESI) m/z: 525 ([M + H]$^+$) |
| 1130 | acetylcyclohexane | 1116 MS(ESI) m/z: 539 ([M + H]$^+$) |
| 1131 | 2-acetyl-1H-pyrrole | 1116 MS(ESI) m/z: 522 ([M + H]$^+$) |
| 1132 | 2-acetyl-1-methylpyrrole | 1116 MS(ESI) m/z: 536 ([M + H]$^+$) |
| 1133 | 2-acetylpyridine | 1116 MS(ESI) m/z: 534 ([M + H]$^+$) |
| 1134 | 3-acetylpyridine | 1116 MS(ESI) m/z: 534 ([M + H]$^+$) |
| 1135 | 4-acetylpyridine | 1116 MS(ESI) m/z: 534 ([M + H]$^+$) |
| 1136 | 4-acetylpyridazine | 1116 MS(ESI) m/z: 535 ([M + H]$^+$) |

TABLE 68-continued

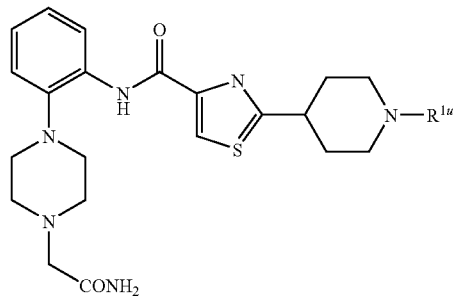

| Ex | R$^{1u}$ | Syn (Sal) Dat |
|---|---|---|
| 1137 | 5-acetylpyrimidine | 1116 MS(ESI) m/z: 535 ([M + H]$^+$) |
| 1138 | 2-acetylthiophene | 1116 MS(ESI) m/z: 539 ([M + H]$^+$) |
| 1139 | 3-acetylthiophene | 1116 MS(ESI) m/z: 539 ([M + H]$^+$) |
| 1140 | acetophenone | 1116 MS(ESI) m/z: 533 ([M + H]$^+$) |
| 1141 | 2'-methylacetophenone | 1116 MS(ESI) m/z: 547 ([M + H]$^+$) |
| 1142 | 3'-methylacetophenone | 1116 MS(ESI) m/z: 547 ([M + H]$^+$) |
| 1143 | 4'-methylacetophenone | 1116 MS(ESI) m/z: 547 ([M + H]$^+$) |
| 1144 | 2'-fluoroacetophenone | 1116 MS(ESI) m/z: 551 ([M + H]$^+$) |
| 1145 | 3'-fluoroacetophenone | 1116 MS(ESI) m/z: 551 ([M + H]$^+$) |
| 1146 | 4'-fluoroacetophenone | 1116 MS(ESI) m/z: 551 ([M + H]$^+$) |

TABLE 68-continued

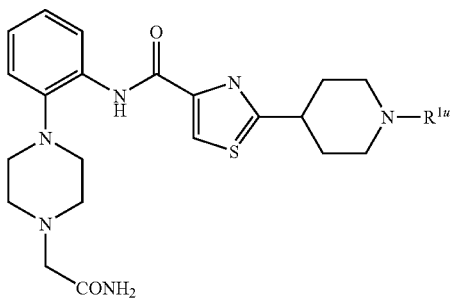

| Ex | R^1u | Syn (Sal) Dat |
|---|---|---|
| 1147 | (2-methoxyphenyl acetyl) | 1116 MS(ESI) m/z: 563 ([M + H]+) |
| 1148 | (3-methoxyphenyl acetyl) | 1116 MS(ESI) m/z: 563 ([M + H]+) |
| 1149 | (4-methoxyphenyl acetyl) | 1116 MS(ESI) m/z: 563 ([M + H]+) |
| 1150 | (2-fluorobenzyl acetone) | 1116 MS(ESI) m/z: 565 ([M + H]+) |
| 1151 | (3-fluorobenzyl acetone) | 1116 MS(ESI) m/z: 565 ([M + H]+) |
| 1152 | (4-fluorobenzyl acetone) | 1116 MS(ESI) m/z: 565 ([M + H]+) |
| 1153 | (cinnamyl methyl ketone) | 1116 MS(ESI) m/z: 559 ([M + H]+) |
| 1154 | (pyridinyl propanone) | 1116 MS(ESI) m/z: 562 ([M + H]+) |

TABLE 68-continued

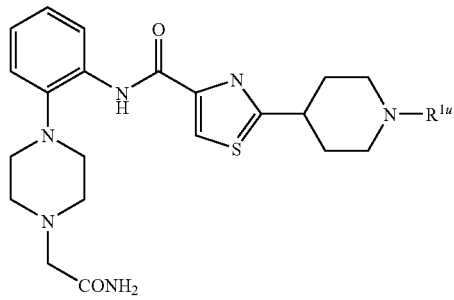

| Ex | R^1u | Syn (Sal) Dat |
|---|---|---|
| 1155 | (phenyl butanone) | 1116 MS(ESI) m/z: 561 ([M + H]+) |
| 1156 | (phenyl pentanone) | 1116 MS(ESI) m/z: 575 ([M + H]+) |
| 1157 | (styryl propanone) | 1116 MS(ESI) m/z: 573 ([M + H]+) |
| 1158 | (phenyl hexanone) | 1116 MS(ESI) m/z: 589 ([M + H]+) |
| 1159 | (2-biphenyl methyl ketone) | 1116 MS(ESI) m/z: 609 ([M + H]+) |
| 1160 | (3-biphenyl methyl ketone) | 1116 MS(ESI) m/z: 609 ([M + H]+) |
| 1161 | (4-biphenyl methyl ketone) | 1116 MS(ESI) m/z: 609 ([M + H]+) |
| 1162 | n-Bu | 1162 MS(ESI) m/z: 471 ([M + H]+) |

TABLE 68-continued

Structure (Ex 1163–1174): 2-[4-(2-{[2-(1-R¹ᵘ-piperidin-4-yl)-1,3-thiazole-4-carbonyl]amino}phenyl)piperazin-1-yl]acetamide Structure (Ex 1175–1184): 2-[4-(2-{[2-(1-R¹ᵘ-piperidin-4-yl)-1,3-thiazole-4-carbonyl]amino}phenyl)piperazin-1-yl]acetamide

| Ex | R¹ᵘ | Syn (Sal) Dat |
|---|---|---|
| 1163 | ethyl-cyclopropyl | 1162 MS(ESI) m/z: 483 ([M + H]⁺) |
| 1164 | –CH(Me)CH(Me)₂ (isobutyl-methyl) | 1162 MS(ESI) m/z: 485 ([M + H]⁺) |
| 1165 | n-pentyl | 1162 MS(ESI) m/z: 485 ([M + H]⁺) |
| 1166 | –CH₂CH₂CH₂OMe | 1162 MS(ESI) m/z: 487 ([M + H]⁺) |
| 1167 | n-hexyl | 1162 MS(ESI) m/z: 499 ([M + H]⁺) |
| 1168 | ethyl-tetrahydrofuran-3-yl | 1162 MS(ESI) m/z: 513 ([M + H]⁺) |
| 1169 | ethyl-(pyridin-4-yl) | 1162 MS(ESI) m/z: 520 ([M + H]⁺) |
| 1170 | ethyl-(3-methylphenyl) | 1162 MS(ESI) m/z: 533 ([M + H]⁺) |
| 1171 | ethyl-(4-methylphenyl) | 1162 MS(ESI) m/z: 533 ([M + H]⁺) |
| 1172 | n-butyl-phenyl | 1162 MS(ESI) m/z: 547 ([M + H]⁺) |
| 1173 | ethyl-(2-methoxyphenyl) | 1162 MS(ESI) m/z: 549 ([M + H]⁺) |
| 1174 | ethyl-(3-methoxyphenyl) | 1162 MS(ESI) m/z: 549 ([M + H]⁺) |
| 1175 | ethyl-(4-methoxyphenyl) | 1162 MS(ESI) m/z: 549 ([M + H]⁺) |
| 1176 | ethyl-(2-carboxyphenyl) | 1162 MS(ESI) m/z: 563 ([M + H]⁺) |
| 1177 | ethyl-(3-carboxyphenyl) | 1162 MS(ESI) m/z: 563 ([M + H]⁺) |
| 1178 | –S(O)₂Me | 1178 MS(ESI) m/z: 507 ([M + H]⁺) |
| 1179 | –S(O)₂Et | 1178 MS(ESI) m/z: 521 ([M + H]⁺) |
| 1180 | –S(O)₂-cyclopropyl | 1178 MS(ESI) m/z: 533 ([M + H]⁺) |
| 1181 | –S(O)₂CH(Me)₂ | 1178 MS(ESI) m/z: 535 ([M + H]⁺) |
| 1182 | –S(O)₂CH₂CH₂Me | 1178 MS(ESI) m/z: 535 ([M + H]⁺) |
| 1183 | –S(O)₂CH₂CH₂CH₂Me | 1178 MS(ESI) m/z: 549 ([M + H]⁺) |
| 1184 | –S(O)₂Ph | 1178 MS(ESI) m/z: 569 ([M + H]⁺) |

TABLE 68-continued

[Structure: 2-(piperazinyl with N-CH2-CONH2)phenyl-NH-C(O)-thiazole-2-(piperidin-4-yl)-N-R^{1u}]

| Ex | R^{1u} | Syn (Sal) Dat |
|---|---|---|
| 1185 | 2-thienyl-SO2- | 1178 MS(ESI) m/z: 575 ([M + H]+) |
| 1186 | 3-thienyl-SO2- | 1178 MS(ESI) m/z: 575 ([M + H]+) |
| 1187 | cyclohexyl-SO2- | 1178 MS(ESI) m/z: 575 ([M + H]+) |
| 1188 | benzyl-SO2- | 1178 MS(ESI) m/z: 583 ([M + H]+) |
| 1189 | 4-fluorophenyl-SO2- | 1178 MS(ESI) m/z: 587 ([M + H]+) |
| 1190 | 2-fluorophenyl-SO2- | 1178 MS(ESI) m/z: 587 ([M + H]+) |
| 1191 | 3-fluorophenyl-SO2- | 1178 MS(ESI) m/z: 587 ([M + H]+) |
| 1192 | cyclohexylmethyl-SO2- | 1178 MS(ESI) m/z: 589 ([M + H]+) |
| 1193 | 2-phenylethyl-SO2- | 1178 MS(ESI) m/z: 597 ([M + H]+) |

TABLE 68-continued

[Structure: 2-(piperazinyl with N-CH2-CONH2)phenyl-NH-C(O)-thiazole-2-(piperidin-4-yl)-N-R^{1u}]

| Ex | R^{1u} | Syn (Sal) Dat |
|---|---|---|
| 1194 | 4-biphenyl-SO2- | 1178 MS(ESI) m/z: 645 ([M + H]+) |
| 1195 | 2-biphenyl-SO2- | 1178 MS(ESI) m/z: 645 ([M + H]+) |
| 1196 | -C(O)-NH-CH(Me)2 | 1196 MS(ESI) m/z: 514 ([M + H]+) |
| 1197 | -C(O)-NH-phenyl | 1196 MS(ESI) m/z: 548 ([M + H]+) |
| 1198 | -C(O)-NH-CH2-phenyl | 1196 MS(ESI) m/z: 562 ([M + H]+) |
| 1199 | -C(S)-NH-Me | 1196 MS(ESI) m/z: 502 ([M + H]+) |
| 1200 | -C(S)-NH-CH(Me)2 | 1196 MS(ESI) m/z: 530 ([M + H]+) |
| 1201 | -C(S)-NH-phenyl | 1196 MS(ESI) m/z: 564 ([M + H]+) |

TABLE 68-continued

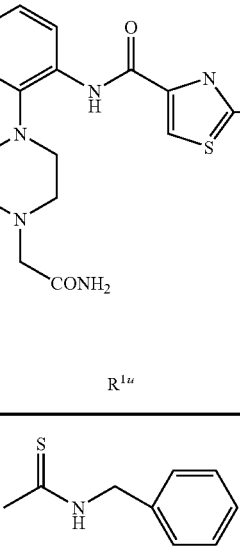

| Ex | R$^{1u}$ | Syn (Sal) Dat |
|---|---|---|
| 1202 | ![structure: S=C(CH3)-NH-CH2-phenyl] | 1196 MS(ESI) m/z: 578 ([M + H]$^+$) |

NMR data of several Example compounds are shown in the following Table 69. For the data, tetramethylsilane was used as an internal standard, and unless otherwise specifically mentioned, δ (ppm) of the peaks in $^1$H-NMR using DMSO-d$_6$ as a measurement solvent is shown.

(CDCl$_3$): δ (ppm) of the peaks in $^1$H-NMR in CDCl$_3$.

TABLE 69

| Ex | Dat(NMR) |
|---|---|
| 11 | 2.65-2.83(4H, m), 2.91-2.97(4H, m), 2.97(2H, s), 3.63(3H, s), 3.68(2H, s), 7.09(1H, dd, J = 8.0, 2.0 Hz), 7.18(1H, brs), 7.13(1H, d, J = 2.0 Hz), 7.25(1H, brs), 7.59-7.64(3H, m), 8.12-8.17(2H, m), 8.40(1H, d, J = 7.5 Hz), 852(1H, s). |
| 32 | (CDCl$_3$) 3.18(2H, t, J = 5.4 Hz), 3.59-3.65(2H, m), 3.78(2H, s), 6.39(1H, brs), 7.13-7.23(2H, m), 7.25-7.30(1H, m), 7.43-7.53(3H, m), 7.92-7.97 (2H, m), 8.20(1H, s), 8.59(1H, dd, J = 8.3, 1.4 Hz), 10.50(1H, brs) |
| 40 | 1.91(2H, d, J = 10.8 Hz), 1.99-2.08(2H, m), 2.33-2.39(1H, m), 2.75 (2H, t, J = 10.8 Hz), 3.04(2H, d, J = 11.6 Hz), 3.17-3.22(2H, m), 3.39-3.44(2H, m), 4.66(1H, t, J = 5.4 Hz), 7.11-7.21(2H, m), 7.34 (1H, d, J = 8 Hz), 7.55-7.58(1H, m), 7.64-7.68(2H, m), 7.84(1H, t, J = 5.4 Hz), 8.13(2H, d, J = 7.6 Hz), 8.50-8.52(2H, m), 10.48(1H, s) |
| 69 | 2.16(2H, q, J = 6.8 Hz), 3.04-3.21(3H, m), 3.27-3.40(2H, m), 6.93 (1H, brs), 7.05-7.14(2H, m), 7.22(1H, d, J = 6.8 Hz), 7.43(1H, brs), 7.54-7.61(3H, m), 8.08-8.10(2H, m), 8.15-8.17(1H, d, J = 9.6 Hz), 8.50(1H, s), 10.19(1H, s) |
| 105 | 1.73-1.90(4H, m), 2.38-2.49(1H, m), 3.09-3.18(2H, m), 3.92-4.03 (2H, m), 6.85(1H, brs), 7.30(1H, brs), 7.40(1H, d, J = 7.0 Hz), 7.53-7.62(4H, m), 8.10-8.14(2H, m), 8.34(1H, d, J = 7.0 Hz), 8.58(1H, s), 8.78(1H, brs), 10.18(1H, brs). |
| 109 | 3.27(4H, brs), 3.40-3.60(2H, m), 3.67-3.70(2H, m), 4.06(2H, s), 7.19-7.28(2H, m), 7.35(1H, d, J = 7.7 Hz), 7.77(1H, brs), 8.20(1H, brs), 8.27(2H, d, J = 6.2 Hz), 8.45(1H, dd, J = 1.5, 8.0 Hz), 8.81(1H, s), 9.02(1H, d, J = 6.0 Hz) |
| 151 | 3.19-3.63(12H, m), 3.80-3.83(4H, m), 3.97(2H, brs), 7.13-7.23(2H, m), 7.31(1H, dd, J = 7.7, 1.0 Hz), 7.71(1H, s), 7.72(1H, brs), 8.13 (1H, brs), 8.43(1H, dd, J = 8.1, 1.5 Hz), 9.73(1H, brs), 10.78(1H, brs) |
| 215 | 1.85-2.00(2H, m), 2.27(2H, d, J = 11.3 Hz), 2.76(2H, t, J = 11.3 Hz), 3.06-3.24(4H, m), 3.28-3.45(3H, m), 3.45-3.55(4H, m), 3.72-3.84 (4H, m), 3.92-4.08(4H, m), 7.07-7.22(2H, m), 7.30(1H, dd, J = 7.7, 1.6 Hz), 7.71(1H, s), 8.42(1H, dd, J = 7.9, 1.6 Hz), 9.64(1H, s), 11.66 (1H, brs) |

TABLE 69-continued

| Ex | Dat(NMR) |
|---|---|
| 229 | 1.76-1.96(4H, m), 2.26-2.38(1H, m), 2.80-2.92(2H, m), 3.10-3.18 (2H, m), 3.47-3.53(4H, m), 3.73-3.81(4H, m), 6.88(1H, brs), 7.40(1H, brs), 7.95(1H, s), 8.62(1H, d, J = 6.5 Hz), 8.74(1H, s), 8.80(1H, d, J = 6.5 Hz), 10.57(1H, s). |
| 234 | 1.51(2H, d, J = 13.0 Hz), 1.85-1.93(2H, m), 3.07-3.24(6H, m), 3.46-3.49(4H, m), 3.73-3.76(4H, m), 5.36(2H, br), 7.22(1H, dd, J = 8.0, 5.2 Hz), 7.73(1H, s), 8.08(1H, dd, J = 5.1, 1.6 Hz), 8.68(1H, dd, J = 8.0, 1.5 Hz), 9.67(1H, s) |
| 311 | 1.54-1.63(2H, m), 1.90-1.95(2H, m), 3.11-3.19(4H, m), 3.36-3.42 (2H, m), 3.63-3.69(4H, m), 3.78-3.85(3H, m), 3.97(2H, s), 4.74(1H, brs), 6.99(1H, dd, J = 11.6, 8.5 Hz), 7.31(1H, ddd, J = 6.2, 8.3, 8.5 Hz), 7.65(1H, s), 7.78(1H, s), 8.31(1H, d, J = 8.3 Hz), 8.39(1H, s), 10.18(1H, s), 10.67(1H, brs) |
| 356 | 3.18-3.30(9H, m), 3.57(3H, s), 3.63-3.74(6H, m), 4.01(2H, brs), 7.12-7.24(2H, m), 7.32(1H, d, J = 7.8 Hz), 8.17(1H, brs), 8.44(1H, dd, J = 8.0, 1.4 Hz), 10.67(1H, brs) |
| 379 | 1.85-2.17(4H, m), 2.88-3.00(1H, m), 3.08-3.24(5H, m), 3.29(3H, s), 3.50-3.66(4H, m), 3.70(2H, t, J = 5.3 Hz), 3.89(2H, d, J = 4.0 Hz), 7.13(1H, td, J = 8.4, 2.7 Hz), 7.31(1H, dd, J = 8.7, 6.5 Hz), 7.49-7.59(2H, m), 7.69(1H, s), 8.06(1H, s), 9.65(1H, s), 9.99(1H, brs) |
| 380 | 1.79-1.90(4H, m), 2.25-2.34(1H, m), 2.77-2.86(2H, m), 3.14(3H, s), 3.22-3.26(2H, m), 3.27(3H, s), 3.61-3.73(4H, m), 6.77(1H, brs), 7.20(1H, dd, J = 8.0, 5.0 Hz), 7.31(1H, brs), 7.57(1H, s), 8.08(1H, dd, J = 4.9, 1.8 Hz), 8.68(1H, d, J = 8.0, 1.5 Hz), 9.73(1H, s) |
| 382 | 3.16(3H, s), 3.30(3H, s), 3.32-3.52(6H, m), 3.61-3.67(4H, m), 3.69-3.74(2H, m), 4.00(2H, s), 7.23(1H, dd, J = 8.0, 5.0 Hz), 7.60(1H, s), 7.74(1H, brs), 8.12(1H, dd, J = 5.0, 1.5 Hz), 8.14(1H, brs), 8.64(1H, dd, J = 8.0, 1.5 Hz), 9.47(1H, s), 10.69(1H, brs). |
| 449 | 1.80-1.88(2H, m), 1.99-2.02(2H, m), 2.74-2.80(2H, m), 2.99-3.02 (2H, m), 3.76(1H, brs), 4.85(1H, d, J = 3.2 Hz), 7.09-7.19(2H, m), 7.29(1H, d, J = 7.2, 1.6 Hz), 7.57-7.65(2H, m), 8.10-8.13(2H, m), 8.39(1H, dd, J = 8.0, 1.6 Hz), 8.93(1H, s), 10.24(1H, s) |
| 462 | 3.21-3.23(2H, m), 3.50-3.78(6H, m), 4.90(2H, brs), 7.05(1H, t, J = 8.2 Hz), 7.30-7.38(1H, m), 7.75(1H, s), 8.26-8.32(2H, m), 8.44-8.45(1H, m), 9.25(1H, s), 9.68(1H, d, J = 5.3 Hz), 9.83(1H, s), 10.06(1H, s) |
| 468 | 1.87-1.90(2H, m), 2.02-2.12(2H, m), 2.31-2.41(1H, m), 2.77(1H, t, J = 10.8 Hz), 2.99-3.03(2H, m), 6.59(1H, d, J = 9.6 Hz), 6.93(1H, brs), 7.09-7.20(2H, m), 7.29-7.31(1H, m, d, J = 7.3 Hz), 7.41(1H, brs), 8.14(1H, d, J = 2.6 Hz), 8.19-8.23(1H, m), 8.37(1H, d, J = 7.4 Hz), 8.80(1H, s), 10.24(1H, brs). |
| 476 | 1.86-1.91(2H, m), 2.05-2.15(2H, m), 2.40-2.51(1H, m), 2.78(2H, t, J = 10.7 Hz), 2.98-3.02(2H, m), 7.10-7.22(2H, m), 7.30-7.33(2H, m), 7.43-7.45(1H, m), 7.84(2H, brs), 8.14(1H, d, J = 6.7 Hz), 8.40-8.43(1H, m), 8.65(1H, brs), 9.16(1H, s), 10.27(1H, brs). |
| 477 | 1.87-1.91(2H, m), 2.03-2.15(2H, m), 2.43-2.51(1H, m), 2.88(2H, t, J = 11.4 Hz), 3.29-3.33(2H, m), 7.21-7.27(2H, m), 7.41-7.43(1H, m), 7.81-7.83(2H, m), 8.08-8.16(2H, m), 8.63-8.66(1H, d, m), 8.77(1H, brs), 9.21(1H, d, J = 1.3 Hz), 9.79(1H, brs). |
| 482 | 3.22(4H, brs), 3.37(4H, brs), 3.49-3.51(4H, m), 3.75-3.77(4H, m), 4.00(2H, s), 7.05(1H, ddd, J = 2.9, 8.9, 11.5 Hz), 7.18(1H, dd, J = 2.9, 10.1 Hz), 7.69(1H, s), 8.10(1H, s), 8.33(1H, s), 8.36(1H, dd, J = 6.0, 8.9 Hz), 9.28(1H, s), 10.77(1H, brs) |
| 492 | 1.81-1.84(2H, m), 1.89-1.99(2H, m), 2.27(1H, dddd, J = 4.1, 4.1, 11.8, 11.8Hz), 2.67-2.74(2H, m), 2.93-2.96(2H, m), 3.48-3.50(4H, m), 3.71-3.73(4H, m), 6.80(1H, s), 7.07(1H, ddd, J = 1.5, 7.6, 8.9 Hz), 7.14(1H, ddd, J = 1.4, 7.9, 8.9Hz), 7.25(1H, dd, J = 1.4, 7.6 Hz), 7.29(1H, s), 8.27(1H, s), 8.37(1H, dd, J = 1.5, 7.9 Hz) |
| 501 | 1.84-1.98(4H, m), 2.33(1H, dddd, J = 4.4, 4.4, 11.6, 11.6 Hz), 2.85-2.91(2H, m), 3.30-3.33(2H, m), 3.48-3.51(4H, m), 3.70-3.73(4H, m), 6.83(1H, brs), 7.24(1H, dd, J = 5.2, 8.1 Hz), 7.34(1H, brs), 8.08(1H, dd, J = 1.6, 5.2 Hz), 8.36(1H, s), 8.66(1H, dd, J = 1.6, 8.2 Hz), 9.55(1H, s) |
| 599 | 1.87-1.92(4H, m), 2.22-2.35(1H, m), 2.73-2.78(2H, m), 3.09(3H, s), 3.19-3.22(2H, m), 3.26(3H, s), 3.57-3.61(4H, m), 6.76(1H, s), 7.14(1H, dd, J = 4.8, 7.6 Hz), 7.28(1H, s), 8.05-8.06(1H, m), 8.23 (1H, s), 8.60-8.62(1H, m), 9.47(1H, s) |

TABLE 69-continued

| Ex | Dat(NMR) |
|---|---|
| 637 | 2.82(3H, d, J = 4.4 Hz), 3.17-3.30(6H, m), 3.54-3.66(2H, m), 7.19(1H, td, J = 7.8, 1.5 Hz), 7.26(1H, td, J = 7.8, 1.5 Hz), 7.33(1H, dd, J = 7.8, 1.5 Hz), 7.82(1H, dd, J = 7.8, 5.4 Hz), 8.43(1H, dd, J = 8.3, 1.4 Hz), 8.59-8.63(1H, m), 8.67(1H, s), 8.85(1H, dd, J = 4.9, 1.5 Hz), 9.40(1H, d, J = 2.0 Hz), 10.25(1H, s), 11.45(1H, brs) |
| 671 | 1.84-1.92(4H, m), 2.24-2.32(1H, m), 2.66-2.73(2H, m), 2.94-2.97 (2H, m), 3.42-3.45(2H, m), 3.86-3.89(2H, m), 3.92(2H, brs), 6.81(1H, brs), 7.08(1H, dd, J = 7.5, 7.6 Hz), 7.15(1H, dd, J = 7.5, 8.1 Hz), 7.28(1H, d, J = 7.6 Hz), 7.34(1H, brs), 7.66(1H, s), 8.31(1H, s), 8.43(1H, d, J = 8.1 Hz), 10.24(1H, s) |
| 701 | 1.82-1.95(2H, m), 1.98-2.13(2H, m), 2.58-3.14(8H, m), 3.32(2H, s), 3.57-3.73(4H, m), 4.90-5.07(1H, m), 7.09-7.19(2H, m), 7.30(1H, dd, J = 7.8, 1.4 Hz), 7.64(1H, s), 8.43(1H, dd, J = 8.1, 1.5 Hz), 10.12(1H, brs) |
| 716 | 1.99-2.13(4H, m), 3.18(3H, brs), 3.40-3.44(2H, m), 3.57-3.68(8H, m), 4.01-4.06(3H, m), 7.13-7.33(3H, m), 7.57(1H, m), 7.74(1H, s), 8.14(1H, s), 8.46(1H, dd, J = 1.2, 7.6 Hz), 9.86(1H, s), 10.61(1H, brs) |
| 722 | 2.79-2.81(4H, m), 3.19-364(8H, m), 3.86-3.89(4H, m), 4.01(1H, brs), 7.15(1H, ddd, J = 1.5, 7.7, 7.8 Hz), 7.21(1H, ddd, J = 1.4, 7.7, 7.9 Hz), 7.32(1H, dd, J = 1.4, 7.8 Hz), 7.67(1H, s), 7.74(1H, brs), 8.14(1H, brs), 8.44(1H, dd, J = 1.5, 7.9 Hz), 9.71(1H, s), 10.74(1H, brs) |
| 862 | 3.23(4H, brs), 3.45-3.65(4H, m), 4.11(2H, brs), 7.15-7.26(3H, m), 7.32(1H, dd, J = 1.4, 7.8 Hz), 7.74(1H, brs), 7.96(1H, s), 8.09(1H, brs, J = 1.6, 7.8 Hz), 8.64(1H, s), 8.90(1H, s), 9.61(1H, brs) |

INDUSTRIAL APPLICABILITY

The compound of the present invention has a potent trkA receptor inhibitory activity, and is useful as a medicine, particularly as an agent for treating urinary frequency, urinary urgency, urinary incontinence, lower urinary tract pain, which are associated with various lower urinary tract diseases including overactive bladder, and various diseases accompanied by pain.

The invention claimed is:

1. A compound or a salt thereof, wherein the compound is selected from the group consisting of:
   methyl (3-[4-(2-amino-2-oxoethyl)piperazin-1-yl]-4-{[(2-phenyl-1,3-thiazol-4-yl)carbonyl]amino}phenyl)acetate,
   N-[2-(3-carbamoylpyrrolidin-1-yl)phenyl]-2-phenyl-1,3-thiazole-4-carboxamide,
   N-{2-[4-(2-amino-2-oxoethyl)piperazin-1-yl]phenyl}-2-morpholin-4-yl-1,3-thiazole-4-carboxamide,
   N-{2-[4-(2-amino-2-oxoethyl)piperazin-1-yl]-3-fluorophenyl}-2-(4-hydroxypiperidin-1-yl)-1,3-thiazole-4-carboxamide,
   N-{2-[4-(2-amino-2-oxoethyl)piperazin-1-yl]phenyl}-2-[(2-methoxyethyl)(methyl)amino]-1,3-thiazole-4-carboxamide,
   1-{3-[({2-[(2-methoxyethyl)(methyl)amino]-1,3-thiazol-4-yl}carbonyl)amino]pyridin-2-yl}piperidine-4-carboxamide,
   N-{2-[4-(2-amino-2-oxoethyl)piperazin-1-yl]pyridin-3-yl}-2-[(2-methoxyethyl)(methyl)amino]-1,3-thiazole-4-carboxamide,
   N-[2-(4-hydroxypiperidin-1-yl)phenyl]-2-phenyl-1,3-oxazole-4-carboxamide,
   1-(2-{[(2-morpholin-4-yl-1,3-oxazol-4-yl)carbonyl]amino}phenyl)piperidine-4-carboxamide,
   1-(3-{[(2-morpholin-4-yl-1,3-oxazol-4-yl)carbonyl]amino}pyridin-2-yl)piperidine-4-carboxamide, and
   N-{2-[4-(2-amino-2-oxoethyl)piperazin-1-yl]phenyl}-2-(3-furyl)-1,3-oxazole-4-carboxamide.

2. A pharmaceutical composition, comprising the compound according to claim 1 or a pharmaceutically acceptable salt thereof, as an active ingredient.

3. The compound according to claim 1 or a salt thereof, wherein said compound is methyl (3-[4-(2-amino-2-oxoethyl)piperazin-1-yl]-4-{[(2-phenyl-1,3-thiazol-4-yl)carbonyl]amino}phenyl)acetate.

4. The compound according to claim 1 or a salt thereof, wherein said compound is N-[2-(3-carbamoylpyrrolidin-1-yl)phenyl]-2-phenyl-1,3-thiazole-4-carboxamide.

5. The compound according to claim 1 or a salt thereof, wherein said compound is N-{2-[4-(2-amino-2-oxoethyl)piperazin-1-yl]phenyl}-2-morpholin-4-yl-1,3-thiazole-4-carboxamide.

6. The compound according to claim 1 or a salt thereof, wherein said compound is N-{2-[4-(2-amino-2-oxoethyl)piperazin-1-yl]-3-fluorophenyl}-2-(4-hydroxypiperidin-1-yl)-1,3-thiazole-4-carboxamide.

7. The compound according to claim 1 or a salt thereof, wherein said compound is N-{2-[4-(2-amino-2-oxoethyl)piperazin-1-yl]phenyl}-2-[(2-methoxyethyl)(methyl)amino]-1,3-thiazole-4-carboxamide.

8. The compound according to claim 1 or a salt thereof, wherein said compound is 1-{3-[({2-[(2-methoxyethyl)(methyl)amino]-1,3-thiazol-4-yl}carbonyl)amino]pyridin-2-yl}piperidine-4-carboxamide.

9. The compound according to claim 1 or a salt thereof, wherein said compound is N-{2-[4-(2-amino-2-oxoethyl)piperazin-1-yl]pyridin-3-yl}-2-[(2-methoxyethyl)(methyl)amino]-1,3-thiazole-4-carboxamide.

10. The compound according to claim 1 or a salt thereof, wherein said compound is N-[2-(4-hydroxypiperidin-1-yl)phenyl]-2-phenyl-1,3-oxazole-4-carboxamide.

11. The compound according to claim 1 or a salt thereof, wherein said compound is 1-(2-{[(2-morpholin-4-yl-1,3-oxazol-4-yl)carbonyl]amino}phenyl)piperidine-4-carboxamide.

12. The compound according to claim 1 or a salt thereof, wherein said compound is 1-(3-{[(2-morpholin-4-yl-1,3-oxazol-4-yl)carbonyl]amino}pyridin-2-yl)piperidine-4-carboxamide.

13. The compound according to claim 1 or a salt thereof, wherein said compound is N-{2-[4-(2-amino-2-oxoethyl)piperazin-1-yl]phenyl}-2-(3-furyl)-1,3-oxazole-4-carboxamide.

14. A method for treating urinary frequency, urinary urgency, urinary incontinence, lower urinary tract pain, which are associated with various lower urinary tract diseases, or osteoarthritis, which comprises administrating an effective amount of the compound according to claim 1 or a pharmaceutically acceptable salt thereof to a patient in need thereof.

15. The method according to claim 14, wherein the lower urinary tract disease is overactive bladder, interstitial cystitis or chronic prostatitis.

16. A method for treating pain, which comprises administrating an effective amount of the compound according to claim 1 or a pharmaceutically acceptable salt thereof to a patient in need thereof.

* * * * *